US011548871B2

(12) United States Patent
Bestvater et al.

(10) Patent No.: US 11,548,871 B2
(45) Date of Patent: Jan. 10, 2023

(54) TRIAZOLE CARBAMATE PYRIDYL SULFONAMIDES AS LPA RECEPTOR ANTAGONISTS AND USES THEREOF

(71) Applicant: Gilead Sciences, Inc., Foster City, CA (US)

(72) Inventors: Brian P. Bestvater, San Mateo, CA (US); Zhimin Du, Belmont, CA (US); Julie Farand, San Mateo, CA (US); Gregory Notte, Redwood City, CA (US); Barton W. Phillips, San Mateo, CA (US); Doris T. Tang, Burlingame, CA (US); Chandrasekar Venkataramani, San Carlos, CA (US); Peiyuan Wang, San Mateo, CA (US); Kin S. Yang, San Mateo, CA (US); Anna Zagorska, Foster City, CA (US)

(73) Assignee: Gilead Sciences, Inc., Foster City, CA (US)

(*) Notice: Subject to any disclaimer, the term of this patent is extended or adjusted under 35 U.S.C. 154(b) by 110 days.

(21) Appl. No.: 17/096,150

(22) Filed: Nov. 12, 2020

(65) Prior Publication Data

US 2021/0171500 A1 Jun. 10, 2021

Related U.S. Application Data

(60) Provisional application No. 62/935,936, filed on Nov. 15, 2019.

(51) Int. Cl.
| | |
|---|---|
| *C07D 498/04* | (2006.01) |
| *C07D 401/04* | (2006.01) |
| *C07D 401/12* | (2006.01) |
| *C07D 401/14* | (2006.01) |
| *C07D 403/04* | (2006.01) |
| *C07D 413/04* | (2006.01) |
| *A61K 31/65* | (2006.01) |
| *A61P 11/00* | (2006.01) |
| *C07D 405/14* | (2006.01) |
| *C07D 409/14* | (2006.01) |
| *C07D 413/14* | (2006.01) |
| *C07D 417/14* | (2006.01) |

(52) U.S. Cl.
CPC ......... *C07D 401/14* (2013.01); *C07D 401/04* (2013.01); *C07D 405/14* (2013.01); *C07D 409/14* (2013.01); *C07D 413/14* (2013.01); *C07D 417/14* (2013.01); *C07B 2200/05* (2013.01)

(58) Field of Classification Search
CPC .. C07D 498/04; C07D 401/04; C07D 401/12; C07D 401/14; C07D 403/04; C07D 413/04; C07D 413/14; A61K 31/65; A61P 11/00

See application file for complete search history.

(56) References Cited

U.S. PATENT DOCUMENTS

| 10,662,172 B2 | 5/2020 | Shi et al. |
| 2003/0092749 A1 | 5/2003 | Dombroski et al. |
| 2017/0360759 A1 | 12/2017 | Cheng et al. |

FOREIGN PATENT DOCUMENTS

| WO | WO-2009135590 A1 | 11/2009 |
| WO | WO-2010068775 A2 | 6/2010 |
| WO | WO-2010077882 A2 | 7/2010 |
| WO | WO-2010077883 A2 | 7/2010 |
| WO | WO-2010141761 A2 | 12/2010 |
| WO | WO-2010141768 A2 | 12/2010 |
| WO | WO-2011017350 A2 | 2/2011 |
| WO | WO-2011037192 A1 | 3/2011 |
| WO | WO-2011041461 A2 | 4/2011 |
| WO | WO-2011041462 A2 | 4/2011 |
| WO | WO-2011041694 A2 | 4/2011 |
| WO | WO-2011041729 A2 | 4/2011 |
| WO | WO-2011053948 A1 | 5/2011 |
| WO | WO-2011159550 A2 | 12/2011 |
| WO | WO-2011159632 A1 | 12/2011 |
| WO | WO-2012039460 A1 | 3/2012 |
| WO | WO-2012078593 A2 | 6/2012 |
| WO | WO-2012078805 A1 | 6/2012 |
| WO | WO-2012100436 A1 | 8/2012 |
| WO | WO-2012138648 A1 | 10/2012 |
| WO | WO-2012138797 A1 | 10/2012 |
| WO | WO-2013025733 A1 | 2/2013 |
| WO | WO-2013085824 A1 | 6/2013 |
| WO | WO-2013189862 A1 | 12/2013 |
| WO | WO-2013189864 A1 | 12/2013 |
| WO | WO-2013189865 A1 | 12/2013 |
| WO | WO-2014037303 A1 | 3/2014 |
| WO | WO-2014072486 A1 | 5/2014 |
| WO | WO-2014104372 A1 | 7/2014 |
| WO | WO-2014113485 A1 | 7/2014 |
| WO | WO-2014145873 A2 | 9/2014 |
| WO | WO-2015025164 A1 | 2/2015 |
| WO | WO-2015066456 A1 | 5/2015 |
| WO | WO-2015199234 A1 | 12/2015 |
| WO | WO-2017086430 A1 | 5/2017 |
| WO | WO-2017177004 A1 | 10/2017 |
| WO | WO-2017223016 A1 | 12/2017 |

(Continued)

OTHER PUBLICATIONS

International Search Report and Written Opinion dated Jul. 26, 2021 for Intl. Appl. No. PCT/US2021/032293.
International Search Report and Written Opinion dated Aug. 10, 2021 for Intl. Appl. No. PCT/US2021/032202.

(Continued)

*Primary Examiner* — Bruck Kifle

(57) ABSTRACT

The present disclosure relates generally to compounds that bind to Lysophosphatidic Acid Receptor 1 (LPAR1) and act as antagonists of LPAR1. The disclosure further relates to the use of the compounds for the preparation of a medicament for the treatment of diseases and/or conditions through binding of LPAR1, including fibrosis and liver diseases such as non-alcoholic steatohepatitis (NASH).

30 Claims, No Drawings

(56) References Cited

FOREIGN PATENT DOCUMENTS

| WO | WO-2019046239 A1 | 3/2019 |
|---|---|---|
| WO | WO-2019126084 A1 | 6/2019 |
| WO | WO-2019126085 A1 | 6/2019 |
| WO | WO-2019126086 A1 | 6/2019 |
| WO | WO-2019126087 A1 | 6/2019 |
| WO | WO-2019126089 A1 | 6/2019 |
| WO | WO-2019126090 A1 | 6/2019 |
| WO | WO-2019126093 A1 | 6/2019 |
| WO | WO-2019126094 A1 | 6/2019 |
| WO | WO-2019126098 A1 | 6/2019 |
| WO | WO-2019126099 A1 | 6/2019 |
| WO | WO-2019126103 A1 | 6/2019 |
| WO | WO-2020060914 A1 | 3/2020 |
| WO | WO-2020060915 A1 | 3/2020 |
| WO | WO-2020060916 A1 | 3/2020 |
| WO | WO-2020081410 A2 | 4/2020 |
| WO | WO-2020257135 A1 | 12/2020 |
| WO | WO-2020257138 A1 | 12/2020 |
| WO | WO-2020257139 A1 | 12/2020 |
| WO | WO-2021020429 A1 | 2/2021 |
| WO | WO-2021110805 A1 | 6/2021 |
| WO | WO-2022013378 A1 | 1/2022 |
| WO | WO-2022034568 A1 | 2/2022 |
| WO | WO-2022100623 A1 | 5/2022 |
| WO | WO-2022100624 A1 | 5/2022 |
| WO | WO-2022100625 A1 | 5/2022 |
| WO | WO-2022174882 A1 | 8/2022 |
| WO | WO-2022174883 A1 | 8/2022 |

OTHER PUBLICATIONS

Gallezot, J. et al. (2018) "Evaluation of the Lysophosphatidic Acid Receptor Type 1 Radioligand 11C-BMT-136088 for Lung Imaging in Rhesus Monkeys" The Journal of Nuclear Medicine, 59(2):327-333.

International Search Report and Written Opinion dated Mar. 26, 2021 for Intl. Appl. No. PCT/US2020/060153.

Cheng, P. et al. (2021) "Discovery of an Oxycyclohexyl Acid Lysophosphatidic Acid Receptor 1 (LPA1) Antagonist BMS-986278 for the Treatment of Pulmonary Fibrotic Diseases" J. Med. Chem., 64, 21, 15549-15581.

International Preliminary Report on Patentability dated May 27, 2022 for Intl. Appl. No. PCT/US2020/060153.

U.S. Appl. No. 17/319,507, filed May 13, 2021, Brian P. Bestvater, et al.

U.S. Appl. No. 17/319,471, filed May 13, 2021, Barton W. Phillips, et al.

U.S. Appl. No. 17/741,991, filed May 11, 2022, Brian P. Bestvater, et al.

U.S. Appl. No. 17/741,222, filed May 10, 2022, Brian P. Bestvater, et al.

U.S. Appl. No. 63/287,252, filed Dec. 8, 2021, Brian P. Bestvater, et al.

TRIAZOLE CARBAMATE PYRIDYL SULFONAMIDES AS LPA RECEPTOR ANTAGONISTS AND USES THEREOF

CROSS-REFERENCE TO RELATED APPLICATIONS

This application claims the benefit under 35 U.S.C. § 119(e) of U.S. provisional application No. 62/935,936, filed on Nov. 15, 2019, which is hereby incorporated herein by reference in its entirety for all purposes.

FIELD

The present disclosure relates to compounds that bind to and act as antagonists of a lysophosphatidic acid (LPA) receptor, such as LPAR1. The disclosure further relates to the use of the compounds for the treatment and/or prophylaxis of diseases and/or conditions associated with one or more LPA receptors, e.g., an LPAR1 associated disease or condition.

BACKGROUND

Lysophosphatidic acids (mono-acyl-glycerol-3-phosphate, LPA) are a class of biologically active phospholipids that can be produced from lysophosphatidyl choline (LPC), e.g., by the enzyme autotaxin. A typical LPA has a glycerol, an ester-linked fatty acid at the sn-1 position, and a phosphate head group at the sn-3 position. LPA with various fatty acids have been identified, including palmitoyl LPA (16:0), stearoyl LPA (18:0), oleoyl LPA (18:1), linoleoyl LPA (18:2) and arachidonyl LPA (20:4). LPA exerts a wide range of cellular responses, such as proliferation, differentiation, survival, migration, adhesion, invasion, and morphogenesis through a family of rhodopsin-like G protein-coupled receptors (GPCRs). Six LPA receptors have been been characterized and were found to differ in their tissue distribution and downstream signaling pathways. These six LPA receptors are often referred to interchangeably as LPAR1-6 (gene) or LPA1-6 (protein). LPA receptor mediated signaling has been shown to influence many biological processes such as wound healing, immunity, carcinogenesis, angiogenesis and neurogenesis.

In vivo studies involving LPA receptor-deficient mice or certain tool compounds have suggested a potential of LPA receptors as possible drug targets in a variety of diseases including cancer, fibrosis, inflammation, pain, and cardiovascular diseases. More recently, LPAR1 antagonists have been studied clinically in connection with fibrotic disease states such as idiopathic pulmonary fibrosis (IPF) and systemic sclerosis.

A need remains for LPA antagonists with desirable selectivity, potency, metabolic stability, or reduced detrimental effects.

SUMMARY

The present disclosure provides compounds useful as inhibitors of Lysophosphatidic Acid Receptor 1 (LPAR1). The disclosure further relates to the use of the compounds for the treatment and/or prophylaxis of diseases and/or conditions through binding of LPAR1 by said compounds.

In one embodiment, provided herein is a compound of Formula (I),

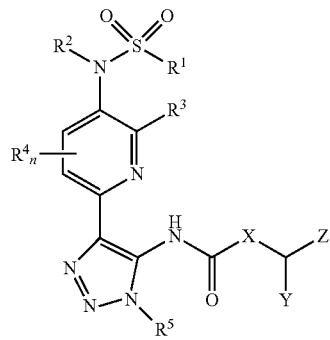

or pharmaceutically acceptable salt thereof,
wherein:

$R^1$ is $C_{1-6}$ alkyl optionally substituted with 1 to 3 substituents independently selected from halogen, cyano, $C_{1-3}$ alkoxy, $-N(R^{1A})_2$, $-C(O)OR^{1A}$, $-C(O)N(R^{1A})_2$, $-NR^{1A}C(O)R^{1A}$, $-NR^{1A}C(O)OR^{1A}$, $-S(O)_{0-2}R^{1A}$, $-S(O)_2N(R^{1A})_2$ and $-NR^{1A}S(O)_2R^{1A}$, wherein each $R^{1A}$ is independently H or $C_{1-6}$ alkyl; or $R^1$ is $C_{3-6}$ cycloalkyl, 6 to 10 membered aryl, 3 to 10 membered heterocyclyl having 1 to 4 heteroatoms independently selected from nitrogen, oxygen, and sulfur, or 5 to 10 membered heteroaryl having 1 to 4 heteroatoms independently selected from nitrogen, oxygen, and sulfur, wherein each cycloalkyl, aryl, heterocyclyl, or heteroaryl is optionally substituted with 1 to 3 substituents independently selected from halogen, cyano, $C_{1-3}$ alkyl, $C_{1-3}$ alkoxy, $-N(R^{1A})_2$, $-C(O)N(R^{1A})_2$, $-NR^{1A}C(O)R^{1A}$, $-S(O)_{0-2}R^{1A}$, $-S(O)_2N(R^{1A})_2$ and $-NR^{1A}S(O)_2R^{1A}$, wherein each $R^{1A}$ is independently H or $C_{1-6}$ alkyl; or $R^1$ is $-O-R^{1B}$ or $-N(R^{1B})_2$, wherein each $R^{1B}$ is independently H, $C_{1-6}$ alkyl, or $C_{3-6}$ cycloalkyl, wherein each $C_{1-6}$ alkyl, or $C_{3-6}$ cycloalkyl is optionally substituted with 1 to 3 substituents independently selected from halogen and $-C(O)N(R^{1C})_2$, wherein each $-R^{1C}$ is independently H or $C_{1-3}$ alkyl;

$R^2$ is hydrogen or $C_{1-6}$ alkyl optionally substituted with 1 to 3 substituents independently selected from deuterium, halogen, cyano, $C_{1-3}$ alkoxy, and $C_{3-10}$ cycloalkyl; or $R^2$ is $C_{3-6}$ cycloalkyl optionally substituted with 1 to 3 substituents independently selected from halogen, cyano, $C_{1-3}$ alkoxy, and $C_{1-6}$ alkyl;

$R^3$ is hydrogen, halogen, $C_{1-6}$ alkyl, $C_{3-6}$ cycloalkyl, $-O-R^{3A}$, or $-N(R^{3A})_2$, wherein the $C_{1-6}$ alkyl is optionally substituted with 1 to 3 substituents independently selected from $C_{1-3}$ alkoxy and halogen, and wherein each $R^{3A}$ is independently $C_{1-3}$ alkyl optionally substituted with 1 to 3 halogens; or each $R^4$ is independently deuterium, halogen, $C_{1-6}$ alkyl, $C_{3-10}$ cycloalkyl, or $C_{1-3}$ alkoxy, wherein the $C_{1-6}$ alkyl or $C_{3-10}$ cycloalkyl, is optionally substituted with 1 to 3 halogens:

n is 0, 1 or 2;

$R^5$ is $C_{1-6}$ alkyl optionally substituted with 1 to 3 substituents independently selected from halogen, cyano, $C_{1-3}$ alkoxy, $-C(O)N(R^{1A})$, and $-N(R^{1A})_2$, wherein each $R^{1A}$ is independently H, $C_{1-6}$ alkyl, or $C_{3-10}$ cycloalkyl; or $R^5$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents independently selected from halogen, cyano, $C_{1-3}$ alkyl and $C_{1-3}$ alkoxy;

X is NH or O;

Y is hydrogen or $C_{1-6}$ alkyl optionally substituted with 1 to 3 substituents independently selected from halogen, cyano, $C_{1-3}$ alkynyl, $C_{1-3}$ alkoxy, and —C(O)NH—$R^y$, wherein $R^y$ is $C_{1-3}$ alkyl; and Z is $C_{1-6}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents independently selected from halogen, cyano, $C_{1-3}$ alkyl, $C_{1-3}$ alkenyl, $C_{1-3}$ alkoxy, and $C_{3-6}$ cycloalkyl, wherein the $C_{1-3}$ alkyl is optionally substituted with 1 to 3 substituents selected from $C_{1-3}$ alkoxy and halogen; or Y and Z together with the carbon to which they are attached form $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents independently selected from cyano, $C_{1-3}$ alkyl, $C_{1-3}$ alkoxy, $C_{6-10}$ aryl and halogen, wherein the $C_{1-3}$ alkyl is optionally substituted with 1 to 3 substituents independently selected from $C_{1-3}$ alkoxy and halogen, and wherein the $C_{6-10}$ aryl is optionally substituted with 1 to 3 substituents independently selected from $C_{1-3}$ alkyl, $C_{1-3}$ alkoxy, and halogen.

In some embodiments, provided herein are pharmaceutical compositions comprising a compound provided herein, or pharmaceutically acceptable salt thereof, and a pharmaceutically acceptable excipient or carrier. In some embodiments, the pharmaceutical compositions comprise a therapeutically effective amount of a compound provided herein, or pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or pharmaceutically acceptable salts thereof. In some embodiments, the pharmaceutical compositions further comprise a therapeutically effective amount of the one or more (e.g., one, two, three, four, one or two, one to three, or one to four) additional therapeutic agents, or pharmaceutically acceptable salts thereof.

In some embodiments, the present disclosure provides methods of inhibiting LPAR1 activity in a subject in need thereof, comprising administering to the subject a therapeutically effective amount of a compound provided herein (e.g., a compound of Formula (I), (Ia), (II), or (IIa)), or pharmaceutically acceptable salt thereof, or a pharmaceutical composition provided herein.

In some embodiments, the present disclosure provides methods of treating a patient having an LPAR1 mediated condition, comprising administering to the patient a therapeutically effective amount of a compound provided herein (e.g., a compound of Formula (I), (Ia), (II), or (IIa)), or pharmaceutically acceptable salt thereof, or a pharmaceutical composition provided herein.

DETAILED DESCRIPTION

The present disclosure relates to LPA receptor antagonists, such as antagonists of LPAR1. The disclosure also relates to compositions and methods relating to LPAR1 antagonists and the use of such compounds for treatment and/or prophylaxis of LPAR1-mediated diseases and conditions. The disclosure also relates to compositions and methods of treating and/or preventing liver disease including an LPAR1 antagonist in combination with one or more additional therapeutic agents.

It is commonly believed that patients with certain LPAR1-mediated diseases, such as cancer, fibrosis, inflammation, pain, and cardiovascular diseases, or liver diseases including non-alcoholic fatty liver disease (NAFLD) and non-alcoholic steatohepatitis (NASH) can benefit from the treatment with an LPAR1 antagonist and optionally one or more additional therapeutic agents.

Definitions and General Parameters

The description below is made with the understanding that the present disclosure is to be considered as an exemplification of the claimed subject matter and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present specification, the following terms and phrases are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring indicates that the point of attachment for a substituent on the ring can be at any ring atom. For example, Ra in the below structure can be attached to any of the five carbon ring atoms or Ra can replace the hydrogen attached to the nitrogen ring atom:

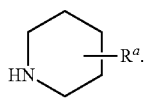

The prefix "$C_{u-v}$" indicates that the following group has from u to v carbon atoms. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula (I), (Ia), (II), or (IIa). Also included are the specific Compounds 1 to 164 provided herein (e.g., Tables 1-7).

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), 1 to 4 carbon atoms (i.e., $C_{1-4}$ alkyl), or 1 to 3 carbon atoms (i.e., $C_{1-3}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_2$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amino" refers to the group —$NR^yR^z$ wherein $R^y$ and $R^z$ are independently selected from the group consisting of hydrogen, alkyl, haloalkyl, aryl, heteroaryl, cycloalkyl, or heterocyclyl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Fused" refers to a ring which is bound to an adjacent ring.

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., $C_{1-20}$ heteroaryl), 3 to 12 carbon ring atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refers to a non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refers to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., $C_{2-20}$ heterocyclyl), 2 to 12 carbon ring atoms (i.e., $C_{2-12}$ heterocyclyl), 2 to 10 carbon ring atoms (i.e., $C_{2-10}$ heterocyclyl), 2 to 8 carbon ring atoms (i.e., $C_{2-8}$ heterocyclyl), 3 to 12 carbon ring atoms (i.e., $C_{3-12}$ heterocyclyl), 3 to 8 carbon ring atoms (i.e., $C_{3-8}$ heterocyclyl), or 3 to 6 carbon ring atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the terms "heterocycle", "heterocyclyl", and "heterocyclic ring" are used interchangeably.

"Hydroxy" or "hydroxyl" refers to the group —OH.

"Oxo" refers to the group (=O) or (O).

"Sulfonyl" refers to the group —S(O)$_2$R$^c$, where R$^c$ is alkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH$_2$ group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, amino, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, amino, alkoxy, halo, oxo, and hydroxyl; "substituted heterocyclyl" refers to a heterocyclyl group having one or more substituents including alkyl, amino, haloalkyl, heterocyclyl, cycloalkyl, aryl, heteroaryl, alkoxy, halo, oxo, and hydroxyl; "substituted aryl" refers to an aryl group having one or more substituents including halo, alkyl, amino, haloalkyl, cycloalkyl, heterocyclyl, heteroaryl, alkoxy, and cyano; "substituted heteroaryl" refers to an heteroaryl group having one or more substituents including halo, amino, alkyl, haloalkyl, cycloalkyl, aryl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

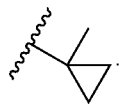

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine, amino acids, or other bases known to persons skilled in the art. The compounds of the present disclosure which contain one or more basic groups, i.e. groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to persons skilled in the art.

If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts.

The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources.

Furthermore, compounds disclosed herein may be subject to tautomerism. Where tautomerism, e.g., keto-enol tautomerism, of compounds or their prodrugs may occur, the individual forms, like, e.g., the keto and enol form, are each within the scope of the disclosure as well as their mixtures in any ratio. The same applies for stereoisomers, like, e.g., enantiomers, cis/trans isomers, diastereomers, conformers, and the like.

The term "protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. The term "deprotecting" refers to removing the protecting group.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound.

In certain embodiments, provided are optical isomers, racemates, or other mixtures thereof of the compounds described herein or a pharmaceutically acceptable salt or a mixture thereof. If desired, isomers can be separated by methods well known in the art, e.g. by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high-pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. "Diastereomers" are stereoisomers that have at least two asymmetric atoms, but which are not mirror-images of each other.

Compounds disclosed herein and their pharmaceutically acceptable salts may, in some embodiments, include an asymmetric center and may thus give rise to enantiomers, diastereomers, and other stereoisomeric forms that may be defined, in terms of absolute stereochemistry, as (R)- or (S)- or, as (D)- or (L)- for amino acids. Some embodiments include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC).

When the compounds described herein contain olefinic double bonds or other centres of geometric asymmetry, and unless specified otherwise, it is intended that the compounds include both E and Z geometric isomers.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphoros, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds disclosed herein, in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g., a human. See, e.g., Foster, "Deuterium Isotope Effects in Studies of Drug Metabolism," Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have beneficial DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the present disclosure provides pharmaceutical compositions comprising a compound of the present disclosure, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure can encompass any composition made by admixing at least one compound of the present disclosure and a pharmaceutically acceptable carrier.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

"IC$_{50}$" or "EC$_{50}$" refers to the inhibitory concentration required to achieve 50% of the maximum desired effect. In many cases here the maximum desired effect is the inhibition of LPA induced LPAR1 activation. This term is obtained using an in vitro assay, such as a calcium mobilization assay, evaluating the concentration-dependent inhibition of LPA induced LPAR1 activity.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival. In some embodiments, the term "treatment" or "treating" means administering a compound or pharmaceutically acceptable salt of Formula (I), (Ia), (II), or (IIa) for the purpose of: (i) delaying the onset of a disease, that is, causing the clinical symptoms of the disease not to develop or delaying the development thereof, (ii) inhibiting the disease, that is, arresting the development of clinical symptoms; and/or (iii) relieving the disease, that is, causing the regression of clinical symptoms or the severity thereof.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to LPAR1 antagonists. The therapeutically effective amount may vary depending on the subject, and disease or condition being treated, the weight and age of the subject, the severity of the disease or condition, and the manner of administering, which can readily be determined by one or ordinary skill in the art.

List of Abbreviations and Acronyms

| Abbreviation | Meaning |
| --- | --- |
| ACN or MeCN | Acetonitrile |
| aq. | Aqueous |
| Bn | Benzyl |
| COPD | Chronic Obstructive Pulmonary Disease |
| DAST | Diethylaminosulfur trifluoride |
| DCM | Dichloromethane |
| DIEA | N, N-Diisopropylethylamine |
| DMF | N,N-Dimethylformamide |
| DMSO | Dimethylsulfoxide |
| DPPA | Diphenylphosphoryl azide |
| EA | Ethyl acetate |
| EDTA | Ethylenediaminetetraacetic acid |
| ESI | Electronspray Ionization |
| Et | Ethyl |
| Et$_2$O | Diethyl ether |
| EtOAc | Ethyl acetate |
| h or hr(s) | Hour(s) |
| HBSS | Hanks' Balanced Salt solution |
| HCC | Hepatocellular carcinoma |
| HPLC | High performance liquid chromatography |
| LCMS or LC/MS | Liquid Chromatography Mass Spectrometry |
| LPA | Lysophosphatidic acid |
| LPC | Lysophosphatidylcholine |
| Me | Methyl |
| MeOH | Methanol |
| MS | Mass Spectrometry |
| m/z | Mass-to-charge ratio |
| NADPH | Dihydronicotinamide-adenine dinucleotide phosphate |
| NAFLD | Non-alcoholic fattyl liver disease |
| NASH | Non-alcoholic steatohepatitis |
| NBS | N-Bromosuccinimide |
| NMR | Nuclear Magnetic Resonance spectroscopy |
| PBC | Primary Biliary Cirrhosis |
| PE | Petroleum ether |
| PSC | Primary Sclerosing Choleangitis |
| RBF | Round Bottom Flask |
| rpm | Revolutions per minute |
| RT or rt | Room temperature |
| sat. | Saturated |

-continued

| Abbreviation | Meaning |
| --- | --- |
| TEMPO | 2,2,6,6-Tetramethylpiperidine 1-oxyl |
| TFA | Trifluoroacetic acid |
| THF | Tetrahydrofuran |
| T$_3$P | Propanephosphonic acid anhydride |

As used herein, an "LPAR1 antagonist" refers to any agent that is capable of binding and inhibiting LPAR1. LPAR1, also known as LPA$_1$, is a GPCR that binds the lipid signaling molecule lysophosphatidic acid (LPA). Exemplary reference sequences for LPAR1 include the NCBI Reference Sequences NP_001392 (human protein), NP_001277415 (mouse protein), NM_001401 (human mRNA), and NM_001290486 (mouse mRNA). LPAR1 antagonists can act as competitive inhibitors of full or partial LPAR1 agonists, or as inverse agonists. The activity of an LPAR antagonist may be measured by methods known in the art, such as those described and cited in Castelino et al., 2010 Arthritis Rheum. 2011 May; 63(5): 1405-1415 or Swaney et al., J Pharmacol Exp Ther. 2011 March; 336(3):693-700.

As used herein, an "ACC inhibitor" refers to any agent that is capable of binding and inhibiting Acetyl-CoA carboxylase (ACC). ACC inhibitors can act as inhibitors or partial inhibitors of ACC. The agent can be a chemical compound or biological molecule (e.g., a protein or antibody). The activity of an ACC inhibitor can be measured by methods known in the art, such as those described and cited in U.S. Pat. No. 8,969,557 and/or in U.S. Pat. No. 10,208,063, both of which are incorporated herein by reference in their entirety.

As referred to herein, an "ASK1 inhibitor" can be any agent that is capable of inactivating an apoptosis signal regulating kinase 1 (ASK1) protein. The agent can be a chemical compound or biological molecule (e.g., a protein or antibody). The ASK1 protein activity can be measured by several different methods. For example, the activity of an ASK1 protein can be determined based on the ability of the ASK1 protein to phosphorylate a substrate protein. Methods for identifying an ASK1 inhibitor are known (see, e.g., U.S. 2007/0276050). Exemplary ASK1 substrate proteins include MAPKK3, MAPKK4, MAPKK6, MAPKK7, or fragments thereof. The ASK1 protein activity can also be measured by the phosphorylation level of the ASK1 protein, for example, the phosphorylation level of a threonine residue in the ASK1 protein corresponding to threonine 838 (T838) of a human full-length ASK1 protein or threonine 845 (T845) of a mouse full-length ASK1 protein. For example, where the ASK1 protein comprises a full-length human ASK1 protein sequence, an ASK1 inhibitor may attenuate phosphorylation of T838 in the full-length human ASK1 protein sequence. A site-specific antibody against human ASK1 T838 or mouse ASK1 T845 may be used to detect the phosphohorylation level.

As used herein, a "FXR agonist" refers to any agent that is capable of binding and activating farnesoid X receptor (FXR) which can be referred to as bile acid receptor (BAR) or NR1H4 (nuclear receptor subfamily 1, group H, member 4) receptor. FXR agonists can act as agonists or partial agonists of FXR. The agent can be a chemical compound or biological molecule (e.g., a protein or antibody). The activity of an FXR agonist can be measured by several different methods, e.g., in an in vitro assay using the fluorescence resonance energy transfer (FRET) cell free assay as described in Pellicciari, et al. Journal of Medicinal Chemistry, 2002 vol. 15, No. 45:3569-72.

Compounds

In one embodiment, provided herein is a compound of Formula (I),

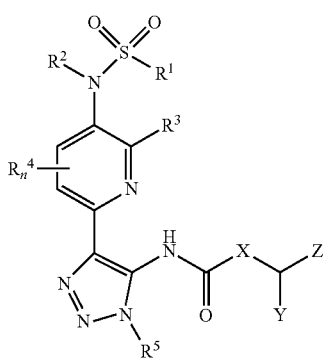

(I)

or a pharmaceutically acceptable salt thereof,
wherein:
- $R^1$ is $C_{1-6}$ alkyl optionally substituted with 1 to 3 substituents independently selected from halogen, cyano, $C_{1-3}$ alkoxy, $-N(R^{1A})_2$, $-C(O)OR^{1A}$, $-C(O)N(R^{1A})_2$, $-NR^{1A}C(O)R^{1A}$, $-NR^{1A}C(O)OR^{1A}$, $-S(O)_{0-2}R^{1A}$, $-S(O)_2N(R^{1A})_2$ and $-NR^{1A}S(O)_2R^{1A}$, wherein each $R^{1A}$ is independently H or $C_{1-6}$ alkyl; or
- $R^1$ is $C_{3-6}$ cycloalkyl, 6 to 10 membered aryl, 3 to 10 membered heterocyclyl having 1 to 4 heteroatoms independently selected from nitrogen, oxygen, and sulfur, or 5 to 10 membered heteroaryl having 1 to 4 heteroatoms independently selected from nitrogen, oxygen, and sulfur, wherein each cycloalkyl, aryl, heterocyclyl, or heteroaryl is optionally substituted with 1 to 3 substituents independently selected from halogen, cyano, $C_{1-3}$ alkyl, $C_{1-3}$ alkoxy, $-N(R^{1A})_2$, $-C(O)N(R^{1A})_2$, $-NR^{1A}C(O)R^{1A}$, $-S(O)_{0-2}R^{1A}$, $-S(O)_2N(R^{1A})_2$ and $-NR^{1A}S(O)_2R^{1A}$, wherein each $R^{1A}$ is independently H or $C_{1-6}$ alkyl; or
- $R^1$ is $-O-R^{1B}$ or $-N(R^{1B})_2$, wherein each $R^{1B}$ is independently H, $C_{1-6}$ alkyl, or $C_{3-6}$ cycloalkyl, optionally substituted with 1 to 3 substituents independently selected from halogen and $-C(O)N(R^{1C})_2$, and wherein each $-R^{1C}$ is independently H or $C_{1-3}$ alkyl;
- $R^2$ is hydrogen or $C_{1-6}$ alkyl optionally substituted with 1 to 3 substituents independently selected from deuterium, halogen, cyano, $C_{1-3}$ alkoxy, and $C_{3-10}$ cycloalkyl; or
- $R^2$ is $C_{3-6}$ cycloalkyl optionally substituted with 1 to 3 substituents independently selected from halogen, cyano, $C_{1-3}$ alkoxy, and $C_{1-6}$ alkyl;
- $R^3$ is hydrogen, halogen, $C_{1-6}$ alkyl, $C_{3-6}$ cycloalkyl, $-O-R^{3A}$, or $-N(R^{3A})_2$, wherein the $C_{1-6}$ alkyl is optionally substituted with 1 to 3 substituents independently selected from $C_{1-3}$ alkoxy and halogen, and wherein each $R^{3A}$ is independently $C_{1-3}$ alkyl optionally substituted with 1 to 3 halogens; or
- each $R^4$ is independently deuterium, halogen, $C_{1-6}$ alkyl, $C_{3-10}$ cycloalkyl, or $C_{1-3}$ alkoxy, wherein the $C_{1-6}$ alkyl or $C_{3-10}$ cycloalkyl, is optionally substituted with 1 to 3 halogens;
- n is 0, 1 or 2;
- $R^5$ is $C_{1-6}$ alkyl optionally substituted with 1 to 3 substituents independently selected from halogen, cyano, $C_{1-3}$ alkoxy, $-C(O)N(R^{1A})$, and $-N(R^{1A})_2$, wherein each $R^{1A}$ is independently H, $C_{1-6}$ alkyl, or $C_{3-10}$ cycloalkyl; or
- $R^5$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents independently selected from halogen, cyano, $C_{1-3}$ alkyl and $C_{1-3}$ alkoxy;
- X is NH or O;
- Y is hydrogen or $C_{1-6}$ alkyl optionally substituted with 1 to 3 substituents independently selected from halogen, cyano, $C_{1-3}$ alkynyl, $C_{1-3}$ alkoxy, and $-C(O)NH-R^y$, wherein $R^y$ is $C_{1-3}$ alkyl; and
- Z is $C_{1-6}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents independently selected from halogen, cyano, $C_{1-3}$ alkyl, $C_{1-3}$ alkenyl, $C_{1-3}$ alkoxy, and $C_{3-6}$ cycloalkyl, wherein the $C_{1-3}$ alkyl is optionally substituted with 1 to 3 substituents selected from $C_{1-3}$ alkoxy and halogen; or
- Y and Z together with the carbon to which they are attached form $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents independently selected from cyano, $C_{1-3}$ alkyl, $C_{1-3}$ alkoxy, $C_{6-10}$ aryl and halogen, wherein the $C_{1-3}$ alkyl is optionally substituted with 1 to 3 substituents independently selected from $C_{1-3}$ alkoxy and halogen, and wherein the $C_{6-10}$ aryl is optionally substituted with 1 to 3 substituents independently selected from $C_{1-3}$ alkyl, $C_{1-3}$ alkoxy, and halogen.

In some embodiments, the compound of Formula (I), or pharmaceutically acceptable salt thereof, is a compound of Formula (Ia)

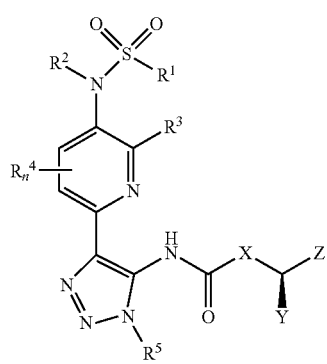

(Ia)

or pharmaceutically acceptable salt thereof.

In some embodiments of the compound of Formula (I) or (Ia), or pharmaceutically acceptable salt thereof, $R^1$ is $C_{1-6}$ alkyl optionally substituted with 1 to 3 substituents independently selected from halogen, cyano, $C_{1-3}$ alkoxy, —N($R^{1A}$)$_2$, —C(O)O$R^{1A}$, —C(O)N($R^{1A}$)$_2$, —N$R^{1A}$C(O)$R^{1A}$, —N$R^{1A}$C(O)O$R^{1A}$, —S(O)$_{0-2}R^{1A}$, —S(O)$_2$N($R^{1A}$)$_2$ and —N$R^{1A}$S(O)$_2R^{1A}$, wherein each $R^{1A}$ is independently H or $C_{1-6}$ alkyl; or $R^1$ is $C_{3-6}$ cycloalkyl, 6 to 10 membered aryl, 3 to 10 membered heterocyclyl having 1 to 4 heteroatoms independently selected from nitrogen, oxygen, and sulfur, or 5 to 10 membered heteroaryl having 1 to 4 heteroatoms independently selected from nitrogen, oxygen, and sulfur, wherein each cycloalkyl, aryl, heterocyclyl, or heteroaryl is optionally substituted with 1 to 3 substituents independently selected from halogen, cyano, $C_{1-3}$ alkyl, $C_{1-3}$ alkoxy, —N($R^{1A}$)$_2$, —C(O)N($R^{1A}$)$_2$—N$R^{1A}$C(O)$R^{1A}$, —S(O)$_{0-2}R^{1A}$; —S(O)$_2$N($R^{1A}$)$_2$ and —N$R^{1A}$S(O)$_2R^{1A}$, wherein each $R^{1A}$ is independently H or $C_{1-6}$ alkyl; or $R^1$ is —O—$R^{1B}$ or —N($R^{1B}$)$_2$, wherein each $R^{1B}$ is independently H, $C_{1-6}$ alkyl, or $C_{3-6}$ cycloalkyl, optionally substituted with 1 to 3 substituents independently selected from halogen and —C(O)N($R^{1C}$)$_2$, and wherein each —$R^{1C}$ is independently H or $C_{1-3}$ alkyl;

$R^2$ is hydrogen or $C_{1-6}$ alkyl optionally substituted with 1 to 3 substituents independently selected from halogen, cyano, $C_{1-3}$ alkoxy, and $C_{3-10}$ cycloalkyl; or $R^2$ is $C_{3-6}$ cycloalkyl optionally substituted with 1 to 3 substituents independently selected from halogen, cyano, $C_{1-3}$ alkoxy, and $C_{1-6}$ alkyl;

$R^3$ is hydrogen, halogen, $C_{1-6}$ alkyl, $C_{3-6}$ cycloalkyl, —O—$R^{3A}$, or —N($R^{3A}$)$_2$, wherein the $C_{1-6}$ alkyl is optionally substituted with 1 to 3 substituents independently selected from $C_{1-3}$ alkoxy and halogen, and wherein each $R^{3A}$ is independently $C_{1-3}$ alkyl optionally substituted with 1 to 3 halogens; or each $R^4$ is independently deuterium, halogen, $C_{1-6}$ alkyl, $C_{3-10}$ cycloalkyl, or $C_{1-3}$ alkoxy, wherein the $C_{1-6}$ alkyl or $C_{3-10}$ cycloalkyl, is optionally substituted with 1 to 3 halogens:

n is 0, 1 or 2;

$R^5$ is $C_{1-6}$ alkyl optionally substituted with 1 to 3 substituents independently selected from halogen, cyano, $C_{1-3}$ alkoxy, —C(O)N($R^{1A}$), and —N($R^{1A}$)$_2$, wherein each $R^{1A}$ is independently H, $C_{1-6}$ alkyl, or $C_{3-10}$ cycloalkyl; or $R^5$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents independently selected from halogen, cyano, $C_{1-3}$ alkyl and $C_{1-3}$ alkoxy;

X is NH or O;

Y is hydrogen or $C_{1-6}$ alkyl optionally substituted with 1 to 3 substituents independently selected from halogen, cyano, $C_{1-3}$ alkynyl, $C_{1-3}$ alkoxy, and —C(O)NH—$R^y$, wherein $R^y$ is $C_{1-3}$ alkyl; and Z is $C_{1-8}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents independently selected from halogen, cyano, $C_{1-3}$ alkyl, $C_{1-3}$ alkoxy, and $C_{3-6}$ cycloalkyl, wherein the $C_{1-3}$ alkyl is optionally substituted with 1 to 3 substituents selected from $C_{1-3}$ alkoxy and halogen; or Y and Z together with the carbon to which they are attached form $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents independently selected from cyano, $C_{1-3}$ alkyl, $C_{1-3}$ alkoxy, $C_{6-10}$ aryl and halogen, wherein the $C_{1-3}$ alkyl is optionally substituted with 1 to 3 substituents independently selected from $C_{1-3}$ alkoxy and halogen, and wherein the $C_{6-10}$ aryl is optionally substituted with 1 to 3 substituents independently selected from $C_{1-3}$ alkyl, $C_{1-3}$ alkoxy, and halogen.

In some embodiments of the compound of Formula (I) or (Ia), or pharmaceutically acceptable salt thereof, $R^1$ is $C_{1-6}$ alkyl optionally substituted with 1 to 3 substituents independently selected from halogen, cyano, and $C_{1-3}$ alkoxy; or $R^1$ is $C_{3-6}$ cycloalkyl, 3 to 6 membered heterocyclyl having 1 or 2 heteroatoms independently selected from nitrogen, oxygen, and sulfur, or 5 to 6 membered heteroaryl having 1 or 2 heteroatoms independently selected from nitrogen, oxygen, and sulfur, wherein the cycloalkyl, heterocyclyl, or heteroaryl are each optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen or $C_{1-3}$ alkoxy;

$R^1$ is —N($R^{1B}$)$_2$, wherein each $R^{1B}$ is independently H, $C_{1-6}$ alkyl, or $C_{3-6}$ cycloalkyl, wherein each $C_{1-6}$ alkyl, or $C_{3-6}$ cycloalkyl is optionally substituted with 1 to 3 halogens.

$R^2$ is hydrogen or $C_{1-3}$ alkyl optionally substituted with 1 to 3 deuteriums or halogens;

$R^3$ is hydrogen, halogen, $C_{1-6}$ alkyl, $C_{1-3}$ alkoxy, wherein the $C_{1-6}$ alkyl is optionally substituted with 1 to 3 substituents independently selected from halogen and $C_{1-3}$ alkoxy;

$R^4$ is halogen;

n is 0 or 1;

$R^5$ is $C_{1-3}$ alkyl optionally substituted with 1 to 3 substituents independently selected from halogen and cyano;

X is NH or O;

Y is hydrogen or $C_{1-3}$ alkyl optionally substituted with 1 to 3 substituents independently selected from halogen, cyano, and $C_{1-3}$ alkoxy; and Z is $C_{1-8}$ alkyl, $C_{3-6}$ cycloalkyl, $C_{6-10}$ aryl, or 5 or 6 membered heteroaryl having 1 to 3 heteroatoms independently selected from nitrogen, oxygen, and sulfur, wherein the $C_{1-8}$ alkyl, $C_{3-6}$ cycloalkyl, $C_{6-10}$ aryl, or 5 or 6 membered heteroaryl is optionally substituted with 1 to 3 substituents independently selected from halogen, $C_{1-3}$ alkyl, $C_{1-3}$ alkenyl, $C_{1-3}$ alkoxy, and $C_{3-6}$ cycloalkyl, wherein the $C_{1-3}$ alkyl is optionally substituted with 1 to 3 substituents independently selected from halogen and $C_{1-3}$ alkoxy; or Y and Z together with the carbon to which they are attached form a 6 to 10 membered aryl, optionally substituted with 1 to 3 halogens.

In some embodiments, the compound of Formula (I), or pharmaceutically acceptable salt thereof, is a compound of Formula (II)

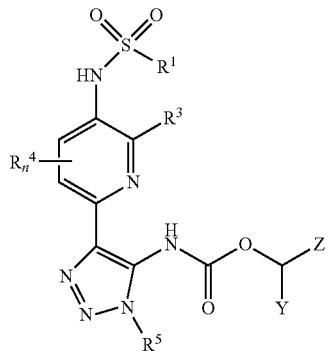

(II)

or pharmaceutically acceptable salt thereof.

In some embodiments, the compound of Formula (I), (Ia) or (II), or pharmaceutically acceptable salt thereof, is a compound of Formula (IIa)

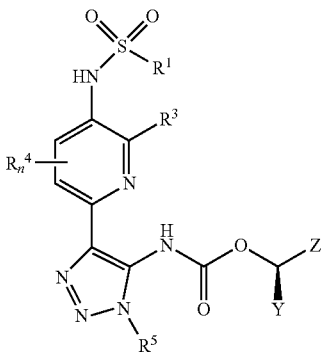

(IIa)

or pharmaceutically acceptable salt thereof.

In some embodiments of the compound of Formula (I), (Ia), (II), or (IIa), or pharmaceutically acceptable salt thereof, $R^1$ is $C_{1-6}$ alkyl optionally substituted with 1 to 3 substituents independently selected from halogen, cyano, and $C_{1-3}$ alkoxy. In some embodiments of the compound of Formula (I), (Ia), (II), or (IIa), or pharmaceutically acceptable salt thereof, $R^1$ is $C_{1-3}$ alkyl optionally substituted 1 to 3 substituents independently selected from halogen and cyano. In some embodiments the 1 to 3 substituents are independently selected from F and cyano. In some embodiments of the compound of Formula (I), (Ia), (II), or (IIa), or pharmaceutically acceptable salt thereof, $R^1$ is $C_{1-3}$ alkyl optionally substituted with cyano. In some embodiments, the $C_{1-3}$ alkyl is selected from methyl, ethyl or isopropyl, each optionally substituted with 1 to 3 substituents independently selected from halogen, cyano, and $C_{1-3}$ alkoxy. In some embodiments, the $C_{1-3}$ alkyl is selected from methyl, ethyl or isopropyl. In some embodiments the $C_{1-3}$ alkoxy is methoxy. In some embodiments, the 1 to 3 halogens are each independently selected from F and Cl. In some embodiments, each of the 1 to 3 halogens is F. In some embodiments of the compound of Formula (I), (Ia), (II), or (IIa), or pharmaceutically acceptable salt thereof, $R^1$ is methyl, ethyl, isopropyl, or cyanomethyl.

In some embodiments of the compound of Formula (I), (Ia), (II), or (IIa), or pharmaceutically acceptable salt thereof, $R^1$ is $C_{3-6}$ cycloalkyl optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, $R^1$ is $C_{3-6}$ cycloalkyl optionally substituted with 1 to 3 halogens. In some embodiments, the 1 to 3 halogens are each independently selected from F and Cl. In some embodiments, each of the 1 to 3 halogens is F. In some embodiments, the $C_{3-6}$ cycloalkyl is cyclopropyl or cyclobutyl optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, $R^1$ is cyclopropyl or cyclobutyl.

In some embodiments of the compound of Formula (I), (Ia), (II), or (IIa), or pharmaceutically acceptable salt thereof, $R^1$ is 3 to 6 membered heterocyclyl having 1 or 2 heteroatoms independently selected from nitrogen, oxygen, and sulfur, wherein the heterocyclyl is optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy. In some embodiments, the 3 to 6 membered heterocyclyl has 1 or 2 heteroatoms independently selected from nitrogen and oxygen. In some embodiments of the compound of Formula (I), (Ia), (II), or (IIa), or pharmaceutically acceptable salt thereof, $R^1$ is oxetanyl or azetidinyl, optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy. In some embodiments each of the 1 to 3 halogens is F. In some embodiments of the compound of Formula (I), (Ia), (II), or (IIa), or pharmaceutically acceptable salt thereof, $R^1$ is oxetanyl or azetidinyl optionally substituted with 1 to 3 substituents independently selected from F and —O—$CH_3$. In some embodiments of the compound of Formula (I), (Ia), (II), or (IIa), or pharmaceutically acceptable salt thereof, $R^1$ is

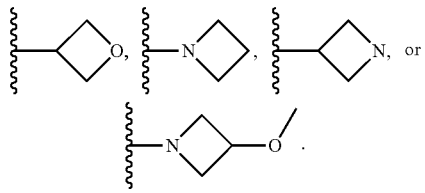

In some embodiments of the compound of Formula (I), (Ia), (II), or (IIa), or pharmaceutically acceptable salt thereof, $R^1$ is

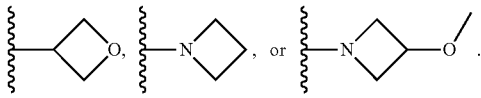

In some embodiments of the compound of Formula (I), (Ia), (II), or (IIa), or pharmaceutically acceptable salt thereof, $R^1$ is

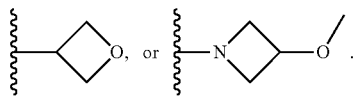

In some embodiments of the compound of Formula (I), (Ia), (II), or (IIa), or pharmaceutically acceptable salt thereof, $R^1$ is a 5 to 6 membered heteroaryl having 1 or 2 heteroatoms independently selected from nitrogen, oxygen, and sulfur, optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, $R^1$ is a 5 membered heteroaryl having 1 or 2 heteroatoms independently selected from nitrogen and sulfur, optionally substituted with 1 or 2 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, $R^1$ is a 5 membered heteroaryl having 1 or 2 heteroatoms independently selected from nitrogen and sulfur, optionally substituted with 1 or 2 substituents independently selected from halogen or $C_{1-3}$ alkyl optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, $R^1$ is thiazolyl optionally substituted with 1 or 2 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, $R^1$ is thiazolyl optionally substituted with 1 or 2 substituents independently selected from halogen or $C_{1-3}$ alkyl optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, $R^1$ is thiazolyl optionally substituted with $-CH_3$. In some embodiments of the compound of Formula (I), (Ia), (II), or (IIa), or pharmaceutically acceptable salt thereof, $R^1$ is

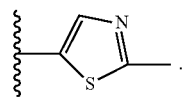 [SMILES: *c1cnc(C)s1]

In some embodiments of the compound of Formula (I), (Ia), (II), or (IIa), or pharmaceutically acceptable salt thereof, $R^1$ is $-O-R^{1B}$ or $-N(R^{1B})_2$, wherein each $R^{1B}$ is independently H, $C_{1-6}$ alkyl, or $C_{3-6}$ cycloalkyl, wherein each $C_{1-6}$ alkyl, or $C_{3-6}$ cycloalkyl is optionally substituted with 1 to 3 substituents independently selected from halogen and $-C(O)N(R^{1C})_2$, wherein each $-R^{1C}$ is independently H or $C_{1-3}$ alkyl. In some embodiments of the compound of Formula (I), (Ia), (II), or (IIa), or pharmaceutically acceptable salt thereof, $R^1$ is $-N(R^{1B})_2$, wherein each $R^{1B}$ is independently H, $C_{1-6}$ alkyl, or $C_{3-6}$ cycloalkyl, wherein each $C_{1-6}$ alkyl, or $C_{3-6}$ cycloalkyl is optionally substituted with 1 to 3 halogens. In some embodiments the halogen is F. In some embodiments of the compound of Formula (I), (Ia), (II), or (IIa), or pharmaceutically acceptable salt thereof, $R^1$ is

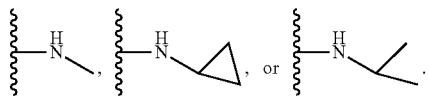

In some embodiments of the compound of Formula (I) or (Ia), or pharmaceutically acceptable salt thereof, $R^2$ is hydrogen.

In some embodiments of the compound of Formula (I) or (Ia), or pharmaceutically acceptable salt thereof, $R^2$ is $C_{1-3}$ alkyl optionally substituted with 1 to 3 halogens. In some embodiments, each of the 1 to 3 halogens is F. In some embodiments of the compound of Formula (I) or (Ia), or pharmaceutically acceptable salt thereof, $R^2$ is methyl, optionally substituted with 1 to 3 F. In some embodiments of the compound of Formula (I) or (Ia), or pharmaceutically acceptable salt thereof, $R^2$ is methyl. In some embodiments of the compound of Formula (I) or (Ia), or pharmaceutically acceptable salt thereof, $R^2$ is $C_{1-3}$ alkyl optionally substituted with 1 to 3 deuteriums. In some embodiments of the compound of Formula (I) or (Ia), or pharmaceutically acceptable salt thereof, $R^2$ is $-CD_3$.

In some embodiments of the compound of Formula (I), (Ia), (II), or (IIa), or pharmaceutically acceptable salt thereof, $R^3$ is hydrogen. In some embodiments of the compound of Formula (I), (Ia), (II), or (IIa), or pharmaceutically acceptable salt thereof, $R^3$ is halogen, $C_{1-6}$ alkyl, $C_{3-6}$ cycloalkyl, $-O-R^{3A}$, or $-N(R^{3A})_2$, wherein the $C_{1-6}$ alkyl is optionally substituted with 1 to 3 substituents independently selected from halogen and $C_{1-3}$ alkoxy, and wherein each $R^{3A}$ is independently H or $C_{1-3}$ alkyl optionally substituted with 1 to 3 halogens. In some embodiments of the compound of Formula (I), (Ia), (II), or (IIa), or pharmaceutically acceptable salt thereof, $R^3$ is halogen, $C_{1-6}$ alkyl, $-O-R^{3A}$, or $-N(R^{3A})_2$, wherein the $C_{1-6}$ alkyl is optionally substituted with 1 to 3 substituents independently selected from halogen and $C_{1-3}$ alkoxy, and wherein each $R^{3A}$ is independently hydrogen or $C_{1-3}$ alkyl optionally substituted with 1 to 3 halogens. In some embodiments of the compound of Formula (I), (Ia), (II), or (IIa), or pharmaceutically acceptable salt thereof, $R^3$ is halogen, $C_{1-6}$ alkyl, $C_{3-6}$ cycloalkyl $-O-R^{3A}$, $-N(R^{3A})_2$, wherein the $C_{1-6}$ alkyl is optionally substituted with 1 to 3 substituents independently selected from halogen and $C_{1-3}$ alkoxy, wherein each $R^{3A}$ is $C_{1-3}$ alkyl optionally substituted with 1 to 3 halogens. In some embodiments of the compound of Formula (I), (Ia), (II), or (IIa), or pharmaceutically acceptable salt thereof, $R^3$ is halogen, $C_{1-6}$ alkyl, or $-O-R^{3A}$, wherein the $C_{1-6}$ alkyl is optionally substituted with 1 to 3 substituents independently selected from halogen and $C_{1-3}$ alkoxy, wherein $R^{3A}$ is $C_{1-3}$ alkyl optionally substituted with 1 to 3 halogens. In some embodiments each halogen is independently selected from F and Cl. In some embodiments, each halogen is F. In some embodiments, the $C_{1-6}$ alkyl is methyl, optionally substituted with 1 to 3 F. In some embodiments, $-O-R^{3A}$ is methoxy. In some embodiments of the compound of Formula (I), (Ia), (II), or (IIa), or pharmaceutically acceptable salt thereof, R³ is —F, —Cl, —CH₃, —C₂H₅, —CHF₂, —CH₂—OCH₃, —O—CH₃, —NH—CH₃, or

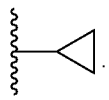

In some embodiments of the compound of Formula (I), (Ia), (II), or (IIa), or pharmaceutically acceptable salt thereof, R³ is —F, —Cl, —CH₃, or —O—CH₃.

In some embodiments of the compound of Formula (I), (Ia), (II), or (IIa), or pharmaceutically acceptable salt thereof, each R⁴ is independently halogen or $C_{1-3}$ alkyl, wherein the $C_{1-3}$ alkyl is optionally substituted with 1 to 3 halogens. In some embodiments of the compound of Formula (I), (Ia), (II), or (IIa), or pharmaceutically acceptable salt thereof, each R⁴ is independently a halogen. In some embodiments of the compound of Formula (I), (Ia), (II), or (IIa), or pharmaceutically acceptable salt thereof, each R⁴ is F. In some embodiments of the compound of Formula (I), (Ia), (II), or (IIa), or pharmaceutically acceptable salt thereof, n is 0 or 1. In some embodiments of the compound of Formula (I), (Ia), (II), or (IIa), or pharmaceutically acceptable salt thereof, n is 0. In some embodiments of the compound of Formula (I), (Ia), (II), or (IIa), or pharmaceutically acceptable salt thereof, n is 1. In some embodiments of the compound of Formula (I), (Ia), (II), or (IIa), or pharmaceutically acceptable salt thereof, n is 2. In some embodiments of the compound of Formula (I), (Ia), (II), or (IIa), or pharmaceutically acceptable salt thereof, n is 2. In some embodiments the two R⁴ are the same. In some embodiments the two R⁴ are different from each other.

In some embodiments of the compound of Formula (I), (Ia), (II), or (IIa), or pharmaceutically acceptable salt thereof, R⁵ is $C_{1-3}$ alkyl optionally substituted with 1 to 3 substituents independently selected from F and cyano. In some embodiments of the compound of Formula (I), (Ia), (II), or (IIa), or pharmaceutically acceptable salt thereof, R⁵ is methyl, ethyl or propyl, each optionally substituted with 1 to 3 substituents independently selected from F and cyano. In some embodiments of the compound of Formula (I), (Ia), (II), or (IIa), or pharmaceutically acceptable salt thereof, R⁵ is methyl, ethyl or propyl, each optionally substituted with cyano. In some embodiments of the compound of Formula (I), (Ia), (II), or (IIa), or pharmaceutically acceptable salt thereof, R⁵ is methyl.

In some embodiments of the compound of Formula (I) or (Ia), or pharmaceutically acceptable salt thereof, X is NH. In some embodiments of the compound of Formula (I) or (Ia), or pharmaceutically acceptable salt thereof, X is O.

In some embodiments of the compound of Formula (I) or (II), or pharmaceutically acceptable salt thereof, Y is hydrogen.

In some embodiments of the compound of Formula (I), (Ia), (II), or (IIa) Y is $C_{1-3}$ alkyl optionally substituted with 1 to 3 substituents independently selected from halogen, cyano, and $C_{1-3}$ alkoxy. In some embodiments of the compound of Formula (I), (Ia), (II), or (IIa) Y is $C_{1-3}$ alkyl optionally substituted with 1 to 3 substituents independently selected from F, Cl, cyano, and methoxy. In some embodiments of the compound of Formula (I), (Ia), (II), or (IIa) Y is methyl optionally substituted with 1 to 3 substituents independently selected from halogen, cyano, and $C_{1-3}$ alkoxy. In some embodiments of the compound of Formula (I), (Ia), (II), or (IIa) Y is methyl optionally substituted with 1 to 3 substituents independently selected from F, Cl, cyano, and methoxy. In some embodiments of the compound of Formula (I), (Ia), (II), or (IIa) Y is —CH₃, —CH₂F, —CHF₂, —CF₃, —CH₂Cl, —CH₂—O—CH₃, or —CH₂—CN. In some embodiments of the compound of Formula (I), (Ia), (II), or (IIa) Y is —CH₂F, —CHF₂, or —CF₃.

In some embodiments of the compound of Formula (I), (Ia), (II), or (IIa), or pharmaceutically acceptable salt thereof, Z is $C_{1-8}$ alkyl, $C_{3-6}$ cycloalkyl, $C_{6-12}$ aryl, or 5 or 6 membered heteroaryl having 1 to 3 heteroatoms independently selected from nitrogen, oxygen, and sulfur, wherein the $C_{1-8}$ alkyl, $C_{3-6}$ cycloalkyl, $C_{6-10}$ aryl, or 5 or 6 membered heteroaryl is optionally substituted with 1 to 3 substituents independently selected from halogen, cyano, $C_{1-3}$ alkyl, $C_{1-3}$ alkenyl, $C_{1-3}$ alkoxy, and $C_{3-6}$ cycloalkyl, wherein the $C_{1-3}$ alkyl is optionally substituted with 1 to 3 substituents independently selected from halogen and $C_{1-3}$ alkoxy.

In some embodiments of the compound of Formula (I), (Ia), (II), or (IIa), or pharmaceutically acceptable salt thereof, Z is $C_{1-8}$ alkyl, $C_{3-6}$ cycloalkyl, $C_{6-12}$ aryl, or 5 or 6 membered heteroaryl having 1 to 3 heteroatoms independently selected from nitrogen, oxygen, and sulfur, wherein the $C_{1-8}$ alkyl, $C_{3-6}$ cycloalkyl, $C_{6-10}$ aryl, or 5 or 6 membered heteroaryl is optionally substituted with 1 to 3 substituents independently selected from halogen, $C_{1-3}$ alkyl, $C_{1-3}$ alkoxy, and $C_{3-6}$ cycloalkyl, wherein the $C_{1-3}$ alkyl is optionally substituted with 1 to 3 substituents independently selected from halogen and $C_{1-3}$ alkoxy.

In some embodiments of the compound of Formula (I), (Ia), (II), or (IIa), or pharmaceutically acceptable salt thereof, Z is $C_{6-10}$ aryl optionally substituted with 1 to 3 substituents independently selected from halogen, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, Z is phenyl optionally substituted with 1 to 3 substituents independently selected from halogen, $C_{1-3}$ alkyl, or $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, Z is phenyl optionally substituted with 1 to 3 substituents independently selected from halogen, $C_{1-3}$ alkyl, or $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, Z is phenyl optionally substituted with 1 to 3 substituents independently selected from F, Cl, methyl and methoxy, wherein the methyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, Z is phenyl optionally substituted with 1 to 3 substituents independently selected from F, Cl, methyl and methoxy, wherein the methyl is optionally substituted with 1 to 3 substituents independently selected from F, Cl and methoxy. In some embodiments of the compound of Formula (I), (Ia), (II), or (IIa), or pharmaceutically acceptable salt thereof, Z is phenyl optionally substituted with 1 to 3 substituents independently selected from F, Cl, —CH₃, —CF₃, —CH₂—O—CH₃, or —O—CH₃. In some embodiments of the compound of Formula (I), (Ia), (II), or (IIa), or pharmaceutically acceptable salt thereof, Z is

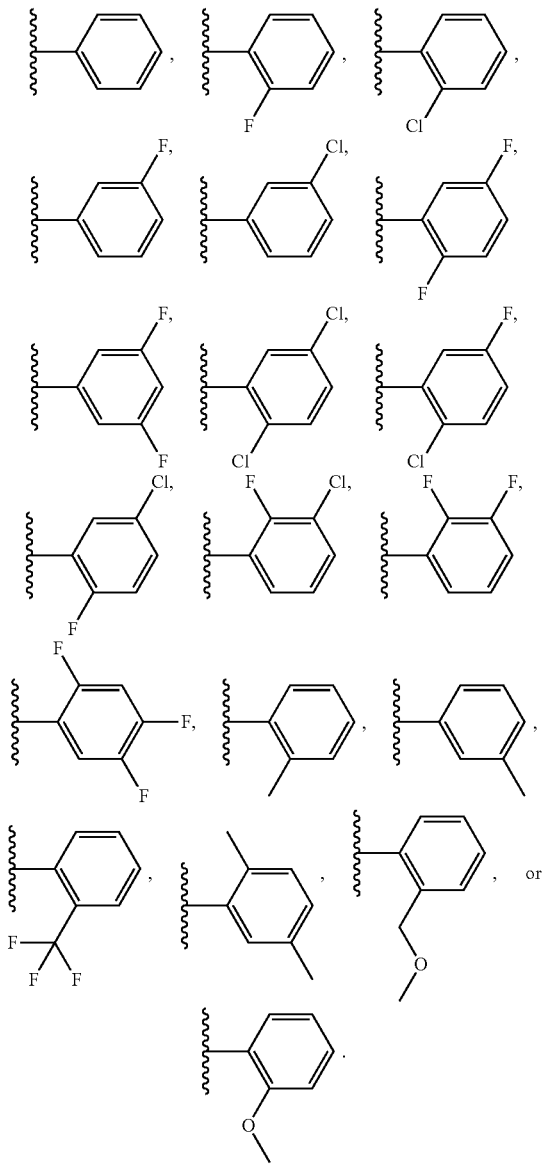

In some embodiments of the compound of Formula (I), (Ia), (II), or (IIa), or pharmaceutically acceptable salt thereof, Z is a 5 or 6 membered heteroaryl having 1-3 heteroatoms independently selected from nitrogen, oxygen, or sulfur, wherein the heteroaryl is optionally substituted with 1 to 3 substituents independently selected from halogen and $C_{1-3}$ alkyl, wherein the $C_{1-3}$ alkyl is optionally substituted with 1 to 3 halogens. In some embodiments, each of the 1 to 3 halogens is F.

In some embodiments of the compound of Formula (I), (Ia), (II), or (IIa), or pharmaceutically acceptable salt thereof, Z is a 5 membered heteroaryl having 1 or 2 heteroatoms independently selected from nitrogen, oxygen, and sulfur, wherein the heteroaryl is optionally substituted with 1 to 3 substituents independently selected from halogen and $C_{1-3}$ alkyl, wherein the $C_{1-3}$ alkyl is optionally substituted with 1 to 3 halogens. In some embodiments, each of the 1 to 3 halogens is F. In some embodiments of the compound of Formula (I), (Ia), (II), or (IIa), or pharmaceutically acceptable salt thereof, Z is thiophenyl, thiazolyl, isothiazolyl, pyrazolyl or oxazolyl, each optionally substituted with 1 or 2 substituents independently selected from —$CH_3$, F and Cl. In some embodiments of the compound of Formula (I), (Ia), (II), or (IIa), or pharmaceutically acceptable salt thereof, Z is thiophenyl, optionally substituted with 1 to 3 substituents independently selected from halogen and $C_{1-3}$ alkyl. In some embodiments of the compound of Formula (I), (Ia), (II), or (IIa), or pharmaceutically acceptable salt thereof, Z is thiophenyl, optionally substituted with 1 or 2 halogens. In some embodiments, the 1 or 2 halogens are independently selected from F and Cl. In some embodiments, the 1 or 2 halogens are Cl. In some embodiments of the compound of Formula (I), (Ia), (II), or (IIa), or pharmaceutically acceptable salt thereof, Z is

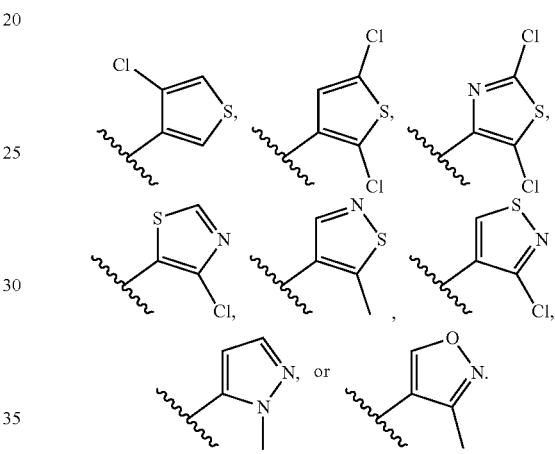

In some embodiments of the compound of Formula (I), (Ia), (II), or (IIa), or pharmaceutically acceptable salt thereof, Z is

In some embodiments of the compound of Formula (I), (Ia), (II), or (IIa), or pharmaceutically acceptable salt thereof, Z is a 6 membered heteroaryl having 1 or 2 heteroatoms independently selected from nitrogen, oxygen, and sulfur, wherein the heteroaryl is optionally substituted with 1 to 3 substituents independently selected from halogen and $C_{1-3}$ alkyl, wherein the $C_{1-3}$ alkyl is optionally substituted with 1 to 3 halogens. In some embodiments, each of the 1 to 3 halogens is F. In some embodiments of the compound of Formula (I), (Ia), (II), or (IIa), or pharmaceutically acceptable salt thereof, Z is pyridyl, pyrimidyl, pyridazinyl, optionally substituted with 1 to 3 substituents independently selected from cyano, halogen, $C_{1-3}$ alkyl, $C_{1-3}$ alkenyl, or $C_{1-3}$ alkoxy, wherein the $C_{1-3}$ alkyl, $C_{1-3}$ alkenyl, or $C_{1-3}$ alkoxy is optionally substituted with 1 to 3 halogens. In some embodiments of the compound of Formula (I), (Ia), (II), or (IIa), or pharmaceutically acceptable salt thereof, Z is pyridyl or pyrimidyl, optionally substituted with 1 to 3 substituents independently selected from halogen and $C_{1-3}$ alkyl, wherein the $C_{1-3}$ alkyl is optionally substituted with 1 to 3 halogens. In some embodiments of the compound of Formula (I), (Ia), (II), or (IIa), or pharmaceutically acceptable salt thereof, Z is pyridyl, optionally substituted with 1 to 3 substituents independently selected from halogen or $C_{1-3}$ alkyl, wherein the $C_{1-3}$ alkyl is optionally substituted with 1 to 3 halogens. In some embodiments of the compound of Formula (I), (Ia), (II), or (IIa), or pharmaceutically acceptable salt thereof, Z is pyrimidyl, optionally substituted with 1 to 3 substituents independently selected from halogen and $C_{1-3}$ alkyl, wherein the $C_{1-3}$ alkyl is optionally substituted with 1 to 3 halogens. In some embodiments each halogen is independently F or Cl. In some embodiments the $C_{1-3}$ alkyl is methyl. In some embodiments of the compound of Formula (I), (Ia), (II), or (IIa), or pharmaceutically acceptable salt thereof, Z is pyridyl, pyrimidyl, pyridazinyl, optionally substituted with 1 to 3 substituents independently selected from F, —Cl, Br, —CH$_3$, —C$_2$H$_5$, —C$_2$H$_4$, —CHF$_2$, —CF$_3$, —OCH$_3$, and —CN. In some embodiments of the compound of Formula (I), (Ia), (II), or (IIa), or pharmaceutically acceptable salt thereof, Z is pyridyl or pyrimidyl, optionally substituted with 1 to 3 substituents independently selected from —F, —Cl, —CH$_3$, and —CF$_3$. In some embodiments of the compound of Formula (I), (Ia), (II), or (IIa), or pharmaceutically acceptable salt thereof, Z is

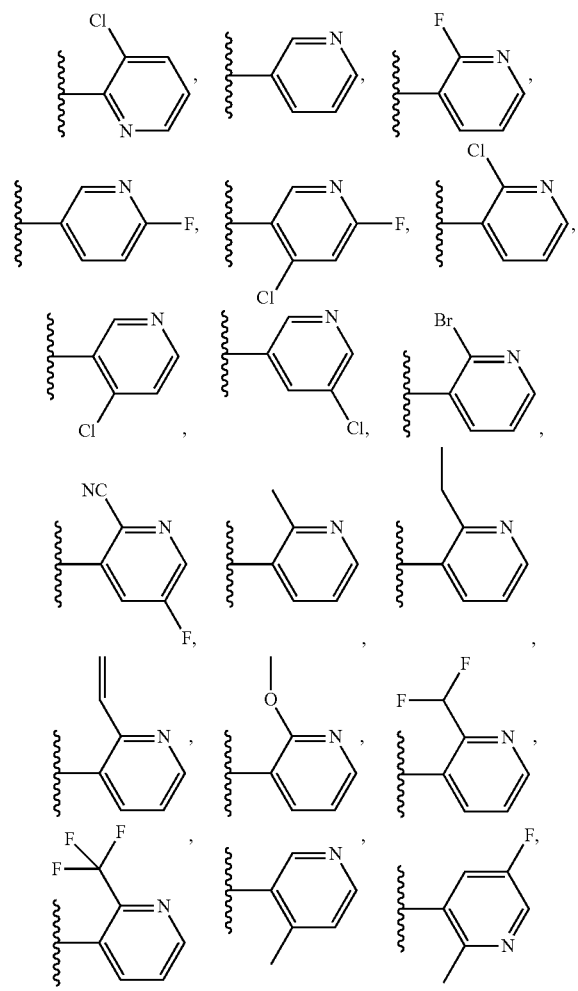

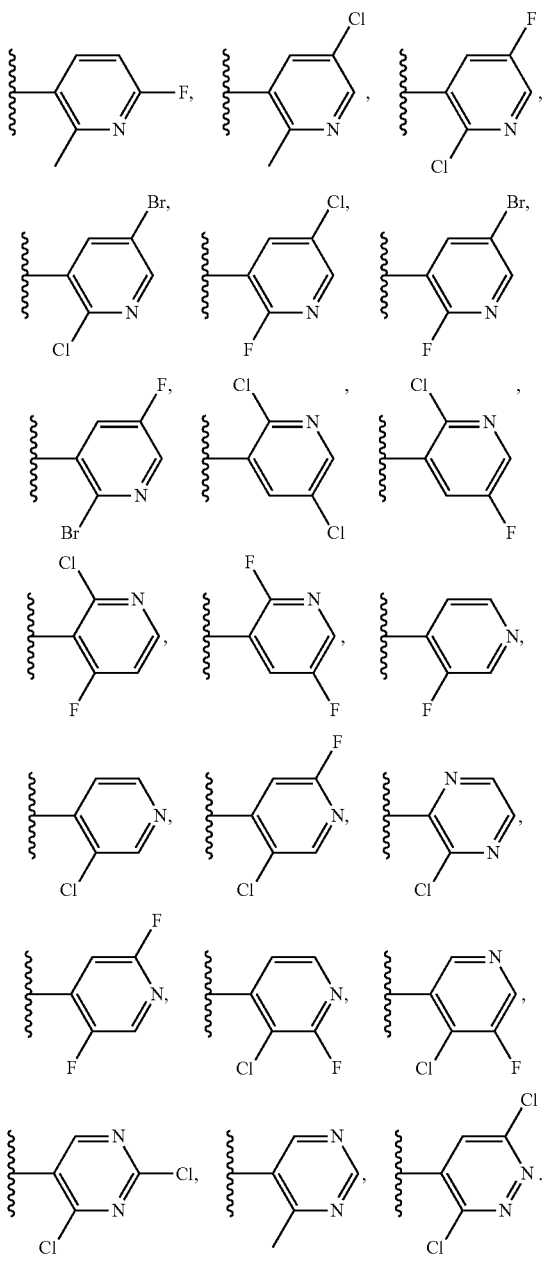

In some embodiments of the compound of Formula (I), (Ia), (II), or (IIa), or pharmaceutically acceptable salt thereof, Z is

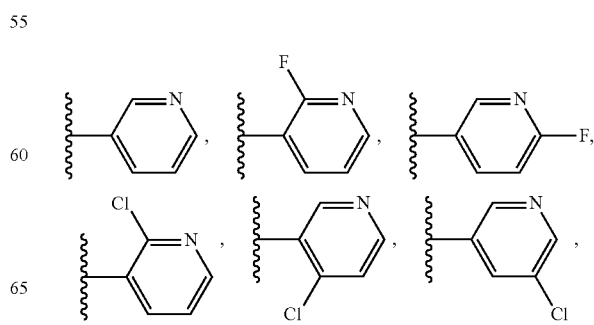

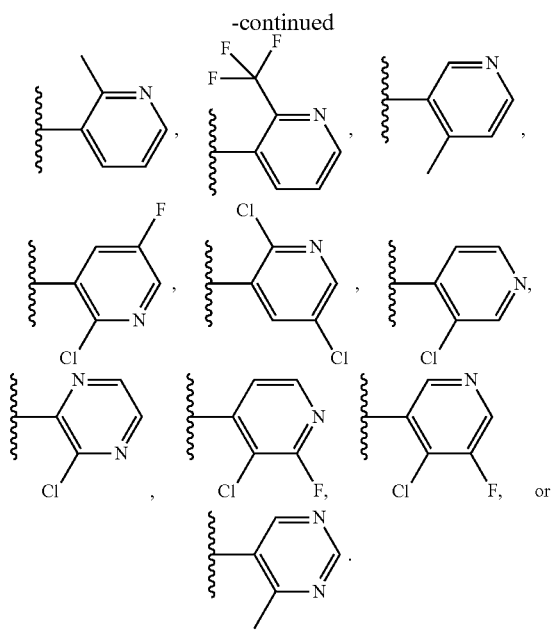

In some embodiments of the compound of Formula (I), (Ia), (II), or (IIa), or pharmaceutically acceptable salt thereof, Z is $C_{3-6}$ cycloalkyl optionally substituted with 1 to 3 substituents independently selected from halogen, $C_{1-3}$ alkyl, $C_{1-3}$ alkoxy, or $C_{3-6}$ cycloalkyl, wherein the $C_{1-3}$ alkyl is optionally substituted with 1 to 3 substituents independently selected from halogen and $C_{1-3}$ alkoxy. In some embodiments, the $C_{3-6}$ cycloalkyl is cyclohexyl. In some embodiments, each halogen is independently Cl or F. In some embodiments the $C_{1-3}$ alkyl is methyl. In some embodiments the $C_{1-3}$ alkoxy is methoxy. In some embodiments, the $C_{3-6}$ cycloalkyl is cyclopropyl or cyclobutyl. In some embodiments of the compound of Formula (I), (Ia), (II), or (IIa), or pharmaceutically acceptable salt thereof, Z is $C_{3-6}$ cycloalkyl optionally substituted with 1 to 3 substituents independently selected from halogen, $C_{1-3}$ alkyl, or $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, Z is cyclohexyl optionally substituted with 1 to 3 substituents independently selected from halogen, $C_{1-3}$ alkyl, $C_{1-3}$ alkoxy, or $C_{3-6}$ cycloalkyl, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, Z is cyclohexyl optionally substituted with 1 to 3 substituents independently selected from halogen, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy. In some embodiments of the compound of Formula (I), (Ia), (II), or (IIa), or pharmaceutically acceptable salt thereof, Z is cyclohexyl optionally substituted with 1 to 3 F.

In some embodiments of the compound of Formula (I), (Ia), (II), or (IIa), or pharmaceutically acceptable salt thereof, Z is $C_{1-8}$ alkyl optionally substituted with 1 to 3 substituents independently selected from halogen, $C_{1-3}$ alkoxy, or $C_{3-6}$ cycloalkyl. In some embodiments of the compound of Formula (I), (Ia), (II), or (IIa), or pharmaceutically acceptable salt thereof, Z is $C_{1-5}$ alkyl optionally substituted with 1 to 3 substituents independently selected from halogen, $C_{1-3}$ alkoxy, or $C_{3-6}$ cycloalkyl. In some embodiments of the compound of Formula (I), (Ia), (II), or (IIa), or pharmaceutically acceptable salt thereof, Z is $C_{1-5}$ alkyl. In some embodiments, each halogen is independently selected from F and Cl. In some embodiments, the $C_{1-3}$ alkoxy is methoxy. In some embodiments, the $C_{3-6}$ cycloalkyl is cyclopropyl or cyclobutyl. In some embodiments of the compound of Formula (I), (Ia), (II), or (IIa), or pharmaceutically acceptable salt thereof, Z is $C_{1-8}$ alkyl substituted with a $C_{3-6}$ cycloalkyl. In some embodiments of the compound of Formula (I), (Ia), (II), or (IIa), or pharmaceutically acceptable salt thereof, Z is $C_{1-3}$ alkyl substituted with cyclopropyl or cyclobutyl. In some embodiments of the compound of Formula (I), (Ia), (II), or (IIa), or pharmaceutically acceptable salt thereof, Z is

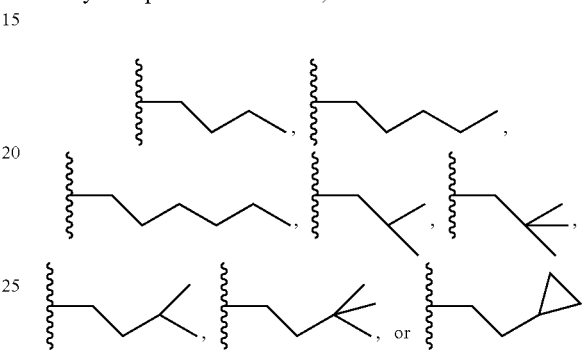

In some embodiments of the compound of Formula (I), (Ia), (II), or (IIa), or pharmaceutically acceptable salt thereof, Y and Z together with the carbon to which they are attached form dihydroindenyl, optionally substituted with 1 to 3 halogens. In some embodiments the 1 to 3 halogens are each independently selected from F and Cl. In some embodiments of the compound of Formula (I), (Ia), (II), or (IIa), or pharmaceutically acceptable salt thereof, Y and Z together with the carbon to which they are attached form dihydroindenyl, optionally substituted with F. In some embodiments of the compound of Formula (I), (Ia), (II), or (IIa), or pharmaceutically acceptable salt thereof, Y and Z together with the carbon to which they are attached form

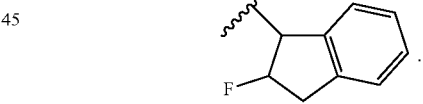

In some embodiments, the compound of Formula (I), (Ia), (II), or (IIa), or pharmaceutically acceptable salt thereof, is selected from the group consisting of:

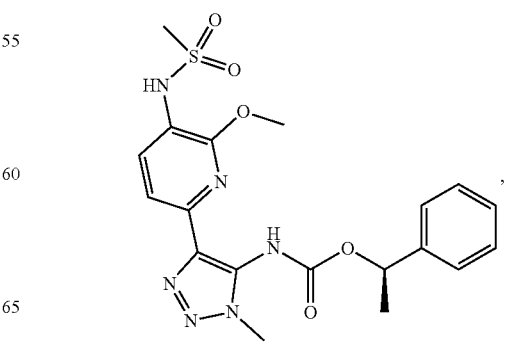

31
-continued
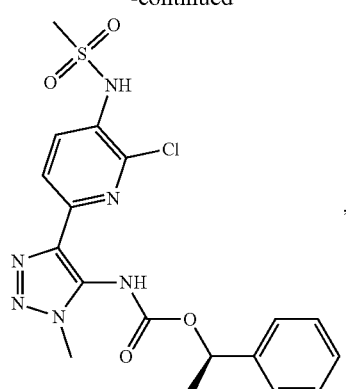
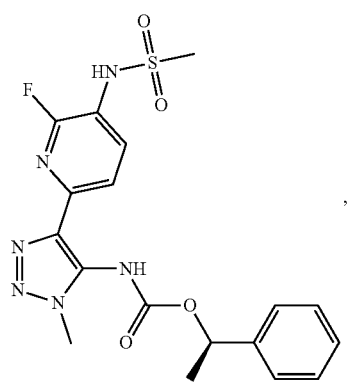
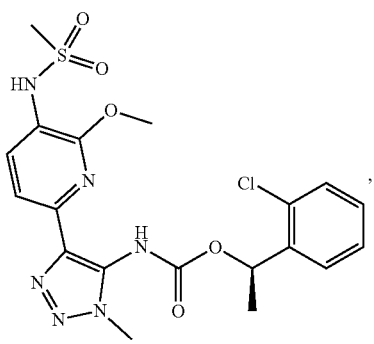
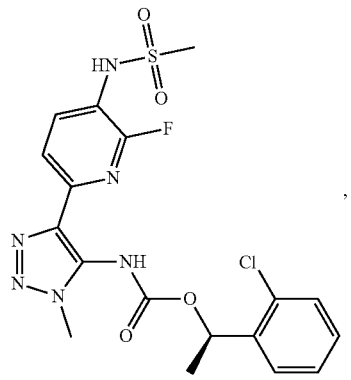
32
-continued
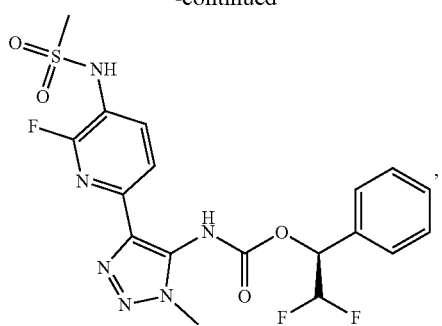
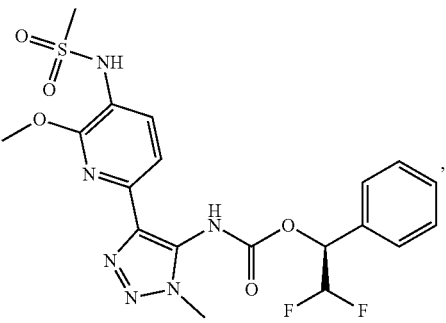
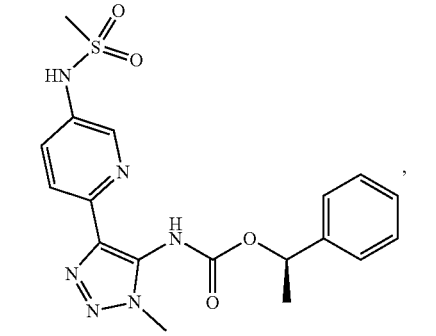
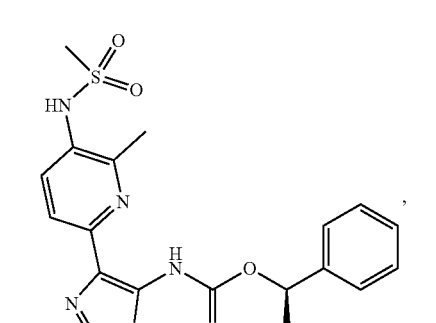
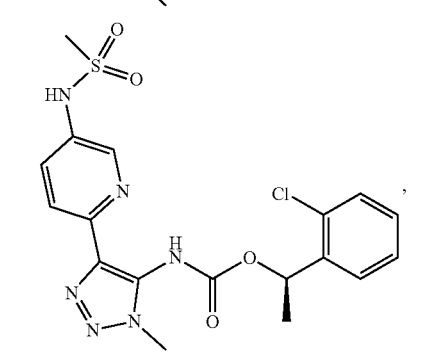

33
-continued
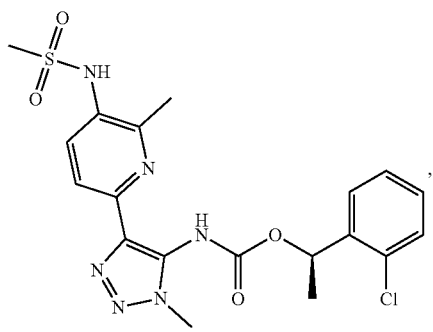
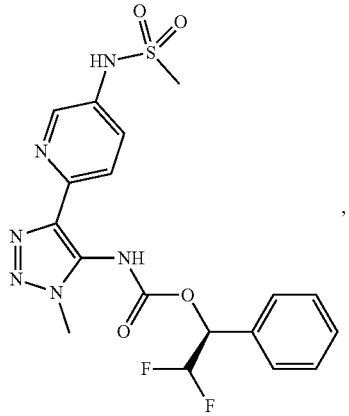 [SMILES: Cn1nnc(-c2ccc(NS(C)(=O)=O)cn2)c1NC(=O)O[C@@H](c1ccccc1)C(F)F]
34
-continued
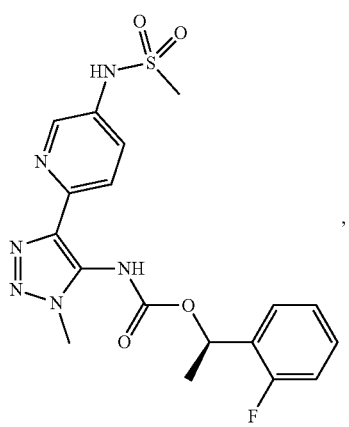
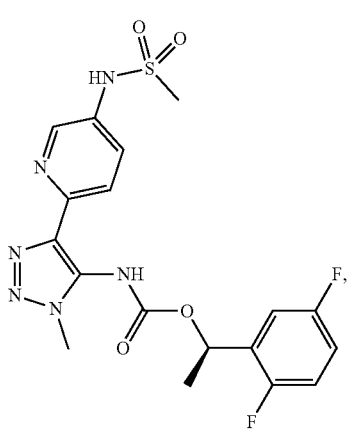
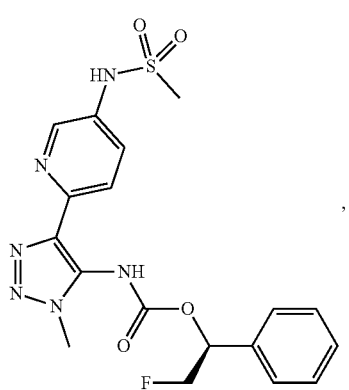

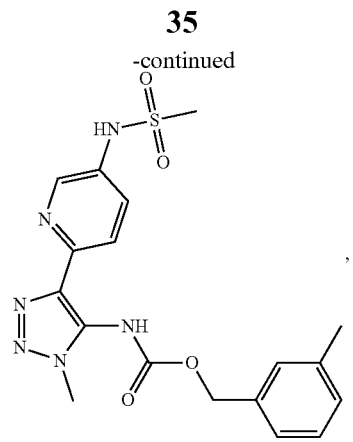
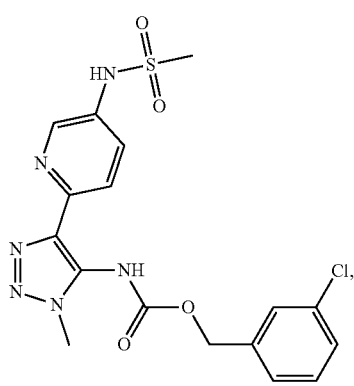
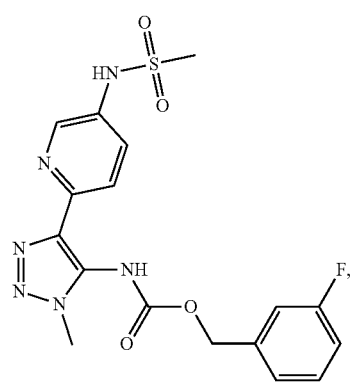
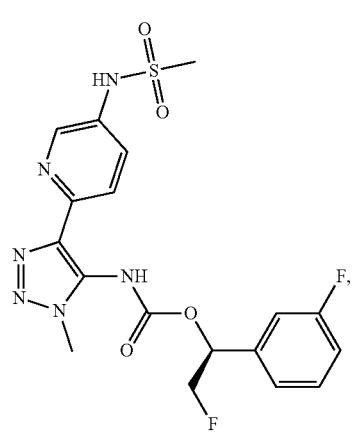
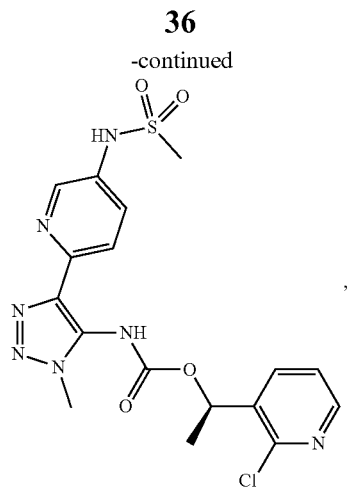
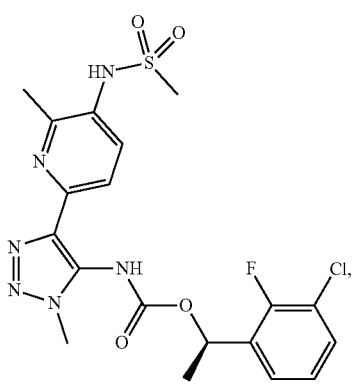
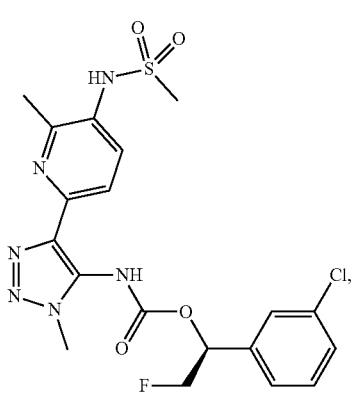
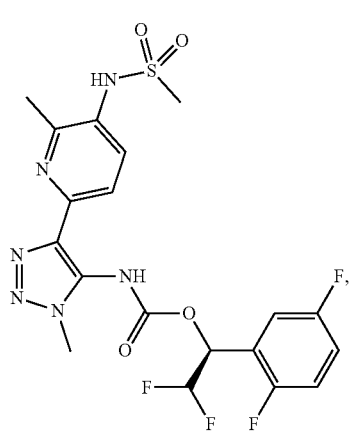

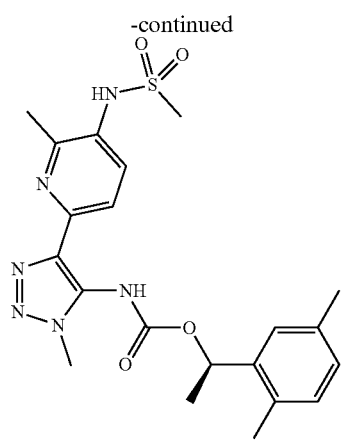
,
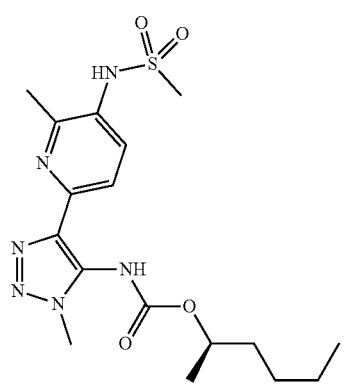
,
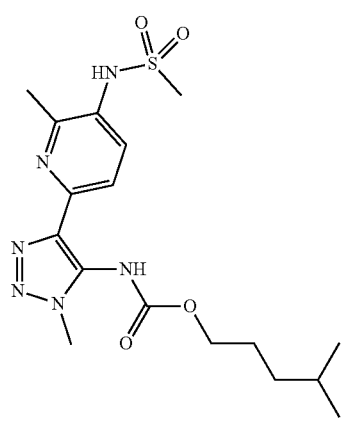
,
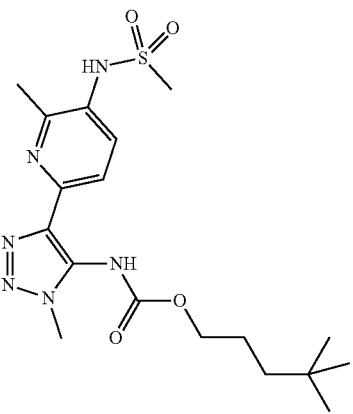
,
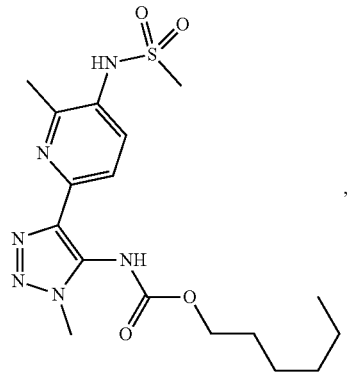
,
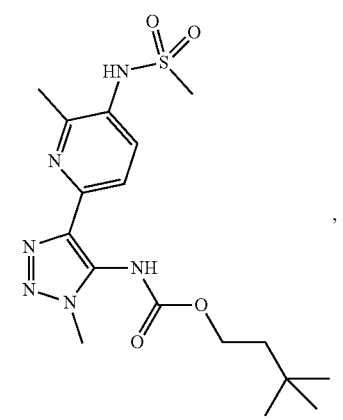
,
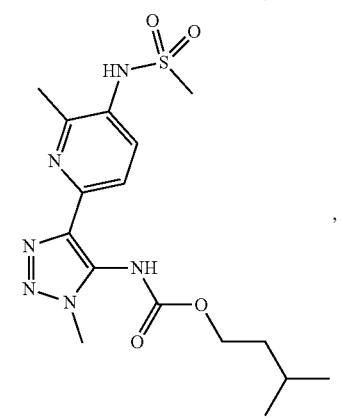
,
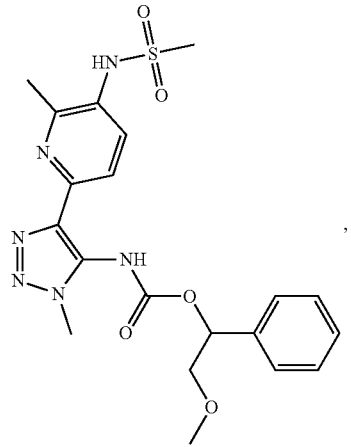
,

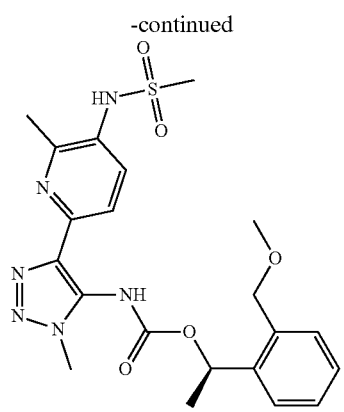
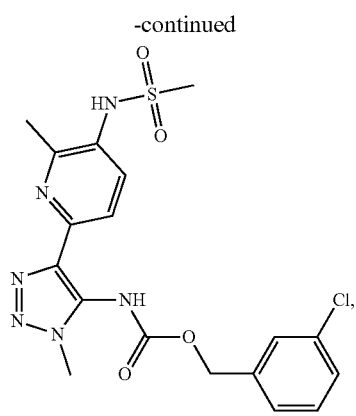
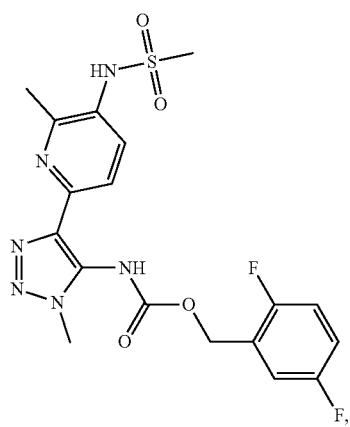
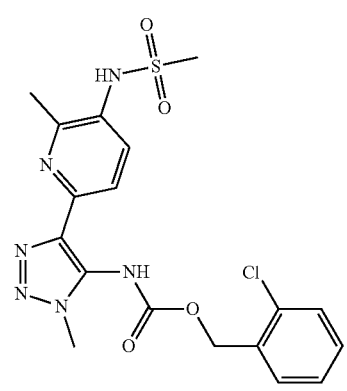
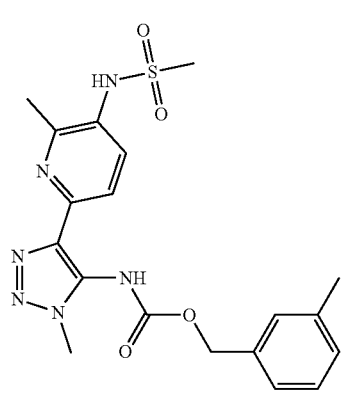
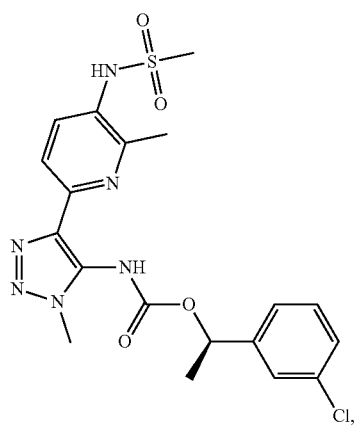
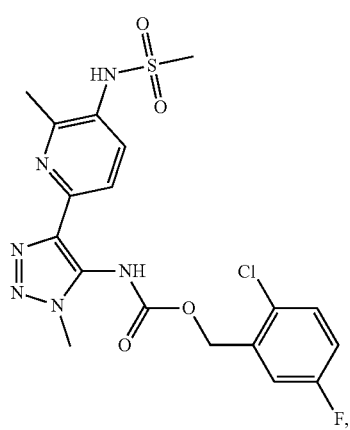
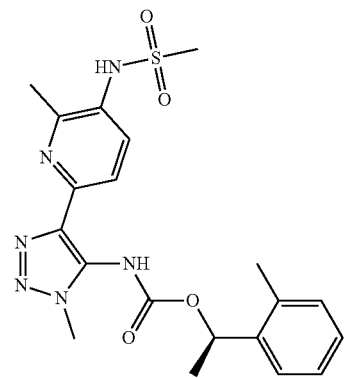

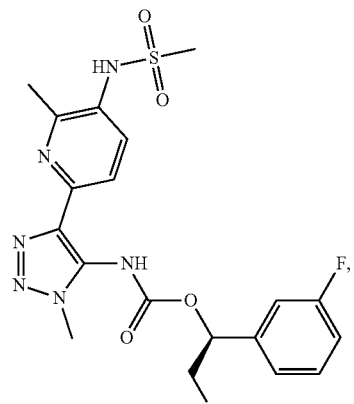
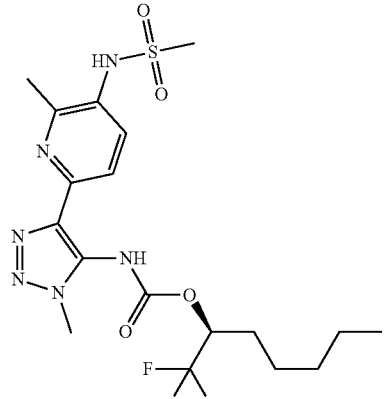
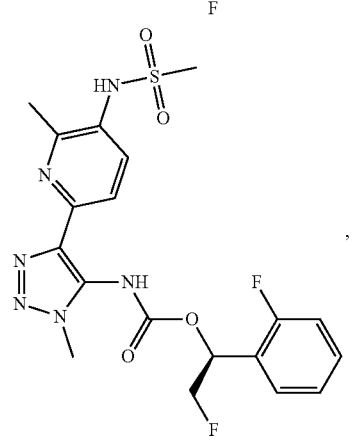
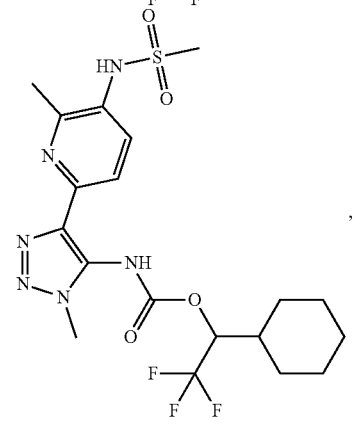
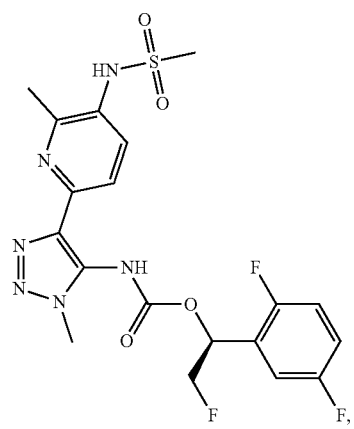
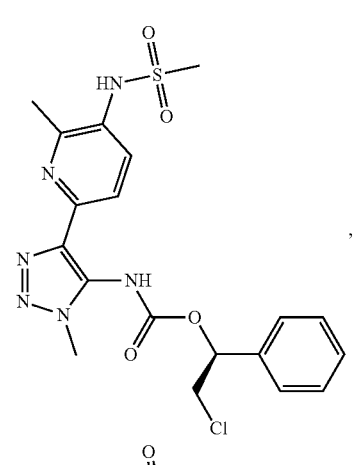
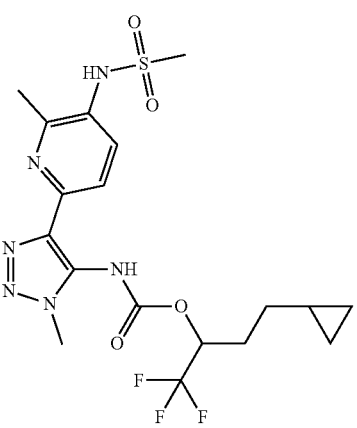
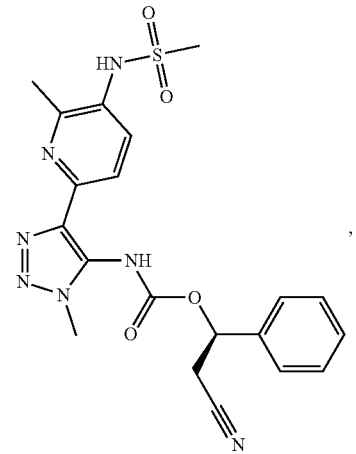

-continued
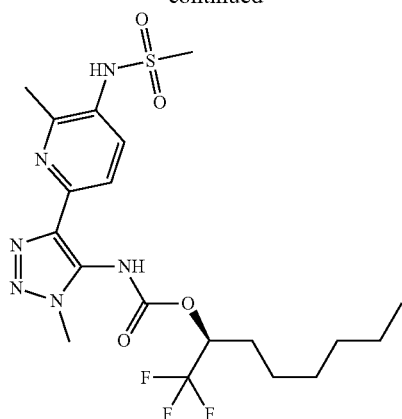
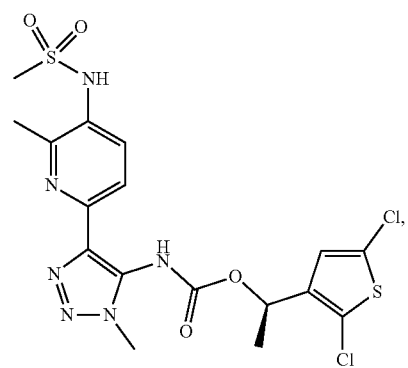
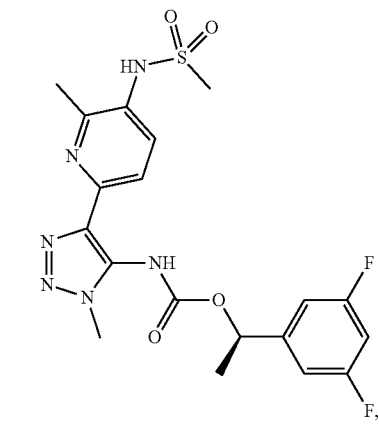
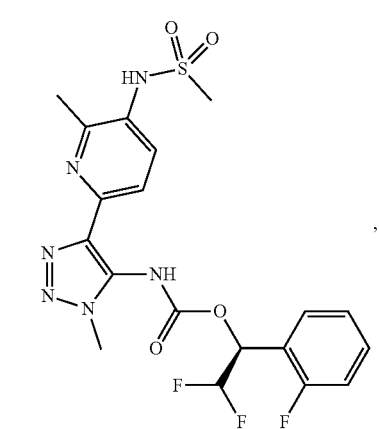
-continued
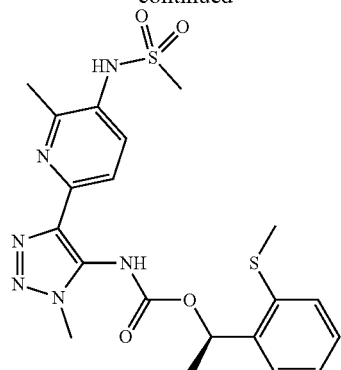
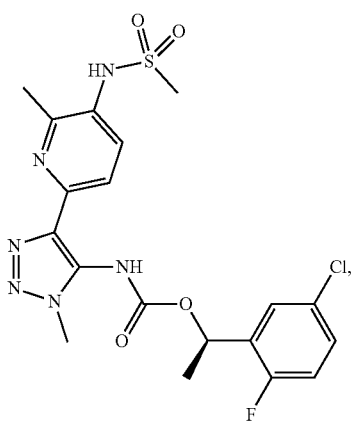
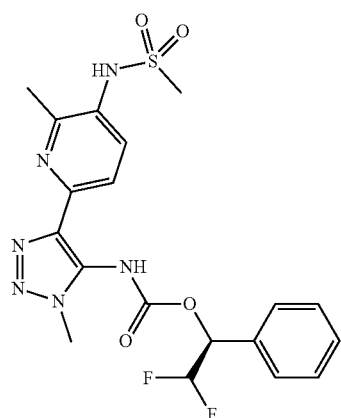
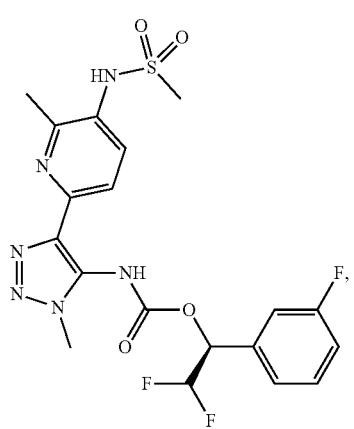

-continued
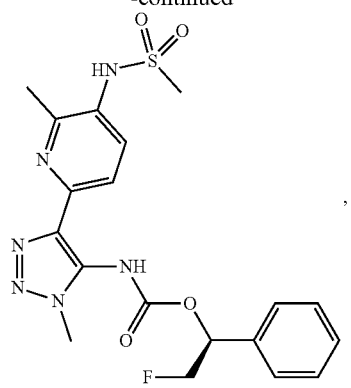
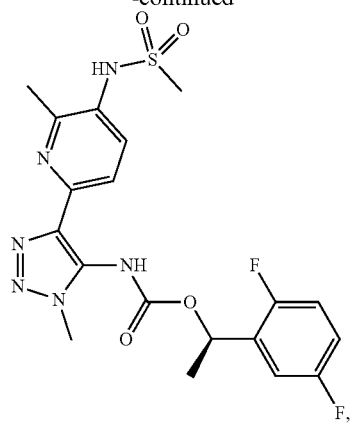
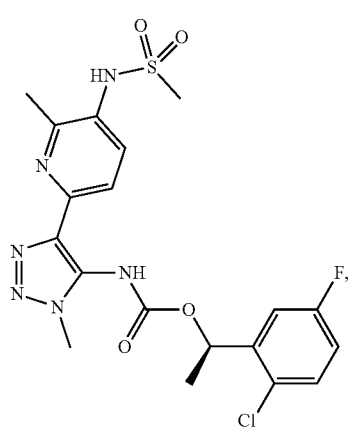
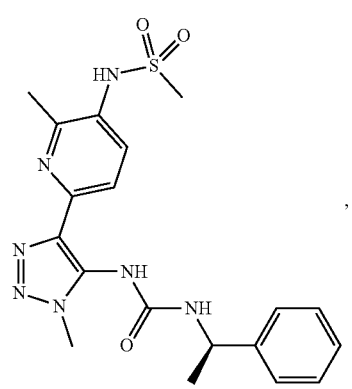
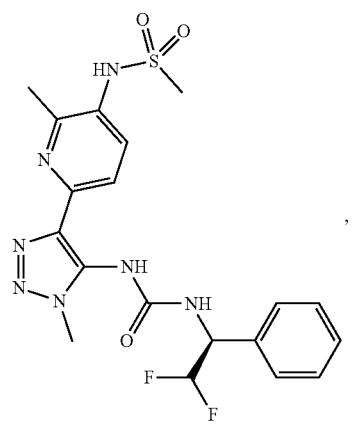
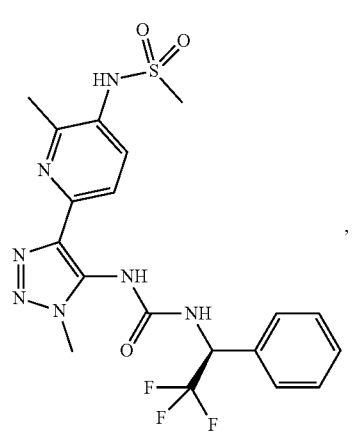

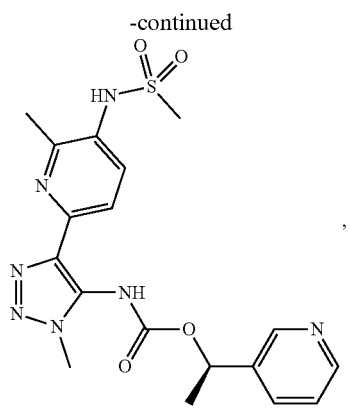
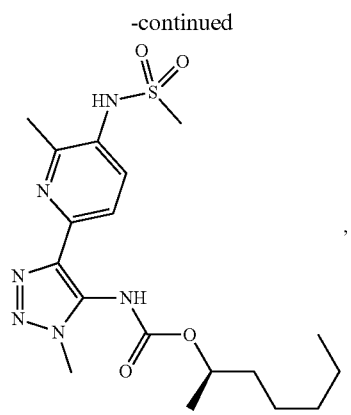
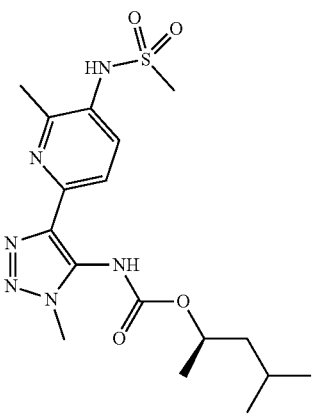
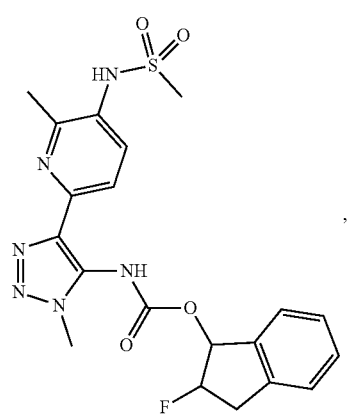
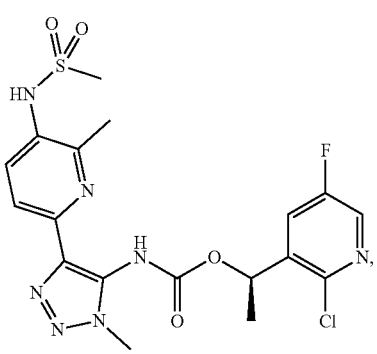

49
-continued
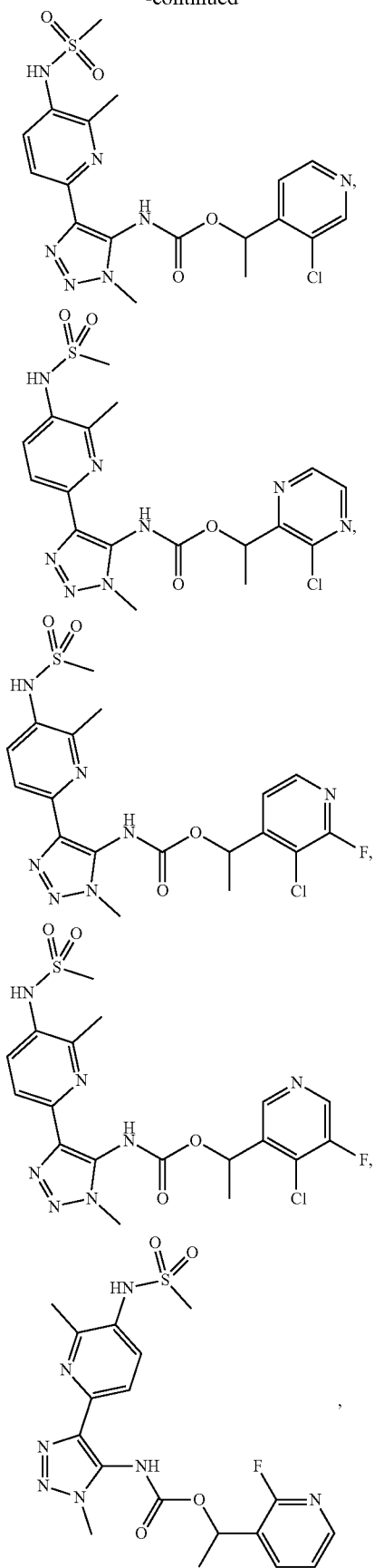
50
-continued
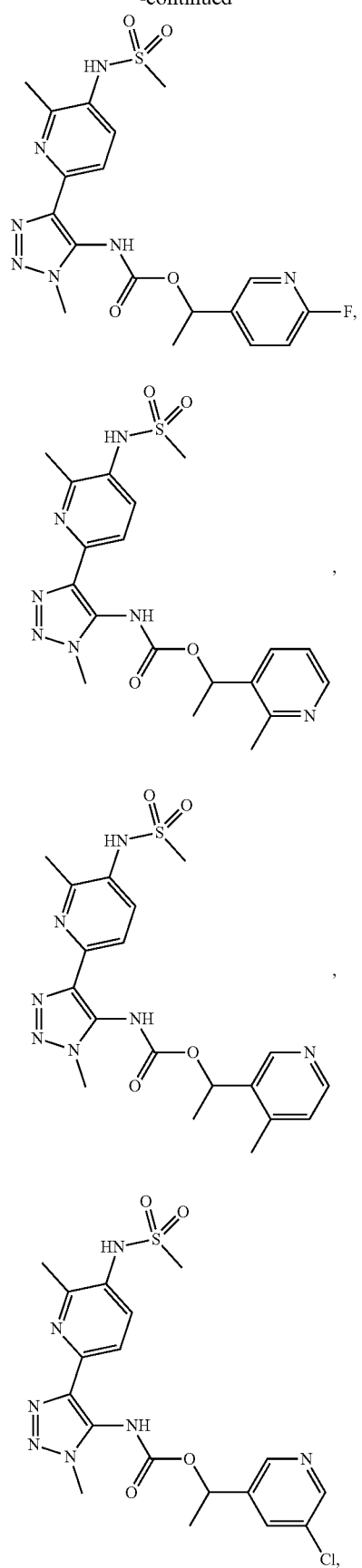

-continued
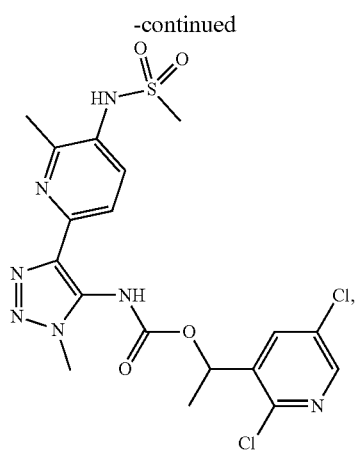
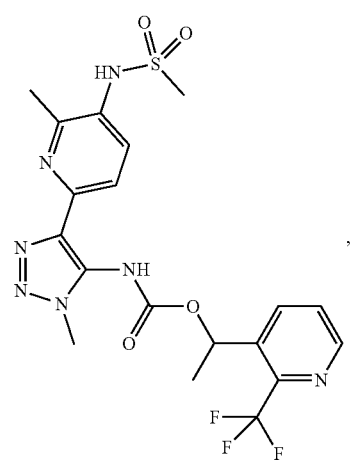
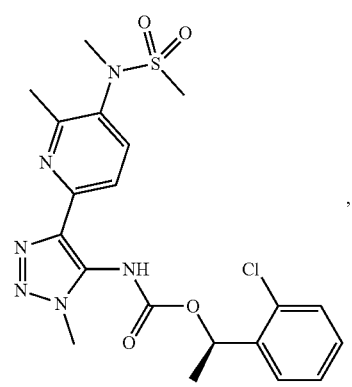
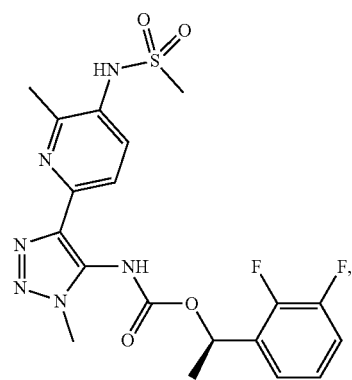
-continued
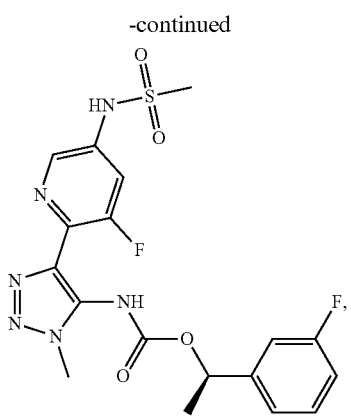
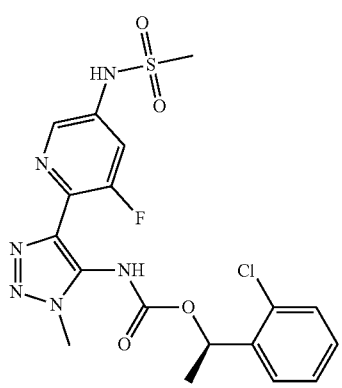
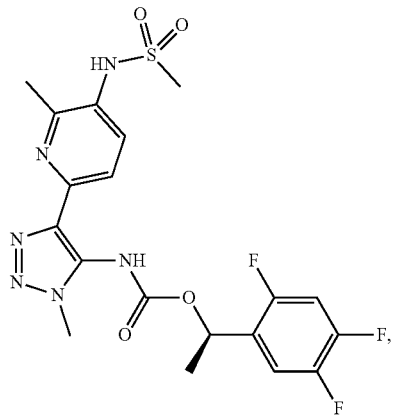
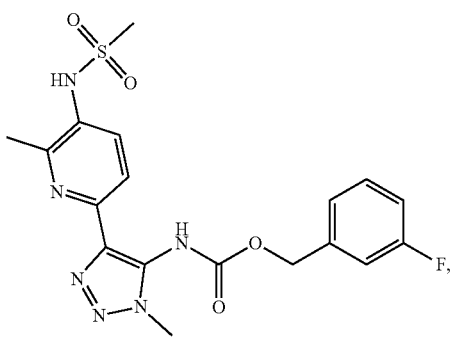

53
-continued
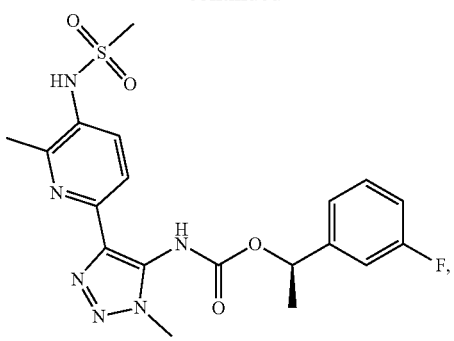 [SMILES: Cc1nc(-c2nnn(C)c2NC(=O)O[C@H](C)c2cccc(F)c2)ccc1NS(C)(=O)=O]
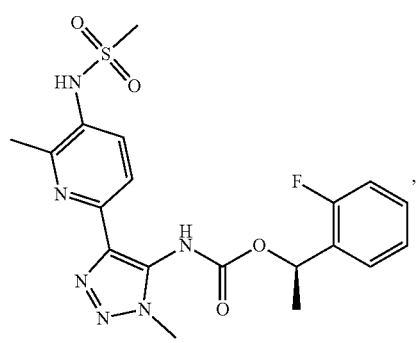
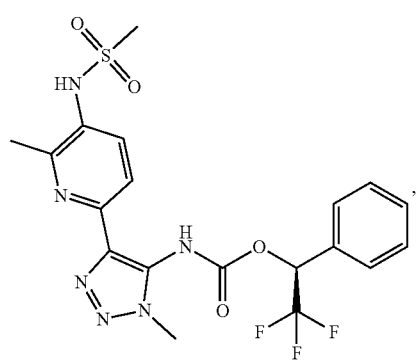
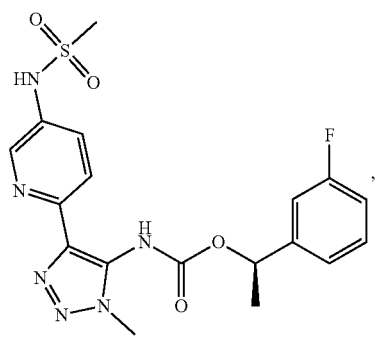
54
-continued
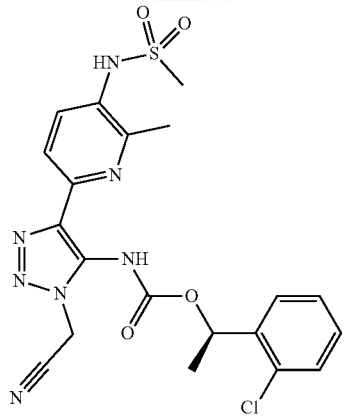
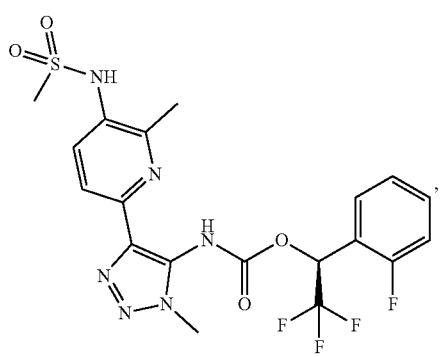
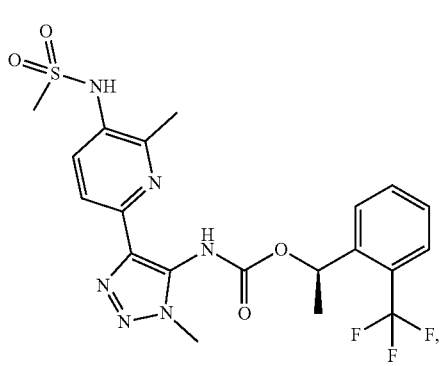
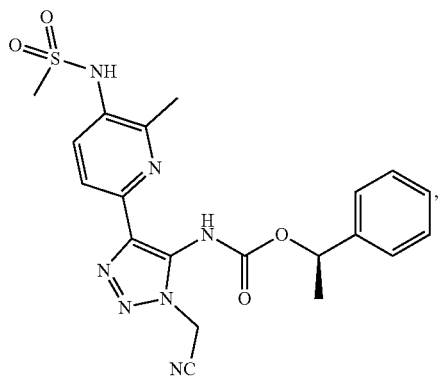

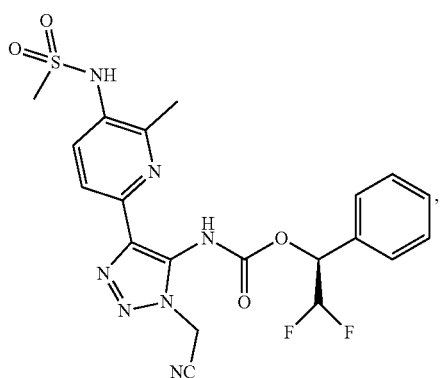
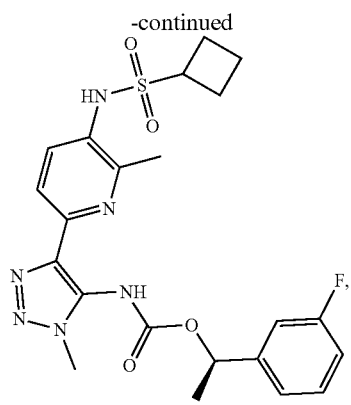
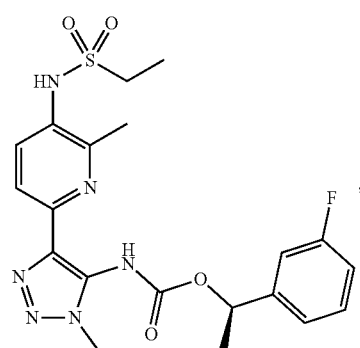
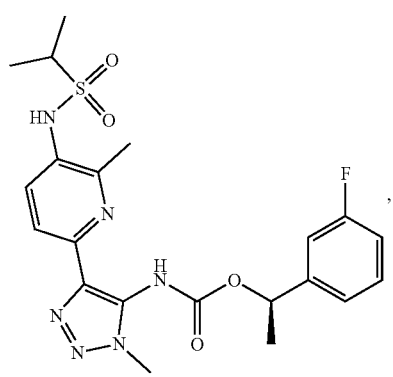
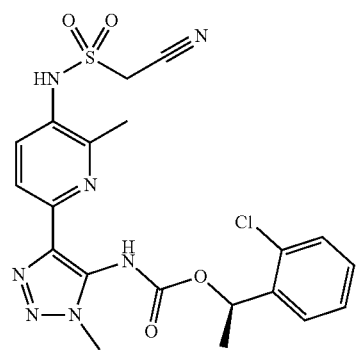
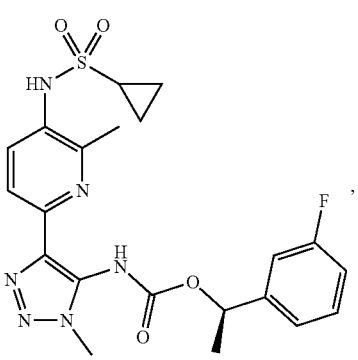
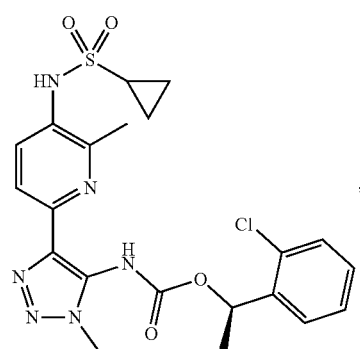
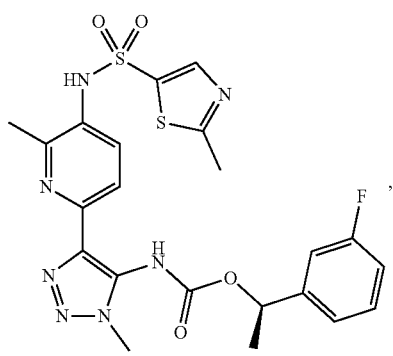

or a pharmaceutically acceptable salt thereof.

In some embodiments, the compound of Formula (I), (Ia), (II), or (Ia), or pharmaceutically acceptable salt thereof, is selected from the group consisting of:

59
-continued
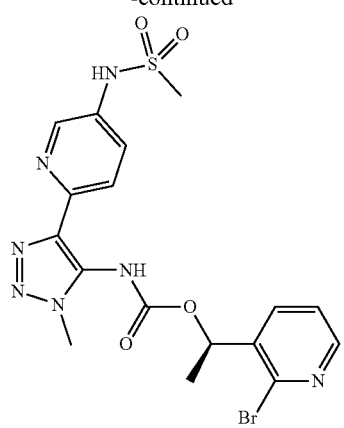
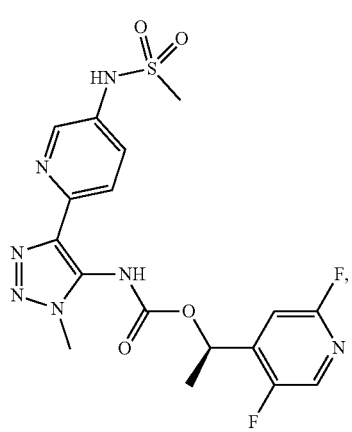
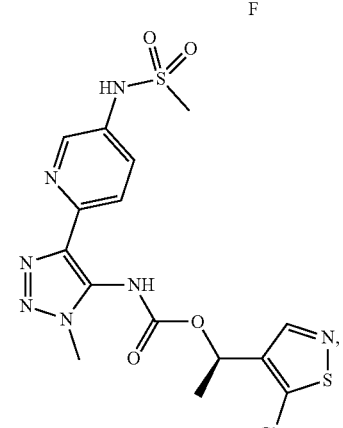
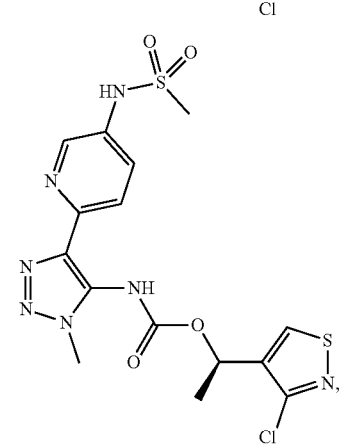
60
-continued
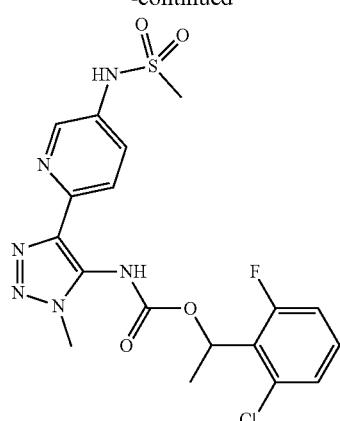
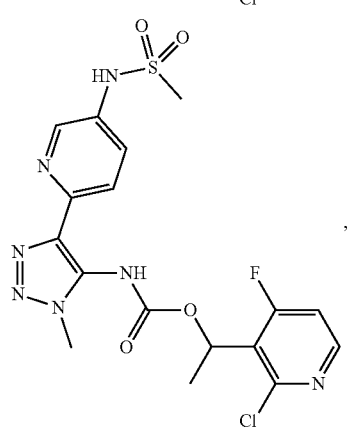
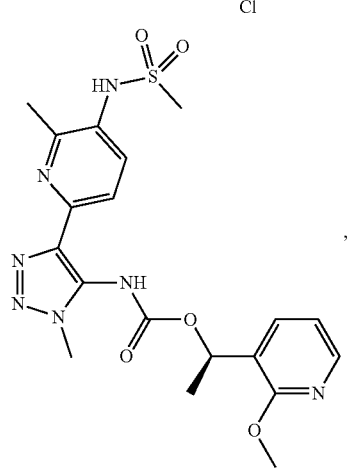
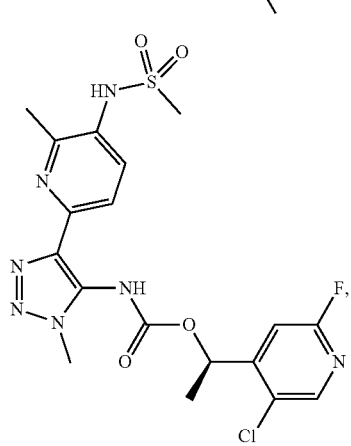

61
-continued
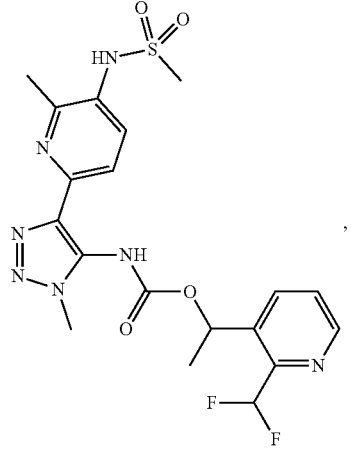
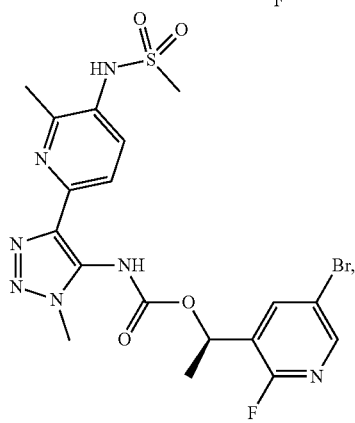
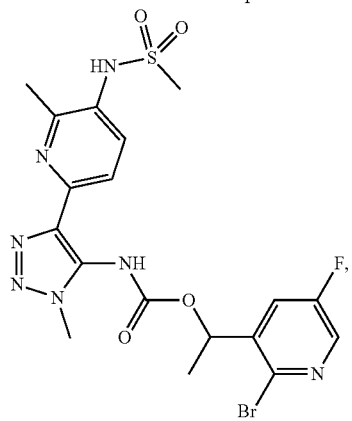
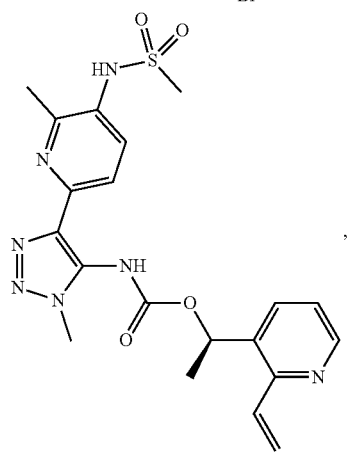
62
-continued
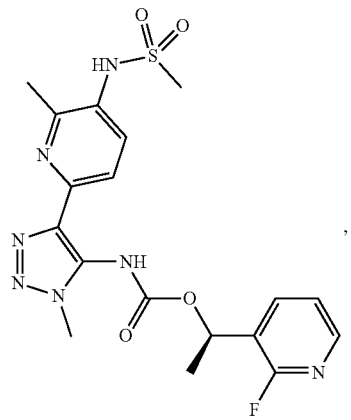
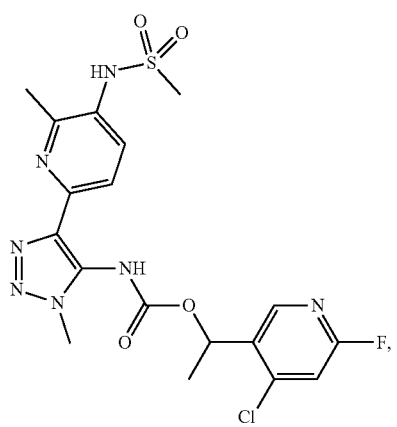
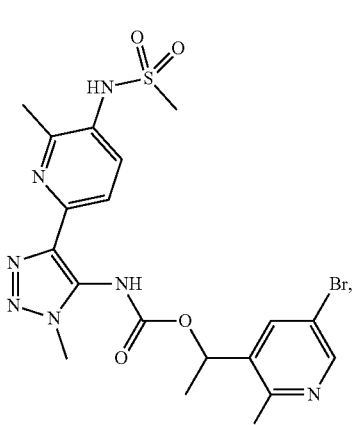
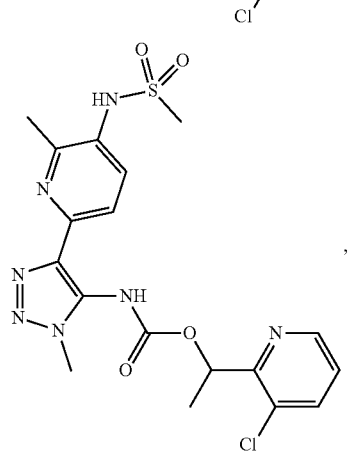

-continued
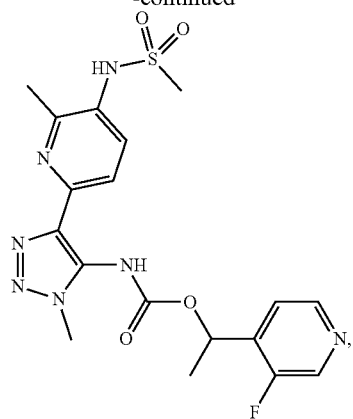
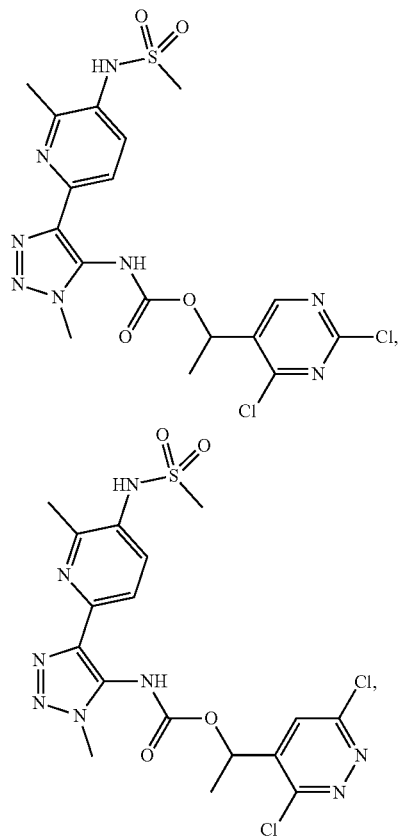
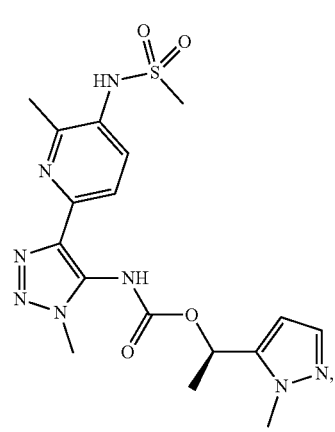
-continued
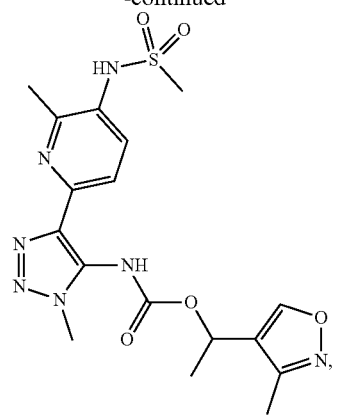
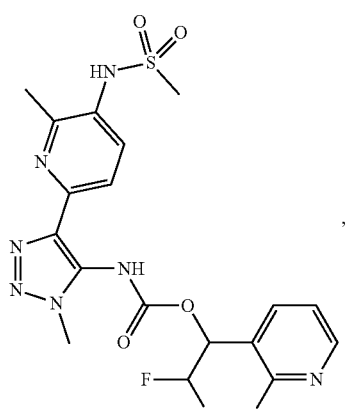
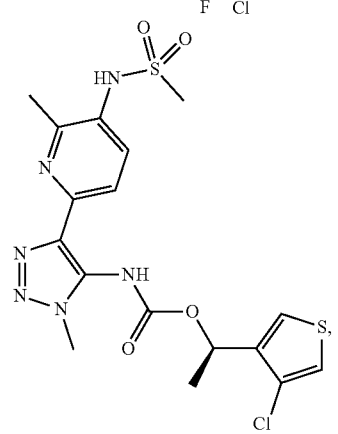
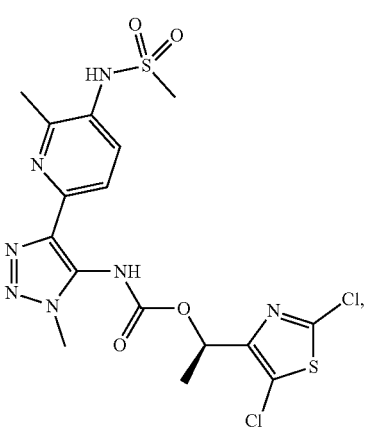

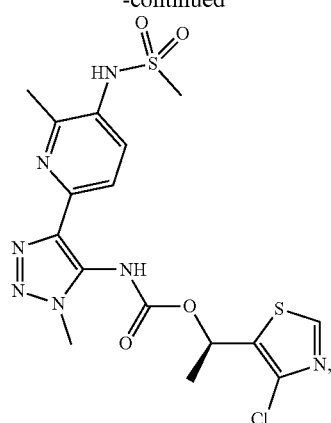
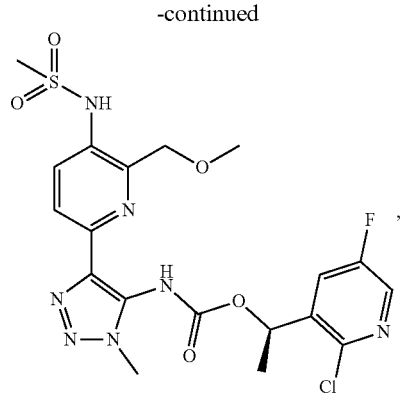
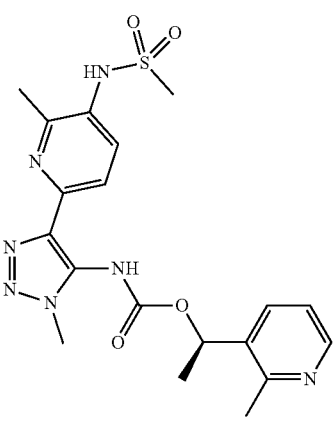
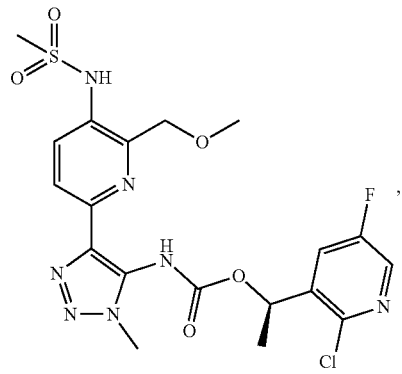
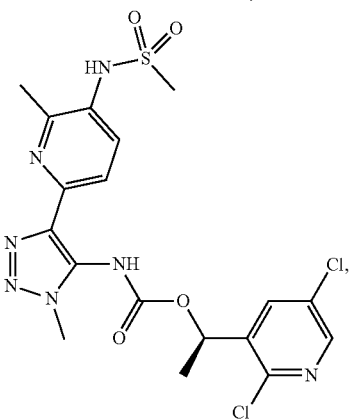
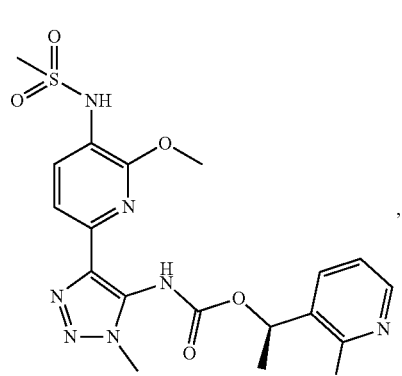
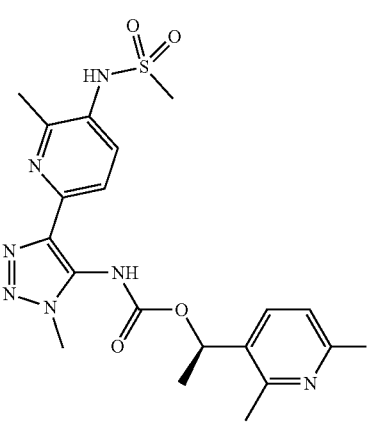
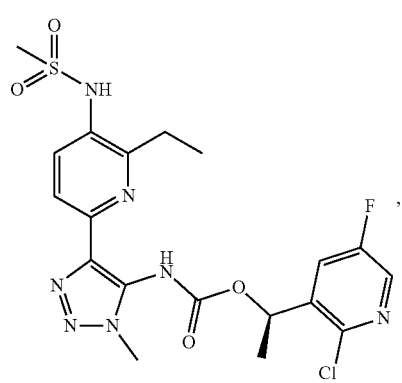

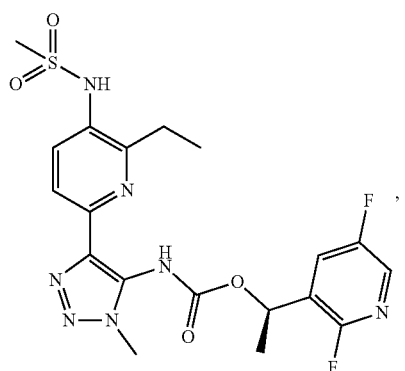
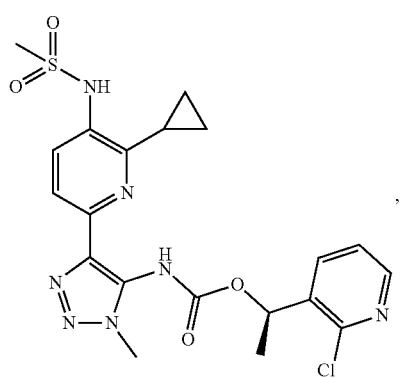
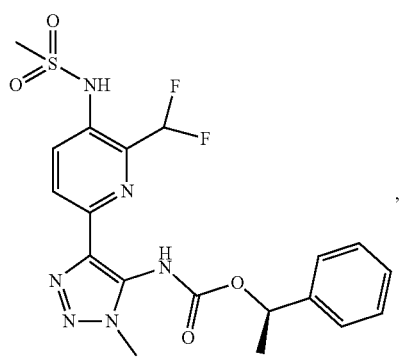
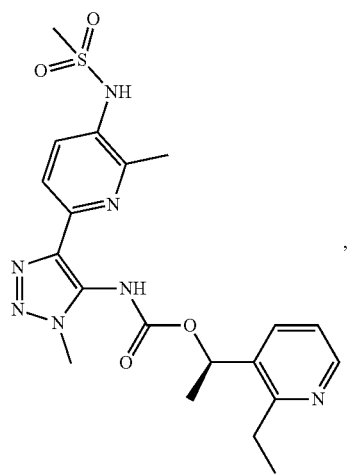
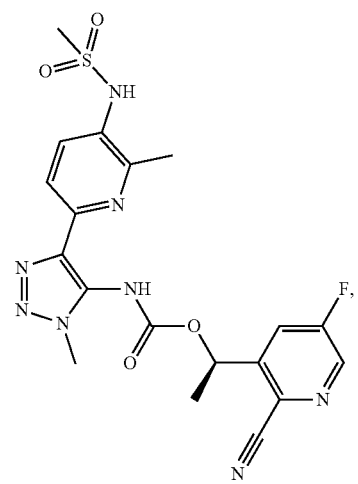
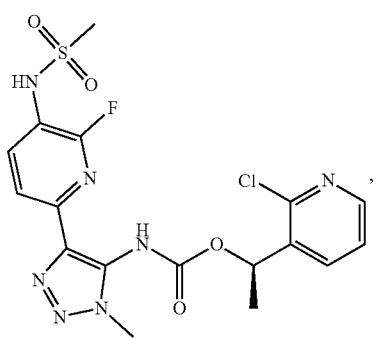
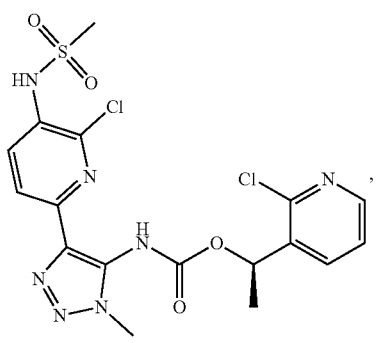
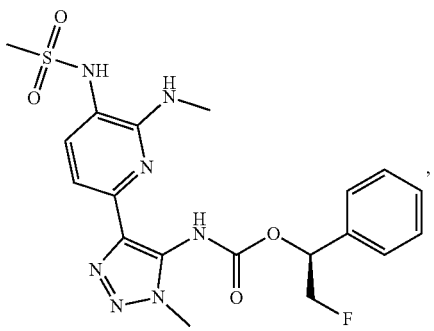

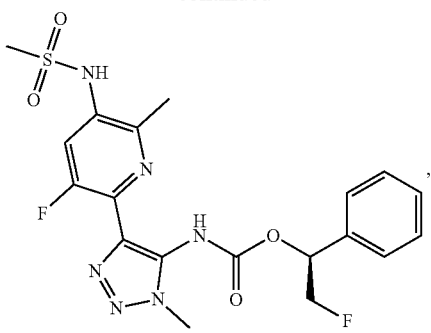
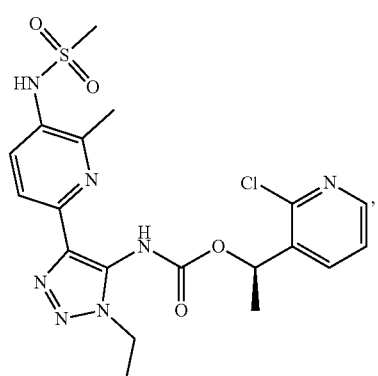
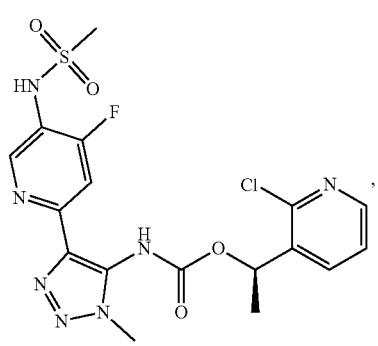
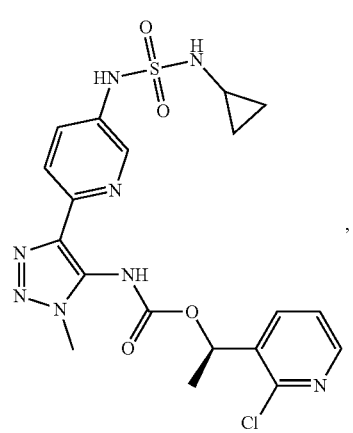
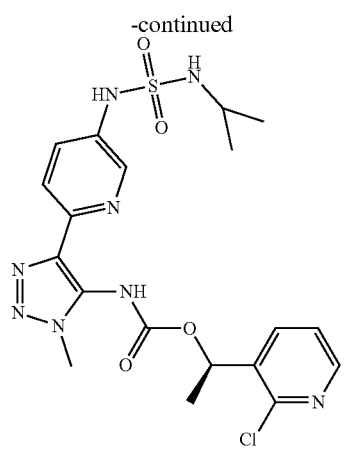
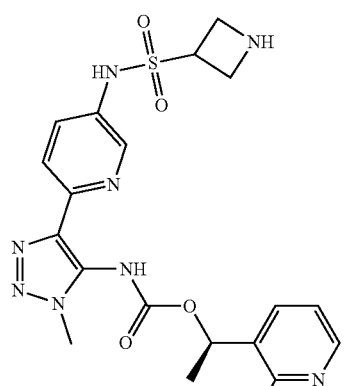
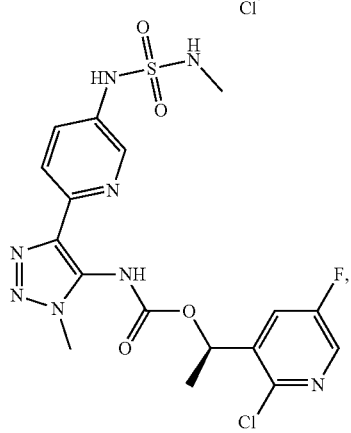
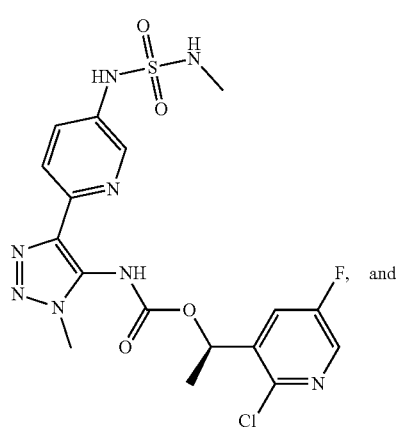
F, and -continued

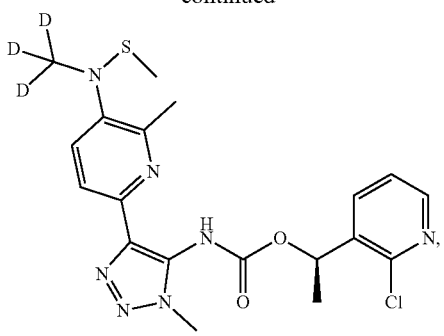

or a pharmaceutically acceptable salt thereof.

In some embodiments, the compound of Formula (I), (Ia), (II), or (IIa), or pharmaceutically acceptable salt thereof, is:

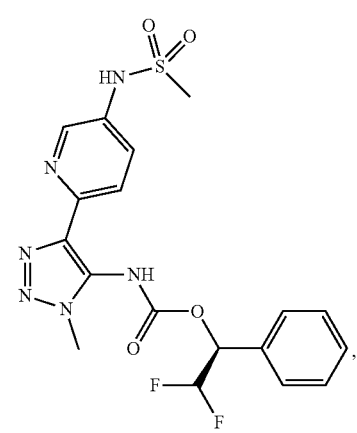

or a pharmaceutically acceptable salt thereof.

In some embodiments, the compound of Formula (I), (Ia), (II), or (IIa), or pharmaceutically acceptable salt thereof, is:

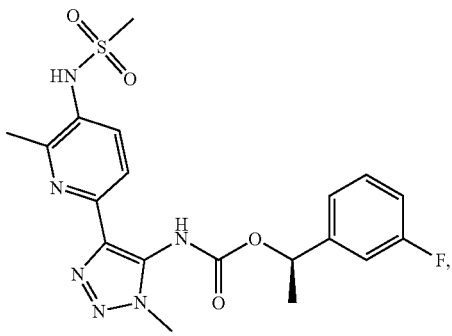

or a pharmaceutically acceptable salt thereof.

In some embodiments, the compound of Formula (I), (Ia), (II), or (IIa), or pharmaceutically acceptable salt thereof, is:

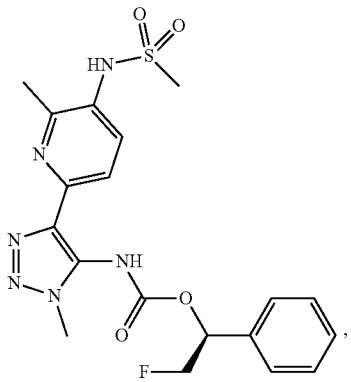 [SMILES: Cc1nc(-c2nnn(C)c2NC(=O)O[C@H](CF)c2ccccc2)ccc1NS(C)(=O)=O]

or a pharmaceutically acceptable salt thereof.

In some embodiments, the compound of Formula (I), (Ia), (II), or (IIa), or pharmaceutically acceptable salt thereof, is:

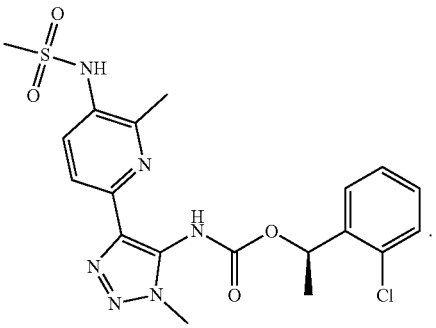 [SMILES: Cc1nc(-c2nnn(C)c2NC(=O)O[C@H](C)c2ccccc2Cl)ccc1NS(C)(=O)=O]

or a pharmaceutically acceptable salt thereof.

In some embodiments, the compound of Formula (I), (Ia), (II), or (IIa), or pharmaceutically acceptable salt thereof, is:

Pharmaceutical Compositions and Modes of Administration

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

The pharmaceutical composition of the present disclosure may additionally comprise one or more other compounds as active ingredients like a prodrug compound or other enzyme inhibitors.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient.

They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

In some embodiments, the compounds of the present disclosure may also be used as salts with various countercations to yield an orally available formulation.

The compounds of the present disclosure may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Treatment Methods and Uses

The disclosure further relates to the use of compounds disclosed herein for the treatment and/or prophylaxis of diseases and/or conditions through binding of LPAR1 by said compounds. Further, the present disclosure relates to the use of said compounds for the preparation of a medicament for the treatment and/or prophylaxis of diseases and/or conditions through binding of LPAR1 by said compounds.

Medicaments as referred to herein may be prepared by conventional processes, including the combination of a compound according to the present disclosure and a pharmaceutically acceptable carrier.

In some embodiments, provided herein is a method of treating and/or preventing an LPAR1-mediated disease or condition in a patient in need thereof, comprising administering to the patient a therapeutically effective amount of a compound of Formula (I), (Ia), (II), or (IIa), or a pharmaceutically acceptable salt thereof, or a composition comprising a compound of Formula (I), (Ia), (II), or (IIa), or a pharmaceutically acceptable salt thereof.

In some embodiments, the LPAR1-mediated disease or condition includes those wherein an absolute or relative excess of LPA is present and/or observed.

In some embodiments, the LPAR1-mediated disease or condition includes fibrosis, wound healing, cancer, pain, respiratory disorders, allergic disorders, nervous system disorders, cardiovascular disorders, or inflammatory disorders.

In some embodiments, the LPAR1-mediated disease or condition is an interstitial lung disease (ILD). In some embodiments, the interstitial lung disease (ILD) is nonspecific interstitial pneumonitis (NSIP), sarcoidosis, asbestosis, an ILD related to an occupational exposure, progressive fibrosing ILD, idiopathic interstitial pneumonia (IIP), connective tissue disease-associated interstitial lung disease (CTD-ILD), rheumatoid arthritis-associated ILD, scleroderma-associated ILD, or extrinsic alveolitis.

In some embodiments, the LPAR1-mediated disease or condition is a chronic kidney disease (CKD). In some embodiments, the chronic kidney disease is complement glomerulopathy, membranous glomerulopathy, polycystic kidney disease, IgA nephropathy, focal segmental glomerulosclerosis (FSGS), or Alport Syndrome.

In some embodiments, the LPAR1-mediated disease or condition includes fibrosis. In some embodiments, fibrosis includes pulmonary fibrosis, renal fibrosis, hepatic fibrosis, ocular fibrosis, or cardiac fibrosis.

In some embodiments, the LPAR1-mediated disease or condition includes pulmonary fibrosis. In some embodiments, pulmonary fibrosis includes idiopathic pulmonary fibrosis (IPF). In some embodiments, pulmonary fibrosis includes pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced).

In some embodiments, the LPAR1-mediated disease or condition includes renal fibrosis. In some embodiments, renal fibrosis includes chronic nephropathies associated with injury/ibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; gut fibrosis, e.g., scleroderma, and radiation induced gut fibrosis.

In some embodiments, the LPAR1-mediated disease or condition includes liver fibrosis. In some embodiments, liver fibrosis includes liver cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis.

In some embodiments, the LPAR1-mediated disease or condition includes head and neck fibrosis, e.g., radiation induced.

In some embodiments, the LPAR1-mediated disease or condition includes corneal scarring, e.g., due to LASIK (laser-assisted in situ keratomileusis), corneal transplantation, or trabeculectomy. In some embodiments, a compound of Formula (I), (Ia), (II), or (IIa), or a pharmaceutically acceptable salt thereof, is used to improve the corneal sensitivity decrease caused by corneal operations such as LASIK or cataract operation, corneal sensitivity decrease caused by corneal degeneration, and dry eye symptom caused thereby. In some embodiments, a compound of Formula (I), (Ia), (II), or (IIa), or a pharmaceutically acceptable salt thereof, is used in the treatment or prevention of ocular inflammation and allergic conjunctivitis, vernal keratoconjunctivitis, and papillary conjunctivitis. In some embodiments, a compound of Formula (I), (Ia), (II), or (IIa), or a pharmaceutically acceptable salt thereof, is used in the treatment or prevention of Sjogren disease or inflammatory disease with dry eyes.

In some embodiments, the LPAR1-mediated disease or condition includes another fibrotic condition, such as hypertrophic scarring and keloids, e.g., burn induced or surgical, sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In some embodiments, the LPAR1-mediated disease or condition includes pain. In some embodiments, pain includes neuropathic pain. In some embodiments, pain includes acute pain. In some embodiments, pain includes chronic pain.

In some embodiments, the LPAR1-mediated disease or condition includes cancer. In some embodiments, cancer includes ovarian cancer, colon cancer, prostate cancer, breast cancer, melanoma, head and neck cancer, bowel cancer (colorectal cancer), and thyroid cancer. In some embodiments, cancer includes solid tumors, such as (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases. In some embodiments, cancer includes, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hair) cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive, neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, the LPAR1-mediated disease or condition includes a respiratory or allergic disorder. In some embodiments, the respiratory or allergic disorder includes asthma, peribronchiolar fibrosis, obliterative bronchiolitis, and chronic obstructive pulmonary disease (COPD). In some embodiments, the COPD includes chronic bronchitis or emphysema, pulmonary hypertension, interstitial lung fibrosis and/or airway inflammation, and cystic fibrosis. In some embodiments, the respiratory disease includes adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, and hypoxia.

In some embodiments, the LPAR1-mediated disease or condition includes a nervous system disorder. In some embodiments, the nervous system disorder includes Alzheimer's Disease, cerebral edema, cerebral ischemia, stroke, multiple sclerosis, neuropathies, Parkinson's Disease, a nervous condition found after blunt or surgical trauma (including post-surgical cognitive dysfunction and spinal cord or brain stem injury), as well as the neurological aspects of disorders such as degenerative disk disease and sciatica.

In some embodiments, the LPAR1-mediated disease or condition includes a cardiovascular disorder. In some embodiments, the cardiovascular disorder includes arrhythmia (atrial or ventricular or both); atherosclerosis and its sequelae; angina; cardiac rhythm disturbances; myocardial ischemia; myocardial infarction; cardiac or vascular aneurysm; vasculitis; stroke; peripheral obstructive arteriopathy of a limb, an organ, or a tissue; reperfusion injury following ischemia of the brain, heart or other organ or tissue; endotoxic, surgical, or traumatic shock; hypertension; valvular heart disease; heart failure; abnormal blood pressure; shock; vasoconstriction (including that associated with migraines); vascular abnormality, and a cardiovascular insufficiency limited to a single organ or tissue.

In some embodiments, the LPAR1-mediated disease or condition includes lung fibrosis, kidney fibrosis, liver fibrosis, scarring, asthma, rhinitis, chronic obstructive pulmonary disease (COPD), pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions.

In some embodiments, the LPAR1-mediated disease or condition is a liver disease. In some embodiments, the liver disease is hepatitis C, liver cancer, familial combined hyperlipidemia, non-alcoholic fatty liver disease (NAFLD), progressive familial intrahepatic cholestasis, primary biliary cirrhosis (PBC), or (PSC). In some embodiments, the liver disease is PSC. In some embodiments the liver disease comprises portal hypertension. In some embodiments, liver cancer comprises hepatocellular carcinoma (HCC), cholangiocarcinoma, angiosarcoma, or hemangiosarcoma. In some embodiments, liver cancer comprises HCC. In some embodiments, NAFLD comprises steatosis. In some embodiments, NAFLD comprises NASH. In some embodiments, NAFLD or NASH comprises liver fibrosis. In some embodiments, NAFLD or NASH comprises liver cirrhosis. In some embodiments, the NAFLD or NASH comprises compensated liver cirrhosis. In some embodiments, the NAFLD or NASH comprises decompensated liver fibrosis. In some embodiments, the NAFLD comprises HCC. In some embodiments, the liver disease is NASH.

In some embodiments, provided herein is a method of treating and/or preventing NAFLD or NASH in a patient in need thereof, comprising administering to the patient a therapeutically effective amount of a compound of Formula (I), (Ia), (II), or (IIa), or pharmaceutically acceptable salt thereof, or a composition comprising a compound of Formula (I), (Ia), (II), or (IIa), or pharmaceutically acceptable salt thereof. In some embodiments, NAFLD or NASH comprise liver fibrosis. In some embodiments, NAFLD or NASH comprise liver cirrhosis. In some embodiments, liver cirrhosis is compensated liver cirrhosis. In some embodiments, liver cirrhosis is decompensated liver cirrhosis. In some embodiments NAFLD or NASH comprise HCC.

In some embodiments, provided herein is a method of preventing a liver disease or condition in a patient in need thereof, comprising administering to the patient a therapeutically effective amount of a compound of Formula (I), (Ia), (II), or (IIa), or pharmaceutically acceptable salt thereof, or a composition comprising a compound of Formula (I), (Ia), (II), or (IIa), or pharmaceutically acceptable salt thereof. In some embodiments, the liver disease or condition is liver fibrosis. In some embodiments, the liver disease or condition is liver cirrhosis. In some embodiments, liver cirrhosis is compensated liver cirrhosis. In some embodiments, liver cirrhosis is decompensated liver cirrhosis. In some embodiments, the liver disease or condition is HCC.

In some embodiments, the present disclosure relates to the use of compounds according to Formula (I), (Ia), (II), or (IIa) in the preparation of a medicament for the prophylaxis and/or treatment of an LPAR1-mediated disease or condition disclosed herein.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing an LPAR1 mediated disease or condition for which compounds of the present disclosure are indicated, generally satisfactory results are obtained when the compounds of the present disclosure are administered at a daily dosage of from about 0.1 milligram to about 300 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 0.1 milligrams to about 200 milligrams. This dosage regimen may be adjusted to provide the optimal therapeutic response. In some embodiments, the total daily dosage is from about 1 milligram to about 900 milligrams, about 1 milligram to about 800 milligrams, about 1 milligram to about 700 milligrams, about 1 milligram to about 600 milligrams, about 1 milligram to about 400 milligrams, about 1 milligram to about 300 milligrams, about 1 milligram to about 200 milligrams, about 1 milligram to about 100 milligrams, about 1 milligram to about 50 milligrams, about 1 milligram to about 20 milligram, or about 1 milligram to about 10 milligrams.

The compounds of the present application or the compositions thereof may be administered once, twice, three, or four times daily, using any suitable mode described above.

Also, administration or treatment with the compounds may be continued for a number of days; for example, commonly treatment would continue for at least 7 days, 14 days, or 28 days, for one cycle of treatment. Treatment cycles are frequently alternated with resting periods of about 1 to 28 days, commonly about 7 days or about 14 days, between cycles. The treatment cycles, in other embodiments, may also be continuous.

In some embodiments, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Combinations

In some embodiments, a compound of Formula (I), (Ia), (II), or (IIa) provided herein, or pharmaceutically acceptable salt thereof, is administered in combination with one or more additional therapeutic agents to treat or prevent a disease or condition disclosed herein. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the pharmaceutical compositions provided herein have a compound of Formula (I), (Ia), (II), or (IIa) provided herein, or pharmaceutically acceptable salt thereof, and one or more additional therapeutic agents. In some embodiments, the one or more additional therapeutic agents are one, two, three, or four additional therapeutic agents. In some embodiments, the one or more additional therapeutic agents are one additional therapeutic agent.

In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the one or more additional therapeutic agents are selected from a(n) angiotensin converting enzyme (ACE) inhibitor, Adenosine A3 receptor agonist, Adiponectin receptor agonist, AKT protein kinase inhibitor, AMP kinase activator, AMP-activated protein kinase (AMPK) activator, Amylin receptor agonist, Angiotensin II AT-1 receptor antagonist, Androgen receptor agonist, Apoptosis signal-regulating kinase 1 (ASK1) inhibitor, ATP citrate lyase inhibitor, Apolipoprotein C3 (APOC3) antagonist, Autophagy protein modulator, Autotaxin inhibitors, Axl tyrosine kinase receptor inhibitor, Bax protein stimulator, Bioactive lipid, Calcitonin agonist, Cannabinoid receptor modulator, Caspase inhibitor, Caspase-3 stimulator, Cathepsin inhibitor (e.g., cathepsin B inhibitor), Caveolin 1 inhibitor, CCR2 chemokine antagonist, CCR3 chemokine antagonist, CCR5 chemokine antagonist, CD3 antagonist, Chloride channel stimulator, cholesterol solubilizer, CNR1 inhibitor, Cyclin D1 inhibitor, Cytochrome P450 7A1 inhibitor, Cytochrome P450 2E1 (CYP2E1) inhibitor, Diacylglycerol O acyltransferase 1 inhibitor (DGAT1) inhibitor, Diacylglycerol O acyltransferase 1 inhibitor (DGAT2) inhibitor, CXCR4 chemokine antagonist, Dipeptidyl peptidase IV inhibitor, Endosialin modulator, Endothelial nitric oxide synthase stimulator, Eotaxin ligand inhibitor, Extracellular matrix protein modulator, Farnesoid X receptor agonist, Fatty acid synthase inhibitors, FGF1 receptor agonist, Fibroblast activation protein (FAP) inhibitor, Fibroblast growth factor receptor ligands (e.g., FGF-15, FGF-19, FGF-21), fish oil, Galectin-3 inhibitor, Glucagon receptor agonist, Glucagon-like peptide 1 receptor agonist, Glucocorticoid receptor antagonist, Glucose 6-phosphate 1-dehydrogenase inhibitor, Glutaminase inhibitor, Glutathione precursor, G-protein coupled bile acid receptor 1 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, HMG CoA reductase inhibitor, 11β-Hydroxysteroid dehydrogenase (11β-HSD1) inhibitor, Hypoxia inducible factor-2 alpha inhibitor, IL-1β antagonist, IL-6 receptor agonist, IL-10 agonist, IL-11 antagonist, IL-17 antagonist, Illeal sodium bile acid cotransporter inhibitor, Insulin sensitizer, Insulin ligand agonist, Insulin receptor agonist, integrin modulator, Integrin antagonist intereukin-1 receptor-associated kinase 4 (IRAK4) inhibitor, Jak2 tyrosine kinase inhibitor, Ketohexokinase (KHK) inhibitors, Klotho beta stimulator, leptin, leptin analog, 5-Lipoxygenase inhibitor, Lipoprotein lipase inhibitor, Liver X receptor, LPL gene stimulator, Lysophosphatidate-1 receptor (LPAR-1) antagonist, Lysyl oxidase homolog 2 (LOXL2) inhibitor, LXR inverse agonist, Macrophage mannose receptor 1 modulator, Matrix metalloproteinase (MMPs) inhibitor, MCH receptor-1 antagonist, MEKK-5 protein kinase inhibitor, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21(miR-21) inhibitor, Mitochondrial uncoupler, Mixed lineage kinase-3 inhibitor, Myelin basic protein stimulator, NACHT LRR PYD domain protein 3 (NLRP3) inhibitor, NAD-dependent deacetylase sirtuin-1 stimulator, NADPH oxidase inhibitor (NOX), Nicotinic acid receptor 1 agonist, P2X7 purinoceptor modulator, P2Y13 purinoceptor stimulator, PDE 3 inhibitor, PDE 4 inhibitor, PDE 5 inhibitor, PDGF receptor beta modulator, Peptidyl-prolyl cis-trans isomerase A inhibitor, Phenylalanine hydroxylase stimulator, Phospholipase C inhibitor, PPAR alpha agonist, PPAR gamma agonist, PPAR delta agonist, PPAR gamma modulator, PPAR alpha/delta agonist, PPAR alpha/gamma/delta agonist, Protease-activated receptor-2 antagonist, Protein kinase modulator, Rho associated protein kinase 2 (ROCK2) inhibitor, Snitrosoglutathione reductase (GSNOR) enzyme inhibitor, Sodium glucose transporter-2 (SGLT2) inhibitor, SREBP transcription factor inhibitor, STAT-1 inhibitor, STAT-3 modulator, Stearoyl CoA desaturase-1 inhibitor, Snitrosoglutathione reductase (GSNOR) enzyme inhibitor, Suppressor of cytokine signalling-1 stimulator, Suppressor of cytokine signalling-3 stimulator, Spleen tyorosine kinase (SYK) inhibitor, Transforming growth factor β (TGF-β), TGF-β antagonist (e.g., TGF-β1 antagonist, TGF-β2 antagonist, TGF-β3 antagonist, latent TGF β complex modulator), TGF-β receptor antagonist, Transforming growth factor β activated Kinase 1 (TAK1), Thyroid hormone receptor beta agonist, Toll-like receptor (TLR)-4 antagonist, Transglutaminase inhibitor, Tumor necrosis factor alpha (TNFα) ligand inhibitor, Tumor Progression Locus 2 (Tpl2) kinase inhibitor, Tyrosine kinase receptor modulator, GPCR modulator, nuclear hormone receptor modulator, WNT modulators, YAP/TAZ modulator, and Zonulin inhibitor.

Non-limiting examples of the one or more additional therapeutic agents include:

ACE inhibitors, such as enalapril;

Acetyl CoA carboxylase (ACC) inhibitors, such as NDI-010976 (firsocostat), DRM-01, gemcabene, PF-05175157, QLT-091382 or PF-05221304;

Acetyl CoA carboxylase/Diacylglycerol O acyltransferase 2 inhibitors, such as PF-07055341;

Acetaldehyde dehydrogenase inhibitors, such as ADX-629;

Adenosine receptor agonists, such as CF-102 (namodenoson), CF-101, CF-502, or CGS21680;

Adiponectin receptor agonists, such as ADP-355 or ADP-399;

Amylin/calcitonin receptor agonists, such as KBP-042 or KBP-089;

AMP activated protein kinase stimulators, such as PXL-770 or 0-304;

AMP kinase activators/ATP citrate lyase inhibitors, such as bempedoic acid (ETC-1002, ESP-55016);

AMP activated protein kinase/Endothelial nitric oxide synthase/NAD-dependent deacetylase sirtuin-1 stimulators, such as NS-0200 (leucine+metformin+sildenafil);

Androgen receptor agonists, such as LPCN-1144;

Angiotensin II AT-1 receptor antagonists, such as irbesartan;

Angiopoietin-related protein-3 inhibitors, such as IONIS-ANGPTL3-LRx;

Autotaxin inhibitors, such as PAT-505, PAT-048, GLPG-1690, X-165, PF-8380, AM-063, or BBT-877;

Axl tyrosine kinase receptor inhibitors, such as bemcentinib (BGB-324, R-428);

Bax protein stimulators, such as CBL-514;

Bioactive lipids, such as DS-102;

Cannabinoid receptor type 1 (CNR1) inhibitors, such as namacizumab, GWP-42004, REV-200, or CRB-4001;

Caspase inhibitors, such as emricasan;

Pan cathepsin B inhibitors, such as VBY-376;

Pan cathepsin inhibitors, such as VBY-825;

CCR2/CCR5 chemokine antagonists, such as cenicriviroc, maraviroc, CCX-872, or WXSH-0213;

CCR2 chemokine antagonists, such as propagermanium;

CCR2 chemokine/Angiotensin II AT-1 receptor antagonists, such as DMX-200, or DMX-250;

CCR2/CCR5 chemokine antagonists and FXR agonists, such as LJC-242 (tropifexor+cenivriviroc); CCR3 chemokine antagonists, such as bertilimumab;

Chloride channel stimulators, such as cobiprostone, or lubiprostone;

CD3 antagonists, such as NI-0401 (foralumab);

CXCR4 chemokine antagonists, such as AD-214;

Diglyceride acyltransferase 1 (DGAT1) inhibitors, such as GSK-3008356;

Diacylglycerol O acyltransferase 1 (DGAT1)/Cytochrome P450 2E1 inhibitors (CYP2E1), such as SNP-610;

Diglyceride acyltransferase 2 (DGAT2) inhibitors, such as IONIS-DGAT2Rx, or PF-06865571;

Dipeptidyl peptidase IV inhibitors, such as linagliptin or evogliptin;

Eotaxin ligand inhibitors, such as bertilimumab or CM-101;

Extracellular matrix protein modulators, such as CNX-024;

Farnesoid X receptor (FXR) agonists, such as AGN-242266, AGN-242256, EP-024297, RDX-023, BWL-200, AKN-083, EDP-305, GNF-5120, GS-9674, LMB-763, obeticholic acid, Px-102, Px-103, M790, M780, M450, M-480, MET-409, PX20606, EYP-001, TERN-101, TC-100, INT-2228;

Farnesoid X receptor (FXR)/G-protein coupled bile acid receptor 1(TGR5) agonists, such as INT-767;

Fatty acid synthase inhibitors, such as TVB-2640;

FGF receptor agonists/Klotho beta stimulators, such as BFKB-8488A (RG-7992);

Fibroblast growth factor 19 (rhFGF19)/cytochrome P450 (CYP)7A1 inhibitors, such as NGM-282;

Fibroblast growth factor 21(FGF-21) ligand, such as BMS-986171, BIO89-100, B-1344, or BMS-986036;

Fibroblast growth factor 21(FGF-21)/glucagon like peptide 1 (GLP-1) agonists, such as YH-25723 (YH-25724; YH-22241) or AKR-001;

Fish oil compositions, such as icosapent ethyl (Vascepa®);

Galectin-3 inhibitors, such as GR-MD-02, GB-1107 (Gal-300), or GB1211 (Gal-400);

Glucagon-like peptide 1 receptor (GLP1R) agonists, such as AC-3174, liraglutide, cotadutide (MEDI-0382), exenatide, SAR-425899, LY-3305677, HM-15211, YH-25723, YH-GLP1, RPC-8844, PB-718, or semaglutide;

Glucocorticoid receptor antagonists, such as CORT-118335 (miricorilant);

Glucose 6-phosphate 1-dehydrogenase inhibitors, such as ST001;

G-protein coupled bile acid receptor 1(TGR5) agonists, such as RDX-009 or INT-777;

Heat shock protein 47 (HSP47) inhibitors, such as ND-L02-s0201;

HMG CoA reductase inhibitors, such as atorvastatin, fluvastatin, pitavastatin, pravastatin, rosuvastatin, or simvastatin;

Hypoxia inducible factor-2 alpha inhibitors, such as PT-2567;

IL-10 agonists, such as peg-ilodecakin;

Ileal sodium bile acid cotransporter inhibitors, such as odevixibat (A-4250), volixibat potassium ethanolate hydrate (SHP-262), GSK2330672, CJ-14199, or elobixibat (A-3309);

Insulin sensitizers, such as, KBP-042, MSDC-0602K, MSDC-5514, Px-102, RG-125 (AZD4076), VVP-100X, CB-4211, or ETI-101;

Insulin ligand/dsInsulin receptor agonists, such as ORMD-0801;

Integrin antagonists, such as IDL-2965;

IL-6 receptor agonists, such as KM-2702;

Ketohexokinase (KHK) inhibitors, such as PF-06835919;

beta Klotho (KLB)-FGF1c agonist, such as MK-3655 (NGM-313);

5-Lipoxygenase inhibitors, such as tipelukast (MN-001), DS-102 (AF-102);

Lipoprotein lipase inhibitors, such as CAT-2003;

LPL gene stimulators, such as alipogene tiparvovec;

Liver X receptor (LXR) modulators, such as PX-L603, PX-L493, BMS-852927, T-0901317, GW-3965, or SR-9238;

Lysophosphatidate-1 receptor antagonists, such as BMT-053011, UD-009 (CP-2090), AR-479, ITMN-10534, BMS-986020, or KI-16198;

Lysyl oxidase homolog 2 inhibitors, such as simtuzumab or PXS-5382A (PXS-5338);

Macrophage mannose receptor 1 modulators, such as tilmanocept-Cy3 (technetium Tc 99m tilmanocept);

Membrane copper amine oxidase (VAP-1) inhibitors, such as TERN-201;

MEKK-5 protein kinase (ASK-1) inhibitors, such as GS-4997, SRT-015, or GS-444217, GST-HG-151;

MCH receptor-1 antagonists, such as CSTI-100 (ALB-127158);

Methionine aminopeptidase-2 inhibitors, such as ZGN-839, ZGN-839, or ZN-1345;

Methyl CpG binding protein 2 modulators, such as mercaptamine;

Mitochondrial uncouplers, such as 2,4-dinitrophenol or HU6;

Mixed lineage kinase-3 inhibitors, such as URMC-099-C;

Myelin basic protein stimulators, such as olesoxime;

NADPH oxidase 1/4 inhibitors, such as GKT-831 or APX-311;

Nicotinic acid receptor 1 agonists, such as ARI-3037MO;

Nitazoxinide;

NACHT LRR PYD domain protein 3 (NLRP3) inhibitors, such as KDDF-201406-03, NBC-6, IFM-514, or JT-194 (JT-349);

Nuclear receptor modulators, such as DUR-928 (DV-928);

P2X7 purinoceptor modulators, such as SGM-1019;

P2Y13 purinoceptor stimulators, such as CER-209;

PDE 3/4 inhibitors, such as tipelukast (MN-001);

PDE 5 inhibitors, such as sildenafil or MSTM-102;

PDGF receptor beta modulators, such as BOT-191 or BOT-509;

Peptidyl-prolyl cis-trans isomerase inhibitors, such as CRV-431 (CPI-432-32), NVP-018, or NV-556 (NVP-025);

Phenylalanine hydroxylase stimulators, such as HepaStem;

PPAR agonists (including PPAR alpha agonists, PPAR alpha/delta agonists, PPAR alpha/delta/gamma agonists, PPAR delta agonists), such as elafibranor (GFT-505), MBX-8025, deuterated pioglitazone R-enantiomer, pioglitazone, DRX-065, saroglitazar, or IVA-337; PPAR alpha agonists, such as aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (fish oil, e.g., icosapent ethyl (Vascepa®), or docosahexaenoic acid), pirinixic acid, GW409544, AZ 242, LY518674, NS-220, AVE8134, BMS-711939, aleglitazar, muraglitzar, or saroglitazar;

PPAR alpha/delta agonists such as elafibranor;

PPAR alpha/delta/gamma agonists such as lanifibranor;

PPAR delta agonists such as seladelpar;

Protease-activated receptor-2 antagonists, such as PZ-235;

Protein kinase modulators, such as CNX-014;

Rho associated protein kinase (ROCK) inhibitors, such as REDX-10178 (REDX-10325) or KD-025;

Semicarbazide-Sensitive Amine Oxidase/Vascular Adhesion Protein-1 (SSAO/VAP-1) Inhibitors, such as PXS-4728A;

S-nitrosoglutathione reductase (GSNOR) enzyme inhibitors, such as SL-891;

Sodium glucose transporter-2(SGLT2) inhibitors, such as ipragliflozin, remogliflozin etabonate, ertugliflozin, dapagliflozin, tofogliflozin, or sotagliflozin;

SREBP transcription factor inhibitors, such as CAT-2003 or MDV-4463; Stearoyl CoA desaturase-1 inhibitors, such as aramchol;

Thyroid hormone receptor (THR) beta agonists, such as resmetriom (MGL-3196), MGL-3745, or VK-2809;

TLR-2/TLR-4 antagonists, such as VB-201 (CI-201);

TLR-4 antagonists, such as JKB-121;

Tyrosine kinase receptor modulators, such as CNX-025 or GFE-2137 (repurposed nitazoxanide);

GPCR modulators, such as CNX-023;

Nuclear hormone receptor modulators, such as Px-102;

Xanthine oxidase/Urate anion exchanger 1 (URAT1) inhibitors, such as RLBN-1001, RLBN-1127; and Zonulin Inhibitors, such as lorazotide acetate (INN-202).

Additional non-limiting examples of the one or more additional therapeutic agents include ACE inhibitors, such as, benazepril, imidapril;

Adenosine A3 receptor antagonists, such as FM-101;

Adropin stimulators, such as RBT-2;

Albumin modulators, such as SYNT-002;

Aldosterone/Mineralocorticoid receptor antagonists, such as MT-3995;

Allogeneic bone marrow-derived mesenchymal stromal cell therapy, such as ORBCEL-M Allogenic expanded adipose-derived stem cell therapy, such as Elixcyte™;

AMP activated protein kinase stimulator/Proprotein convertase PC9 inhibitors, such as O-304;

AMP activated protein kinase stimulators, such as DZCY-01, MK-8722, PXL-770;

Angiotensin II AT-1 receptor/CCR2 chemokine antagonists, such as DMX-200;

Angiotensin II AT-2 receptor agonists, such as MOR-107, irbesartan;

Angiotensin II receptor antagonists, such as losartan;

Angiotensinogen ligand inhibitors, such as ALN-AGT;

anti-C1 antibodies, such as BIVV-009 (sutimlimab);

anti-CB1 antibodies, such as GFB-024;

anti-CX3CR1 nanobodies, such as BI-655088;

anti-IL-6 antibodies, such as COR-001;

anti-VEGF-B antibodies, such as CSL-346;

APOA1 gene stimulators/Bromodomain containing protein 2/Bromodomain containing protein 4 inhibitors, such as apabetalone;

Bone morphogenetic protein-7 ligand modulators, such as BMP-7;

Calcium channel inhibitors, such as TBN (xiaotongqin);

Cannabinoid CB1 receptor antagonists, such as JNJ-2463;

CB1 inverse agonists, such as CRB-4001;

Chymase inhibitors, such as fulacimstat (BAY-1142524);
Cyclooxygenase 1 inhibitors, such as GLY-230;
Cyclooxygenase 2/Epoxide hydrolase inhibitors, such as COX-2/soluble epoxide hydrolase;
Cytochrome P450 11B2 inhibitors, such as aldosterone synthase inhibitors;
Ectonucleotide pyrophosphatase-PDE-2 inhibitors, such as BLD-0409;
Endothelin ET-A/Endothelin ET-B receptor antagonists, such as aprocitentan;
Enteropeptidase inhibitors, such as SCO-792;
Erythropoietin receptor antagonists, such as EPO-018B;
Farnesoid X receptor agonists, such as LMB-763;
FGF/PDGF/beta receptor antagonist/p38 MAP kinase inhibitors, such as pirfenidone;
GHR/IGF1 gene inhibitors, such as atesidorsen sodium;
GPR40 agonist/GPR84 antagonists, such as PBI-4050;
G-protein beta subunit inhibitors, such as galleon;
G-protein coupled receptor 84 modulators, such as PBI-4425;
Growth hormone ligand/Growth hormone receptor agonist, such as Jintropin AQ™;
Growth hormone receptor agonists, such as LAT-8881;
Guanylate cyclase receptor agonist/Guanylate cyclase stimulators, such as praliciguat;
Guanylate cyclase stimulators, such as MRL-001, runcaciguat;
Heme oxygenase 1 modulators, such as RBT-1;
HIF prolyl hydroxylase inhibitors, such as TRGX-154;
Insulin sensitizer/Kallikrein 1 modulators, such as DM-199;
Integrin alpha-V/beta-3 antagonists, such as VPI-2690B;
Interleukin 33 ligand inhibitors, such as MEDI-3506;
Kelch like ECH associated protein 1 modulator/Nuclear erythroid 2-related factor 2 stimulators, such as SFX-01;
LDHA gene inhibitors, such as nedosiran;
5-Lipoxygenase activating protein inhibitors, such as AZD-5718;
Lysophosphatidate-1 receptor antagonists, such as BMS-002, EPGN-696;
Matrix extracell phosphoglycoprotein modulator/Phosphatonin receptor agonist, such as TPX-200;
MEKK-5 protein kinase inhibitors, such as selonsertib;
Membrane copper amine oxidase inhibitors, such as UD-014;
Midkine ligand inhibitors, such as CAB-101;
Mineralocorticoid receptor antagonists, such as AZD-9977, esaxerenone, finerenone, KBP-5074;
Myosin 2 inhibitor, such as DeciMab™;
NADPH oxidase 1 inhibitors/NADPH oxidase 4 inhibitors, such as setanaxib;
NADPH oxidase inhibitors, such as APX-115;
NK1 receptor antagonist/Opioid receptor kappa agonist/Opioid receptor mu antagonist, such as AV-104;
Nuclear erythroid 2-related factor 2 stimulator/TGF beta ligand inhibitors, such as CU01-1001;
Nuclear factor kappa B inhibitors, such as mefunidone, bardoxolone methyl (NSC-713200);
PDE 4 inhibitors, such as ART-648, PCS-499;
PDGF receptor beta modulators, such as BOT-191;
PDGF/VEGF receptor antagonists, such as ANG-3070;
PR84 antagonist/GPR40 (FFAR1)/GPR120 (FFAR4) agonist/and a partial activator of peroxisome proliferator-activated receptors (PPAR), such as PBI-4547;
PRKAA2 gene stimulators/AMPK activators, such as PF-06679142, PF-06685249;
Prostacyclin (PGI2) agonists, such as YS-1402;
Protein C activator/Glycoprotein Ib (GPIb) antagonist, such as AB-002;
Protein NOV homolog modulators, such as BLR-200;
Protein tyrosine phosphatase-1B inhibitors, such as MSI-1436;
Reactive oxygen species modulator inhibitors, such as SUL-121;
Renin inhibitors, such as imarikiren hydrochloride;
Rho associated protein kinase 2 inhibitors, such as ANG-4201, RXC-007;
Sodium glucose transporter-2 inhibitors, such as canagliflozin, dapagliflozin propanediol, empagliflozin;
Thromboxane A2 receptor antagonist/Thromboxane synthesis inhibitors, such as SER-150;
Tissue transglutaminase inhibitors, such as ZED-1227;
TRP cation channel C5 inhibitors, such as GFB-887;
TRP cation channel C6 inhibitors, such as ALGX-2224;
Cell adhesion molecule inhibitors, such as glycoside bacterial adhesin antagonists;
Urate anion exchanger 1 (URAT1)/SLC22A12 inhibitors, such as verinurad (RDEA3170);
VIP 1/VIP 2 receptor agonists, such as LBT-3627; and
Xanthine oxidase inhibitors, such as TMX-049, TMX-049DN.

In some embodiments, the one or more additional therapeutic agents are selected from A-4250, AC-3174, acetylsalicylic acid, AK-20, alipogene tiparvovec, AMX-342, AN-3015, aramchol, ARI-3037MO, ASP-8232, AZD-2693, bertilimumab, Betaine anhydrous, BI-1467335, BMS-986036, BMS-986171, BMT-053011, BOT-191, BTT-1023, CAT-2003, cenicriviroc, CBW-511, CER-209, CF-102, CGS21680, CNX-014, CNX-023, CNX-024, CNX-025, cobiprostone, colesevelam, dapagliflozin, DCR-LIV1, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, fluasterone (ST-002), FT-4101, GKT-831, GNF-5120, GRI-0621, GR-MD-02, GS-300, GS-4997, GS-9674, HTD-1801, HST-202, HST-201, hydrochlorothiazide, icosabutate (PRC-4016), icosapent ethyl ester, IMM-124-E, INT-767, INV-240, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452 (tropifexor), LM-011, LM-002 (CVI-LM-002), LMB-763, LYN-100, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-160, norursodeoxycholic acid, NVP-022, 0-304, obeticholic acid (OCA), 25HC3S, olesoxime, PAT-505, PAT-048, PBI-4547, pegilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), RPI-500, saroglitazar, semaglutide, simtuzumab, solithromycin, sotagliflozin, statins (atorvastatin, fluvastatin, pitavastatin, pravastatin, rosuvastatin, simvastatin), symbiotic, TCM-606F, TEV-45478, TQA-3526, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, XRx-117, ZGN-839, ZG-5216, ZSYM-008, and ZYSM-007.

In some embodiments, the methods and pharmaceutical compositions provided herein include a therapeutically effective amount of an Apoptosis Signal-Regulating Kinase 1 (ASK1) inhibitor and a therapeutically effective amount of an LPAR1 antagonist, wherein the LPAR1 antagonist is a compound of Formula (I) (Ia), (II), or (IIa) provided herein or a pharmaceutically acceptable salt thereof.

In some embodiments of the methods and pharmaceutical compositions disclosed herein, the ASK1 inhibitor is GS-4997 (selonsertib, SEL).

ASK1 inhibitors can be synthesized and characterized using methods known to those of skill in the art, such as those described in U.S. 2007/0276050, U.S. 2011/0009410, and U.S. 2013/0197037.

In some embodiments, the methods and pharmaceutical compositions provided herein include a therapeutically effective amount of an Acetyl-CoA Carboxylase (ACC) inhibitor and a therapeutically effective amount of an LPAR1 antagonist, wherein the LPAR1 antagonist is a compound of Formula (I) (Ia), (II), or (IIa) provided herein or a pharmaceutically acceptable salt thereof.

In some embodiments of the methods and pharmaceutical compositions disclosed herein, the ACC inhibitor is GS-0976 (firsocostat, FIR).

ACC inhibitors can be synthesized and characterized using methods known to those of skill in the art, such as those described in U.S. Pat. Nos. 9,453,026 and 10,183,951.

In some embodiments, the methods and compositions provided herein include a therapeutically effective amount of a PPAR agonist (e.g., PPAR alpha agonist, PPAR alpha/delta agonist, PPARalpha/delta/gamma agonist, PPAR delta agonist) or fish oil, a therapeutically effective amount of an Acetyl CoA Carboxylase (ACC) inhibitor, such as GS-0976 (firsocostat, FIR), and a therapeutically effective amount of an LPAR1 antagonist, wherein the LPAR1 antagonist is a compound of Formula (I) (Ia), (II), or (IIa) provided herein or a pharmaceutically acceptable salt thereof. In some embodiments, the PPAR agonist is a PPAR alpha agonist. In some embodiments, the PPAR alpha agonist is selected from aluminum clofibrate, bezafibrate, ciprofibrate, choline fenofibrate, clinofibrate, clofibrate, clofibride, fenofibrate, gemfibrozil, pemafibrate, ronifibrate, simfibrate, pirinixic acid, GW409544, AZ 242, LY518674, NS-220, AVE8134, BMS-711939, aleglitazar, muraglitzar, and saroglitazar. In some embodiments, the PPAR agonist (e.g., PPAR alpha agonist) is a fibrate. In some embodiments, the PPAR agonist (e.g., PPAR alpha agonist) is fenofibrate. In some embodiments, the PPAR agonist is a PPAR alpha/delta agonist (e.g., elafibranor). In some embodiments, the PPAR agonist is a PPAR alpha/delta/gamma agonist (e.g., lanifibranor). In some embodiments, the PPAR agonist is a PPAR delta agonist (e.g., seladelpar). In some embodiments the fish oil is an omega-3 fatty acid or docosahexaenoic acid. In some embodiments, the fish oil is icosapent ethyl (e.g., Vascepa©).

In some embodiments, the methods and compositions provided herein include a therapeutically effective amount of a Farnesoid X Receptor (FXR) agonist and a therapeutically effective amount of an LPAR1 antagonist, wherein the LPAR1 antagonist is a compound of Formula (I), (Ia), (II), or (IIa) provided herein or a pharmaceutically acceptable salt thereof.

In some embodiments of the methods and pharmaceutical compositions disclosed herein, the FXR agonist is GS-9674 (cilofexor, CILO).

In some embodiments of the methods and pharmaceutical compositions disclosed herein, the FXR agonist is a compound having the structure:

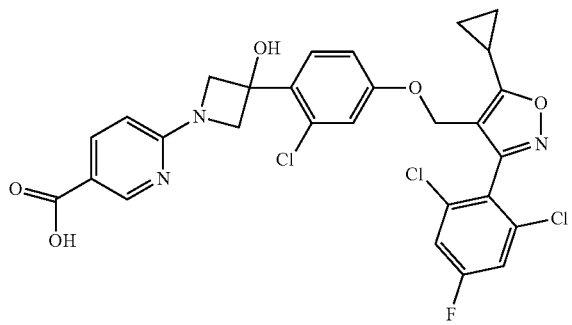 [SMILES: O=C(O)c1ccc(N2CC(O)(c3ccc(OCc4c(-c5c(Cl)cc(F)cc5Cl)noc4C4CC4)cc3Cl)C2)nc1]

or a pharmaceutically acceptable salt thereof.

In some embodiments, the methods and compositions provided herein include a therapeutically effective amount of a GLP-1 receptor agonist and a therapeutically effective amount of an LPAR1 antagonist, wherein the LPAR1 antagonist is a compound of Formula (I), (Ia), (II), or (IIa) provided herein or a pharmaceutically acceptable salt thereof. In some embodiments, the GLP-1 receptor agonist is liraglutide or semaglutide. In some embodiments, the GLP-1 receptor agonist is semaglutide.

In some embodiments, the methods and compositions provided herein include a therapeutically effective amount of a TGFβ antagonist and a therapeutically effective amount of an LPAR1 antagonist, wherein the LPAR1 antagonist is a compound of Formula (I), (Ia), (II), or (IIa) provided herein or a pharmaceutically acceptable salt thereof. In some embodiments, the TGFβ antagonist is a TGFβ1-specific antibody. TGFβ1-specific antibodies can be prepared and characterized using methods known to those of skill in the art, such as those described in PCT International Application Publication No. WO 2018/129329 and in U.S. Pat. No. 9,518,112. In some embodiments, the TGFβ antagonist binds to a TGFβ latency-associated peptide (LAP), e.g., TGFβ1-LAP. TGFβ1-LAP-specific antibodies can be prepared and characterized using methods known to those of skill in the art, such as those described in U.S. Pat. No. 8,198,412 or U.S. Pat. No. 10,017,567. In some embodiments, the TGFβ antagonist binds to TGFβ (e.g., TGFβ 1) in a context independent manner (e.g., independent of the presentation of TGFβ in a specific tissue or organ). In some embodiments, the TGFβ antagonist binds to TGFβ (e.g., TGFβ1) in a context-dependent manner. In some embodiments, the TGFβ antagonist blocks activation of latent TGFβ(e.g., latent TGFβ 1) that is localized in extracellular matrix, e.g., in connective tissue of the liver. In some embodiments, the TGFβ antagonist blocks activation of latent TGFβ (e.g., latent TGFβ1) that is localized in the thymus, a lymph node, or in a tumor microenvironment (e.g., in a patient having liver cancer). In some embodiments, the TGFβ antagonist blocks activation of latent TGFβ (e.g., latent TGFβ1) by Latent TGFβ Binding Protein (LTBP). In some embodiments, the TGFβ antagonist blocks activation of latent TGFβ (e.g., latent TGFβ1) by Glycoprotein-A Repetitions Predominant protein (GARP), as described, e.g., in U.S. Pat. No. 10,000,572. In some embodiments, the TGFβ antagonist is ARGX-115. In some embodiments, the TGFβ antagonist is an anti-latency-associated peptide (LAP) antibody that specifically binds to a LAP-TGFβ1 complex. In some embodiments, the anti-LAP antibody specifically binds to LAP-TGFβ 1 complexes in extracellular matrix (ECM), e.g., of connective tissue in the liver. In some embodiments, the anti-LAP antibody specifically binds to LAP-TGFβ1 complexes on the surfaces of certain immunosuppressive cell types, such as regulatory T cells (Tregs), tumor-associated macrophages, or myeloid-derived suppressor cells, e.g., in a tumor microenvironment. In some embodiments, the anti-LAP antibody is a TLS-β1 antibody. In some embodiments, the anti-LAP antibody specifically binds to LAP-TGFβ1 complexes in any context. In some embodiments, the anti-LAP antibody is a TLS-02 antibody. In some embodiments, the TGFβ antagonist comprises a TGFβ receptor. In some embodiments, the TGFβ antagonist is a TGFβ receptor-Fc fusion protein. In some embodiments, the TGFβ antagonist is an antibody comprising a TGFβ receptor. TGFβ antagonists comprising a TGFβ receptor that can be useful in connection with the compositions and methods provided herein have been described, e.g., in PCT International Publication Nos. WO 2019/113123 A1 and WO 2019/113464 A1. In some embodiments the methods and compositions provided herein include a therapeutically effective amount of an LPAR1 antagonist and of an additional therapeutic agent selected from an ACE inhibitor, adenosine A3 receptor antagonist, adropin stimulator, albumin modulator, aldosterone antagonist, AMP activated protein kinase stimulator, angiotensin II AT-2 receptor agonist, angiotensin II receptor antagonist, angiotensinogen ligand inhibitor, APOA1 gene stimulator, apolipoprotein L1 modulator, bone morphogenetic protein-7 ligand modulator, bromodomain containing protein 2 inhibitor, bromodomain containing protein 4 inhibitor, calcium channel inhibitors, cannabinoid CB1 receptor antagonists, CB1 inverse agonists, CCR2 chemokine antagonist, chymase inhibitor, complement C1s subcomponent inhibitor, CX3CR1 chemokine antagonist, cyclooxygenase 1 inhibitor, cyclooxygenase 2 inhibitor, cytochrome P450 11B2 inhibitor, ectonucleotide pyrophosphatase-PDE-2 inhibitor, endothelin ET-A receptor antagonist, endothelin ET-B receptor antagonist, enteropeptidase inhibitor, epoxide hydrolase inhibitor, erythropoietin receptor antagonist, farnesoid X receptor agonist, FGF receptor antagonists, free fatty acid receptor 1 agonist, GHR gene inhibitor, glycoprotein Ib (GPIb) antagonist, GPR40 agonist, GPR84 antagonist, G-protein beta subunit inhibitor, G-protein coupled receptor 120 agonist, G-protein coupled receptor 84 modulator, growth hormone ligand, growth hormone receptor agonist, guanylate cyclase receptor agonists, guanylate cyclase stimulator, heme oxygenase 1 modulator, HIF prolyl hydroxylase inhibitor, IGF1 gene inhibitors, IgG receptor FcRn large subunit p51 modulator, IL-6 receptor antagonist, integrin alpha-V/beta-3 antagonist, interleukin 33 ligand inhibitor, Kelch-like ECH associated protein 1 modulator, LDHA gene inhibitor, 5-lipoxygenase activating protein inhibitor, lysophosphatidate-1 receptor antagonist, matrix extracellular phosphoglycoprotein modulator, membrane copper amine oxidase inhibitor, midkine ligand inhibitor, mineralocorticoid receptor antagonist, myosin 2 inhibitors, NADPH oxidase 1 inhibitor, NADPH oxidase 4 inhibitor, NADPH oxidase inhibitor, NK1 receptor antagonist, nuclear erythroid 2-related factor 2 stimulator, nuclear factor kappa B inhibitor, opioid receptor kappa agonist, opioid receptor mu antagonists p38 MAP kinase inhibitor, PDE4 inhibitor, PDGF receptor antagonist, PDGF receptor beta modulator, phosphatonin receptor agonist, PRKAA2 gene stimulator, proprotein convertase PC9 inhibitor, prostacyclin (PGI2) agonist, protein C activator, protein NOV homolog modulator, protein tyrosine phosphatase-1B inhibitor, reactive oxygen species modulator inhibitor, renin inhibitor, Rho associated protein kinase 2 inhibitor, SLC22A12 inhibitor, sodium glucose transporter-2 inhibitor, solute carrier family inhibitor, TGF beta ligand inhibitor, TGF beta receptor antagonist, thromboxane A2 receptor antagonist, thromboxane synthesis inhibitor, tissue transglutaminase inhibitor, TRP cation channel C5 inhibitor, TRP cation channel C6 inhibitor, tryptophanase inhibitor, unspecified cell adhesion molecule inhibitor, urate anion exchanger 1 inhibitor, vasopressin V1a receptor antagonist, VEGF receptor antagonist, VIP 1 receptor agonist, VIP 2 receptor agonist, and Xanthine oxidase inhibitor.

In some embodiments the methods and compositions provided herein include a therapeutically effective amount of an LPAR1 antagonist and of an additional therapeutic agent selected from a VEGFR inhibitor, a FGFR inhibitor, a PDGFR inhibitor, an autaxin inhibitor, a GPR84 agonist, a PASK inhibitor, a CFTR agonist, a JAK1 inhibitor, an ADAMTS5 inhibitor, a TOL2/3 inhibitor, a CTGF inhibitor, a soluble PTX2, an anti-galectin-3 antibody, an integrin-$\alpha_V$-$\beta_6$/$\alpha_V$-$\beta_1$ antagonist, a JNK1 inhibitor, a mineralocorticoid receptor antagonist, a Nrf2 activator, a chymase inhibitor, a PDE inhibitor, a NOX1/4 inhibitor, a leukotriene/thromboxane receptor antagonist, SLC22A12 inhibitor, an sGC inhibitor, and a xanthine oxidase inhibitor.

In some embodiments the methods and compositions provided herein include a therapeutically effective amount of an LPAR1 antagonist and of an additional therapeutic agent selected from nintedanib, pirfenidone, pamrevlumab, PRM-151, GB-0139, PLN-74809, CC-90001, finerenone, BAY1142524, PCS-499, setanaxib, SER150, RDEA3170, praliciguat, TMX-049, GLPG1690, GLPG1205, GLPG1972, GLPG4059, GLPG2737, GLPG3970, and filgotinib.

In some embodiments the methods and compositions provided herein include a therapeutically effective amount of an LPAR1 antagonist and of an additional therapeutic agent selected from A-717, ACF-TEI, alanyl-glutamine, ALLN-346, anti-SCF248 antibody, anti-TAGE monoclonal antibodies, anti-TGF beta antibodies, AST-120, BAY-2327949, BI-685509, DP-001, DZ-4001, GDT-01, LNP-1892, MEDI-8367, microRNA-targeting antisense oligonucleotide therapy, MK-2060, MPC-300-IV, NAV-003, Neo-Kidney Augment™ (NKA), NP-135, NP-160, NP-251, NRF-803, PBI-4610, PHN-033, R-HSC-010, salvianolic acid, SGF-3, SPD-01, Sugaheal variant, SZ-005, TCF-12, UMC119-06, VAR-400, veverimer, VS-105, and XRx-221.

ADDITIONAL EXEMPLARY EMBODIMENTS

Embodiment 1: A compound of Formula (I),

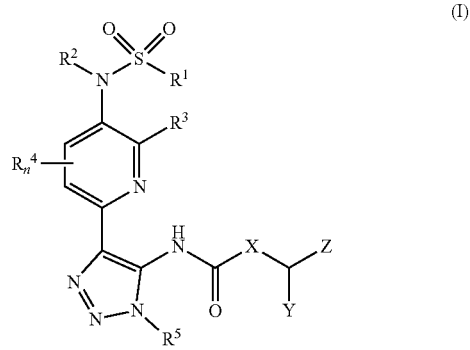

or a pharmaceutically acceptable salt thereof,
wherein:
$R^1$ is $C_{1-6}$ alkyl optionally substituted with 1 to 3 substituents independently selected from halogen, cyano, $C_{1-3}$ alkoxy, $-N(R^{1A})_2$, $-C(O)OR^{1A}$, $-C(O)N(R^{1A})_2$, $-NR^{1A}C(O)R^{1A}$, $-NR^{1A}C(O)OR^{1A}$, $-S(O)_{0-2}R^{1A}$, $-S(O)_2N(R^{1A})_2$ and $-NR^{1A}S(O)_2R^{1A}$, wherein each $R^{1A}$ is independently H or $C_{1-6}$ alkyl; or $R^1$ is $C_{3-6}$ cycloalkyl, 6 to 10 membered aryl, 3 to 10 membered heterocyclyl having 1 to 4 heteroatoms independently selected from nitrogen, oxygen, and sulfur, or 5 to 10 membered heteroaryl having 1 to 4 heteroatoms independently selected from nitrogen, oxygen, and sulfur, wherein each cycloalkyl, aryl, heterocyclyl, or heteroaryl is optionally substituted with 1 to 3 substituents independently selected from halogen, cyano, $C_{1-3}$ alkyl, $C_{1-3}$ alkoxy, $-N(R^{1A})_2$, $-C(O)N(R^{1A})_2$, $-NR^{1A}C(O)RA$, $-S(O)_{0-2}R^{1A}$, $-S(O)_2N(R^{1A})_2$ and $-NR^{1A}S(O)_2R^{1A}$ wherein each $R^{1A}$ is independently H or $C_{1-6}$ alkyl; or $R^1$ is $-O-R^{1B}$ or $-N(R^{1B})_2$, wherein each $R^{1B}$ is independently H, $C_{1-6}$ alkyl, or $C_{3-6}$ cycloalkyl, wherein each $C_{1-6}$ alkyl, or $C_{3-6}$ cycloalkyl is optionally substituted with 1 to 3 substituents independently selected from halogen and $-C(O)N(R^{1C})_2$, wherein each $-R^{1C}$ is independently H or $C_{1-3}$ alkyl;

$R^2$ is hydrogen or $C_{1-6}$ alkyl optionally substituted with 1 to 3 substituents independently selected from halogen, cyano, $C_{1-3}$ alkoxy, and $C_{3-10}$ cycloalkyl; or $R^2$ is $C_{3-6}$ cycloalkyl optionally substituted with 1 to 3 substituents independently selected from halogen, cyano, $C_{1-3}$ alkoxy, and $C_{1-6}$ alkyl;

$R^3$ is hydrogen, halogen, $C_{1-6}$ alkyl, $C_{3-6}$ cycloalkyl, $-O-R^{3A}$, or $-N(R^{3A})_2$, wherein the $C_{1-6}$ alkyl is optionally substituted with 1 to 3 substituents independently selected from $C_{1-3}$ alkoxy and halogen, and wherein each $R^{3A}$ is independently $C_{1-3}$ alkyl optionally substituted with 1 to 3 halogens; or each $R^4$ is independently deuterium, halogen, $C_{1-6}$ alkyl, $C_{3-10}$ cycloalkyl, or $C_{1-3}$ alkoxy, wherein the $C_{1-6}$ alkyl or $C_{3-10}$ cycloalkyl, is optionally substituted with 1 to 3 halogens:

n is 0, 1 or 2;

$R^5$ is $C_{1-6}$ alkyl optionally substituted with 1 to 3 substituents independently selected from halogen, cyano, $C_{1-3}$ alkoxy, $-C(O)N(R^{1A})$, and $-N(R^{1A})_2$, wherein each $R^{1A}$ is independently H, $C_{1-6}$ alkyl, or $C_{3-10}$ cycloalkyl; or $R^5$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents independently selected from halogen, cyano, $C_{1-3}$ alkyl and $C_{1-3}$ alkoxy;

X is NH or O;

Y is hydrogen or $C_{1-6}$ alkyl optionally substituted with 1 to 3 substituents independently selected from halogen, cyano, $C_{1-3}$ alkynyl, $C_{1-3}$ alkoxy, and $-C(O)NH-R^y$, wherein $R^y$ is $C_{1-3}$ alkyl; and Z is $C_{1-8}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents independently selected from halogen, cyano, $C_{1-3}$ alkyl, $C_{1-3}$ alkoxy, and $C_{3-6}$ cycloalkyl, wherein the $C_{1-3}$ alkyl is optionally substituted with 1 to 3 substituents selected from $C_{1-3}$ alkoxy and halogen; or Y and Z together with the carbon to which they are attached form $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents independently selected from cyano, $C_{1-3}$ alkyl, $C_{1-3}$ alkoxy, $C_{6-10}$ aryl and halogen, wherein the $C_{1-3}$ alkyl is optionally substituted with 1 to 3 substituents independently selected from $C_{1-3}$ alkoxy and halogen, and wherein the $C_{6-10}$ aryl is optionally substituted with 1 to 3 substituents independently selected from $C_{1-3}$ alkyl, $C_{1-3}$ alkoxy, and halogen.

Embodiment 2: The compound or pharmaceutically acceptable salt thereof of Embodiment 1, wherein the compound is of Formula (Ia):

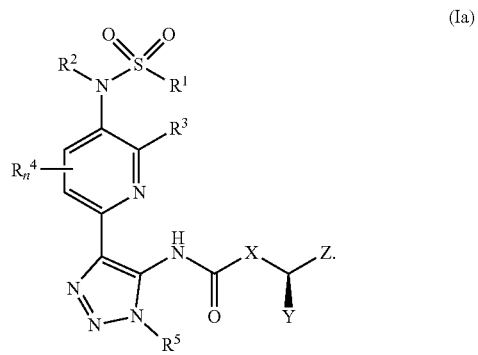

(Ia)

Embodiment 3: The compound or pharmaceutically acceptable salt thereof of Embodiment 1 or Embodiment 2, wherein:

$R^1$ is $C_{1-6}$ alkyl optionally substituted with 1 to 3 substituents independently selected from halogen, cyano, and $C_{1-3}$ alkoxy; or $R^1$ is $C_{3-6}$ cycloalkyl, 3 to 6 membered heterocyclyl having 1 or 2 heteroatoms independently selected from nitrogen, oxygen, and sulfur, or 5 to 6 membered heteroaryl having 1 or 2 heteroatoms independently selected from nitrogen, oxygen, and sulfur, wherein the cycloalkyl, heterocyclyl, or heteroaryl are each optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen or $C_{1-3}$ alkoxy;

$R^2$ is hydrogen or $C_{1-3}$ alkyl optionally substituted with 1 to 3 halogens;

$R^3$ is hydrogen, halogen, $C_{1-6}$ alkyl, $C_{1-3}$ alkoxy, wherein the $C_{1-6}$ alkyl is optionally substituted with 1 to 3 substituents independently selected from halogen and $C_{1-3}$ alkoxy;

$R^4$ is halogen;

n is 0 or 1;

$R^5$ is $C_{1-3}$ alkyl optionally substituted with 1 to 3 substituents independently selected from halogen and cyano;

X is NH or O;

Y is hydrogen or $C_{1-3}$ alkyl optionally substituted with 1 to 3 substituents independently selected from halogen, cyano, and $C_{1-3}$ alkoxy; and Z is $C_{1-6}$ alkyl, $C_{3-6}$ cycloalkyl, $C_{6-10}$ aryl, or 5 or 6 membered heteroaryl having 1 to 3 heteroatoms independently selected from nitrogen, oxygen, and sulfur, wherein the $C_{1-8}$ alkyl, $C_{3-6}$ cycloalkyl, $C_{6-10}$ aryl, or 5 or 6 membered heteroaryl is optionally substituted with 1 to 3 substituents independently selected from halogen, $C_{1-3}$ alkyl, $C_{1-3}$ alkoxy, and $C_{3-6}$ cycloalkyl, wherein the $C_{1-3}$ alkyl is optionally substituted with 1 to 3 substituents independently selected from halogen and $C_{1-3}$ alkoxy; or Y and Z together with the carbon to which they are attached form a 6 to 10 membered aryl, optionally substituted with 1 to 3 halogens.

Embodiment 4: The compound or pharmaceutically acceptable salt thereof of Embodiment 1, wherein the compound is of Formula (II):

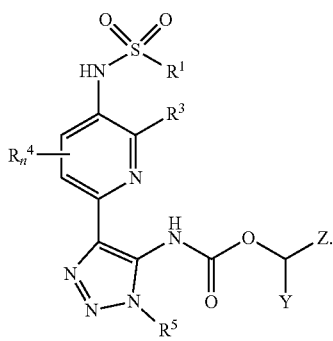

(II)

Embodiment 5: The compound or pharmaceutically acceptable salt thereof of anyone of Embodiments 1-3, wherein the compound is of Formula (IIa):

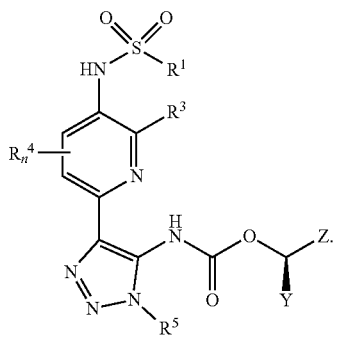

(IIa)

Embodiment 6: The compound or pharmaceutically acceptable salt thereof of any one of Embodiments 1-5, wherein $R^1$ is $C_{1-6}$ alkyl optionally substituted with 1 to 3 substituents independently selected from halogen, cyano, and $C_{1-3}$ alkoxy.

Embodiment 7: The compound or pharmaceutically acceptable salt thereof of anyone of Embodiments 1-6, wherein $R^1$ is $C_{1-3}$ alkyl optionally substituted with 1 to 3 substituents independently selected from F and cyano.

Embodiment 8: The compound or pharmaceutically acceptable salt thereof of anyone of Embodiments 1-7, wherein $R^1$ is $C_{1-3}$ alkyl optionally substituted with cyano.

Embodiment 9: The compound or pharmaceutically acceptable salt thereof of anyone of Embodiments 1-8, wherein $R^1$ is methyl, ethyl, isopropyl, or cyanomethyl.

Embodiment 10: The compound or pharmaceutically acceptable salt thereof of anyone of Embodiments 1-5, wherein $R^1$ is $C_{3-6}$ cycloalkyl optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy.

Embodiment 11: The compound or pharmaceutically acceptable salt thereof of anyone of Embodiments 1-5 and 10, wherein $R^1$ is $C_{3-6}$ cycloalkyl optionally substituted with 1 to 3 F.

Embodiment 12: The compound or pharmaceutically acceptable salt thereof of any one of Embodiments 1-5 and 10-11, wherein $R^1$ is cyclopropyl or cyclobutyl.

Embodiment 13: The compound or pharmaceutically acceptable salt thereof of anyone of Embodiments 1-5, wherein $R^1$ is 3 to 6 membered heterocyclyl having 1 or 2 heteroatoms independently selected from nitrogen, oxygen, and sulfur, wherein the heterocyclyl is optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy.

Embodiment 14: The compound or pharmaceutically acceptable salt thereof of any one of Embodiments 1-5 and 13, wherein $R^1$ is oxetanyl or azetidinyl, optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy.

Embodiment 15: The compound or pharmaceutically acceptable salt thereof of anyone of Embodiments 1-5 and 13-14, wherein $R^1$ is oxetanyl or azetidinyl optionally substituted with —O—$CH_3$.

Embodiment 16: The compound or pharmaceutically acceptable salt thereof of any one of Embodiments 1-5 and 13-15, wherein $R^1$ is

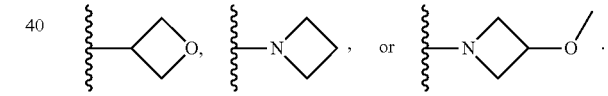

Embodiment 17: The compound or pharmaceutically acceptable salt thereof of anyone of Embodiments 1-5, wherein $R^1$ is 5 to 6 membered heteroaryl having 1 or 2 heteroatoms independently selected from nitrogen, oxygen, or sulfur, optionally substituted with 1 to 3 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy.

Embodiment 18: The compound or pharmaceutically acceptable salt thereof of anyone of Embodiments 1-5 and 17, wherein $R^1$ is thiazolyl optionally substituted with 1 or 2 substituents independently selected from halogen, cyano, $C_{1-3}$ alkyl, and $C_{1-3}$ alkoxy, wherein the $C_{1-3}$ alkyl is optionally substituted with 1 to 3 substituents independently selected from halogen and $C_{1-3}$ alkoxy.

Embodiment 19: The compound or pharmaceutically acceptable salt thereof of anyone of Embodiments 1-5 and 17-18, wherein $R^1$ is thiazolyl optionally substituted with —$CH_3$.

Embodiment 20: The compound or pharmaceutically acceptable salt thereof of any one of Embodiments 1-5 and 17-19, wherein $R^1$ is

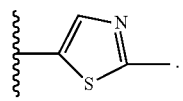

Embodiment 21: The compound or pharmaceutically acceptable salt thereof of anyone of embodiments 1-3 and 6-20, wherein $R^2$ is hydrogen.

Embodiment 22: The compound or pharmaceutically acceptable salt thereof of any one of Embodiments 1-3 and 6-20, wherein $R^2$ is $C_{1-3}$ alkyl optionally substituted with 1 to 3 halogens.

Embodiment 23: The compound or pharmaceutically acceptable salt thereof of anyone of Embodiments 1-3, 6-20 and 22, wherein $R^2$ is methyl optionally substituted with 1 to 3 F.

Embodiment 24: The compound or pharmaceutically acceptable salt thereof of anyone of Embodiments 1-3, 6-20 and 22-23, wherein $R^2$ is methyl.

Embodiment 25: The compound or pharmaceutically acceptable salt thereof of anyone of Embodiments 1-24, wherein $R^3$ is hydrogen.

Embodiment 26: The compound or pharmaceutically acceptable salt thereof of any one of Embodiments 1-24, wherein $R^3$ is halogen, $C_{1-6}$ alkyl, —O—$R^{3A}$, or —N($R^{3A}$)$_2$, wherein the $C_{1-6}$ alkyl is optionally substituted with 1 to 3 substituents independently selected from halogen and $C_{1-3}$ alkoxy, and wherein each $R^{3A}$ is independently H or $C_{1-3}$ alkyl optionally substituted with 1 to 3 halogens.

Embodiment 27: The compound or pharmaceutically acceptable salt thereof of anyone of Embodiments 1-24 and 26, wherein $R^3$ is halogen, $C_{1-6}$ alkyl, or —O—$R^{3A}$, wherein the $C_{1-6}$ alkyl is optionally substituted with 1 to 3 substituents independently selected from halogen and $C_{1-3}$ alkoxy, wherein $R^{3A}$ is $C_{1-3}$ alkyl optionally substituted with 1 to 3 halogens.

Embodiment 28: The compound or pharmaceutically acceptable salt thereof of anyone of Embodiments 1-24 and 26-27, wherein $R^3$ is —F, —Cl, —CH$_3$, or —O—CH$_3$.

Embodiment 29: The compound or pharmaceutically acceptable salt thereof of anyone of Embodiments 1-2 and 4-28, wherein n is 0 or 1.

Embodiment 30: The compound or pharmaceutically acceptable salt thereof of anyone of Embodiments 1-29, wherein n is 0.

Embodiment 31: The compound or pharmaceutically acceptable salt thereof of any one of Embodiments 1-30, wherein $R^4$ is halogen or $C_{1-3}$ alkyl optionally substituted with 1 to 3 halogens.

Embodiment 32: The compound or pharmaceutically acceptable salt thereof of any one of Embodiments 1-31, wherein $R^4$ is halogen.

Embodiment 33: The compound or pharmaceutically acceptable salt thereof of any one Embodiments 1-32, wherein $R^4$ is —F.

Embodiment 34: The compound or pharmaceutically acceptable salt thereof of any one of Embodiments 1-33, wherein $R^5$ is $C_{1-3}$ alkyl optionally substituted with 1 to 3 substituents independently selected from cyano and F.

Embodiment 35: The compound or pharmaceutically acceptable salt thereof of any one of Embodiments 1-34, wherein $R^5$ is methyl, ethyl or propyl, each optionally substituted with cyano.

Embodiment 36: The compound or pharmaceutically acceptable salt thereof of any one of Embodiments 1-35, wherein $R^5$ is —CH$_3$.

Embodiment 37: The compound or pharmaceutically acceptable salt thereof of anyone of Embodiments 1-3 and 6-36, wherein X is NH.

Embodiment 38: The compound or pharmaceutically acceptable salt thereof of any one of Embodiments 1-37, wherein Y is hydrogen.

Embodiment 39: The compound or pharmaceutically acceptable salt thereof of any one of Embodiments 1-37, wherein Y is $C_{1-3}$ alkyl optionally substituted with 1 to 3 substituents independently selected from halogen, cyano, and $C_{1-3}$ alkoxy.

Embodiment 40: The compound or pharmaceutically acceptable salt thereof of any one of Embodiments 1-37 and 39, wherein Y is methyl optionally substituted with 1 to 3 substituents independently selected from F, Cl, cyano, and methoxy.

Embodiment 41: The compound or pharmaceutically acceptable salt thereof of any one of Embodiments 1-37 and 39-40, wherein Y is —CH$_3$, —CH$_2$F, —CHF$_2$, —CF$_3$, —CH$_2$Cl, —CH$_2$—O—CH$_3$, or —CH$_2$—CN.

Embodiment 42: The compound or pharmaceutically acceptable salt thereof of any one of Embodiments 1-41, wherein Z is $C_{1-8}$ alkyl, $C_{3-6}$ cycloalkyl, $C_{6-12}$ aryl, or 5 or 6 membered heteroaryl having 1 to 3 heteroatoms independently selected from nitrogen, oxygen, and sulfur, wherein the $C_{1-8}$ alkyl, $C_{3-6}$ cycloalkyl, $C_{6-10}$ aryl, or 5 or 6 membered heteroaryl is optionally substituted with 1 to 3 substituents independently selected from halogen, $C_{1-3}$ alkyl, $C_{1-3}$ alkoxy, and $C_{3-6}$ cycloalkyl, wherein the $C_{1-3}$ alkyl is optionally substituted with 1 to 3 substituents independently selected from halogen and $C_{1-3}$ alkoxy.

Embodiment 43: The compound or pharmaceutically acceptable salt thereof of anyone of Embodiments 1-42, wherein Z is $C_{6-10}$ aryl optionally substituted with 1 to 3 substituents independently selected from halogen, $C_{1-3}$ alkyl, or $C_{1-3}$ alkoxy, wherein the $C_{1-3}$ alkyl is optionally substituted with 1 to 3 substituents independently selected from halogen and $C_{1-3}$ alkoxy.

Embodiment 44: The compound or pharmaceutically acceptable salt thereof of any one of Embodiments 1-43, wherein Z is phenyl optionally substituted with 1 to 3 substituents independently selected from halogen, $C_{1-3}$ alkyl, or $C_{1-3}$ alkoxy, wherein the $C_{1-3}$ alkyl is optionally substituted with 1 to 3 substituents independently selected from halogen and $C_{1-3}$ alkoxy Embodiment 45: The compound or pharmaceutically acceptable salt thereof of any one of Embodiments 1-44, wherein Z is phenyl optionally substituted with 1 to 3 substituents independently selected from —F, —Cl, —CH$_3$, —CF$_3$, —CH$_2$—O—CH$_3$, or —O—CH$_3$.

Embodiment 46: The compound or pharmaceutically acceptable salt thereof of any one of Embodiments 1-45, wherein Z is

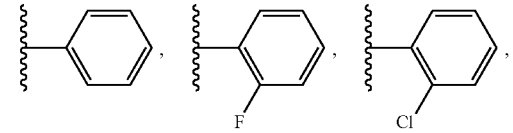

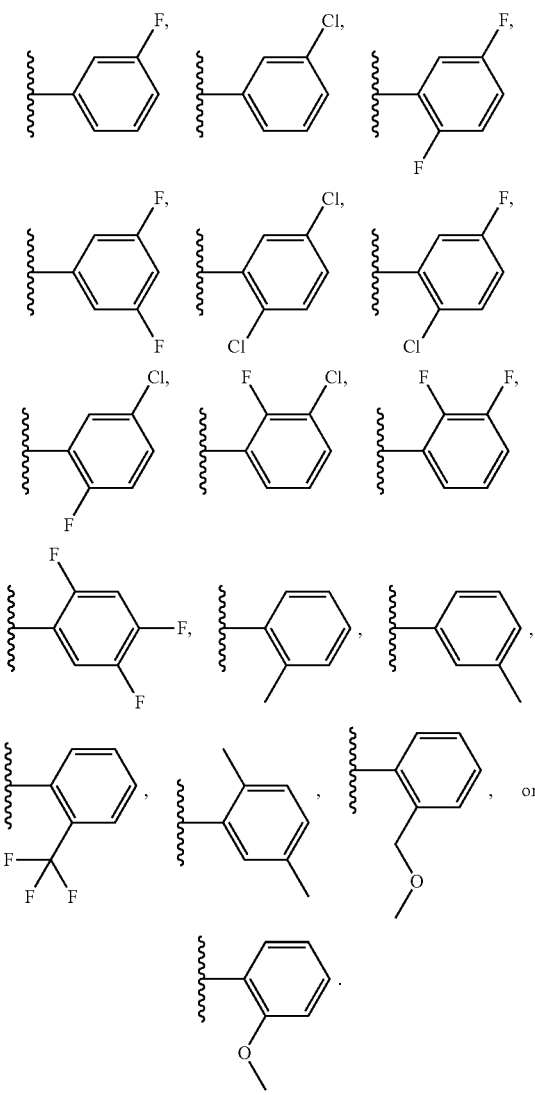

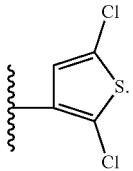 [SMILES: *c1cc(Cl)sc1Cl]

Embodiment 47: The compound or pharmaceutically acceptable salt thereof of any one of Embodiments 1-42, wherein Z is 5 or 6 membered heteroaryl having 1-3 heteroatoms independently selected from nitrogen, oxygen, and sulfur, wherein the heteroaryl is optionally substituted with 1 to 3 substituents independently selected from halogen and $C_{1-3}$ alkyl.

Embodiment 48: The compound or pharmaceutically acceptable salt thereof of any one of Embodiments 1-42 and 47, wherein Z is a 5 membered heteroaryl having 1 or 2 heteroatoms independently selected from nitrogen, oxygen, and sulfur, wherein the heteroaryl is optionally substituted with 1 to 3 substituents independently selected from halogen and $C_{1-3}$ alkyl.

Embodiment 49: The compound or pharmaceutically acceptable salt thereof of any one of Embodiments 1-42 and 47-48, wherein Z is thiophenyl, optionally substituted with 1 or 2 halogens independently selected from F and Cl.

Embodiment 50: The compound or pharmaceutically acceptable salt thereof of any one of Embodiments 1-42 and 47-49, wherein Z is Embodiment 51: The compound or pharmaceutically acceptable salt thereof of any one of Embodiments 1-42 and 47, wherein Z is pyridyl or pyrimidyl, optionally substituted with 1 to 3 substituents independently selected from halogen or $C_{1-3}$ alkyl, wherein the $C_{1-3}$ alkyl is optionally substituted with 1 to 3 halogens.

Embodiment 52: The compound or pharmaceutically acceptable salt thereof of any one of Embodiments 1-42, 47 and 51, wherein Z is pyridyl or pyrimidyl, optionally substituted with 1 to 3 substituents independently selected from F, —Cl, —$CH_3$, and —$CF_3$.

Embodiment 53: The compound or pharmaceutically acceptable salt thereof of any one of Embodiments 1-42, 47 and 51-52, wherein Z is Embodiment 54: The compound or pharmaceutically acceptable salt thereof of any one of Embodiments 1-42, wherein Z is a $C_{3-6}$ cycloalkyl optionally substituted with 1 to 3 substituents independently selected from halogen, $C_{1-3}$ alkyl, $C_{1-3}$ alkoxy, and $C_{3-6}$ cycloalkyl, wherein the $C_{1-3}$ alkyl is optionally substituted with 1 to 3 substituents independently selected from halogen and $C_{1-3}$ alkoxy.

Embodiment 55: The compound or pharmaceutically acceptable salt thereof of any one of Embodiments 1-42 and 54, wherein Z is cyclohexyl optionally substituted with 1 to 3 substituents independently selected from halogen, $C_{1-3}$ alkyl, and $C_{1-3}$ alkoxy.

Embodiment 56: The compound or pharmaceutically acceptable salt thereof of any one of Embodiments 1-42 and 54-55, wherein Z is cyclohexyl, optionally substituted with 1 to 3 F.

Embodiment 57: The compound or pharmaceutically acceptable salt thereof of anyone of Embodiments 1-42, wherein Z is $C_{1-3}$ alkyl optionally substituted with 1 to 3 substituents independently selected from halogen, $C_{1-3}$ alkoxy, and $C_{3-6}$ cycloalkyl.

Embodiment 58: The compound or pharmaceutically acceptable salt thereof of any one of Embodiments 1-42 and 57, wherein Z is $C_5$ alkyl optionally substituted with 1 to 3 substituents independently selected from halogen, $C_{1-3}$ alkoxy, and $C_{3-6}$ cycloalkyl.

Embodiment 59: The compound or pharmaceutically acceptable salt thereof of any one of Embodiments 1-42 and 57-58, wherein Z is $C_{1-3}$ alkyl optionally substituted with $C_{3-6}$ cycloalkyl.

Embodiment 60: The compound or pharmaceutically acceptable salt thereof of any one of Embodiments 1-42 and 57-59, wherein Z is $C_{1-3}$ alkyl optionally substituted with cyclopropyl.

Embodiment 61: The compound or pharmaceutically acceptable salt thereof of any one of Embodiments 1-42 and 57-60, wherein Z is

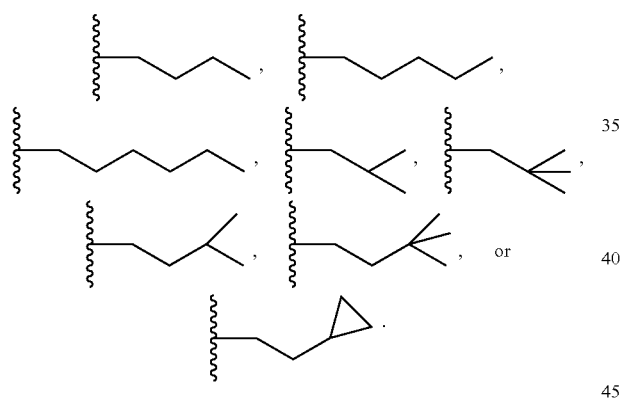

Embodiment 62: The compound or pharmaceutically acceptable salt thereof of any one of Embodiments 1-42, wherein Y and Z together with the carbon to which they are attached form a dihydroindenyl, optionally substituted with 1 to 3 halogens.

Embodiment 63: The compound or pharmaceutically acceptable salt thereof of any one of Embodiments 1-42 and 62, wherein the dihydroindenyl is optionally substituted with F.

Embodiment 64: The compound or pharmaceutically acceptable salt thereof of any one of Embodiments 1-42 and 62-63, wherein Y and Z together with the carbon to which they are attached form

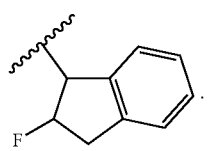 [SMILES: *C1c2ccccc2CC1F]

Embodiment 65: A compound selected from the group consisting of:

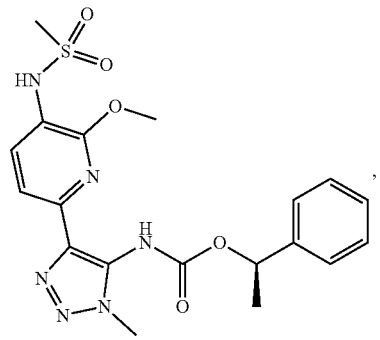

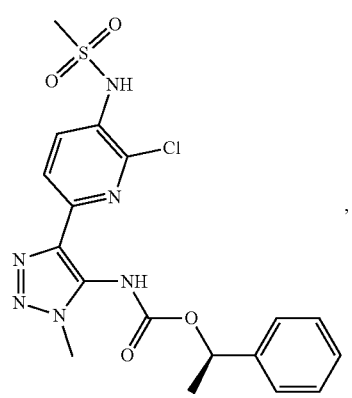

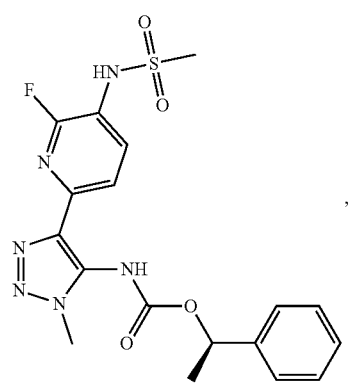

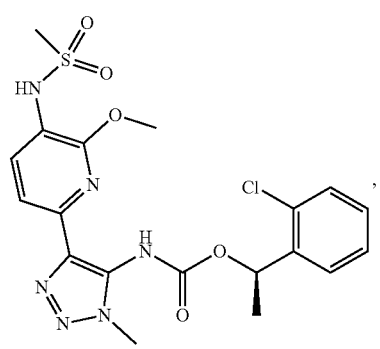

-continued
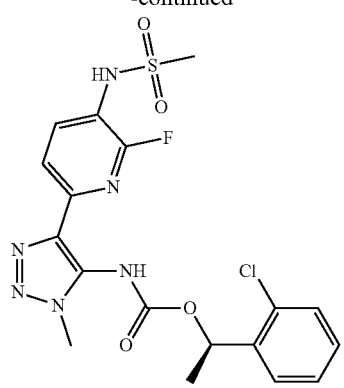
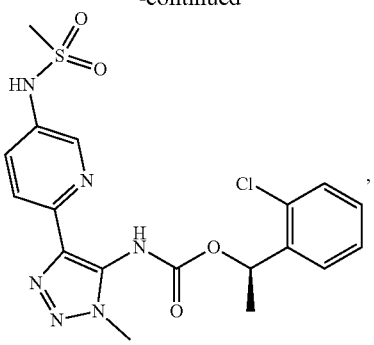
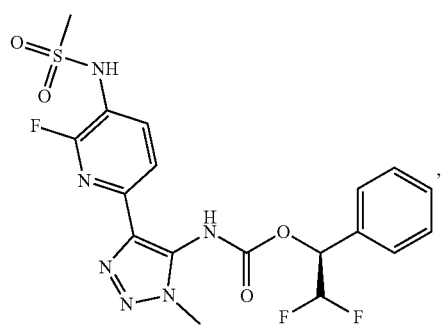
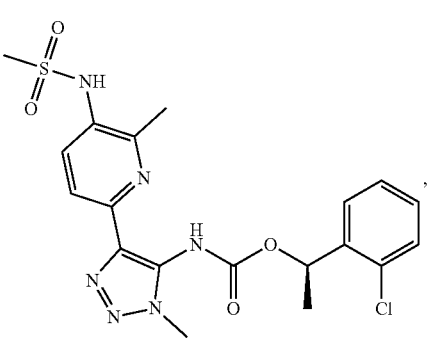
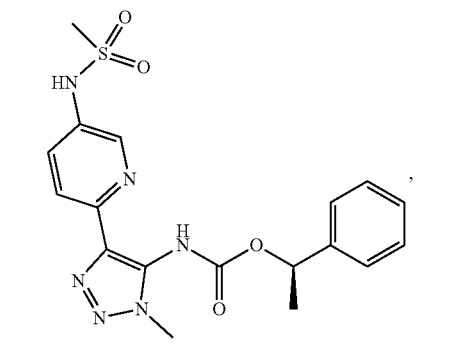
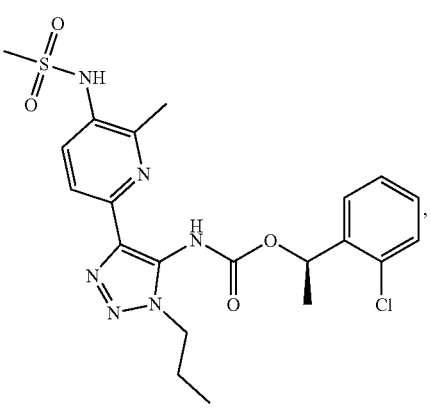
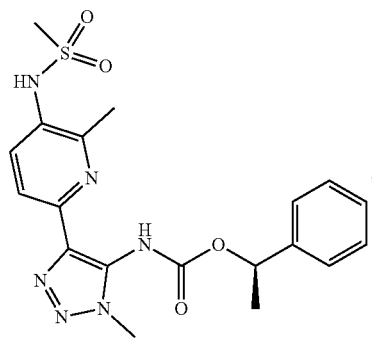

103
-continued
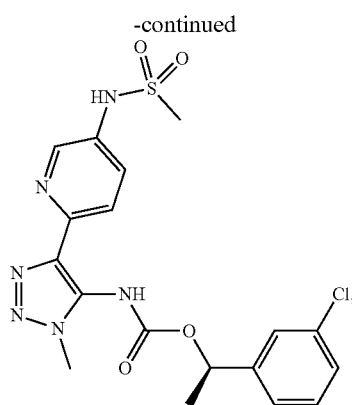
,
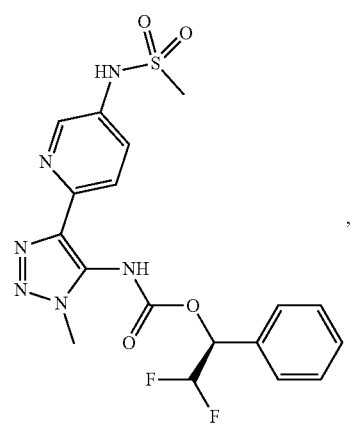 [SMILES: Cn1nnc(-c2ccc(NS(C)(=O)=O)cn2)c1NC(=O)O[C@@H](c1ccccc1)C(F)F]
,
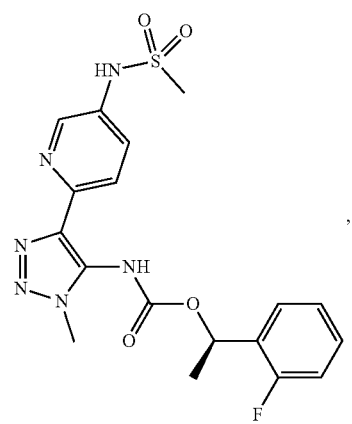
,
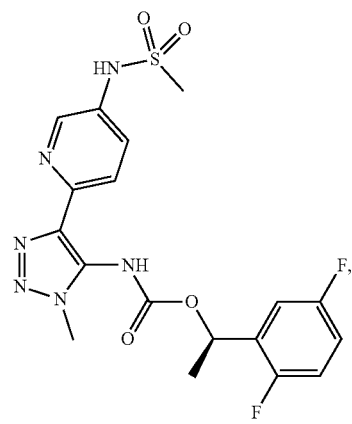
,
104
-continued
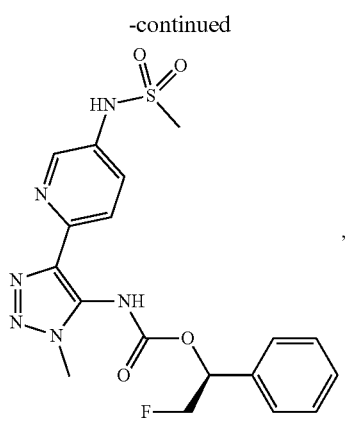
,
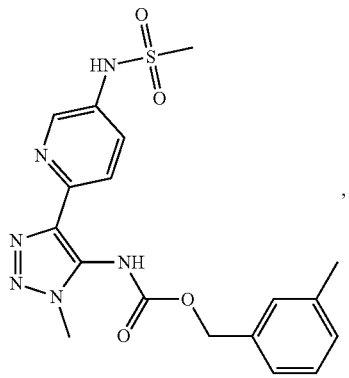
,
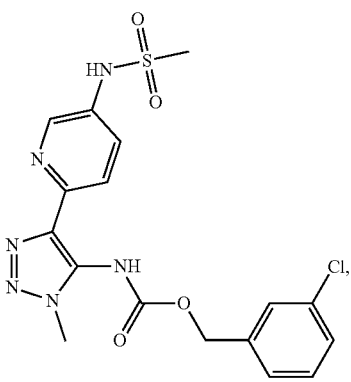
,
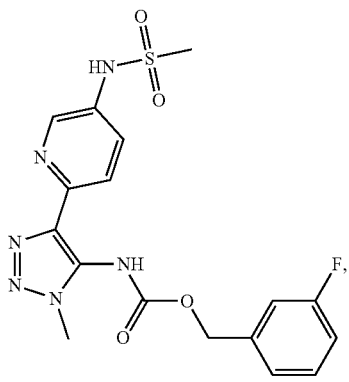
,

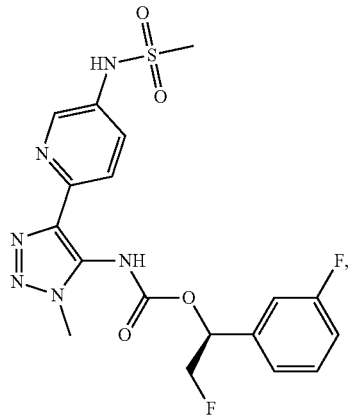
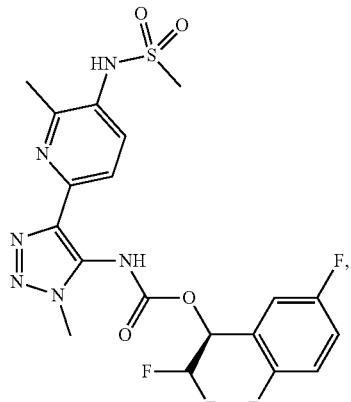
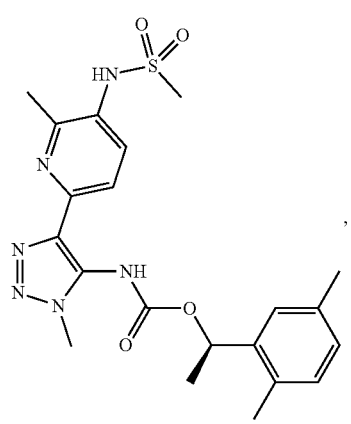
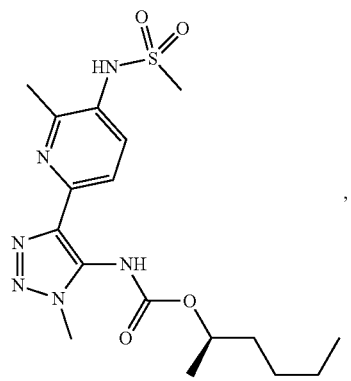
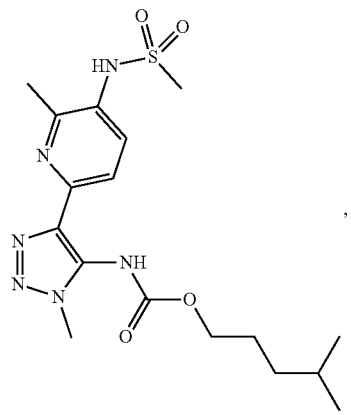

107
-continued
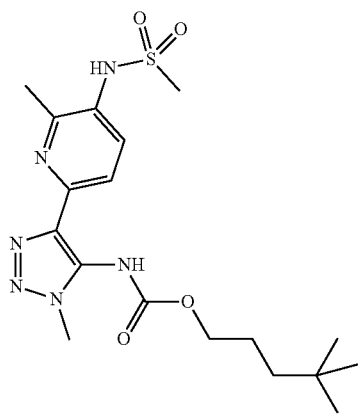
108
-continued
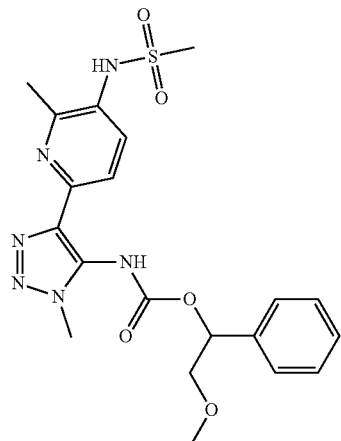
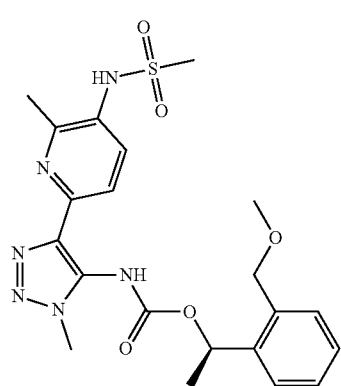
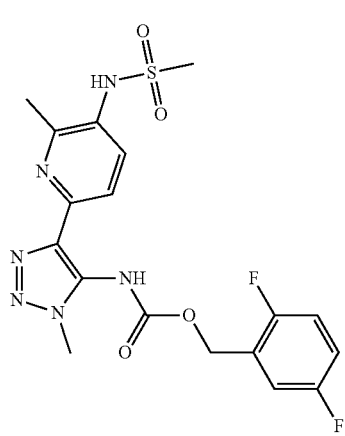
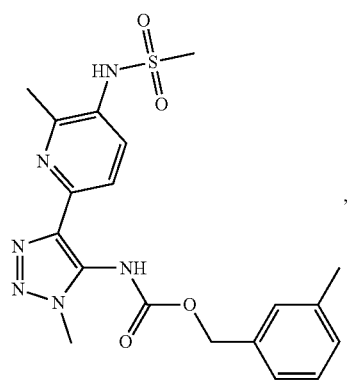

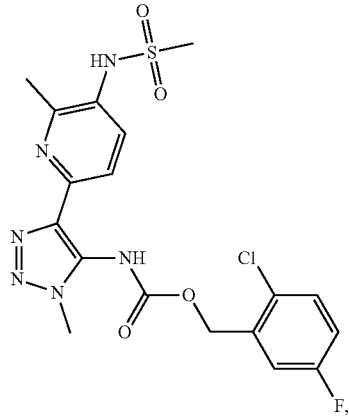
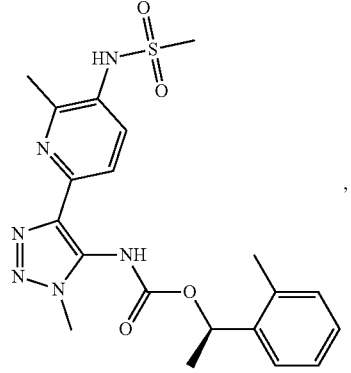
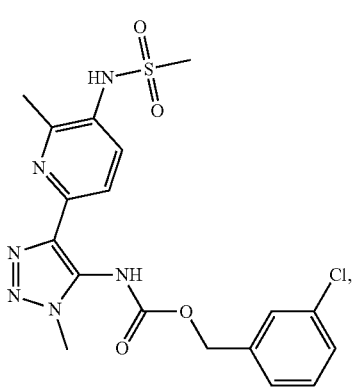
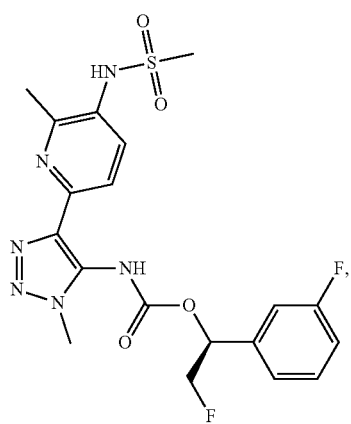
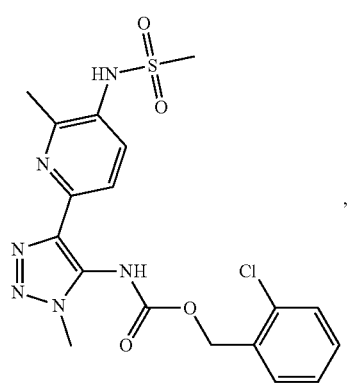
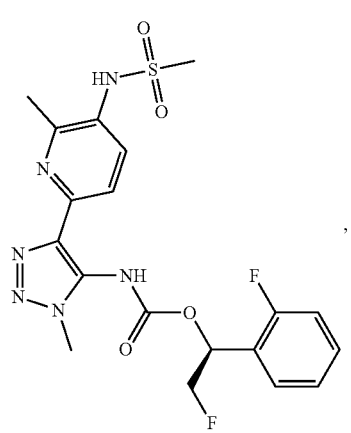
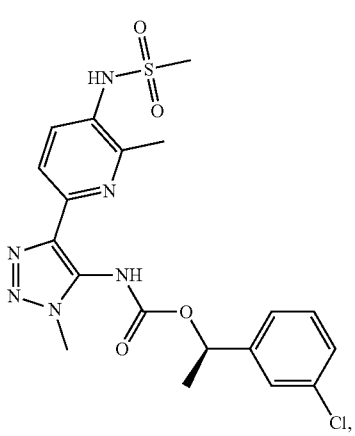
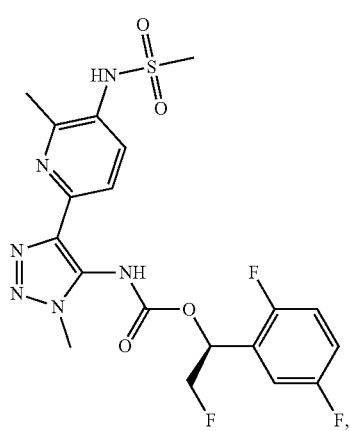

111
-continued
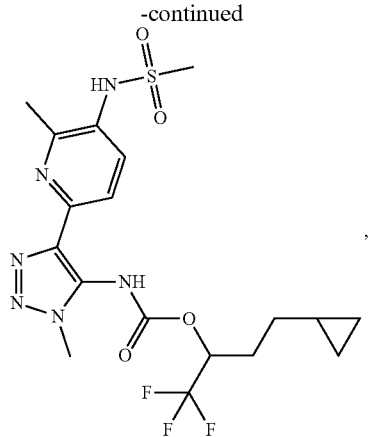
,
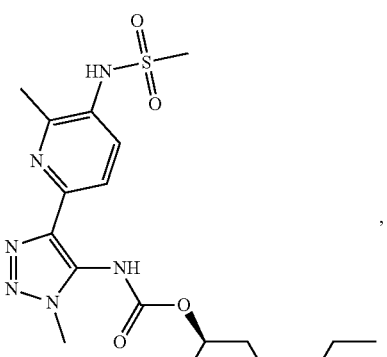
,
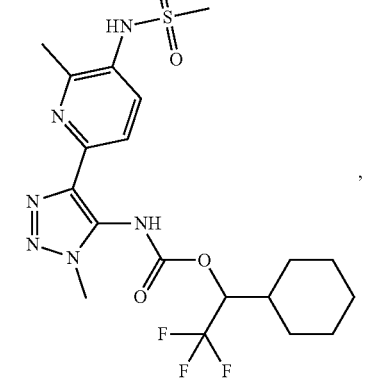
,
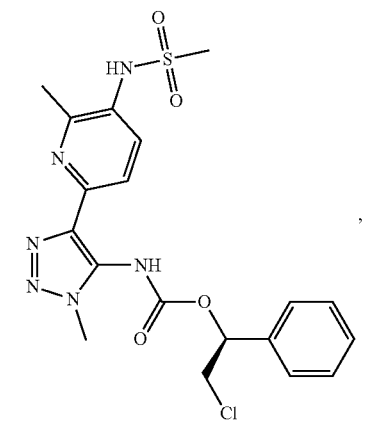
,
112
-continued
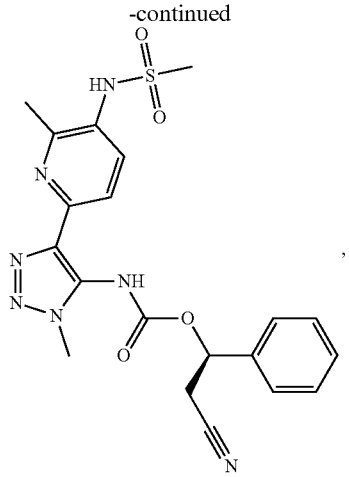
,
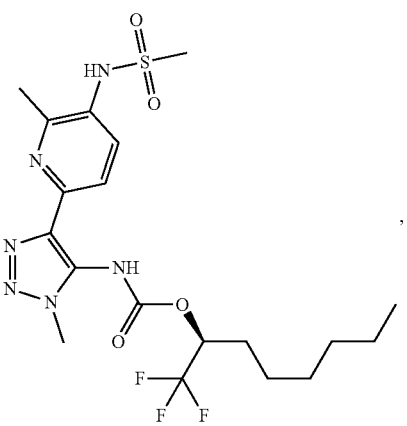
,
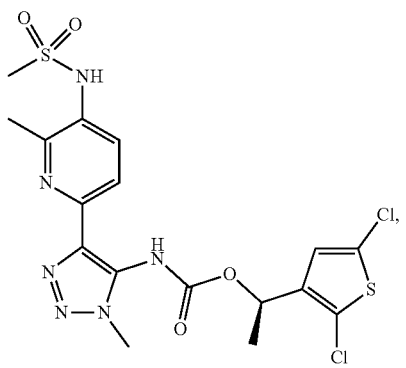
,
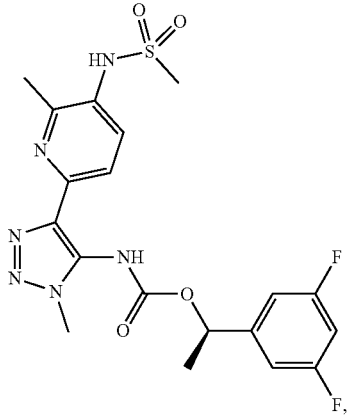
, -continued
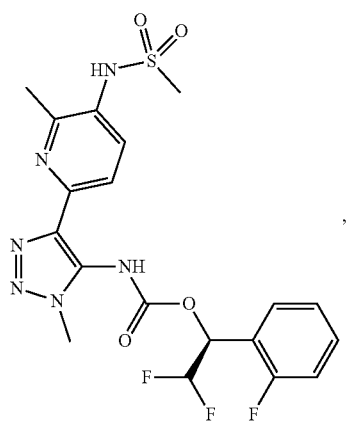
,
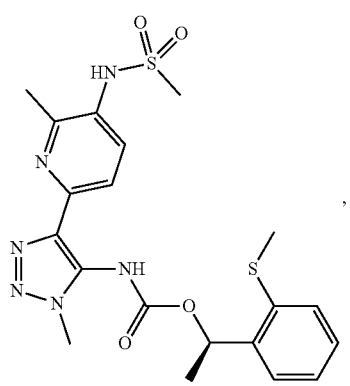
,
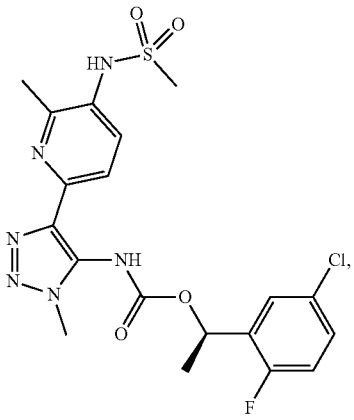
,
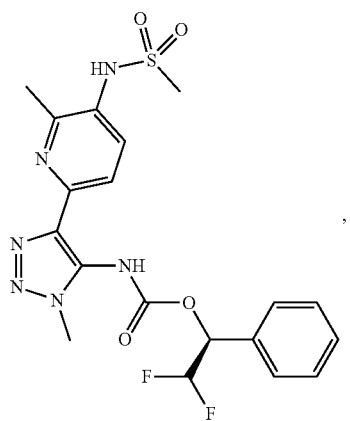
,
-continued
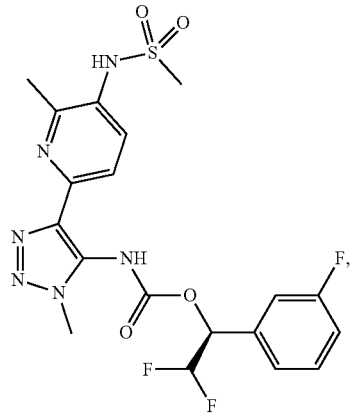
,
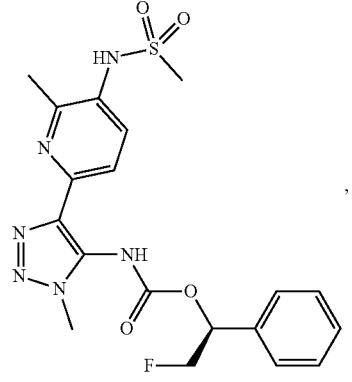 [SMILES: Cc1nc(-c2nnn(C)c2NC(=O)O[C@H](CF)c2ccccc2)ccc1NS(C)(=O)=O]
,

,

, 115
-continued
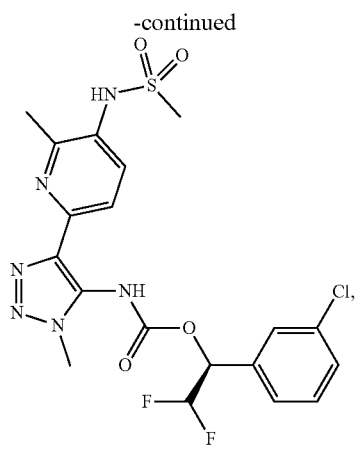
116
-continued
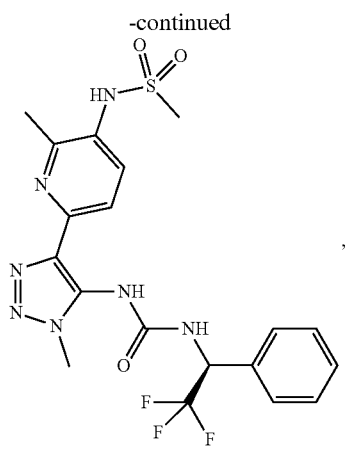
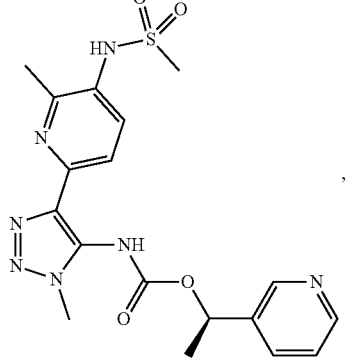
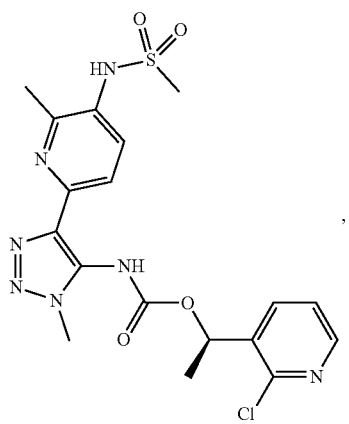 [SMILES: Cc1nc(-c2nnn(C)c2NC(=O)O[C@H](C)c2cccnc2Cl)ccc1NS(C)(=O)=O]
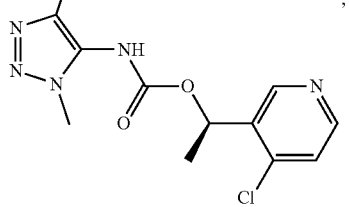

117
-continued
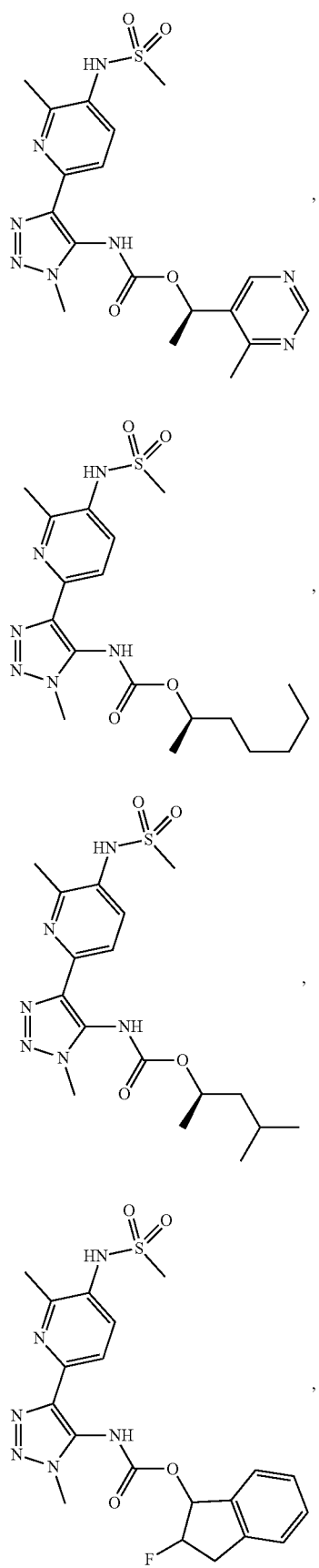
118
-continued
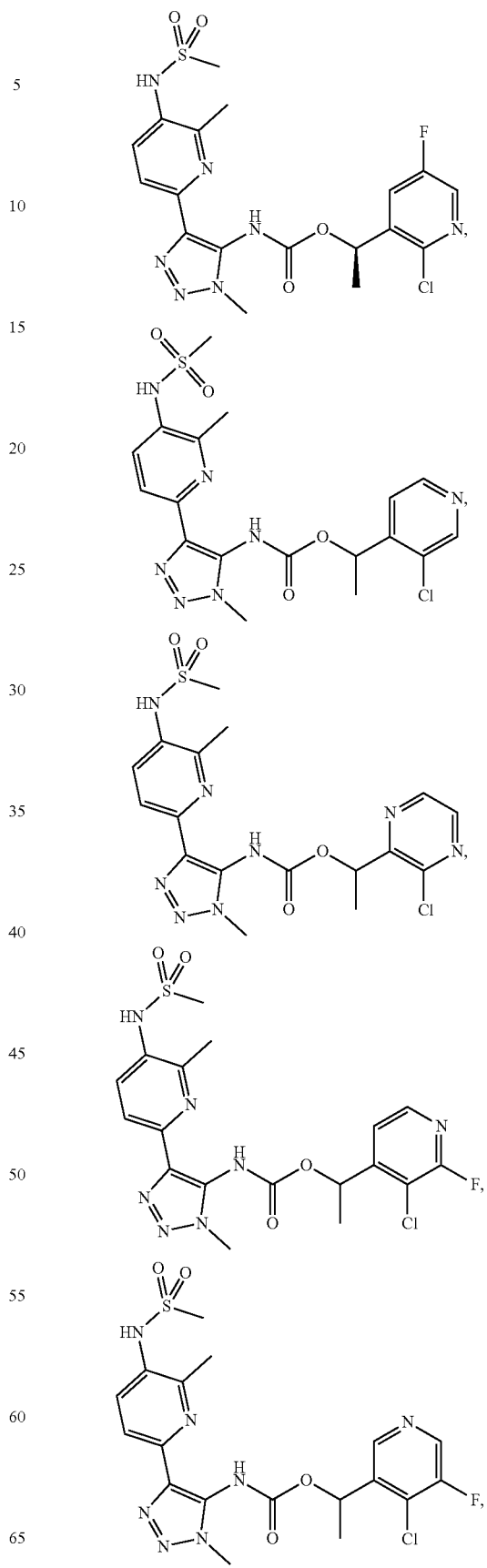

119
-continued
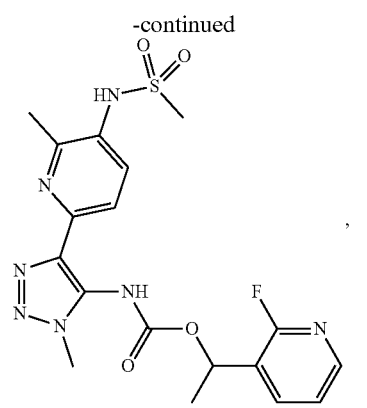
,
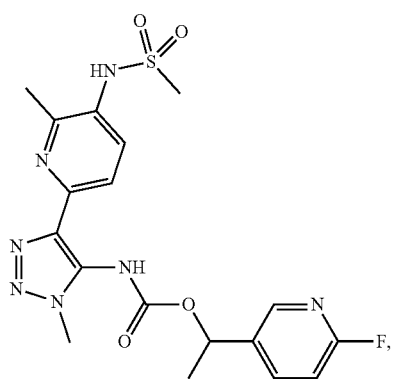
,
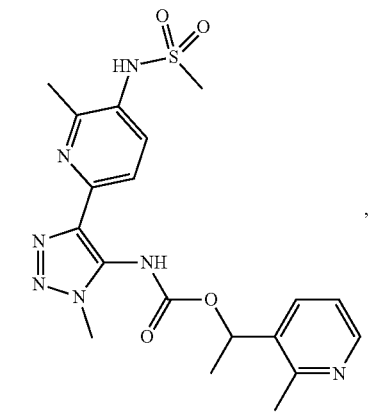
,
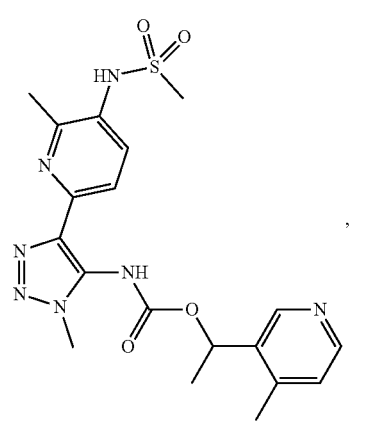
,
120
-continued
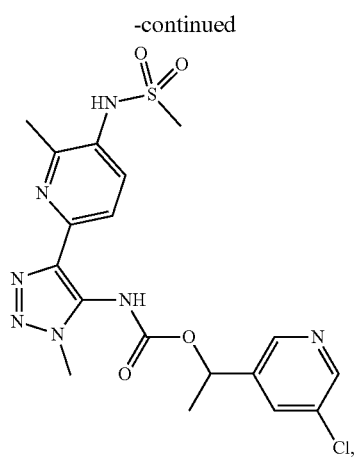
,
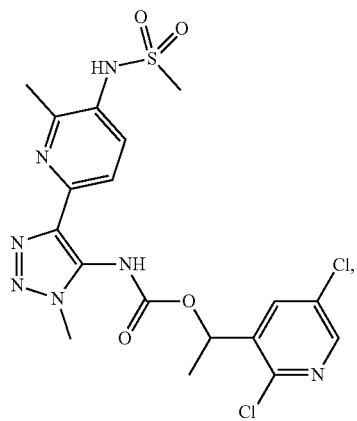
,
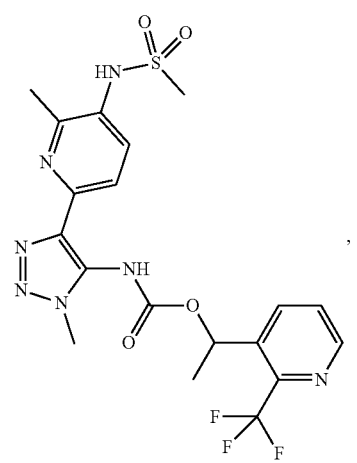
,
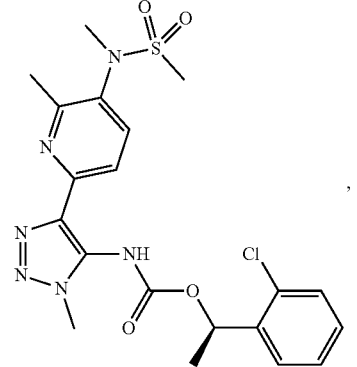
, 121
-continued
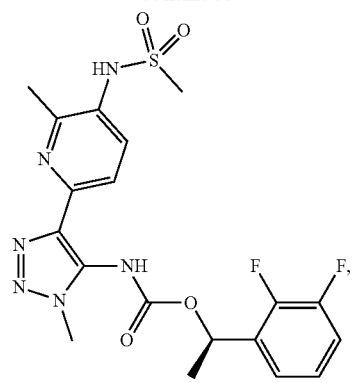
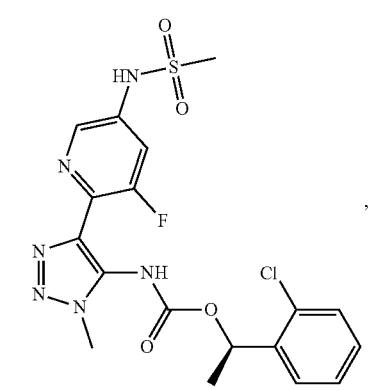
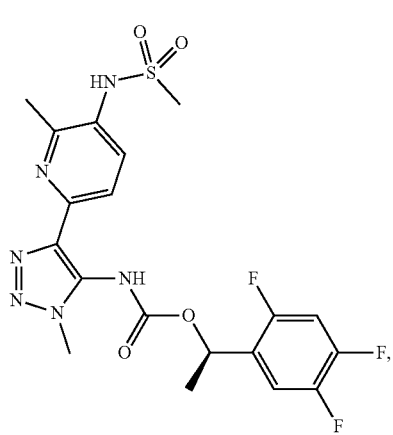
122
-continued
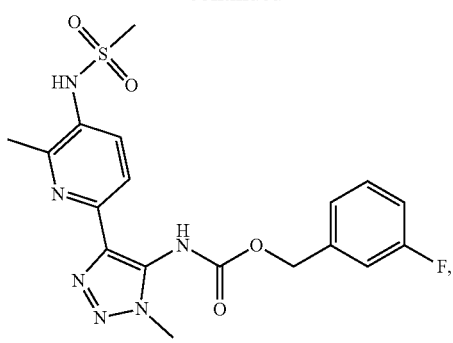
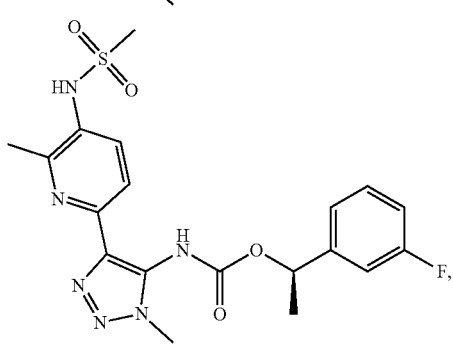
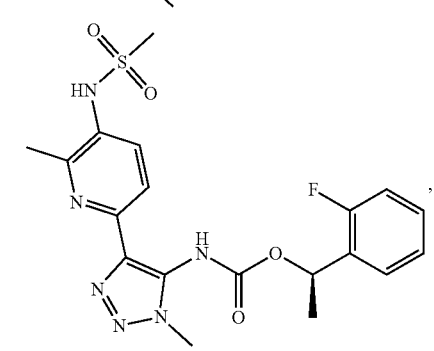
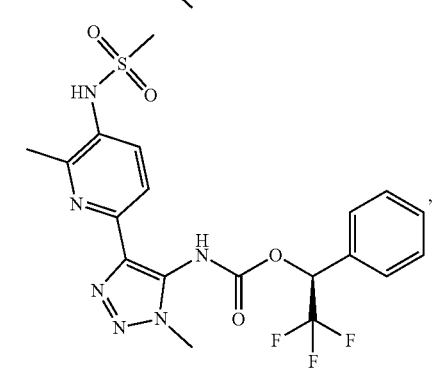
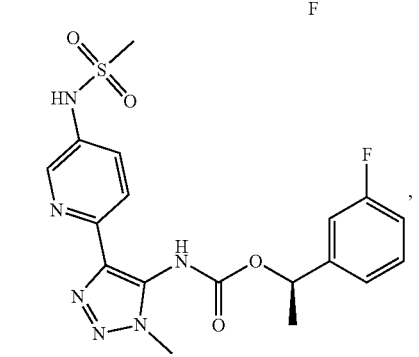

123
-continued
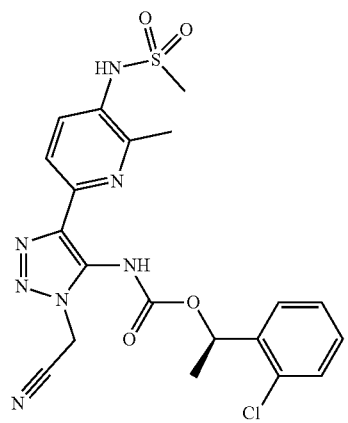
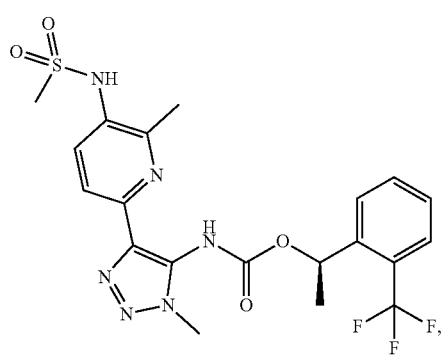
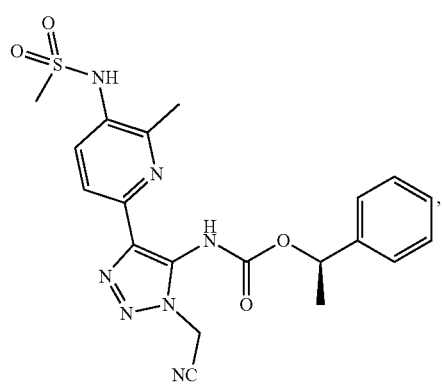
124
-continued
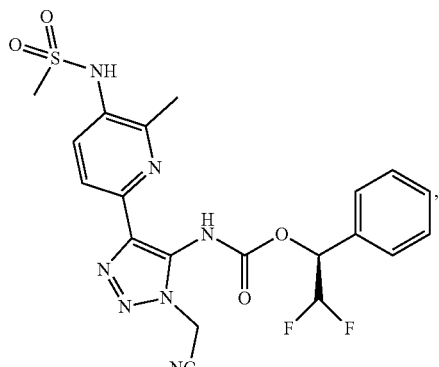
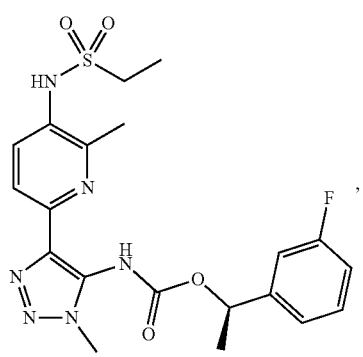
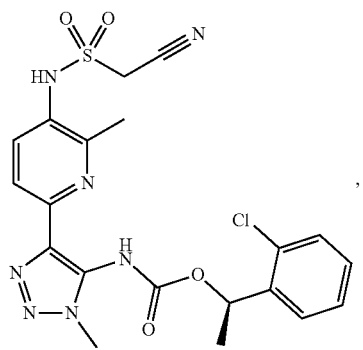
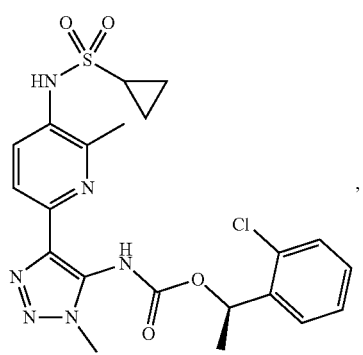

125
-continued
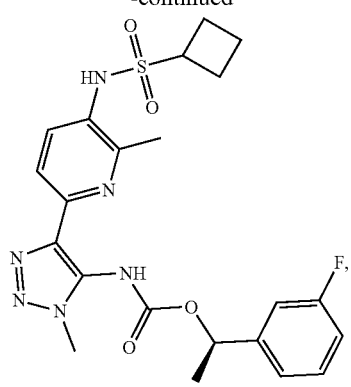
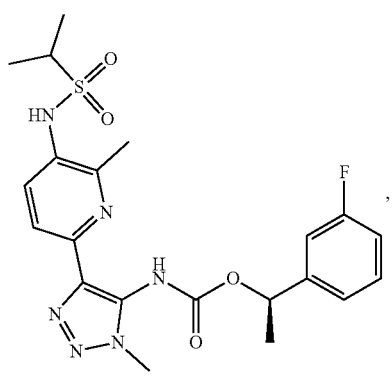
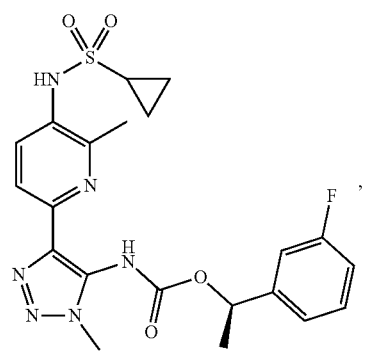
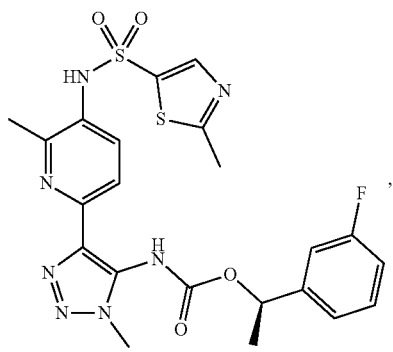
126
-continued
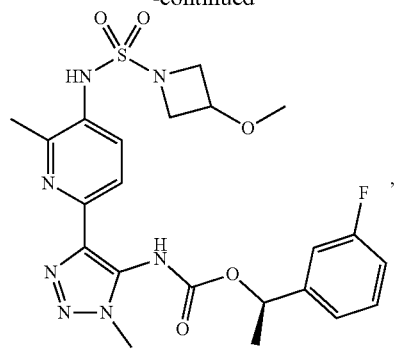
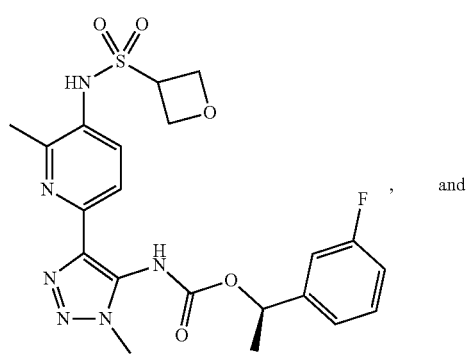
or a pharmaceutically acceptable salt thereof.
Embodiment 66: A compound or pharmaceutically acceptable salt thereof of Embodiment 1, wherein the compound is Embodiment 67: A compound or pharmaceutically acceptable salt thereof of Embodiment 1, wherein the compound is

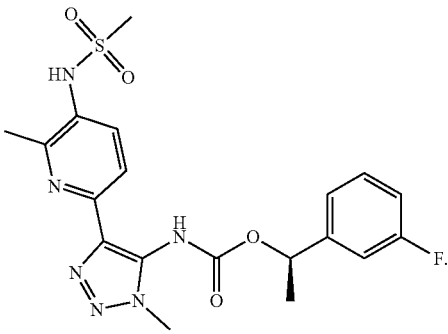

Embodiment 68: A compound or pharmaceutically acceptable salt thereof of Embodiment 1, wherein the compound is

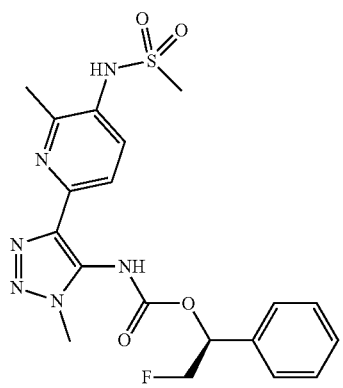

Embodiment 69: A compound or pharmaceutically acceptable salt thereof of Embodiment 1, wherein the compound is

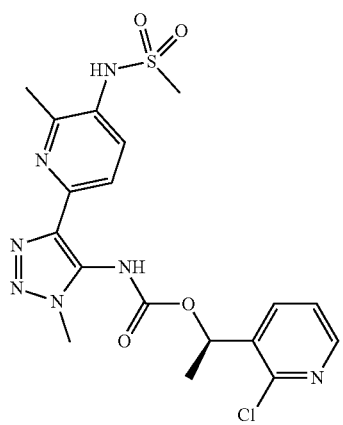

Embodiment 70: A compound or pharmaceutically acceptable salt thereof of Embodiment 1, wherein the compound is

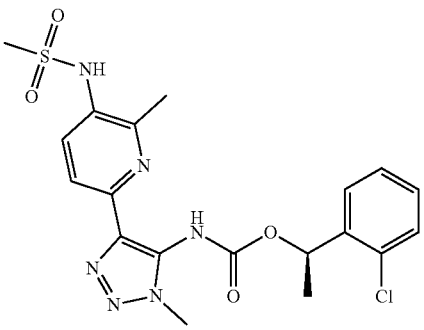

Embodiment 71: A pharmaceutical composition comprising a therapeutically effective amount of a compound, or pharmaceutically acceptable salt thereof, of any one of Embodiments 1 to 70, and a pharmaceutically acceptable excipient.

Embodiment 72: The pharmaceutical composition of Embodiments 71, further comprising an additional therapeutic agent.

Embodiment 73: A method of treating, stabilizing, or lessening the severity or progression of an LPAR1 mediated disease or condition comprising administering to a patient in need thereof a therapeutically effective amount of a compound of any one of Embodiments 1 to 70, or a pharmaceutically acceptable salt thereof, or a pharmaceutical composition of Embodiments 71 or 72.

Embodiment 74: The method of Embodiment 73, wherein the LPAR1 mediated disease or condition is selected from the gdiaroup consisting of wound healing, cancer, pain, respiratory disorder, allergic disorder, nervous system disorder, cardiovascular disorder, and inflammatory disorder.

Embodiment 75: The method of Embodiment 73, wherein the LPAR1 mediated disease or condition comprises fibrosis.

Embodiment 76: The method of embodiment 75, wherein fibrosis is pulmonary fibrosis, renal fibrosis, hepatic fibrosis, ocular fibrosis, cardiac fibrosis, or systemic sclerosis.

Embodiment 77: The method of Embodiment 76, wherein pulmonary fibrosis is idiopathic pulmonary fibrosis (IPF).

Embodiment 78: The method of Embodiment 77, wherein the pulmonary fibrosis is secondary to a systemic inflammatory disease.

Embodiment 79: The method of Embodiment 78, wherein the systemic inflammatory disease is rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury or acute respiratory distress.

Embodiment 80: The method of Embodiment 76, wherein the renal fibrosis is associated with diabetic kidney disease.

Embodiment 81: The method of Embodiment 73, wherein the LPAR1 mediated disease or condition is a liver disease.

Embodiment 82: The method of Embodiment 81, wherein the liver disease comprises liver fibrosis.

Embodiment 83: The method of Embodiment 81 or 82, wherein the liver disease comprises non-alcoholic fatty liver disease (NAFLD).

Embodiment 84: The method of any one of Embodiments 81 to 83, wherein the liver disease comprises steatosis.

Embodiment 85: The method of any one of Embodiments 81 to 84, wherein the liver disease comprises non-alcoholic steatoheptitis (NASH).

Embodiment 86: The method of any one of Embodiments 81 to 85, wherein the liver disease comprises liver cirrhosis.

Embodiment 87: The method of Embodiment 86, wherein the liver cirrhosis is compensated liver cirrhosis.

Embodiment 88: The method of Embodiment 86, wherein the liver cirrhosis is decompensated liver cirrhosis.

Embodiment 89: The method of any one of Embodiments 81 to 88, wherein the liver disease comprises hepatocellular carcinoma (HCC).

Embodiment 90: The method of any one of Embodiments 81 to 89, wherein the liver disease comprises Primary Biliary Cirrhosis (PBC) or Primary Sclerosing Choleangitis (PSC).

Embodiment 91: The method of any one of Embodiments 81 to 89, wherein the liver disease comprises portal hypertension.

Embodiment 92: The method of anyone of Embodiments 83 to 91, wherein the compound or pharmaceutically acceptable salt thereof is administered in combination with an additional therapeutic agent.

Embodiment 93: The pharmaceutical composition of Embodiment 72 or the method of Embodiments 92, wherein the additional therapeutic agent is one, two, three, or four additional therapeutic agents.

Embodiment 94: The pharmaceutical composition of Embodiment 72, or the method of embodiment 92 or 93, wherein the additional therapeutic agent comprises an acetyl-CoA carboxylase (ACC) inhibitor, an apoptotic signal-regulating kinase (ASK-1) inhibitor, a farnesoid X receptor (FXR) agonist, fish oil, a glucagon-like peptide-1 receptor agonist, a peroxisome proliferator-activated receptor alpha (PPARα) agonist, or a TGFβ antagonist.

Embodiment 95: The pharmaceutical composition or method of Embodiment 94, wherein the ACC inhibitor is firsocostat.

Embodiment 96: The pharmaceutical composition or method of Embodiment 94, wherein the ASK1 inhibitor is selonsertib.

Embodiment 97: The pharmaceutical composition or method of Embodiment 94, wherein the FXR agonist is cilofexor.

Embodiment 98: The pharmaceutical composition or method of Embodiment 94, wherein the PPARα agonist is a fibrate.

Embodiment 99: The pharmaceutical composition or method of Embodiment 94, wherein the fish oil is icosapent ethyl.

Embodiment 100: The pharmaceutical composition or method of Embodiment 94, wherein the GLP-1 receptor agonist is liraglutide or semaglutide.

Embodiment 101: The pharmaceutical composition or method of Embodiment 94, wherein the TGFβ antagonist is an anti-TGFβ1 specific antibody.

Embodiment 102: The pharmaceutical composition or method of Embodiment 94, wherein the TGFβ antagonist is a TGFβ receptor.

Embodiment 103: The pharmaceutical composition or method of Embodiment 94, wherein the additional therapeutic agent comprises firsocostat and cilofexor.

Embodiment 104: The pharmaceutical composition or method of Embodiment 94, wherein the additional therapeutic agents comprise firsocostat and liraglutide or semaglutide.

Embodiment 105: The pharmaceutical composition or method of Embodiment 92 or 94, wherein the additional therapeutic agents comprise a fibrate or icosapent ethyl.

Embodiment 106: The pharmaceutical composition or method of Embodiment 94, wherein the additional therapeutic agent comprises cilofexor and liraglutide or semaglutide.

Embodiment 107: Use of a compound or pharmaceutically acceptable salt thereof of any one of Embodiments 1 to 70 for the manufacture of a medicament for the treatment of an LPAR1 mediated disease or condition.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that these examples are exemplary and not exhaustive. Many changes can be made in the specific embodiments which are disclosed and still obtain a like or similar result without departing from the spirit and scope of the disclosure.

Compounds disclosed herein can be prepared according to the procedures of the following Schemes and Examples, using appropriate materials and are further exemplified by the following specific examples. Moreover, by utilizing the procedures described herein, in conjunction with ordinary skills in the art, additional compounds of the present disclosure claimed herein can be readily prepared. The examples further illustrate details for the preparation of the compounds of the present disclosure. Those skilled in the art will readily understand that known variations of the conditions and processes of the following preparative procedures can be used to prepare these compounds. For synthesizing compounds which are embodiments described in the present disclosure, inspection of the structure of the compound to be synthesized will provide the identity of each substituent group. In some cases, the identity of the final product can render apparent the identity of the necessary starting materials by a process of inspection, given the examples herein. Compounds can be isolated in the form of their pharmaceutically acceptable salts, such as those described above. Compounds described herein are typically stable and isolatable at room temperature and pressure.

An illustration of the preparation of compounds disclosed herein is shown below. Unless otherwise indicated, variables have the same meaning as described above. The examples presented below are intended to illustrate particular embodiments of the disclosure. Suitable starting materials, building blocks and reagents employed in the synthesis as described below are commercially available from AbovChem, Acros Organics, Astatech, Combi Blocks, Oakwood Chemical, or Sigma-Aldrich, for example, or can be routinely prepared by procedures described in the literature, for example in "March's Advanced Organic Chemistry: Reactions, Mechanisms, and Structure", 5$^{th}$ Edition; John Wiley & Sons or T. Eicher, S. Hauptmann "The Chemistry of Heterocycles; Structures, Reactions, Synthesis and Application", 2$^{nd}$ edition, Wiley-VCH 2003; Fieser et al. "Fiesers' Reagents for organic Synthesis" John Wiley & Sons 2000.

General Schemes

Scheme A

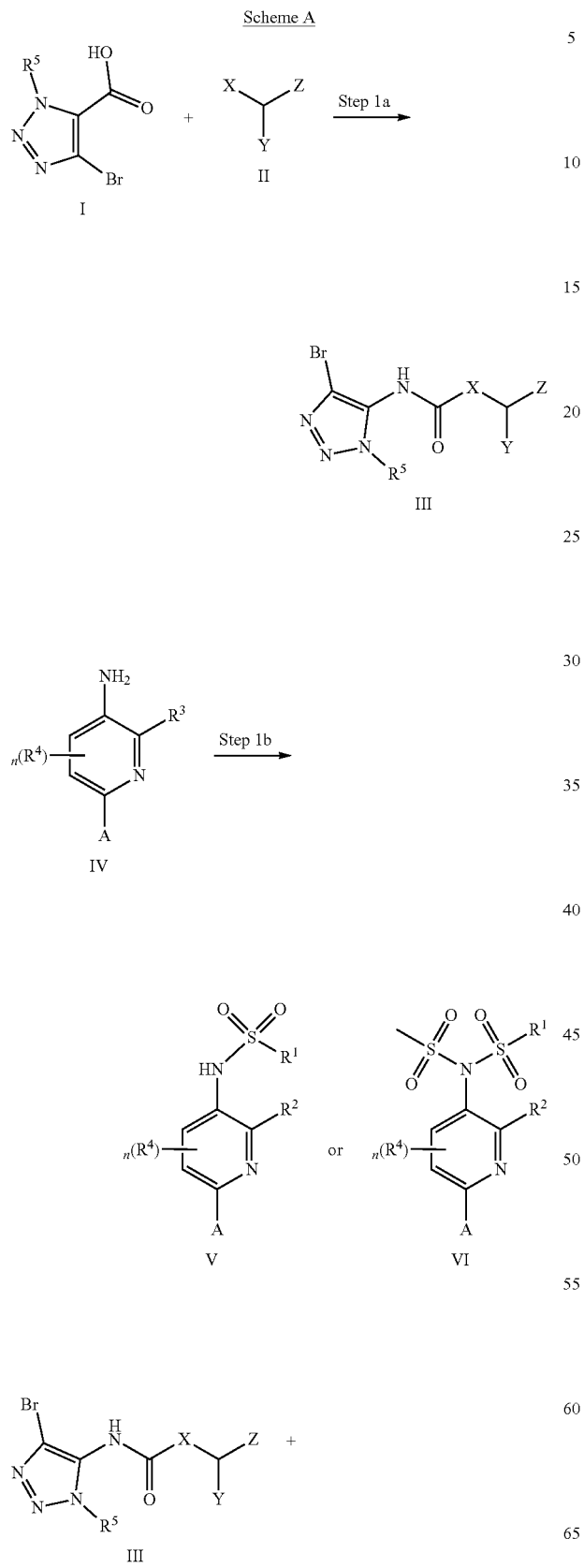

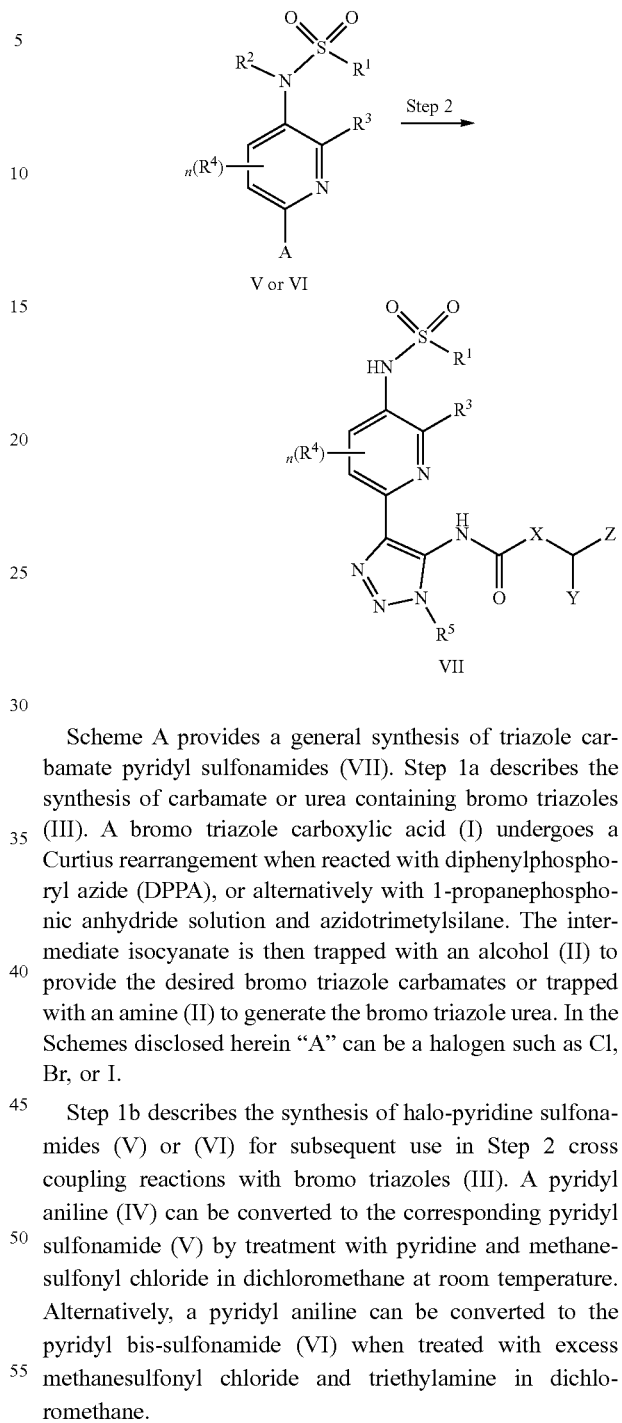

Scheme A provides a general synthesis of triazole carbamate pyridyl sulfonamides (VII). Step 1a describes the synthesis of carbamate or urea containing bromo triazoles (III). A bromo triazole carboxylic acid (I) undergoes a Curtius rearrangement when reacted with diphenylphosphoryl azide (DPPA), or alternatively with 1-propanephosphonic anhydride solution and azidotrimetylsilane. The intermediate isocyanate is then trapped with an alcohol (II) to provide the desired bromo triazole carbamates or trapped with an amine (II) to generate the bromo triazole urea. In the Schemes disclosed herein "A" can be a halogen such as Cl, Br, or I.

Step 1b describes the synthesis of halo-pyridine sulfonamides (V) or (VI) for subsequent use in Step 2 cross coupling reactions with bromo triazoles (III). A pyridyl aniline (IV) can be converted to the corresponding pyridyl sulfonamide (V) by treatment with pyridine and methanesulfonyl chloride in dichloromethane at room temperature. Alternatively, a pyridyl aniline can be converted to the pyridyl bis-sulfonamide (VI) when treated with excess methanesulfonyl chloride and triethylamine in dichloromethane.

In Step 2, halo-pyridine sulfonamide (V) or (VI) (Y=H or —SO$_2$CH$_3$) is converted to the corresponding pinacol ester via Miaura borylation, or corresponding Stannane using hexamethylditin. In the same pot, the intermediate organometallic reagent is treated with a carbamate containing bromo triazole (III), and additional palladium catalyst to undergo the desired cross coupling reaction (e.g., Suzuki or Stille), to provide the desired triazole carbamate pyridyl sulfonamides (VII).

Scheme B1

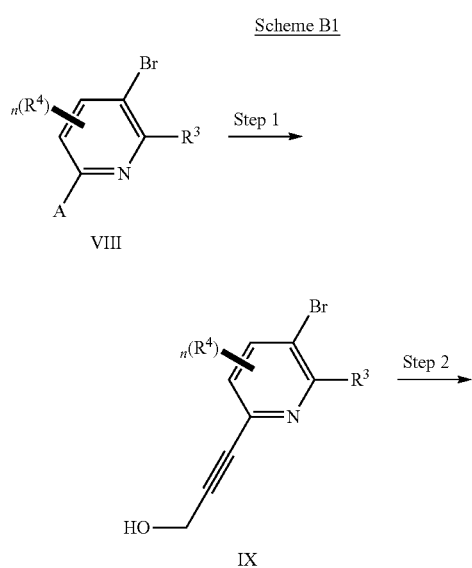

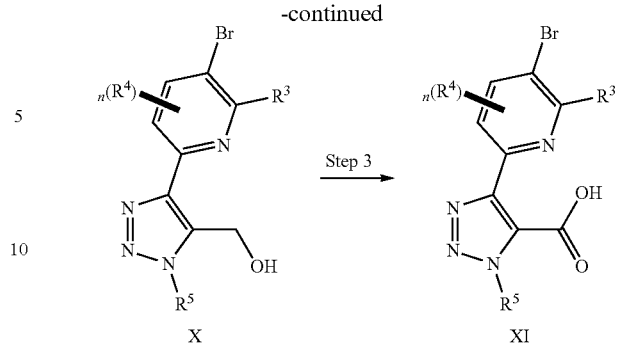

Scheme B1 describes the synthesis of Bromo-pyridine triazole carboxylic acids (XI). First, a dihalo-pyridine (VIII) undergoes a Sonagashira coupling with propargyl alcohol to generate the aklynl-pyridine (IX). The alkyne then ungoes a thermal or catalytic cycloaddition with an azide to generate the corresponding hydroxymethyl triazoles (X). Finally, oxidation of the primary alcohol via tetramethylpiperidinyloxy (TEMPO), and sodium chlorite provides the bromo-pyridine triazole carboxylic acid (XI).

Scheme B2a

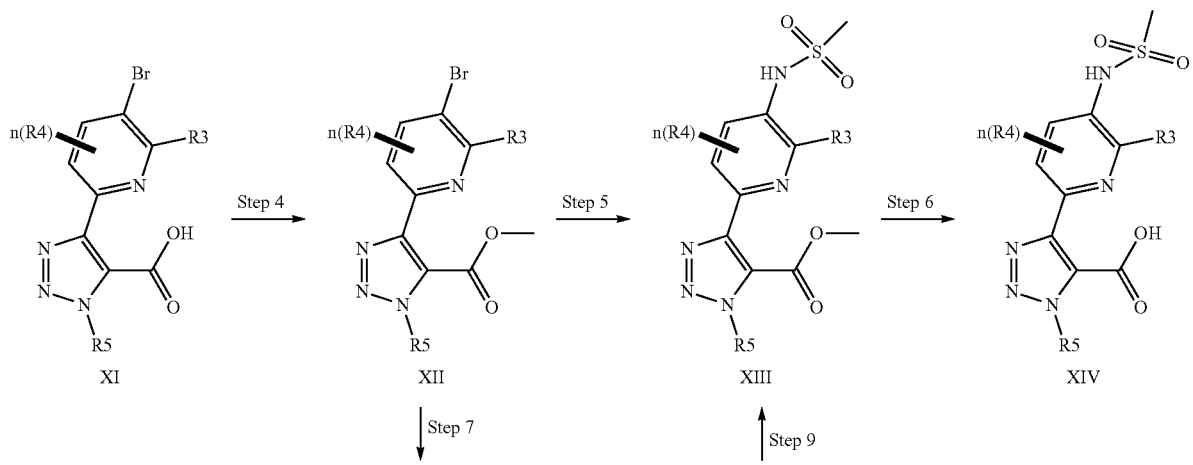

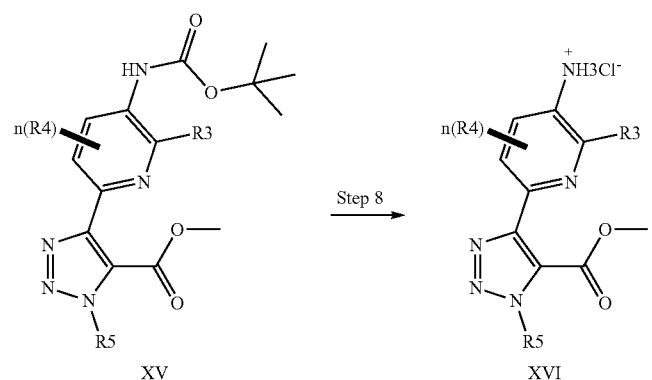

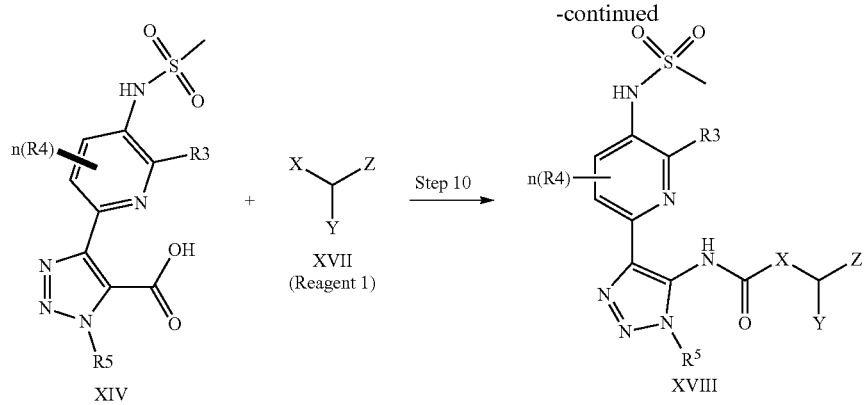

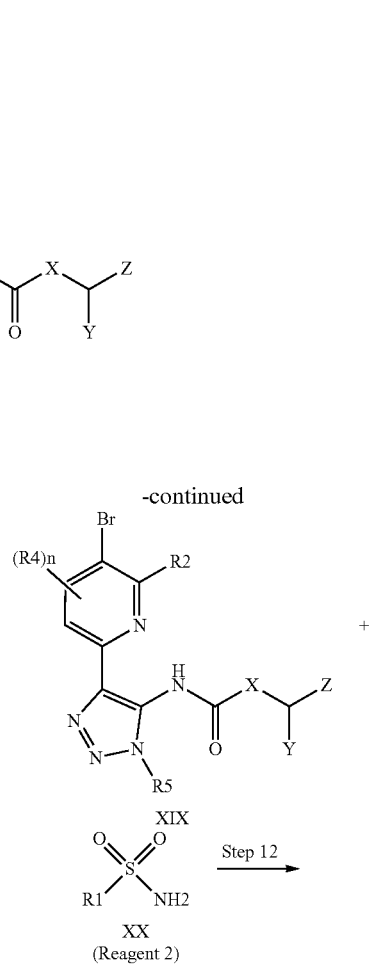

Scheme B2a describes the general synthesis of pyridyl sulfonamide triazole carboxylic acids (XIV). First, a bromo-pyridine triazole carboxylic acid (XI) is protected as a methyl ester (XII) by treatment with thionyl chloride. In Step 5, the pyridyl-bromide (XII) then undergoes a Buchwald-type amination with methanesulfonamide to provide the pyridyl-methanesulfonamide (XIII). Alternatively, in step 7 pyridyl-bromide (XII) can undergo a Buchwald-type amination with tert-butyl carbamate to generate the Boc-protected aniline (XV). Exposure of protected aniline (XV) to hydrochloric acid reveals the aniline-hydrochloride salt (XVI), which can be reacted with methane sulfonyl chloride to provide pyridyl-methanesulfonamide (XIII). Next, base hydrolysis of the ester (XIII) provides the pyridyl sulfonamide triazole carboxylic acid (XIV).

Step 10 describes the general synthesis of pyridyl sulfonamide triazole carbamates and ureas (XVIII). Pyridyl sulfonamide triazole carboxylic acid (XIV) undergoes a Curtius rearrancement via treatment with 1-propanephosphonic anhydride solution and azidotrimetylsilane and heat. The intermediate isocyanate is trapped with either an alcohol (XVII, Reagent 1) to provide the desired pyridyl sulfonamide triazole carbamate (XVIII), or an amine (XVII, Reagent 1) to provide the desired pyridyl sulfonamide triazole urea (XVIII).

Scheme B2b

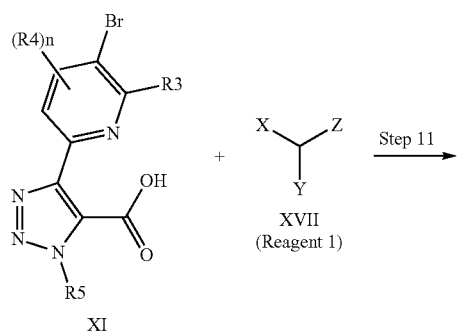

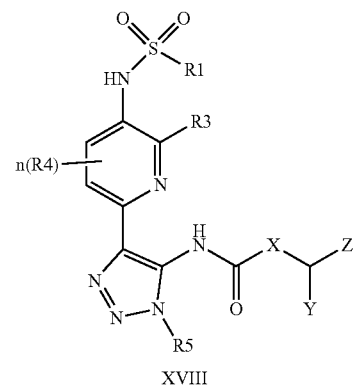

Scheme B2b describes an alternative synthesis for pyridyl sulfonamide triazole carbamates (XVIII). In Step 11, a bromopyridine triazole carboxylic acid (XI) undergoes a Curtius rearrangement via treatment with propanephosphonic acid anhydride and azidotrimethyl silane. The intermediate isocyanate is trapped with an alcohol (XVII, Reagent 1) to generate the corresponding bromo pyridine triazole carbamate (XIX). In Step 12, the pyridyl bromide is undergoes a Buchwald-type amination with an alkyl sulfonamide (XX, Reagent 2) to provide the desired pyridyl sulfonamide triazole carbamate (XVIII).

Example 1: Preparation of 4-bromo-1-methyl-1H-1,2,3-triazole-5-carboxylic acid

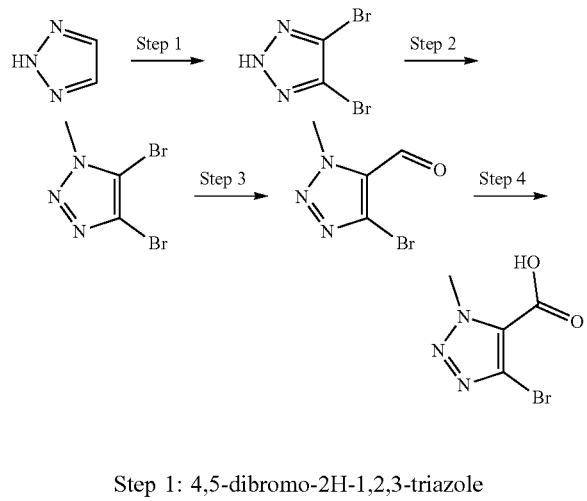

Step 1: 4,5-dibromo-2H-1,2,3-triazole

Br$_2$ (2.8 mol) was added to a solution of 2H-1,2,3-triazole (1.4 mol) in water (600 ml) at 40° C. The resulting mixture was stirred for 2 h at 40° C. After cooling to room temperature, the precipitate was collected by filtration. The solid was washed with water (2×300 ml) and dried under vacuum to give 4,5-dibromo-2H-1,2,3-triazole.

Step 2: 4,5-dibromo-1-methyl-1H-1,2,3-triazole

To a mixture of 4,5-dibromo-2H-1, 2, 3-triazole (704.0 mmol) and K$_2$CO$_3$ (1.4 mol) in THF (1000 ml), iodomethane (1.0 mol) was added. The mixture was stirred for 12 h at room temperature. The mixture was filtered and the filter cake was washed with ethyl acetate (2×500 ml), the filtrate was concentrated under 40° C. to afford a crude product, which was purified by column chromatography to give 4,5-dibromo-1-methyl-1H-1,2,3-triazole.

Step 3: 4-bromo-1-methyl-1H-1,2,3-triazole-5-carbaldehyde

To a solution of 4,5-dibromo-1-methyl-1H-1,2,3-triazole (168.0 mmol) in THE (600 ml) was added isopropylmagnesium chloride (252.0 mmol) at −10° C. The mixture was stirred for 15 min, DMF (840 mmol) was added. After 1 h, the mixture was treated with 250 ml of saturated ammonium chloride and extracted with DCM (2×350 ml). The combined organics were washed with 250 ml of brine, dried over Na2SO4, filtered and concentrated to give 4-bromo-1-methyl-1H-1,2,3-triazole-5-carbaldehyde.

Step 4: 4-bromo-1-methyl-1H-1,2,3-triazole-5-carboxylic acid

Oxone (651 mmol) was added to a solution of 4-bromo-1-methyl-1H-1, 2, 3-triazole-5-carbaldehyde (535.7 mmol) in DMF (800 mL) and the resulting suspension was stirred at room temperature overnight. The mixture reaction was diluted with H$_2$O (1000 ml), was adjusted to pH 3 with 1N HCl, and the aqueous phase was extracted with ethyl acetate (3×800 ml). The combined organics were washed with saturated Na$_2$CO$_3$ (2×500 ml), the aqueous phase was adjusted to pH 3 with 1N HCl. The precipitate was isolated by filtration and dried under reduced pressure to provide 4-bromo-1-methyl-1H-1,2,3-triazole-5-carboxylic acid.

Example 2: Preparation of 4-bromo-1-propyl-1H-1,2,3-triazole-5-carboxylic acid

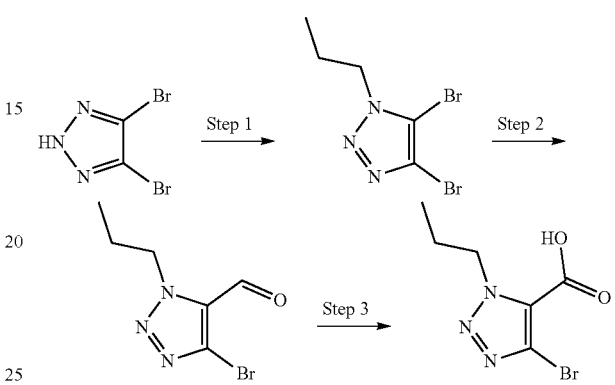

Step 1: 4,5-dibromo-1-propyl-1H-1,2,3-triazole

Following the procedure described in Example 1 (Step 2) for the synthesis of 4,5-dibromo-1-methyl-1H-1,2,3-triazole, using 1-bromopropane (102 mmol) in place of iodomethane, 4,5-dibromo-1-propyl-1H-1,2,3-triazole was obtained.

Step 2: 4-bromo-1-propyl-1H-1,2,3-triazole-5-carbaldehyde

Following the procedure described in Example 1 (Step 3), for the synthesis of 4-bromo-1-methyl-1H-1,2,3-triazole-5-carbaldehyde, using 4,5-dibromo-1-propyl-1H-1,2,3-triazole (3.7 mmol), in place of 4,5-dibromo-1-methyl-1H-1,2, 3-triazole, 4-bromo-1-propyl-1H-1,2,3-triazole-5-carbaldehyde was obtained.

Step 3: 4-bromo-1-propyl-1H-1,2,3-triazole-5-carboxylic acid

Following the procedure described in Example 1 (Step 4) for the synthesis of 4-bromo-1-methyl-1H-1,2,3-triazole-5-carboxylic acid, using 4-bromo-1-propyl-1H-1, 2, 3-triazole-5-carbaldehyde (3.7 mmol), in place of 4-bromo-1-methyl-1H-1, 2, 3-triazole-5-carbaldehyde, 4-bromo-1-propyl-1H-1,2,3-triazole-5-carboxylic acid was obtained.

Example 3: Preparation of (R)-1-phenylethyl (4-bromo-1-methyl-1H-1,2,3-triazol-5-yl)carbamate (Intermediate 1)

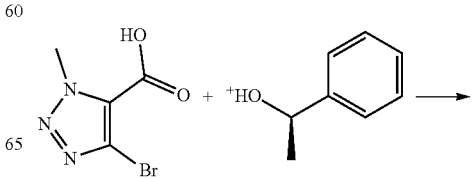

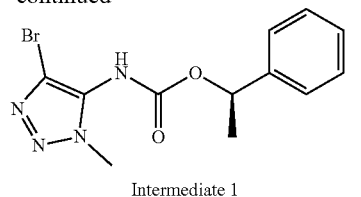

Intermediate 1

Intermediates 1-4 (Examples 3-6) were generally prepared according to Scheme A, Step 1a.

To a suspension of 4-bromo-1-methyl-1H-1,2,3-triazole-5-carboxylic acid (97 mmol) in toluene (500 mL) was added diphenylphosphoryl azide (DPPA) (107 mmol), N,N-diisopropylethylamine (DIEA) (194 mmol), and (R)-1-phenylethan-1-ol (194 mmol). The mixture was heated at 80° C. for 6 h. After cooling to room temperature, the mixture was filtered and the filtrate was concentrated in vacuo. The residue was purified by silica chromatography to afford (R)-1-phenylethyl (4-bromo-1-methyl-1H-1,2,3-triazol-5-yl)carbamate (Intermediate 1). LCMS M/Z (M+1)=325.1.

Example 4: Preparation of (R)-1-(2-chlorophenyl) ethyl (4-bromo-1-methyl-1H-1,2,3-triazol-5-yl)carbamate (Intermediate 2)

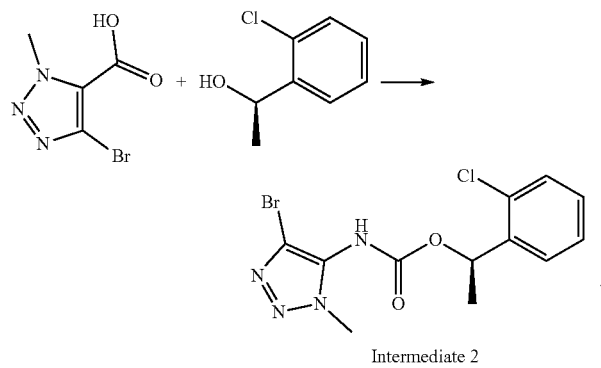

Intermediate 2

Following the synthesis described in Example 3 for (R)-1-phenylethyl (4-bromo-1-methyl-1H-1,2,3-triazol-5-yl)carbamate, Intermediate 1), using (R)-1-(2-chlorophenyl)ethan-1-ol (36 mmol) in place of (R)-1-phenylethan-1-ol, (R)-1-(2-chlorophenyl)ethyl (4-bromo-1-methyl-1H-1,2,3-triazol-5-yl)carbamate (Intermediate 2) was obtained. LCMS M/Z (M+1)=359.0.

Example 5: (R)-1-(2-chlorophenyl)ethyl (4-bromo-1-propyl-1H-1,2,3-triazol-5-yl)carbamate (Intermediate 3)

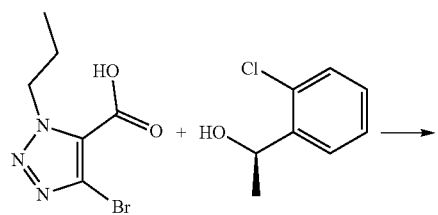

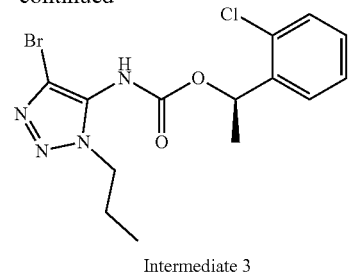

Intermediate 3

Following the synthesis described in Example 3 for (R)-1-phenylethyl (4-bromo-1-methyl-1H-1,2,3-triazol-5-yl)carbamate, Intermediate 1), using 4-bromo-1-propyl-1H-1,2,3-triazole-5-carboxylic acid (0.86 mmol) in place of 4-bromo-1-methyl-1H-1,2,3-triazole-5-carboxylic acid, (R)-1-(2-chlorophenyl)ethyl (4-bromo-1-propyl-1H-1,2,3-triazol-5-yl)carbamate (Intermediate 3) was obtained. LCMS M/Z (M+1)=387.1.

Example 6: (S)-2,2-difluoro-1-phenylethyl (4-bromo-1-methyl-1H-1,2,3-triazol-5-yl)carbamate (Intermediate 4)

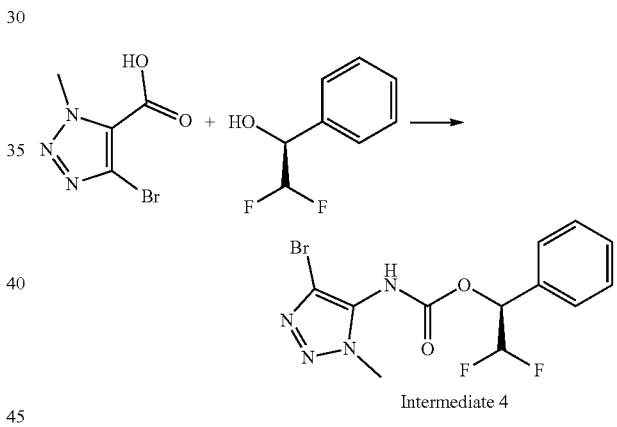

Intermediate 4

4-Bromo-1-methyl-1H-1,2,3-triazole-5-carboxylic acid (3.9 mmol), 50% 1-propanephosphonic anhydride solution (5.8 mmol) in DMF, and azidotrimethylsilane (5.8 mmol), were suspended in THF (10 ml). Triethylamine (9.7 mmol) was added dropwise and the mixture was stirred for 30 min at 70° C. The mixture was then cooled to room temperature and (S)-2,2-difluoro-1-phenylethan-1-ol (5.8 mmol) was added and the mixture was heated again to 70° C. for 4 h. The reaction mixture was cooled to room temperature, and ethyl acetate (25 ml) and water (25 ml) were added. The organic layer was separated, and the aqueous layer was extracted with 25 mL ethyl acetate. The combined organics were dried over sodium sulfate, filtered. The filtrate was concentrated and purified by column chromatography to provide (S)-2,2-difluoro-1-phenylethyl (4-bromo-1-methyl-1H-1,2,3-triazol-5-yl)carbamate (Intermediate 4). LCMS M/Z (M+1)=361.08.

Example 7: Preparation of 4-(5-bromopyridin-2-yl)-1-methyl-1H-1,2,3-triazole-5-carboxylic acid (Intermediate 5)

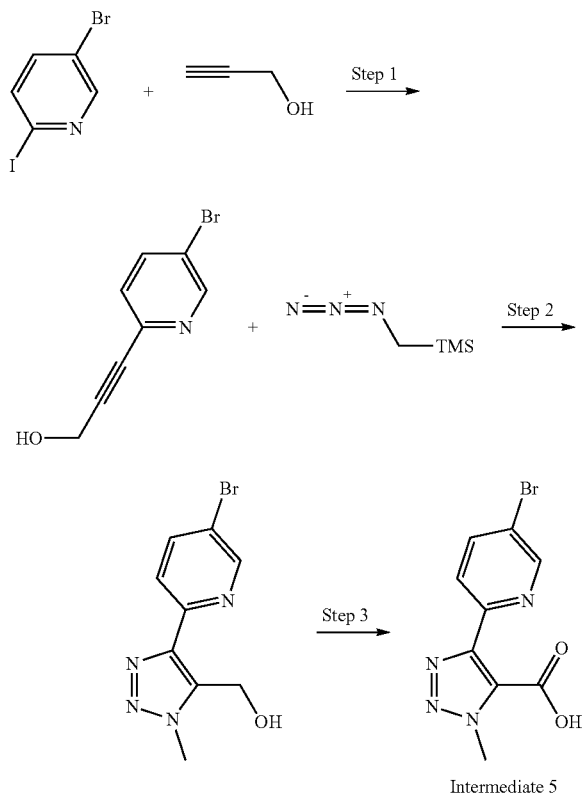

Intermediate 5

Intermediate 5 was generally prepared according to Scheme B1.

Step 1: 3-(5-bromopyridin-2-yl)prop-2-yn-1-ol

To a mixture of 5-bromo-2-iodopyridine (352.2 mmol) in THF (400 mL) was added compound prop-2-yn-1-ol (370 mmol), triethylamine (1.06 mol), cuprous iodide (17.6 mmol) and bis(triphenylphosphine) palladium(II) chloride (10.6 mmol) under nitrogen atmosphere. The reaction mixture was stirred at room temperature for 16 h. After completion of the reaction, the mixture was diluted with water (500 ml) and the solid was filtered. The filtrate was extracted with ethyl acetate (3×500 ml). The organic layer was dried over anhydrous sodium sulfate and concentrated under reduced pressure. The residue was triturated with ethyl acetate and ether and stirred for 2 h and filtered. The filter cake was washed with ether to give 3-(5-bromopyridin-2-yl)prop-2-yn-1-ol.

Step 2: (4-(5-bromopyridin-2-yl)-1-methyl-1H-1,2,3-triazol-5-yl)methanol

Cuprous iodide (0.94 mmol) and tetrabutylammonium iodide (0.94 mmol) were mixed together and dissolved in THF (30 mL), stirred for 20 min to yield a solution. Then, 3-(5-bromo-2-pyridyl)prop-2-yn-1-ol (9.43 mmol) was added and the reaction was sparged with argon for 2 min. Pentamethylcyclopentadienylbis(triphenylphosphine)ruthenium(II) chloride (0.47 mmol) and azidomethyltrimethylsilane (24 mmol) were added and the reaction was sealed and heated to 80° C. for 16 h. The reaction mixture was concentrated in vacuo, and then re-dissolved in TH (50 mL). Tetrabutylammonium fluoride (10 mL of a 1M solution in THF) was added dropwise at room temperature and stirred for 1 h. The mixture was quenched with saturated solution of sodium bicarbonate (100 mL) and extracted with DCM (3×100 mL). The organic layer was dried over anhydrous sodium sulfate and concentrated under reduced pressure. The residue was purified by silica gel chromatography to provide (4-(5-bromopyridin-2-yl)-1-methyl-1H-1,2,3-triazol-5-yl)methanol.

Step 3: 4-(5-bromopyridin-2-yl)-1-methyl-1H-1,2,3-triazole-5-carboxylic acid (Intermediate 5)

[5-(5-bromo-2-pyridyl)-3-methyl-triazol-4-yl]methanol (4.83 mmol), 2,2,6,6-tetramethylpiperidinyloxy (TEMPO) (0.48 mmol), and sodium phosphate monobasic (12.08 mmol) were suspended in acetonitrile (50 ml) and water (40 ml). The solution was heated to 45° C. Then, 10 ml of a 1M aqueous solution of sodium chlorite and a separate solution of sodium hypochlorite (10 ml of 0.01 M solution in water), were added simultaneously over 1 h. The reaction was stirred at 45° C. for 16 h. The mixture was cooled to room temperature and concentrated to remove acetonitrile. The product was filtered and the filter cake was washed with water (2×50 mL), and diethyl ether (50 mL) to provide 4-(5-bromopyridin-2-yl)-1-methyl-1H-1,2,3-triazole-5-carboxylic acid (Intermediate 5). LCMS M/Z (M+1)=283.1.

Example 8: Preparation of 1-methyl-4-(5-(methylsulfonamido)pyridin-2-yl)-1H-1,2,3-triazole-5-carboxylic acid (Intermediate 6)

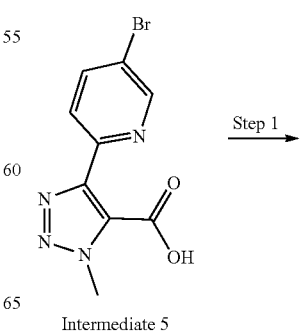

Intermediate 5

143

-continued

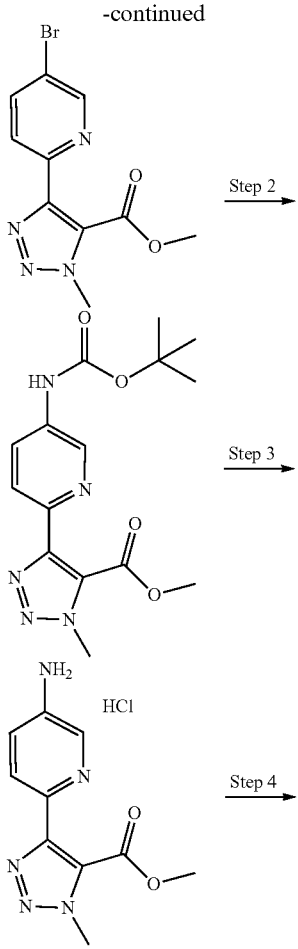

Intermediate 6 was generally prepared according to Scheme B2a.

Step 1: methyl 4-(5-bromopyridin-2-yl)-1-methyl-1H-1,2,3-triazole-5-carboxylate 4-(5-bromopyridin-2-yl)-1-methyl-1H-1,2,3-triazole-5-carboxylic acid (Intermediate 5) (14.1 mmol) was dissolved in 40 ml of methanol. The solution was cooled to 0° C. with an ice bath. Trimethylsilyldiazomethane (18.4 mmol) was added dropwise over 15 min. The ice bath was removed and the reaction was stirred for 5 h. The reaction was quenched by the addition of saturated aqueous sodium bicarbonate and extracted with ethyl acetate. The organic layer was dried over anhydrous sodium sulfate and concentrated under reduced pressure. The residue was purified by silica gel chromatography to provide methyl 4-(5-bromopyridin-2-yl)-1-methyl-1H-1,2,3-triazole-5-carboxylate.

Step 2: Methyl 4-(5-((tert-butoxycarbonyl)amino)pyridin-2-yl)-1-methyl-1H-1,2,3-triazole-5-carboxylate Methyl 4-(5-bromopyridin-2-yl)-1-methyl-1H-1,2,3-triazole-5-carboxylate (11.1 mmol), tert-butyl carbamate (33 mmol), cesium carbonate (33 mmol), and Xantphos Pd G3 precatalyst (1.1 mmol) were suspended in dioxane (50 ml). The suspension was sparged with argon for 10 min and then heated to 95° C. for 4 h. After completion of the reaction, the mixture was cooled and diluted with water (100 ml) and extracted with ethyl acetate (2×100 ml). The organic layer was dried over anhydrous sodium sulfate and concentrated under reduced pressure. The residue was purified by silica gel chromatography to provide methyl 4-(5-((tert-butoxycarbonyl)amino)pyridin-2-yl)-1-methyl-1H-1,2,3-triazole-5-carboxylate.

Step 3: Methyl 4-(5-aminopyridin-2-yl)-1-methyl-1H-1,2,3-triazole-5-carboxylate hydrochloride salt To methyl 4-(5-((tert-butoxycarbonyl)amino)pyridin-2-yl)-1-methyl-1H-1,2,3-triazole-5-carboxylate (6 mmol), was added 4M HCl in dioxanes (14 mL) and the reaction was stirred vigorously at room temperature for 3 h. After completion of the reaction, the solution was concentrated in vacuo to provide methyl 4-(5-aminopyridin-2-yl)-1-methyl-1H-1,2,3-triazole-5-carboxylate hydrochloride salt.

Step 4: 1-methyl-4-(5-(methylsulfonamido)pyridin-2-yl)-1H-1,2,3-triazole-5-carboxylic acid (Intermediate 6)

Methyl 4-(5-aminopyridin-2-yl)-1-methyl-1H-1,2,3-triazole-5-carboxylate hydrochloride salt (6 mmol), was suspended in DCM (32 ml), and pyridine (5 ml). Methanesulfonyl chloride (12 mmol) was added dropwise over 15 min and the reaction was stirred at room temperature for 16 h. After complete conversion to the desired sulfonamide, the reaction was concentrated in vacuo and dissolved in THF (35 ml). 1 M aqueous solution of sodium hydroxide (24 ml) was then added and the reaction was stirred vigorously for 30 min. The reaction was neutralized by the addition of an aqueous 6 N solution hydrochloric acid (1 ml) to pH ~5. THF was removed by rotary evaporation, and the resulting precipitate collected by vacuum filtration. The collected material was washed with ethyl ether (50 mL) and water (50 mL) and dried in vacuo to afford 1-methyl-4-(5-(methylsulfonamido)pyridin-2-yl)-1H-1,2,3-triazole-5-carboxylic acid (Intermediate 6). LCMS M/Z (M+1)=298.1

Example 9: Preparation of 4-(5-bromo-6-methylpyridin-2-yl)-1-methyl-1H-1,2,3-triazole-5-carboxylic acid (Intermediate 7)

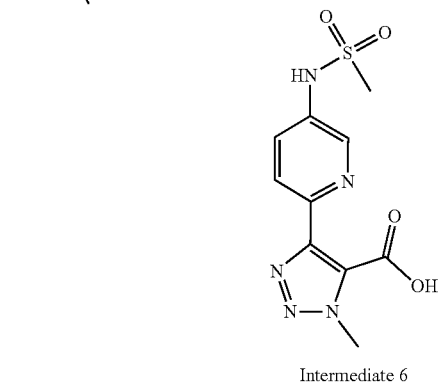

Intermediate 6

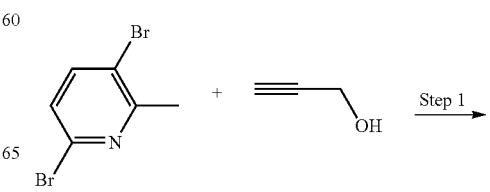

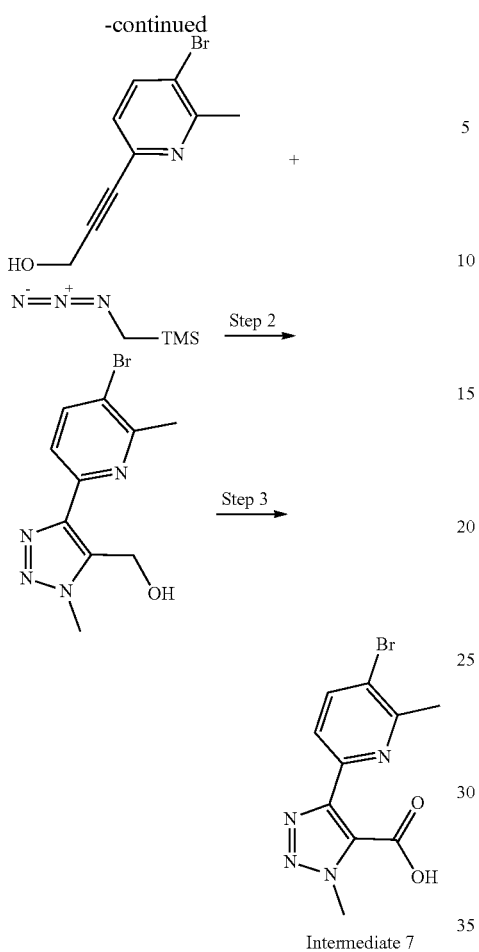

Intermediate 7

Intermediate 7 was generally prepared according to Scheme B1.

Step 1: 3-(5-bromo-6-methylpyridin-2-yl)prop-2-yn-1-ol

To a mixture of 3,6-dibromo-2-methylpyridine (398.6 mmol) in THF (300 mL) was added propargyl alcohol (418.4 mmol), triethylamine (1.19 mol), cuprous iodide (19.9 mmol) and bis(triphenylphosphine) palladium(II) chloride (11.9 mmol) under nitrogen atmosphere. The reaction mixture was stirred at room temperature for 16 h. After completion of the reaction, the mixture was diluted with water (500 ml) and the solid was filtered. The filtrate was extracted with ethyl acetate (3×300 ml). The organic layer was dried over anhydrous sodium sulfate and concentrated under reduced pressure. The residue was added into DCM (300 ml) and stirred for 5 min and then filtered. The filter cake was washed with ether (3×200 ml) and concentrated under reduced pressure to afford 3-(5-bromo-6-methylpyridin-2-yl)prop-2-yn-1-ol.

Step 2: (4-(5-bromo-6-methylpyridin-2-yl)-1-methyl-1H-1,2,3-triazol-5-yl)methanol To a mixture of 3-(5-bromo-6-methylpyridin-2-yl)prop-2-yn-1-ol (176.9 mmol) in THF (400 ml) was added azidomethyltrimethylsilane (619.3 mmol), cuprous iodide (17.9 mmol), tetrabutylammonium iodide (17.7 mmol) and pentamethylcyclopentadienylbis(triphenyl phosphine)ruthenium(II) chloride (8.84 mmol) under nitrogen atmosphere. The reaction mixture was stirred at 40° C. for 16 h. After concentration, the residue was dissolved in tetrahydrofuran (500 ml) at 0° C. and then tetrabutylammonium fluoride (1 M in THF, 212 mmol) was added. The reaction mixture was stirred at 0° C. for 1 h. After completion of the reaction, the mixture was quenched with saturated solution of sodium bicarbonate (500 ml) and extracted with DCM (4×300 ml). The organic layer was dried over anhydrous sodium sulfate and concentrated under reduced pressure. The residue was purified by silica gel chromatography to provide (4-(5-bromo-6-methylpyridin-2-yl)-1-methyl-1H-1,2,3-triazol-5-yl)methanol.

Step 3: 4-(5-bromo-6-methylpyridin-2-yl)-1-methyl-1H-1,2,3-triazole-5-carboxylic acid (Intermediate 7)

To a mixture of (4-(5-bromo-6-methylpyridin-2-yl)-1-methyl-1H-1,2,3-triazol-5-yl)methanol (105.9 mmol) in acetonitrile (300 ml) and water (225 ml) was added TEMPO (31.8 mmol), sodium phosphate monobasic (264.9 mmol) and sodium chlorite (317.9 mmol). The reaction mixture was stirred at 50° C. for 16 h. After completion of the reaction, the solid was filtered and washed with DCM (2×100 ml). The filter cake was dried under reduced pressure to provide (5-bromo-6-methylpyridin-2-yl)-1-methyl-1H-1,2,3-triazole-5-carboxylic acid (Intermediate 7). LCMS M/Z (M+1)= 297.2.

Example 10: Preparation of 4-(5-bromo-3-fluoropyridin-2-yl)-1-methyl-1H-1,2,3-triazole-5-carboxylic acid (Intermediate 8)

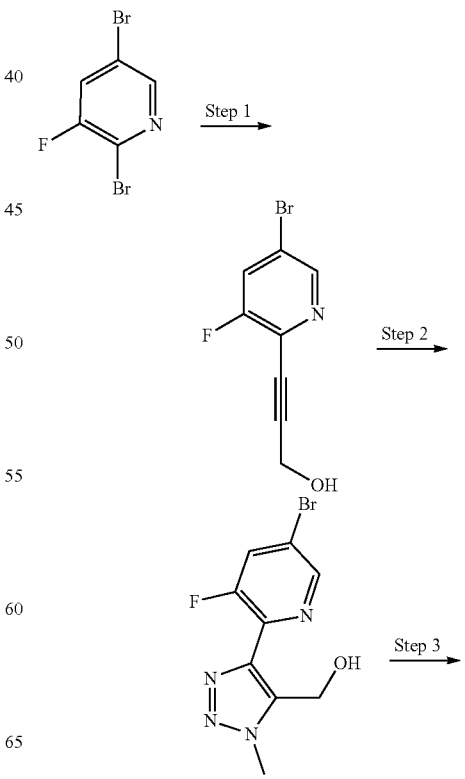

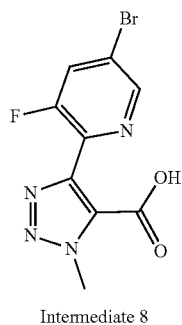

Intermediate 8

Intermediate 8 was generally prepared according to Scheme B1.

Step 1: 3-(5-bromo-3-fluoro-2-pyridyl)prop-2-yn-1-ol

To a mixture of 2,5-dibromo-3-fluoro-pyridine (40 mmol) in tetrahydrofuran (50 ml) was added prop-2-yn-1-ol (43 mmol), triethylamine (130 mmol), cuprous iodide (1.2 mmol) and bis(triphenylphosphine) palladium(II) chloride (2.0 mmol) under nitrogen atmosphere. The reaction mixture was heated to 70° C. for 4 h. After completion of the reaction, the mixture was cooled and filtered through a pad of celite. The filtrate was diluted with water (50 ml) and extracted with ethyl acetate (3×500 ml). The organic layer was dried over anhydrous sodium sulfate and concentrated under reduced pressure. The residue was purified by column chromatography to provide 3-(5-bromo-3-fluoro-2-pyridyl)prop-2-yn-1-ol.

Step 2: (4-(5-bromo-3-fluoropyridin-2-yl)-1-methyl-1H-1,2,3-triazol-5-yl)methanol Cuprous iodide (0.87 mmol) and tetrabutylammonium iodide (0.87 mmol) were dissolved in THF (40 mL) and stirred for 20 min to yield a solution. Then, 3-(5-bromo-3-fluoro-2-pyridyl)prop-2-yn-1-ol (8.7 mmol) was added and the reaction was sparged with argon for 2 min. Pentamethylcyclopentadienylbis(triphenylphosphine)ruthenium(II) chloride (0.45 mmol) and azidomethyltrimethylsilane (22 mmol) were added and the reaction was sealed and heated to 80° C. for 16 h. The reaction mixture was concentrated in vacuo, and then dissolved in THF (50 ml). Tetrabutylammonium fluoride (9 ml of a 1M solution in THF) was added dropwise at room temperature and stirred for 1 h. The mixture was quenched with saturated solution of sodium bicarbonate (100 ml) and extracted with DCM (3×100 ml). The organic layer was dried over anhydrous sodium sulfate and concentrated under reduced pressure. The residue was purified by silica gel chromatography to provide (4-(5-bromo-3-fluoropyridin-2-yl)-1-methyl-1H-1,2,3-triazol-5-yl)methanol.

Step 3: 4-(5-bromo-3-fluoropyridin-2-yl)-1-methyl-1H-1,2,3-triazole-5-carboxylic acid (Intermediate 8)

(4-(5-bromo-3-fluoropyridin-2-yl)-1-methyl-1H-1,2,3-triazol-5-yl)methanol (4.9 mmol), TEMPO (1 mmol), and sodium phosphate monobasic (12.2 mmol) were suspended in acetonitrile (50 ml), and water (40 ml). The solution was heated to 45° C. Then, 10 ml of a 1M aqueous solution of sodium chlorite and a separate solution of sodium hypochlorite (10 ml of 0.01 M solution in water), were added simultaneously over 1 h. The reaction was stirred at 45° C. for 16 h. The mixture was cooled to room temperature and concentrated to remove acetonitrile. The product was filtered and the filter cake was washed with water (2×50 ml) and diethyl ether (50 ml) to provide 4-(5-bromo-3-fluoropyridin-2-yl)-1-methyl-1H-1,2,3-triazole-5-carboxylic acid (Intermediate 8). LCMS M/Z (M+1)=301.0.

Example 11: Preparation of 4-(5-bromo-6-methylpyridin-2-yl)-1-(cyanomethyl)-1H-1,2,3-triazole-5-carboxylic acid (Intermediate 9)

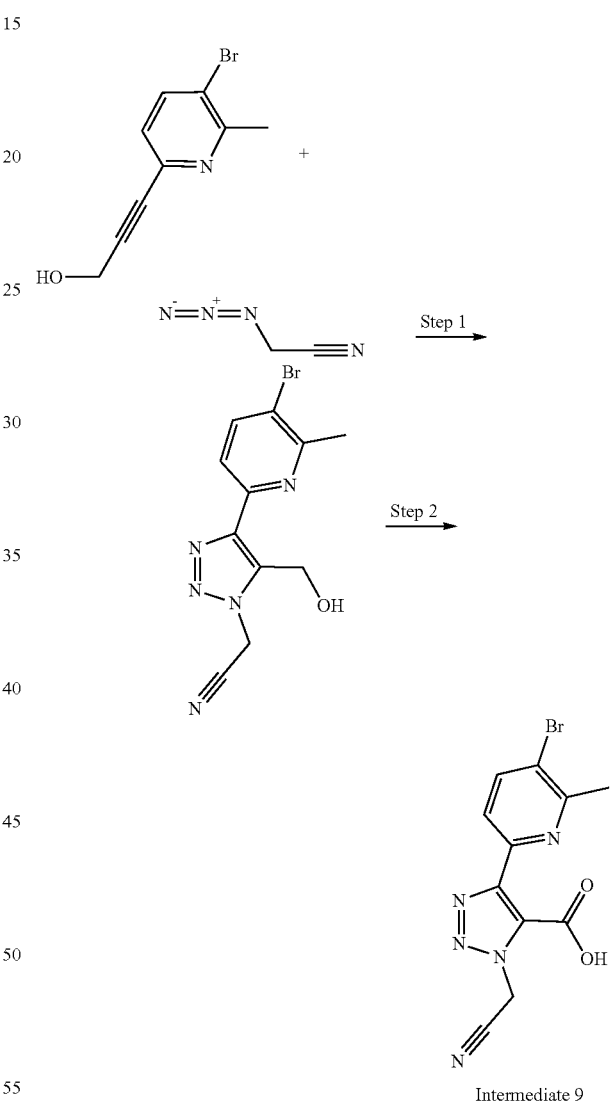

Intermediate 9

Intermediate 9 was generally prepared according to Scheme B1.

Step 1: 2-(4-(5-bromo-6-methylpyridin-2-yl)-5-(hydroxymethyl)-1H-1,2,3-triazol-1-yl)acetonitrile To a mixture of 3-(5-bromo-6-methylpyridin-2-yl)prop-2-yn-1-ol (4.4 mmol) in THF (20 ml) was added 2-azidoacetonitrile (5.3 mmol), cuprous iodide (0.44 mmol), tetrabutylammonium iodide (0.44 mmol) and pentamethylcyclopentadienylbis(triphenylphosphine)ruthenium(II) chloride (0.22 mmol) under nitrogen atmosphere. The reaction mixture was stirred at room temperature for 16 h. The reaction was filtered through a silica plug and rinsed with ethyl acetate, and concentrated. The residue was purified by silica gel chromatography to provide 2-(4-(5-bromo-6-methylpyridin-2-yl)-5-(hydroxymethyl)-1H-1,2,3-triazol-1-yl)acetonitrile.

Step 2: 4-(5-bromo-6-methylpyridin-2-yl)-1-(cyanomethyl)-1H-1,2,3-triazole-5-carboxylic acid (Intermediate 9)

Following the procedure described in Example 15 for the synthesis of 4-(5-bromo-6-methylpyridin-2-yl)-1-methyl-1H-1,2,3-triazole-5-carboxylic acid (Intermediate 7), using 2-(4-(5-bromo-6-methylpyridin-2-yl)-5-(hydroxymethyl)-1H-1,2,3-triazol-1-yl)acetonitrile in place of (4-(5-bromo-6-methylpyridin-2-yl)-1-methyl-1H-1,2,3-triazol-5-yl)methanol, 4-(5-bromo-6-methyl pyridin-2-yl)-1-(cyanomethyl)-1H-1,2,3-triazole-5-carboxylic acid (Intermediate 9) was obtained. LCMS M/Z (M+1)=322.0.

Example 12: Preparation of 1-methyl-4-(6-methyl-5-(methylsulfonamido)pyridin-2-yl)-1H-1,2,3-triazole-5-carboxylic acid (Intermediate 10)

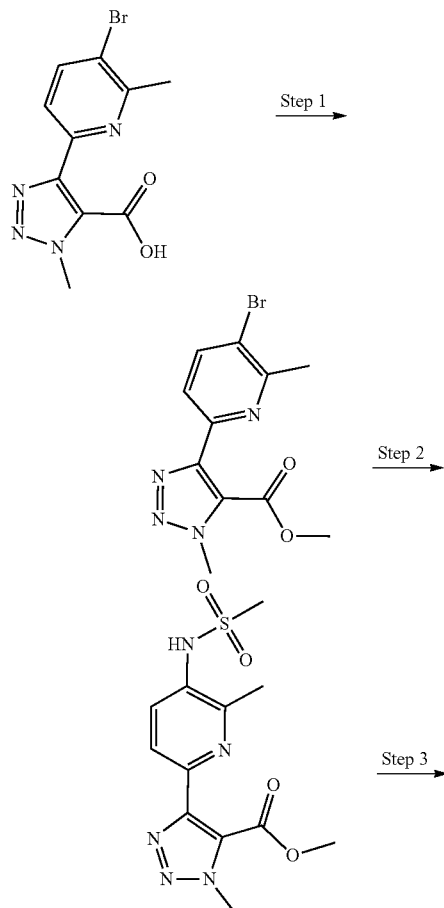

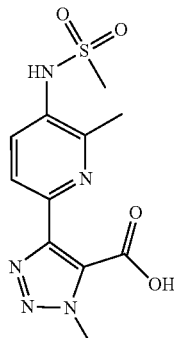

Intermediate 10

Intermediate 10 was generally prepared according to Scheme B2a.

Step 1: Methyl 4-(5-bromo-6-methylpyridin-2-yl)-1-methyl-1H-1,2,3-triazole-5-carboxylate 4-(5-Bromo-6-methylpyridin-2-yl)-1-methyl-1H-1,2,3-triazole-5-carboxylic acid (Intermediate 7) (0.02 mol), was dissolved in MeOH and cooled in an ice bath for 10 min. Thionyl chloride (0.07 mol) was added dropwise. The reaction was warmed to room temperature, and then heated to 75° C. for 5 h. The reaction was concentrated and dissolved in ethyl acetate (100 ml) and aqueous saturated sodium bicarbonate solution (50 ml). The organic layer was separated and the aqueous layer was extracted with ethyl acetate (2×50 ml). The combined organic layer was dried over anhydrous sodium sulfate and concentrated under reduced pressure. The residue was purified by silica gel chromatography to provide methyl 4-(5-bromo-6-methylpyridin-2-yl)-1-methyl-1H-1,2,3-triazole-5-carboxylate.

Step 2: Methyl 1-methyl-4-(6-methyl-5-(methylsulfonamido)pyridin-2-yl)-1H-1,2,3-triazole-5-carboxylate A 150 ml screw cap pressure vessel was charged with methyl 4-(5-bromo-6-methylpyridin-2-yl)-1-methyl-1H-1,2,3-triazole-5-carboxylate (1.61 mmol), methanesulphonamide (4.82 mmol), allylpalladium chloride dimer (0.4 mmol), 2-di-tert-butylphosphino-2',4',6'-triisopropylbiphenyl (1.61 mmol), potassium carbonate (4.02 mmol), and tetrahydrofuran (50 ml). The mixture was degassed for 5 min, sealed under an atmosphere of argon and heated to 80° C. with magnetic stirring for 10 h. The crude mixture was cooled to room temperature, precipitated product was redissolved with ethyl acetate and methanol. The mixture was filtered through celite, and volatiles removed in vacuo. The crude material was purified by silica gel column chromatography to give methyl 1-methyl-4-(6-methyl-5-(methylsulfonamido)pyridin-2-yl)-1H-1,2,3-triazole-5-carboxylate.

Step 3: 1-Methyl-4-(6-methyl-5-(methylsulfonamido)pyridin-2-yl)-1H-1,2,3-triazole-5-carboxylic acid (Intermediate 10)

A 200 ml round bottom flask was charged with methyl 1-methyl-4-(6-methyl-5-(methylsulfonamido)pyridin-2-yl)-1H-1,2,3-triazole-5-carboxylate (1.28 mmol) and dissolved in tetrahydrofuran (42 ml). 2 M aqueous sodium hydroxide (2.55 mmol) was then added and allowed to stir for 30 min followed by the addition of a 6 N aqueous solution of hydrochloric acid (2.55 mmol) to pH ~5. Tetrahydrofuran was removed by rotary evaporation and the resulting precipitate collected by vacuum filtration. The collected material was washed with ethyl ether (50 ml) and water (50 ml) and dried in vacuo to afford 1-methyl-4-(6-methyl-5-(methylsulfonamido)pyridin-2-yl)-1H-1,2,3-triazole-5-carboxylic acid (Intermediate 10). LCMS M/Z (M+1)=312.1.

Example 13: Preparation of 1-methyl-4-(6-methyl-5-(N-methylmethylsulfonamido)pyridin-2-yl)-1H-1,2,3-triazole-5-carboxylic acid (Intermediate 11)

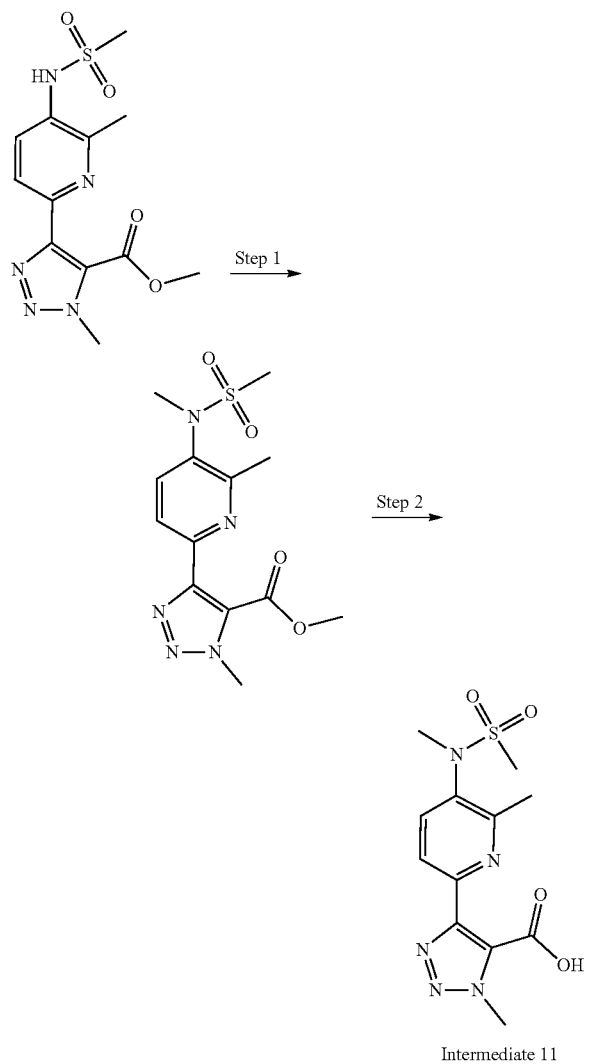

Intermediate 11

Intermediate 11 was generally prepared according to Scheme B2a.

Step 1: Methyl 1-methyl-4-(6-methyl-5-(N-methylmethylsulfonamido)pyridin-2-yl)-1H-1,2,3-triazole-5-carboxylate A 50 mL RBF was charged with methyl 1-methyl-4-(6-methyl-5-(methylsulfonamido)pyridin-2-yl)-1H-1,2,3-triazole-5-carboxylate (0.965 mmol) (Example 12, Step 2), cesium carbonate (1.06 mmol) and acetonitrile (5.0 mL). Iodomethane (0.97 mmol) was added and the reaction was stirred at room temperature for 18 h. The reaction was diluted with DCM, filtered over celite and concentrated. The crude product was purified by silica gel chromatography to provide methyl 1-methyl-4-(6-methyl-5-(N-methylmethylsulfonamido) pyridin-2-yl)-1H-1,2,3-triazole-5-carboxylate.

Step 2: 1-Methyl-4-(6-methyl-5-(N-methylmethylsulfonamido)pyridin-2-yl)-1H-1,2,3-triazole-5-carboxylic acid (Intermediate 11)

Following the procedure described in Example 12 (Step 3) for the synthesis of 1-methyl-4-(6-methyl-5-(methylsulfonamido)pyridin-2-yl)-1H-1,2,3-triazole-5-carboxylic acid (Intermediate 10), using methyl 1-methyl-4-(6-methyl-5-(N-methylmethylsulfonamido)pyridin-2-yl)-1H-1,2,3-triazole-5-carboxylate in place of methyl 1-methyl-4-(6-methyl-5-(methylsulfonamido)pyridin-2-yl)-1H-1,2,3-triazole-5-carboxylate, 1-methyl-4-(6-methyl-5-(N-methylmethylsulfonamido)pyridin-2-yl)-1H-1,2,3-triazole-5-carboxylic acid (Intermediate 11) was obtained.

Example 14: N-(6-bromo-2-methoxy-3-pyridyl)methanesulfonamide

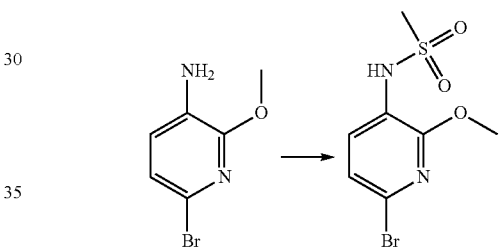

6-bromo-2-methoxy-pyridin-3-amine (5.4 mmol) was dissolved in 25 ml DCM and 5 ml pyridine. Methanesulfonyl chloride (16 mmol) was added dropwise and the reaction was stirred at room temperature overnight. The reaction was worked up with aqueous saturated sodium bicarbonate and the layers were separated, dried over Na2SO4, concentrated, and purified via column chromatography to provide the title compound.

Example 15: N-(6-bromo-2-fluoropyridin-3-yl)-N-(methylsulfonyl)methanesulfonamide

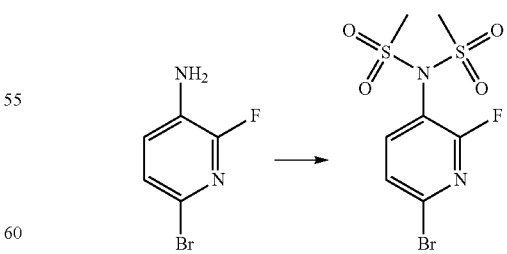

6-bromo-2-fluoropyridin-3-amine (5.2 mmol) was dissolved in DCM (25 ml). Triethylamine (42 mmol) was added and the solution was submerged in an ice batch and stirred for 15 min. Methanesulfonyl chloride (16 mmol) was added dropwise over 15 min. The ice bath was removed, and the solution was allowed to warm to room temperature. After 2 h, the mixture was diluted with water (10 ml) and extracted with dichloromethane (2×25 ml). The organic layer was dried over anhydrous sodium sulfate and concentrated under reduced pressure. The residue was purified by silica gel chromatography to provide N-(6-bromo-2-fluoropyridin-3-yl)-N-(methylsulfonyl)methanesulfonamide.

Example 16: N-(6-bromo-2-chloropyridin-3-yl)-N-(methylsulfonyl)methanesulfonamide

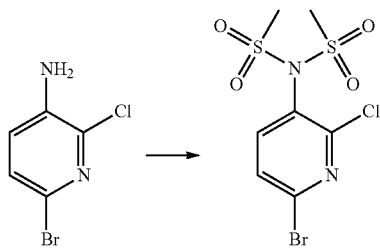 [SMILES: Nc1ccc(Br)nc1Cl ; CS(=O)(=O)N(c1ccc(Br)nc1Cl)S(C)(=O)=O]

Following the synthesis described in Example 14 for N-(6-bromo-2-fluoropyridin-3-yl)-N-(methylsulfonyl)methanesulfonamide, using 6-bromo-2-chloropyridin-3-amine (1.04 mmol) in place of 6-bromo-2-fluoropyridin-3-amine, N-(6-bromo-2-chloropyridin-3-yl)-N-(methylsulfonyl)methanesulfonamide was prepared (Scheme A, Step 1b).

Example 17: N-(6-bromo-2-methylpyridin-3-yl)methanesulfonamide

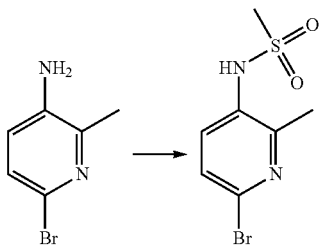

Following the synthesis described in Example 13 for N-(6-bromo-2-methoxy-3-pyridyl)methanesulfonamide, using 6-bromopyridin-3-amine (8.6 mmol) in place of 6-bromo-2-methoxypyridin-3-amine, N-(6-bromo-2-methylpyridin-3-yl)methanesulfonamide was prepared (Scheme A, Step 1b).

Example 18: N-(6-bromopyridin-3-yl)methanesulfonamide

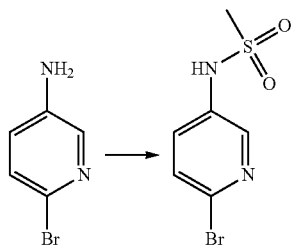

Following the synthesis described in Example 13 for N-(6-bromo-2-methoxy-3-pyridyl)methanesulfonamide, 6-bromo-2-methylpyridin-3-amine (5.4 mmol) in place of 6-bromo-2-methoxypyridin-3-amine, N-(6-bromopyridin-3-yl)methanesulfonamide was prepared (Scheme A, Step 1b).

Example 19: Preparation of Compounds 1 to 7

Compounds 1 to 7 were generally synthesized according Scheme A, Step 2. For example, ((R)-1-phenylethyl (4-(6-methoxy-5-(methylsulfonamido)pyridin-2-yl)-1-methyl-1H-1,2,3-triazol-5-yl)carbamate (Compound 1) was prepared as follows.

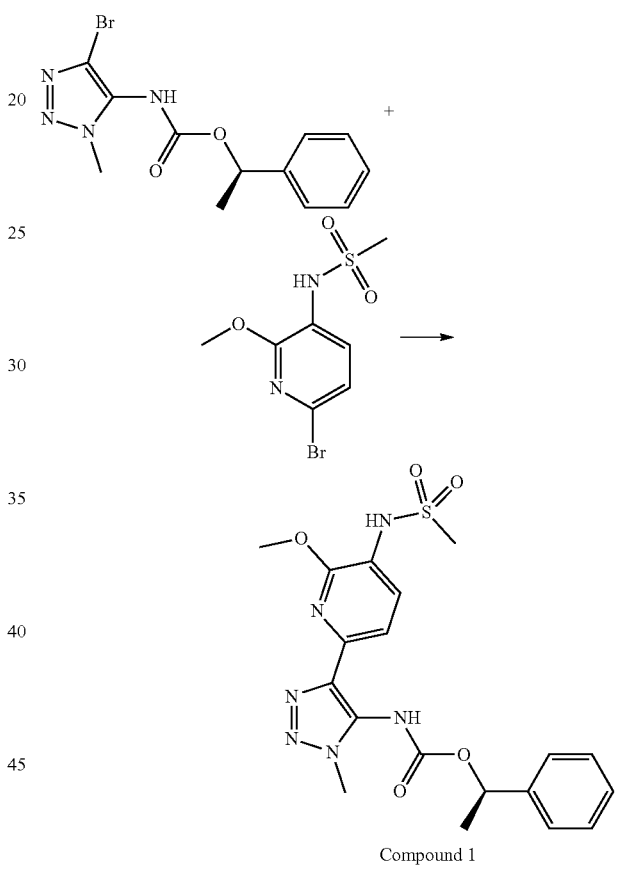

Compound 1

N-(6-bromo-2-methoxy-3-pyridyl)methanesulfonamide (Example 13) (1 mmol) was mixed with Bis(pinacolato)diboron (2 mmol), potassium acetate (3 mmol), and $PdCl_2$(dppf) (0.1 mmol). The mixture was suspended in dioxane (6 ml), and sparged with argon gas for 5 min. The reaction was sealed and heated to 95° C. for 2 h. After complete borylation, the reaction was cooled and (R)-1-phenylethyl (4-bromo-1-methyl-1H-1,2,3-triazol-5-yl)carbamate (Intermediate 1) (0.5 mmol), potassium carbonate (3 mmol), and XPhos Pd G2 precatalyst (0.1 mmol), and water (0.5 mL) were added. The reaction mixture was sparged with argon for 5 minutes, sealed, and heated to 95° C. for 4 h. The mixture was cooled and diluted with water (10 ml) and was extracted with ethyl acetate (2×15 ml). The organic layer was dried over anhydrous sodium sulfate and concentrated under reduced pressure. The residue was purified by silica gel chromatography to provide ((R)-1-phenylethyl (4-(6-methoxy-5-(methylsulfonamido)pyridin-2-yl)-1-methyl-1H-1,2,3-triazol-5-yl)carbamate (Compound 1). (MS (m/z) 447.1 [M+H]$^+$). 1H NMR (400 MHz, Methanol-d4) δ 7.79 (d, J=8.0 Hz, 1H), 7.60 (d, J=8.0 Hz, 1H), 7.39 (s, 5H), 5.86 (s, 1H), 3.97 (s, 3H), 3.89 (s, 3H), 2.99 (s, 3H), 1.45 (s, 3H).

Compounds 2-7 (Table 1) were similarly prepared according to Scheme A, by reacting Intermediate 1 (Example 3), Intermediate 2 (Example 4), Intermediate 3 (Example 5), or Intermediate 4 (Example 6) with a compound of Examples 14 to 16 following the general process described for Compound 1.

TABLE 1

Compounds prepared according to Scheme A

| Name | Structure | LCMS M/Z (M + 1) | NMR |
| --- | --- | --- | --- |
| Compound 1 (R)-1-phenylethyl (4-(6-methoxy-5-(methylsulfonamido)pyridin-2-yl)-1-methyl-1H-1,2,3-triazol-5-yl)carbamate | 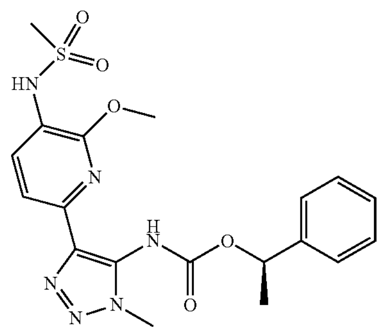 [SMILES: COc1nc(-c2nnn(C)c2NC(=O)O[C@H](C)c2ccccc2)ccc1NS(C)(=O)=O] | 447.1 | 1H NMR (400 MHz, Methanol-d4) δ 7.79 (d, J = 8.0 Hz, 1H), 7.60 (d, J = 8.0 Hz, 1H), 7.39 (s, 5H), 5.86 (s, 1H), 3.97 (s, 3H), 3.89 (s, 3H), 2.99 (s, 3H), 1.45 (s, 3H). |
| Compound 2 (R)-1-phenylethyl (4-(6-chloro-5-(methylsulfonamido)pyridin-2-yl)-1-methyl-1H-1,2,3-triazol-5-yl)carbamate | 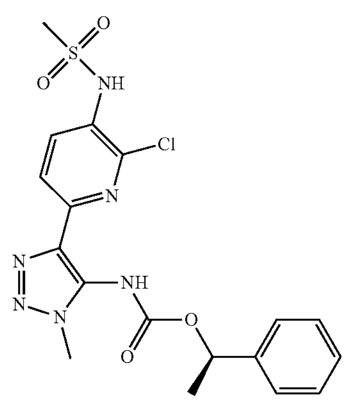 [SMILES: C[C@@H](OC(=O)Nc1c(-c2ccc(NS(C)(=O)=O)c(Cl)n2)nnn1C)c1ccccc1] | 451.0 | 1H NMR (400 MHz, Methanol-d4) δ 7.97 (d, J = 8.4 Hz, 1H), 7.92 (d, J = 8.3 Hz, 1H), 7.56-6.99 (m, 5H), 5.90-5.70 (m, 1H), 3.94 (s, 3H), 3.07 (s, 3H), 1.57 (s, 3H). |
| Compound 3 (R)-1-phenylethyl (4-(6-fluoro-5-(methylsulfonamido)pyridin-2-yl)-1-methyl-1H-1,2,3-triazol-5-yl)carbamate | | 435.1 | 1H NMR (400 MHz, Methanol-d4) δ 7.99 (t, J = 9.1 Hz, 1H), 7.83 (d, J = 8.3 Hz, 1H), 7.30 (d, J = 24.5 Hz, 5H), 5.91-5.71 (m, 1H), 3.92 (s, 3H), 3.07 (s, 3H), 1.57 (s, 3H). |

TABLE 1-continued

Compounds prepared according to Scheme A

| Name | Structure | LCMS M/Z (M + 1) | NMR |
|---|---|---|---|
| Compound 4 (R)-1-(2-chlorophenyl)ethyl (4-(6-methoxy-5-(methyl-sulfonamido)pyridin-2-yl)-1-methyl-1H-1,2,3-triazol-5-yl)carbamate | 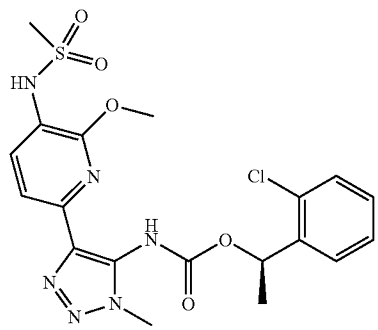 [SMILES: COc1nc(-c2nnn(C)c2NC(=O)O[C@H](C)c2ccccc2Cl)ccc1NS(C)(=O)=O] | 481.1 | 1H NMR (400 MHz, Methanol-d4) δ 7.78 (d, J = 8.1 Hz, 1H), 7.59 (d, J = 8.1 Hz, 1H), 7.37 (s, 4H), 6.19 (s, 1H), 4.15-3.64 (m, 6H), 2.98 (s, 3H), 1.56 (s, 3H). |
| Compound 5 (R)-1-(2-chlorophenyl)ethyl (4-(6-fluoro-5-(methyl-sulfonamido)pyridin-2-yl)-1-methyl-1H-1,2,3-triazol-5-yl)carbamate | 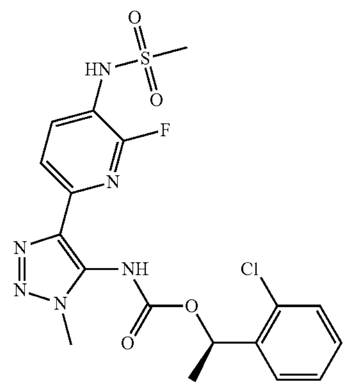 [SMILES: C[C@@H](OC(=O)Nc1c(-c2ccc(NS(C)(=O)=O)c(F)n2)nnn1C)c1ccccc1Cl] | 469.0 | 1H NMR (400 MHz, Methanol-d4) δ 8.01 (t, J = 9.1 Hz, 1H), 7.86 (d, J = 8.3 Hz, 1H), 7.76-7.06 (m, 4H), 6.16 (q, J = 6.5 Hz, 1H), 3.94 (s, 3H), 3.07 (s, 3H), 1.57 (s, 3H). |
| Compound 6 (S)-2,2-difluoro-1-phenylethyl (4-(6-fluoro-5-(methylsulfonamido)pyridin-2-yl)-1-methyl-1H-1,2,3-triazol-5-yl)carbamate | 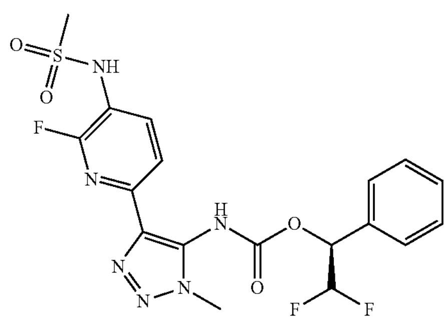 [SMILES: Cn1nnc(-c2ccc(NS(C)(=O)=O)c(F)n2)c1NC(=O)O[C@@H](c1ccccc1)C(F)F] | 471.1 | 1H NMR (400 MHz, Methanol-d4) δ 8.02 (t, J = 9.1 Hz, 1H), 7.88 (dd, J = 8.2, 1.2 Hz, 1H), 7.77-6.85 (m, 5H), 6.58-5.64 (m, 2H), 3.96 (s, 3H), 3.08 (s, 3H). |
| Compound 7 (S)-2,2-difluoro-1-phenylethyl (4-(6-methoxy-5-(methylsulfonamido)pyridin-2-yl)-1-methyl-1H-1,2,3-triazol-5-yl)carbamate | 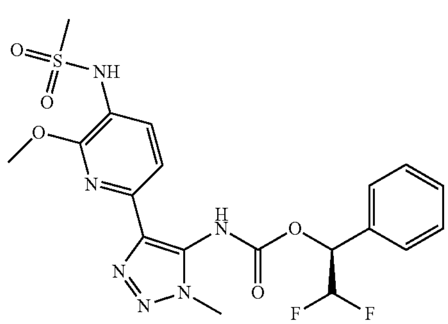 [SMILES: COc1nc(-c2nnn(C)c2NC(=O)O[C@@H](c2ccccc2)C(F)F)ccc1NS(C)(=O)=O] | 483.1 | 1H NMR (400 MHz, Methanol-d4) δ 7.80 (d, J = 8.0 Hz, 1H), 7.74-6.79 (m, 6H), 6.45-5.59 (m, 2H), 4.20-3.55 (m, 6H), 2.99 (s, 3H). |

Example 20: Preparation of Compounds 8 to 12

Compounds 8 to 12 were generally synthesized according to Scheme A. For example, ((R)-1-phenylethyl (1-methyl-4-(5-(methylsulfonamido)pyridin-2-yl)-1H-1,2,3-triazol-5-yl) carbamate (Compound 8) was prepared as follows.

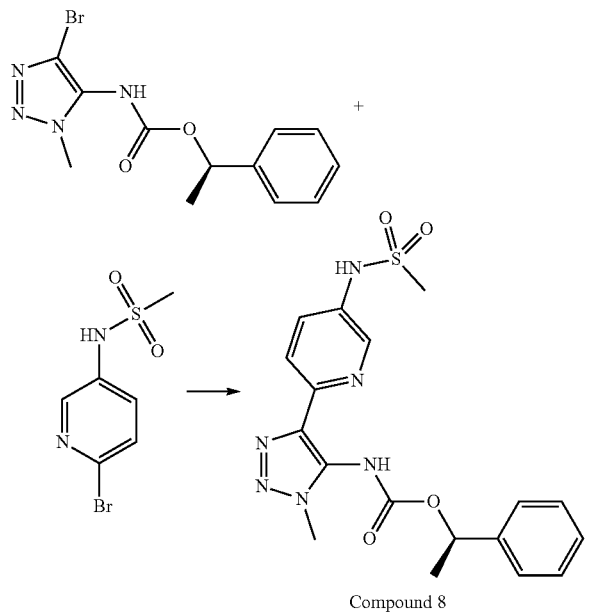

Compound 8

In a pressure tube, to a solution of N-(6-bromopyridin-3-yl)methanesulfonamide (0.81 mmol) (Example 18) in dioxane (2 ml), hexamethylditin (1.62 mmol) was added at room temperature. The resulting solution was degassed with $N_2$ gas. Then $Pd(PPh_3)_4$ (0.081 mmol) was added and the mixture was heated to 100° C. for 3 h. The reaction mixture was used directly for the next step. (R)-1-phenylethyl (4-bromo-1-methyl-1H-1,2,3-triazol-5-yl)carbamate (Intermediate 1, Example 3) (0.58 mmol) and Pd(XPhos)G2 precatalyst (0.145 mmol) were added. The reaction was degassed again with argon and heated back to 100° C. for 1 h. The reaction mixture was cooled to room temperature and filtered from Celite. The filtrate was concentrated and purified by silica gel column chromatography followed by prep-HPLC with Gilson prep HPLC (Gemini column, 30-90% $CH_3CN$ in H2O with 0.1% TFA) to give the title compound. (MS (m/z) 416.9 [M+H]$^+$). 1H NMR (400 MHz, Methanol-d4) δ 8.48 (s, 1H), 7.89 (s, 1H), 7.78 (d, 1H), 7.51-7.21 (m, 5H), 5.83 (q, 1H), 3.95 (s, 3H) 3.06 (s, 3H), 1.68-1.48 (m, 3H).

Compounds 9-12 (Table 2) were similarly prepared according to Scheme 3 by reacting Intermediate 1 (Example 3), Intermediate 2 (Example 4), or Intermediate 3 (Example 5) with a compound of Example 17 or 18 following the general process described for Compound 8.

TABLE 2

Compounds prepared according to Scheme A

| Name | Structure | LCMS M/Z (M + 1) | NMR |
|---|---|---|---|
| Compound 8 (R)-1-phenylethyl (1-methyl-4-(5-(methylsulfonamido)pyridin-2-yl)-1H-1,2,3-triazol-5-yl)carbamate | | 416.9 | 1H NMR (400 MHz, Methanol-d4) δ 8.48 (s, 1H), 7.89 (s, 1H), 7.78 (d, 1H), 7.51-7.21 (m, 5H), 5.83 (q, 1H), 3.95 (s, 3H) 3.06 (s, 3H), 1.68-1.48 (m, 3H). |
| Compound 9 (R)-1-phenylethyl (1-methyl-4-(6-methyl-5-(methylsulfonamido)pyridin-2-yl)-1H-1,2,3-triazol-5-yl)carbamate | 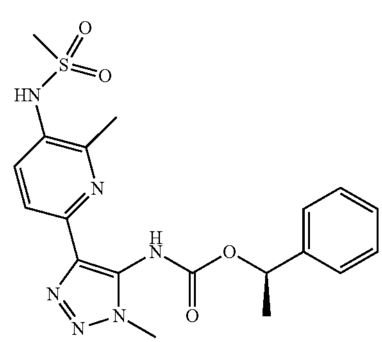 [SMILES: Cc1nc(-c2nnn(C)c2NC(=O)O[C@H](C)c2ccccc2)ccc1NS(C)(=O)=O] | 431.2 | 1H NMR (400 MHz, Methanol-d4) δ 7.95 (d, J = 8.5 Hz, 1H), 7.73 (d, J = 8.5 Hz, 1H), 7.56-6.99 (m, 5H), 5.80 (q, J = 6.6 Hz, 1H), 3.96 (s, 3H), 3.07 (s, 3H), 2.60 (s, 3H), 1.55 (s, 3H). |

TABLE 2-continued

Compounds prepared according to Scheme A

| Name | Structure | LCMS M/Z (M + 1) | NMR |
| --- | --- | --- | --- |
| Compound 10 (R)-1-(2-chlorophenyl) ethyl (1-methyl-4-(5-(methylsulfonamido) pyridin-2-yl)-1H-1,2,3-triazol-5-yl)carbamate | 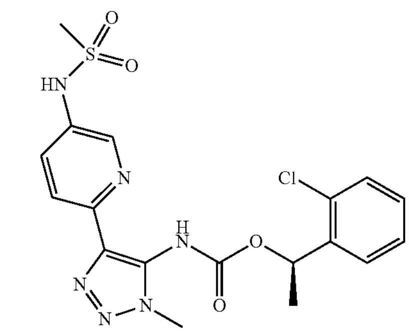 [SMILES: C[C@@H](OC(=O)Nc1c(-c2ccc(NS(C)(=O)=O)cn2)nnn1C)c1ccccc1Cl] | 450.1 | 1H NMR (400 MHz, Methanol-d4) δ 8.50 (s, 1H), 7.92 (s, 1H), 7.82-7.08 (m, 5H), 6.16 (q, 1H), 3.98 (s, 3H), 3.05 (s, 3H), 1.58 (s, 5H). |
| Compound 11 (R)-1-(2-chlorophenyl) ethyl (1-methyl-4-(6-methyl-5-(methyl-sulfonamido)pyridin-2-yl)-1H-1,2,3-triazol-5-yl)carbamate | 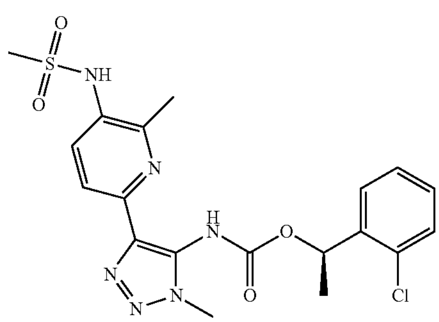 [SMILES: Cc1nc(-c2nnn(C)c2NC(=O)O[C@H](C)c2ccccc2Cl)ccc1NS(C)(=O)=O] | 465.1 | 1H NMR (400 MHz, Methanol-d4) δ 7.79 (s, 2H), 7.66-7.12 (m, 4H), 6.24-6.13 (m, 1H), 4.00 (s, 3H), 3.04 (s, 3H), 2.57 (s, 3H), 1.74-1.39 (m, 3H). |
| Compound 12 (R)-1-(2-chlorophenyl) ethyl (4-(6-methyl-5-(methylsulfonamido) pyridin-2-yl)-1-propyl-1H-1,2,3-triazol-5-yl) carbamate | 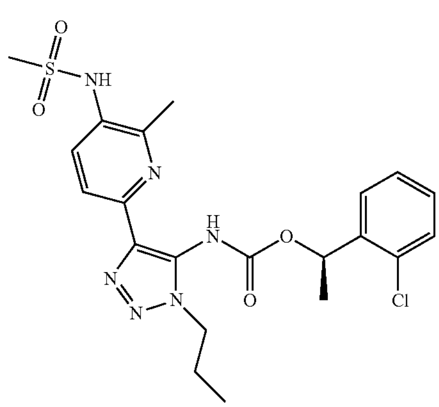 [SMILES: CCCn1nnc(-c2ccc(NS(C)(=O)=O)c(C)n2)c1NC(=O)O[C@H](C)c1ccccc1Cl] | 493.2 | 1H NMR (400 MHz, Methanol-d4) δ 7.90-7.73 (m, 2H), 7.31 (d, J = 38.5 Hz, 4H), 6.22-6.05 (m, 1H), 4.29 (t, J = 7.1 Hz, 2H), 3.04 (s, 3H), 2.54 (s, 3H), 2.03-1.87 (m, 2H), 1.56 (s, 3H), 0.94 (t, J = 7.4 Hz, 3H). |

Example 21: Preparation of (S)-2,2-difluoro-1-phenylethyl(4-(5-((cyanomethyl)sulfonamido)pyridin-2-yl)-1-methyl-1H-1,2,3-triazol-5-yl)carbamate (Compound 13)

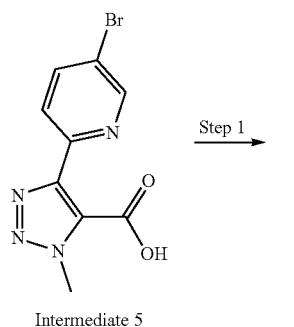

Intermediate 5

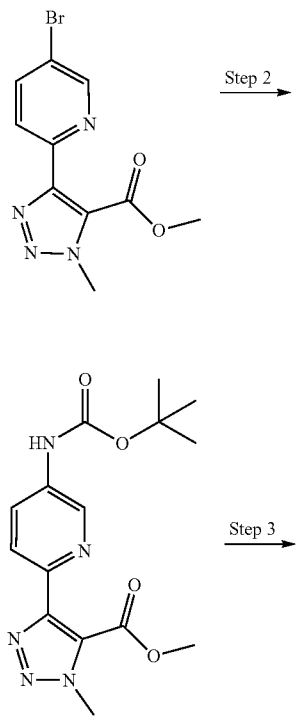

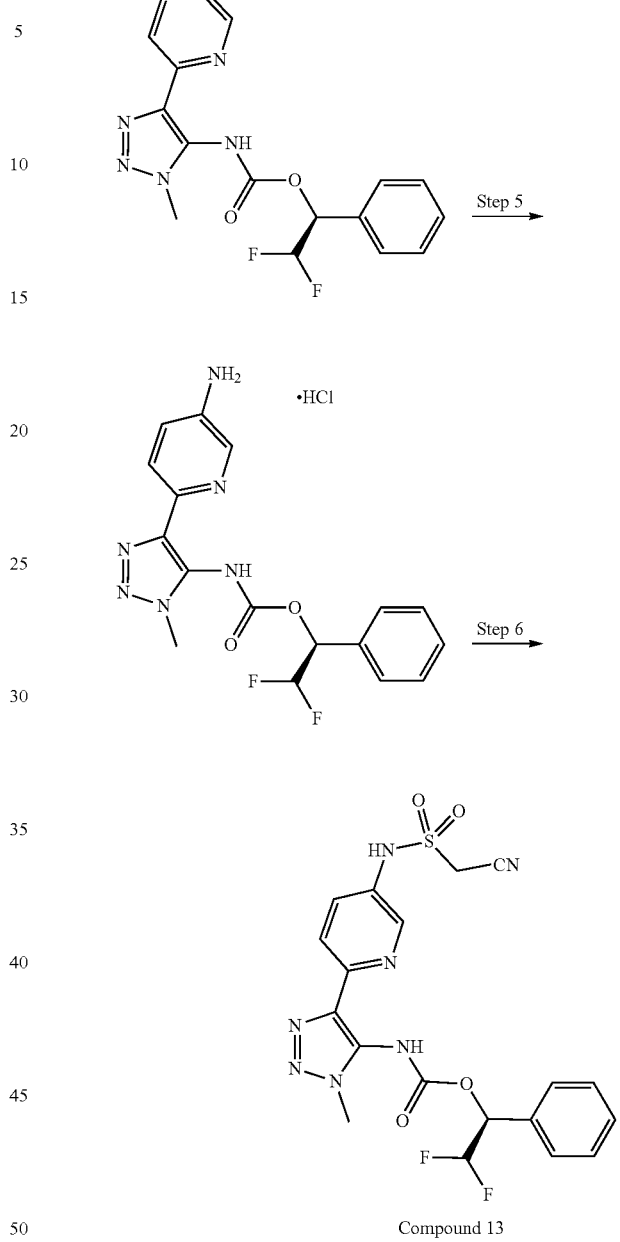

Compound 13

Step 1: methyl 4-(5-bromopyridin-2-yl)-1-methyl-1H-1,2,3-triazole-5-carboxylate 4-(5-bromopyridin-2-yl)-1-methyl-1H-1,2,3-triazole-5-carboxylic acid (Intermediate 5) (14.1 mmol) was dissolved in 40 ml of methanol. The solution was cooled to 0° C. with an ice bath. Trimethylsilyldiazomethane (18.4 mmol) was added dropwise over 15 min. The ice bath was removed and the reaction was stirred for 5 h. The reaction was quenched by the addition of saturated aqueous sodium bicarbonate and extracted with ethyl acetate. The organic layer was dried over anhydrous sodium sulfate and concentrated under reduced pressure. The residue was purified by silica gel chromatography to provide methyl 4-(5-bromopyridin-2-yl)-1-methyl-1H-1,2,3-triazole-5-carboxylate.

Step 2: Methyl 4-(5-((tert-butoxycarbonyl)amino)pyridin-2-yl)-1-methyl-1H-1,2,3-triazole-5-carboxylate Methyl 4-(5-bromopyridin-2-yl)-1-methyl-1H-1,2,3-triazole-5-carboxylate (11.1 mmol), tert-butyl carbamate (33 mmol), cesium carbonate (33 mmol), and Xantphos Pd G3 precatalyst (1.1 mmol) were suspended in dioxane (50 ml). The suspension was sparged with argon for 10 min and then heated to 95° C. for 4 h. After completion of the reaction, the mixture was cooled and diluted with water (100 ml) and extracted with ethyl acetate (2×100 ml). The organic layer was dried over anhydrous sodium sulfate and concentrated under reduced pressure. The residue was purified by silica gel chromatography to provide methyl 4-(5-((tert-butoxycarbonyl)amino)pyridin-2-yl)-1-methyl-1H-1,2,3-triazole-5-carboxylate.

Step 3: 4-(5-((tert-butoxycarbonyl)amino)pyridin-2-yl)-1-methyl-1H-1,2,3-triazole-5-carboxylic acid Methyl 4-(5-((tert-butoxycarbonyl)amino)pyridin-2-yl)-1-methyl-1H-1,2,3-triazole-5-carboxylate (2.2 mmol) was dissolved in THF (20 ml). 2 M aqueous sodium hydroxide (4.5 mmol) was then added and the solution was stirred for 30 min. 6 N aqueous solution of hydrochloric acid (4.5 mmol) was added to adjust the pH ~5. THE was removed by rotary evaporation and the resulting precipitate collected by vacuum filtration. The collected material was washed with ethyl ether (50 ml) and water (50 ml) and dried in vacuo to afford 4-(5-((tert-butoxycarbonyl)amino)pyridin-2-yl)-1-methyl-1H-1,2,3-triazole-5-carboxylic acid.

Step 4: (S)-2,2-difluoro-1-phenylethyl (4-(5-((tert-butoxycarbonyl)amino)pyridin-2-yl)-1-methyl-1H-1,2,3-triazol-5-yl)carbamate To a flask charged with 4-(5-((tert-butoxycarbonyl)amino)pyridin-2-yl)-1-methyl-1H-1,2,3-triazole-5-carboxylic acid (0.31 mmol), 1-propanephosphonic acid cyclic anhydride (50% in DMF, 0.47 mmol), azidotrimethysilane (0.47 mmol) acid and THF (1.0 mL) was added triethylamine (0.65 mmol) dropwise. The reaction mixture was stirred at room temperature for 30 min. (S)-2,2-Difluoro-1-phenylethan-1-ol (0.47 mmol) was added and the flask was heated at 90° C. for 2 h. The reaction was cooled to room temperature, diluted with water, extracted with EtOAc (3×10 ml), washed with brine, dried over MgSO₄, filtered and concentrated. The residue was purified by silica gel chromatography to afford the title compound.

Step 5: (S)-2,2-difluoro-1-phenylethyl (4-(5-((tert-butoxycarbonyl)amino)pyridin-2-yl)-1-methyl-1H-1,2,3-triazol-5-yl)carbamate A solution of (S)-2,2-difluoro-1-phenylethyl (4-(5-((tert-butoxycarbonyl)amino)pyridin-2-yl)-1-methyl-1H-1,2,3-triazol-5-yl)carbamate (0.16 mmol) and 4M HCl in 1,4-dioxane (2.3 mL) was stirred for 18 h at room temperature. The reaction was concentrated to afford (S)-2,2-difluoro-1-phenylethyl (4-(5-((tert-butoxycarbonyl)amino)pyridin-2-yl)-1-methyl-1H-1,2,3-triazol-5-yl)carbamate, which was used in the next step without further purification.

Step 6: (S)-2,2-difluoro-1-phenylethyl (4-(5-((cyanomethyl)sulfonamido)pyridin-2-yl)-1-methyl-1H-1,2,3-triazol-5-yl)carbamate (Compound 13)

To a mixture of (S)-2,2-difluoro-1-phenylethyl (4-(5-aminopyridin-2-yl)-1-methyl-1H-1,2,3-triazol-5-yl)carbamate hydrochloride (0.16 mmol), pyridine (0.81 mmol) and DCM (5.0 mL) was added cyanomethanesulfonyl chloride (0.20 mmol). The mixture was stirred at room temperature for 6 h. The reaction was concentrated and purified by reverse phase chromatography (30-98% ACN/water with 0.1% TFA, then 40-65% ACN/water with 0.1% TFA). The residue was lyophilized to afford (S)-2,2-difluoro-1-phenylethyl (4-(5-((cyanomethyl)sulfonamido)pyridin-2-yl)-1-methyl-1H-1,2,3-triazol-5-yl)carbamate (Compound 13). (MS (m/z) 478.1 [M+H]$^+$). 1H NMR (400 MHz, DMSO-d$_6$) δ 11.02 (s, 1H), 10.16 (bs, 1H), 8.36 (s, 1H), 7.98 (d, J=8.6 Hz, 1H), 7.72 (dd, J=8.6, 2.7 Hz, 1H), 7.66-7.20 (bm, 5H), 6.73-6.19 (bm, 1H), 5.94 (bm, 1H), 5.04 (s, 2H), 3.85 (s, 3H).

Example 22: Preparation of Compounds 14 to 86 and 111 to 143

Compounds 14 to 86 and 111 to 143 were generally prepared according to Scheme B2a by reacting Intermediate 6 (Example 8) with a Reagent 1 listed in Table 3. For example, (R)-1-(3-chlorophenyl)ethyl (1-methyl-4-(5-(methylsulfonamido)pyridin-2-yl)-1H-1,2,3-triazol-5-yl)carbamate (Compound 14) was prepared as follows. To a solution of 1-methyl-4-(5-(methylsulfonamido)pyridin-2-yl)-1H-1,2,3-triazole-5-carboxylic acid (Intermediate 6) (0.168 mmol) in THE (1 mL) was added triethylamine (0.589 mmol), 50% v/v propanephosphonic acid anhydride (1.57 M) in THE (0.336 mmol), and trimethylsilyl azide (0.336 mmol). The mixture was stirred for 30 min at 70° C., or until cessation of gas evolution. The mixture was then cooled to room temperature and (R)-1-(3-chlorophenyl)ethan-1-ol (0.336 mmol) was added. The mixture was then reheated to 70° C. for 1 h. The reaction solution was cooled to room temperature, the volatiles removed in vacuo and the remaining residue was chromatographed by silica gel column chromatography to give (R)-1-(3-chlorophenyl)ethyl (1-methyl-4-(5-(methylsulfonamido)pyridin-2-yl)-1H-1,2, 3-triazol-5-yl)carbamate. (MS (m/z) 451.1 [M+H]$^+$). 1H NMR (400 MHz, Methanol-d4) δ 8.46 (s, 1H), 7.90 (d, J=8.6 Hz, 1H), 7.75 (dd, J=8.6, 2.6 Hz, 1H), 7.31 (s, 4H), 5.79 (d, J=6.7 Hz, 1H), 3.96 (s, 3H), 3.03 (s, 3H), 1.56 (s, 3H).

Compounds 15-23 and 111-121 (Table 3) were similarly prepared according to Scheme B2a by reacting Intermediate 6 (Example 8) with a Reagent listed in Table 3 following the general process described for Compound 14.

Compounds 24-85 and 122-143 (Table 4) were similarly prepared according to Scheme B2a by reacting Intermediate 10 (Example 12) with a Reagent listed in Table 4 following the general process described for Compound 14.

Compound 86 (Table 5) was similarly prepared according to Scheme B2a by reacting Intermediate 11 (Example 13) with the Reagent listed in Table 5 following the general process described for Compound 14.

TABLE 3

Compounds prepared according to Scheme B2a (using Intermediate 6)

| Name | Structure | Reagent 1 | LCMS M/Z (M + 1) | NMR |
|---|---|---|---|---|
| Compound 14 (R)-1-(3-chlorophenyl)ethyl (1-methyl-4-(5-(methylsulfonamido)pyridin-2-yl)-1H-1,2,3-triazol-5-yl)carbamate | 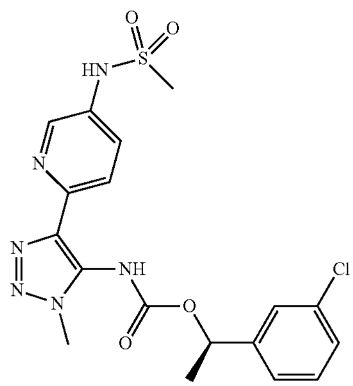 [SMILES: C[C@@H](OC(=O)Nc1c(-c2ccc(NS(C)(=O)=O)cn2)nnn1C)c1cccc(Cl)c1] | | 451.1 | 1H NMR (400 MHz, Methanol-d4) δ 8.46 (s, 1H), 7.90 (d, J = 8.6 Hz, 1H), 7.75 (dd, J = 8.6, 2.6 Hz, 1H), 7.31 (s, 4H), 5.79 (d, J = 6.7 Hz, 1H), 3.96 (s, 3H), 3.03 (s, 3H), 1.56 (s, 3H). |
| Compound 15 (S)-2,2-difluoro-1-phenylethyl (1-methyl-4-(5-(methylsulfonamido)pyridin-2-yl)-1H-1,2,3-triazol-5-yl)carbamate | 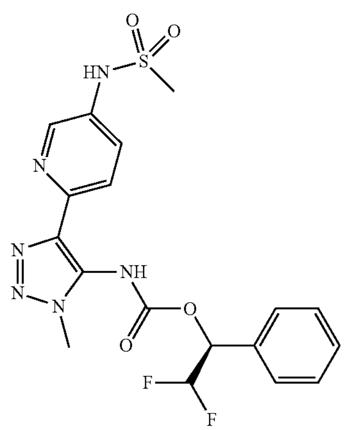 [SMILES: Cn1nnc(-c2ccc(NS(C)(=O)=O)cn2)c1NC(=O)O[C@@H](c1ccccc1)C(F)F] | | 453.2 | 1H NMR (400 MHz, Methanol-d4) δ 8.41 (s, 1H), 7.89 (dd, J = 8.6, 0.7 Hz, 1H), 7.72 (dd, J = 8.6, 2.7 Hz, 1H), 7.43 (s, 5H), 6.45-5.71 (m, 2H), 3.97 (s, 3H), 3.02 (s, 3H). |
| Compound 16 (R)-1-(2-fluorophenyl)ethyl (1-methyl-4-(5-(methylsulfonamido)pyridin-2-yl)-1H-1,2,3-triazol-5-yl)carbamate | 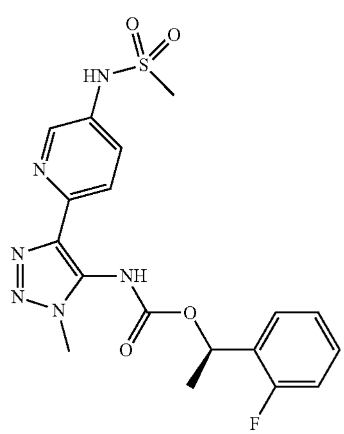 [SMILES: C[C@@H](OC(=O)Nc1c(-c2ccc(NS(C)(=O)=O)cn2)nnn1C)c1ccccc1F] | | 435.2 | 1H NMR (400 MHz, Methanol-d4) δ 8.45 (d, J = 2.6 Hz, 1H), 7.89 (dd, J = 8.6, 0.8 Hz, 1H), 7.73 (dd, J = 8.6, 2.7 Hz, 1H), 7.65-6.91 (m, 4H), 6.07 (t, J = 6.6 Hz, 1H), 3.95 (s, 3H), 3.03 (s, 3H), 1.58 (s, 3H). |

TABLE 3-continued

Compounds prepared according to Scheme B2a (using Intermediate 6)

| Name | Structure | Reagent 1 | LCMS M/Z (M + 1) | NMR |
|---|---|---|---|---|
| Compound 17 (R)-1-(2,5-difluoro-phenyl)ethyl (1-methyl-4-(5-(methylsulfonamido)pyridin-2-yl)-1H-1,2,3-triazol-5-yl)carbamate | 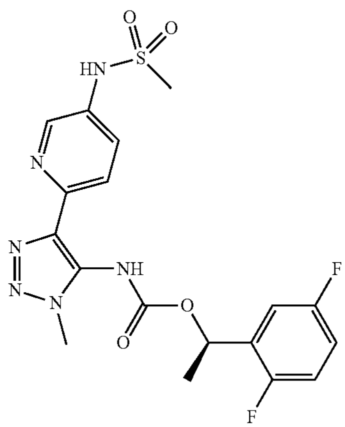 [SMILES: C[C@@H](OC(=O)Nc1c(-c2ccc(NS(C)(=O)=O)cn2)nnn1C)c1cc(F)ccc1F] | | 453.2 | 1H NMR (400 MHz, Methanol-d4) δ 8.47 (s, 1H), 7.93 (dd, J = 8.6, 0.8 Hz, 1H), 7.76 (dd, J = 8.6, 2.7 Hz, 1H), 7.11 (s, 3H), 6.04 (d, J = 6.4 Hz, 1H), 3.99 (s, 3H), 3.05 (s, 3H), 1.59 (s, 3H). |
| Compound 18 (S)-2-fluoro-1-phenyl-ethyl (1-methyl-4-(5-(methylsulfonamido)pyridin-2-yl)-1H-1,2,3-triazol-5-yl)carbamate | 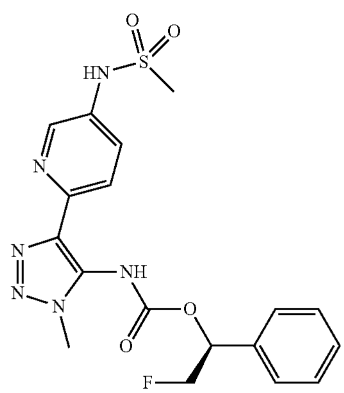 [SMILES: Cn1nnc(-c2ccc(NS(C)(=O)=O)cn2)c1NC(=O)O[C@H](CF)c1ccccc1] | | 435.1 | 1H NMR (400 MHz, Methanol-d4) δ 8.47 (s, 1H), 7.90 (d, J = 8.7 Hz, 1H), 7.80 (dd, J = 8.7, 2.6 Hz, 1H), 7.40 (s, 5H), 6.00 (dt, J = 16.5, 5.3 Hz, 1H), 4.65 (d, J = 46.8 Hz, 2H), 3.99 (s, 3H), 3.07 (s, 3H). |
| Compound 19 3-methylbenzyl (1-methyl-4-(5-(methyl-sulfonamido)pyridin-2-yl)-1H-1,2,3-triazol-5-yl)carbamate | 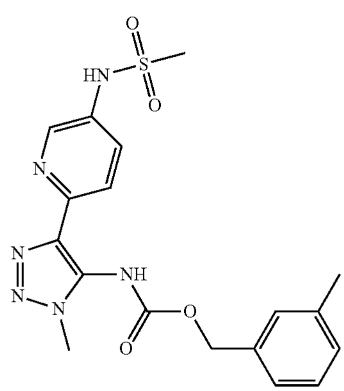 [SMILES: Cc1cccc(COC(=O)Nc2c(-c3ccc(NS(C)(=O)=O)cn3)nnn2C)c1] | | 417.1 | 1H NMR (400 MHz, Methanol-d4) δ 8.44 (d, J = 2.6 Hz, 1H), 7.89 (dd, J = 8.6, 0.8 Hz, 1H), 7.73 (dd, J = 8.6, 2.7 Hz, 1H), 7.30-7.02 (m, 4H), 5.14 (s, 2H), 3.97 (s, 3H), 3.02 (s, 3H), 2.32 (s, 3H). |

TABLE 3-continued

Compounds prepared according to Scheme B2a (using Intermediate 6)

| Name | Structure | Reagent 1 | LCMS M/Z (M + 1) | NMR |
|---|---|---|---|---|
| Compound 20 3-chlorobenzyl (1-methyl-4-(5-(methyl-sulfonamido)pyridin-2-yl)-1H-1,2,3-triazol-5-yl)carbamate | 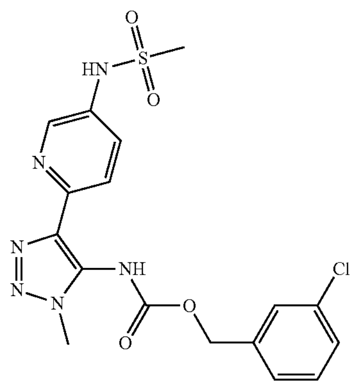 [SMILES: Cn1nnc(-c2ccc(NS(C)(=O)=O)cn2)c1NC(=O)OCc1cccc(Cl)c1] | 3-chlorobenzyl alcohol | 437.9 | 1H NMR (400 MHz, Methanol-d4) δ 8.46 (d, J = 2.6 Hz, 1H), 7.92 (dd, J = 8.6, 0.8 Hz, 1H), 7.75 (dd, J = 8.6, 2.7 Hz, 1H), 7.47-7.18 (m, 4H), 5.18 (s, 2H), 3.98 (s, 3H), 3.02 (s, 4H). |
| Compound 21 3-fluorobenzyl (1-methyl-4-(5-(methyl-sulfonamido)pyridin-2-yl)-1H-1,2,3-triazol-5-yl)carbamate | 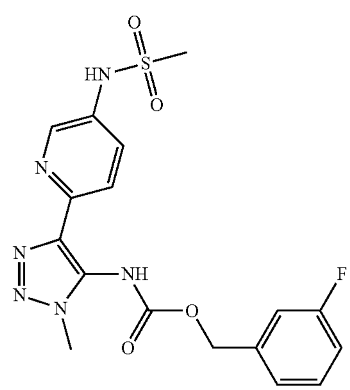 [SMILES: Cn1nnc(-c2ccc(NS(C)(=O)=O)cn2)c1NC(=O)OCc1cccc(F)c1] | 3-fluorobenzyl alcohol | 421.1 | 1H NMR (400 MHz, Methanol-d4) δ 8.44 (d, J = 2.6 Hz, 1H), 7.90 (d, J = 8.5 Hz, 1H), 7.73 (dd, J = 8.6, 2.7 Hz, 1H), 7.47-6.79 (m, 4H), 5.20 (s, 2H), 3.98 (s, 3H), 3.02 (s, 3H). |
| Compound 22 (S)-2-fluoro-1-(3-fluorophenyl)ethyl (1-methyl-4-(5-(methyl-sulfonamido)pyridin-2-yl)-1H-1,2,3-triazol-5-yl)carbamate | 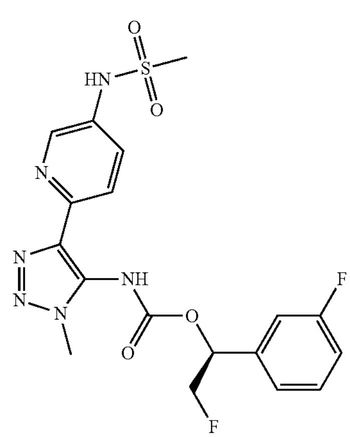 [SMILES: Cn1nnc(-c2ccc(NS(C)(=O)=O)cn2)c1NC(=O)O[C@H](CF)c1cccc(F)c1] | (S)-2-fluoro-1-(3-fluorophenyl)ethanol | 453.1 | 1H NMR (400 MHz, Methanol-d4) δ 8.45 (s, 1H), 7.92 (d, J = 8.6 Hz, 1H), 7.75 (dd, J = 8.6, 2.7 Hz, 1H), 7.53-6.86 (m, 4H), 6.13-5.80 (m, 1H), 3.99 (s, 3H), 3.04 (s, 3H). |

TABLE 3-continued

Compounds prepared according to Scheme B2a (using Intermediate 6)

| Name | Structure | Reagent 1 | LCMS M/Z (M + 1) | NMR |
|---|---|---|---|---|
| Compound 23 (R)-1-(2-chloro-pyridin-3-yl)ethyl (1-methyl-4-(5-(methyl-sulfonamido)pyridin-2-yl)-1H-1,2,3-triazol-5-yl)carbamate | 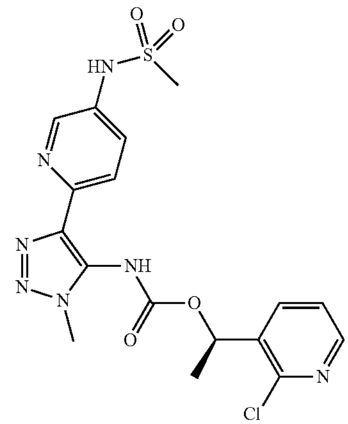 [SMILES: C[C@@H](OC(=O)Nc1c(-c2ccc(NS(C)(=O)=O)cn2)nnn1C)c1cccnc1Cl] | | 452.0 | 1H NMR (400 MHz, Methanol-d4) δ 8.48 (s, 1H), 8.33 (s, 1H), 8.10 (dd, J = 8.9, 2.6 Hz, 1H), 7.94 (dd, J = 8.5, 0.7 Hz, 1H), 7.74 (dd, J = 8.6, 2.7 Hz, 1H), 7.47 (s, 1H), 6.08 (d, J = 6.8 Hz, 1H), 3.99 (s, 3H), 3.06 (s, 3H), 1.61 (s, 3H). |
| Compound 111 (R)-1-(5-chloro-2-fluoropyridin-3-yl)ethyl (1-methyl-4-(5-(methyl-sulfonamido)pyridin-2-yl)-1H-1,2,3-triazol-5-yl)carbamate | 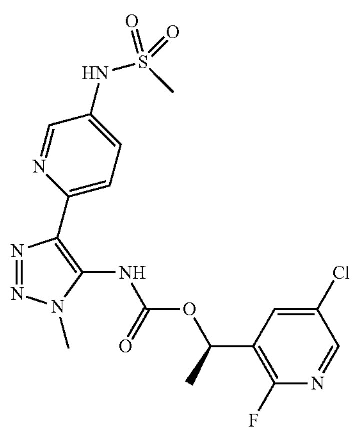 [SMILES: C[C@@H](OC(=O)Nc1c(-c2ccc(NS(C)(=O)=O)cn2)nnn1C)c1cc(Cl)cnc1F] | | 470.0 | 1H NMR (400 MHz, Methanol-d4) δ 8.46 (s, 1H), 8.28-7.82 (m, 3H), 7.76 (dd, J = 8.7, 2.7 Hz, 1H), 5.95 (d, J = 7.2 Hz, 1H), 4.00 (s, 3H), 3.05 (s, 3H), 1.62 (s, 3H). |
| Compound 112 (R)-1-(5-fluoro-2-methylpyridin-3-yl)ethyl (1-methyl-4-(5-(methyl-sulfonamido)pyridin-2-yl)-1H-1,2,3-triazol-5-yl)carbamate | 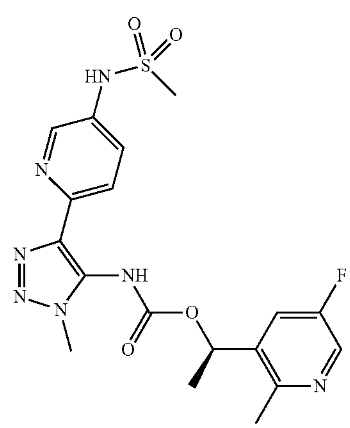 [SMILES: Cc1ncc(F)cc1[C@@H](C)OC(=O)Nc1c(-c2ccc(NS(C)(=O)=O)cn2)nnn1C] | | 449.9 | 1H NMR (400 MHz, Methanol-d4) δ 8.43 (s, 1H), 8.28 (s, 1H), 8.01-7.51 (m, 3H), 5.98 (d, J = 6.9 Hz, 1H), 3.98 (s, 3H), 3.05 (s, 3H), 2.57 (s, 3H), 1.59 (s, 3H). |

TABLE 3-continued

Compounds prepared according to Scheme B2a (using Intermediate 6)

| Name | Structure | Reagent 1 | LCMS M/Z (M + 1) | NMR |
|---|---|---|---|---|
| Compound 113 (R)-1-(5-chloro-2-methylpyridin-3-yl)ethyl (1-methyl-4-(5-(methylsulfonamido)pyridin-2-yl)-1H-1,2,3-triazol-5-yl)carbamate | | | 466.0 | 1H NMR (400 MHz, Methanol-d4) δ 8.40 (d, J = 32.3 Hz, 2H), 8.17-7.48 (m, 3H), 5.98 (d, J = 6.7 Hz, 1H), 3.98 (s, 3H), 3.05 (s, 3H), 2.57 (s, 3H), 1.59 (s, 3H). |
| Compound 114 (R)-1-(2,5-difluoropyridin-3-yl)ethyl (1-methyl-4-(5-(methylsulfonamido)pyridin-2-yl)-1H-1,2,3-triazol-5-yl)carbamate | | | 453.9 | 1H NMR (400 MHz, Methanol-d4) δ 8.46 (s, 1H), 8.23-7.48 (m, 4H), 5.95 (d, J = 7.1 Hz, 1H), 4.00 (s, 3H), 3.06 (s, 3H), 1.62 (s, 3H). |
| Compound 115 (R)-1-(2-chloro-5-fluoropyridin-3-yl)ethyl (1-methyl-4-(5-(methylsulfonamido)pyridin-2-yl)-1H-1,2,3-triazol-5-yl)carbamate | | | 470.0 | 1H NMR (400 MHz, Acetonitrile-d3) δ 8.49 (d, J = 2.6 Hz, 1H), 8.40 (s, 1H), 8.27 (d, J = 3.0 Hz, 1H), 8.07 (d, J = 8.6 Hz, 1H), 7.87 (s, 1H), 7.83 (dd, J = 8.7, 2.6 Hz, 1H), 7.76 (s, 1H), 6.01 (q, J = 6.5 Hz, 1H), 3.97 (s, 3H), 3.05 (s, 3H), 1.62-1.55 (m, 3H). |

TABLE 3-continued

Compounds prepared according to Scheme B2a (using Intermediate 6)

| Name | Structure | Reagent 1 | LCMS M/Z (M + 1) | NMR |
|---|---|---|---|---|
| Compound 116 (R)-1-(2-bromo-pyridin-3-yl)ethyl (1-methyl-4-(5-(methyl-sulfonamido)pyridin-2-yl)-1H-1,2,3-triazol-5-yl)carbamate | 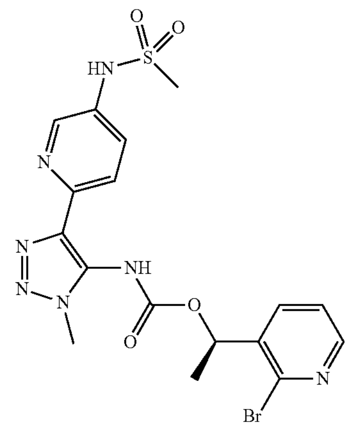 | | 496.0 | 1H NMR (400 MHz, DMSO-d6) δ 12.02 (s, 1H), 10.14 (s, 1H), 9.82 (s, 1H), 8.37 (d, J = 2.6 Hz, 1H), 8.00 (s, 1H), 7.93 (dd, J = 8.6, 0.7 Hz, 1H), 7.67 (dd, J = 8.6, 2.7 Hz, 1H), 7.58 (s, 1H), 5.82 (s, 1H), 3.89 (s, 3H), 3.07 (s, 3H), 2.48 (s, 3H), 1.56 (s, 3H). |
| Compound 117 (R)-1-(2,5-difluoro-pyridin-4-yl)ethyl (1-methyl-4-(5-(methyl-sulfonamido)pyridin-2-yl)-1H-1,2,3-triazol-5-yl)carbamate | 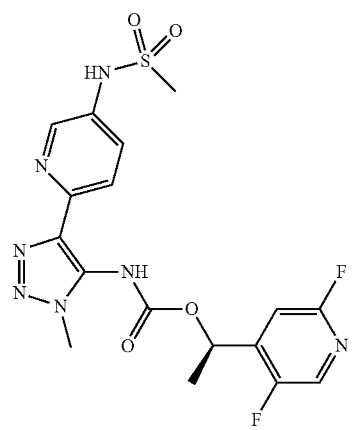 [SMILES: C[C@@H](OC(=O)Nc1c(-c2ccc(NS(C)(=O)=O)cn2)nnn1C)c1cc(F)ncc1F] | | 454.0 | 1H NMR (400 MHz, Acetoni-trile-d3) δ 8.49 (d, J = 2.6 Hz, 1H), 8.11-8.04 (m, 2H), 7.88-7.78 (m, 2H), 7.15 (s, 1H), 6.01 (q, J = 6.7 Hz, 1H), 3.97 (s, 3H), 3.63 (s, 3H), 3.04 (s, 3H), 1.62-1.56 (m, 3H). |
| Compound 118 (R)-1-(5-chloroiso-thiazol-4-yl)ethyl (1-methyl-4-(5-(methyl-sulfonamido)pyridin-2-yl)-1H-1,2,3-triazol-5-yl)carbamate | 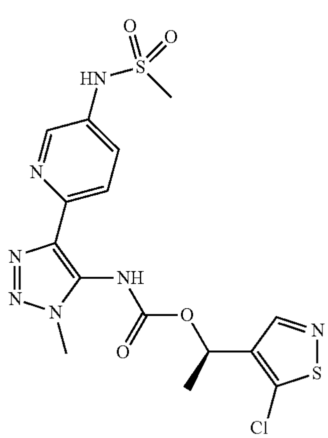 [SMILES: C[C@@H](OC(=O)Nc1c(-c2ccc(NS(C)(=O)=O)cn2)nnn1C)c1cnsc1Cl] | | 457.9 | 1H NMR (400 MHz, Methanol-d4) δ 8.46 (s, 1H), 7.93 (d, J = 8.6 Hz, 1H), 7.79 (dd, J = 8.6, 2.6 Hz, 1H), 5.98 (d, J = 6.8 Hz, 1H), 3.99 (s, 3H), 3.08 (s, 3H), 1.66 (s, 3H). |

TABLE 3-continued

Compounds prepared according to Scheme B2a (using Intermediate 6)

| Name | Structure | Reagent 1 | LCMS M/Z (M + 1) | NMR |
|---|---|---|---|---|
| Compound 119 (R)-1-(3-chloroiso-thiazol-4-yl)ethyl (1-methyl-4-(5-(methyl-sulfonamido)pyridin-2-yl)-1H-1,2,3-triazol-5-yl)carbamate | | | 457.9 | 1H NMR (400 MHz, Methanol-d4) δ 9.01 (s, 1H), 8.49 (s, 1H), 7.94 (d, J = 8.7 Hz, 1H), 7.81 (dd, J = 8.7, 2.6 Hz, 1H), 5.96 (q, J = 6.6 Hz, 1H), 4.00 (s, 3H), 3.08 (s, 3H), 1.65 (s, 3H). |
| Compound 120 1-(2-chloro-6-fluorophenyl)ethyl (1-methyl-4-(5-(methyl-sulfonamido)pyridin-2-yl)-1H-1,2,3-triazol-5-yl)carbamate | | | 469.0 | 1H NMR (400 MHz, Methanol-d4) δ 8.45 (s, 1H), 7.89 (d, J = 8.7 Hz, 1H), 7.86-7.76 (m, 1H), 7.33 (q, J = 7.4 Hz, 1H), 7.27-7.22 (m, 1H), 7.17-7.03 (m, 1H), 6.32 (qd, J = 6.8, 1.1 Hz, 1H), 3.98 (s, 3H), 3.09 (s, 3H), 1.89-1.59 (m, 3H). |
| Compound 121 1-(2-chloro-4-fluoropyridin-3-yl)ethyl (1-methyl-4-(5-(methyl-sulfonamido)pyridin-2-yl)-1H-1,2,3-triazol-5-yl)carbamate | | | 470.0 | 1H NMR (400 MHz, Methanol-d4) δ 8.42 (d, J = 4.2 Hz, 1H), 8.34 (s, 1H), 7.90 (d, J = 8.6 Hz, 1H), 7.85-7.70 (m, 1H), 7.25 (s, 1H), 6.23 (q, J = 6.9 Hz, 1H), 3.98 (s, 2H), 3.07 (d, J = 11.0 Hz, 3H), 1.84-1.59 (m, 3H). |

TABLE 4

Exemplary compounds prepared according to Scheme B2a (using Intermediate 10)

| Name | Structure | Reagent 1 | LCMS M/Z (M + 1) | NMR |
|---|---|---|---|---|
| Compound 24 (R)-1-(3-chloro-2-fluorophenyl)ethyl (1-methyl-4-(6-methyl-5-(methyl-sulfonamido)pyridin-2-yl)-1H-1,2,3-triazol-5-yl)carbamate | | | 483.1 | 1H NMR (400 MHz, Methanol-d4) δ 7.79 (s, 2H), 7.27 (d, J = 107.9 Hz, 3H), 6.06 (d, J = 7.8 Hz, 1H), 3.98 (s, 3H), 3.03 (s, 3H), 2.54 (s, 3H), 1.58 (s, 3H). |
| Compound 25 (S)-1-(3-chlorophenyl)-2-fluoroethyl (1-methyl-4-(6-methyl-5-(methyl-sulfonamido)pyridin-2-yl)-1H-1,2,3-triazol-5-yl)carbamate | | | 483.2 | 1H NMR (400 MHz, Methanol-d4) δ 7.87-7.74 (m, 2H), 7.35 (s, 4H), 5.99 (d, J = 17.4 Hz, 1H), 4.64 (d, J = 44.5 Hz, 2H), 3.99 (s, 3H), 3.02 (s, 3H), 2.50 (s, 3H). |
| Compound 26 (S)-1-(2,5-difluorophenyl)-2,2-difluoroethyl (1-methyl-4-(6-methyl-5-(methyl-sulfonamido)pyridin-2-yl)-1H-1,2,3-triazol-5-yl)carbamate | | | 503.1 | 1H NMR (400 MHz, Methanol-d4) δ 7.90-7.68 (m, 2H), 7.31 (d, J = 72.7 Hz, 3H), 6.22 (s, 1H), 4.01 (s, 3H), 3.04 (s, 3H), 2.50 (s, 3H). |

TABLE 4-continued

Exemplary compounds prepared according to Scheme B2a (using Intermediate 10)

| Name | Structure | Reagent 1 | LCMS M/Z (M + 1) | NMR |
| --- | --- | --- | --- | --- |
| Compound 27 (R)-1-(2,5-dimethylphenyl)ethyl (1-methyl-4-(6-methyl-5-(methyl-sulfonamido)pyridin-2-yl)-1H-1,2,3-triazol-5-yl)carbamate | 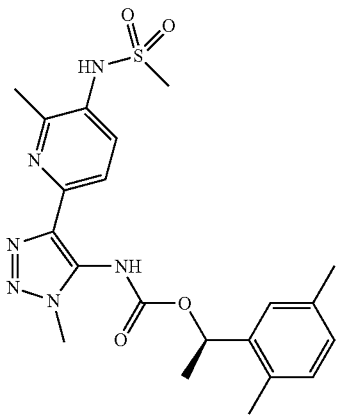 [SMILES: Cc1ccc(C)c([C@@H](C)OC(=O)Nc2c(-c3ccc(NS(C)(=O)=O)c(C)n3)nnn2C)c1] | | 459.2 | 1H NMR (400 MHz, Methanol-d4) δ 7.79 (s, 2H), 7.01 (t, J = 8.4 Hz, 3H), 6.03 (q, J = 6.5 Hz, 1H), 3.98 (s, 3H), 3.04 (s, 3H), 2.54 (s, 3H), 2.28 (d, J = 21.9 Hz, 6H), 1.52 (s, 3H). |
| Compound 28 (R)-hexan-2-yl (1-methyl-4-(6-methyl-5-(methyl-sulfonamido)pyridin-2-yl)-1H-1,2,3-triazol-5-yl)carbamate | 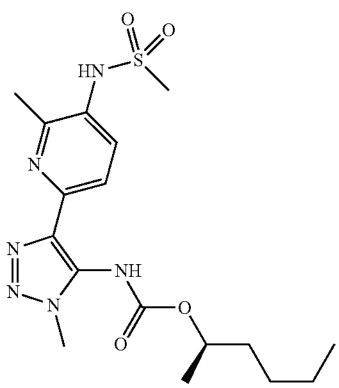 [SMILES: CCCC[C@@H](C)OC(=O)Nc1c(-c2ccc(NS(C)(=O)=O)c(C)n2)nnn1C] | | 411.1 | 1H NMR (400 MHz, Methanol-d4) δ 7.82 (s, 2H), 4.83 (s, 1H), 4.00 (s, 3H), 3.04 (s, 3H), 2.61 (s, 3H), 2.00-1.04 (m, 9H), 0.88 (s, 3H). |
| Compound 29 4-methylpentyl (1-methyl-4-(6-methyl-5-(methyl-sulfonamido)pyridin-2-yl)-1H-1,2,3-triazol-5-yl)carbamate | 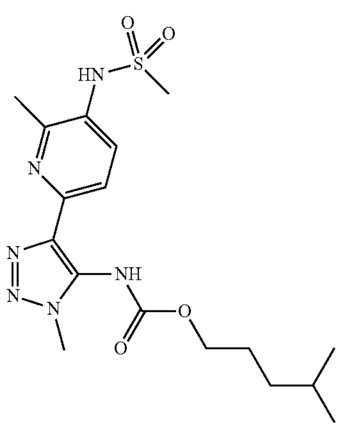 [SMILES: Cc1nc(-c2nnn(C)c2NC(=O)OCCCC(C)C)ccc1NS(C)(=O)=O] | | 411.2 | 1H NMR (400 MHz, Methanol-d4) δ 7.85 (d, J = 1.4 Hz, 2H), 4.15 (s, 2H), 4.03 (s, 3H), 3.06 (s, 3H), 2.63 (s, 3H), 1.85-1.06 (m, 5H), 0.90 (s, 6H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 30 4,4-dimethylpentyl (1-methyl-4-(6-methyl-5-(methyl-sulfonamido)pyridin-2-yl)-1H-1,2,3-triazol-5-yl)carbamate | 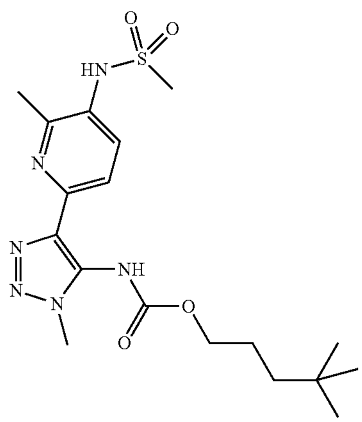 [SMILES: Cc1nc(-c2nnn(C)c2NC(=O)OCCCC(C)(C)C)ccc1NS(C)(=O)=O] | | 425.2 | 1H NMR (400 MHz, Methanol-d4) δ 7.85 (d, J = 2.0 Hz, 2H), 4.14 (s, 2H), 4.03 (s, 3H), 3.06 (s, 3H), 2.63 (s, 3H), 1.44 (d, J = 153.8 Hz, 4H), 1.03-0.75 (m, 9H). |
| Compound 31 hexyl (1-methyl-4-(6-methyl-5-(methyl-sulfonamido)pyridin-2-yl)-1H-1,2,3-triazol-5-yl)carbamate | 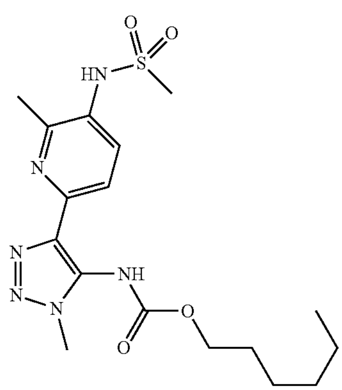 [SMILES: CCCCCCOC(=O)Nc1c(-c2ccc(NS(C)(=O)=O)c(C)n2)nnn1C] | | 411.2 | 1H NMR (400 MHz, Methanol-d4) δ 7.84 (s, 2H), 4.17 (s, 2H), 4.03 (s, 3H), 3.06 (s, 3H), 2.62 (s, 3H), 1.65 (s, 2H), 1.32 (s, 6H), 0.91 (s, 3H). |
| Compound 32 3,3-dimethylbutyl (1-methyl-4-(6-methyl-5-(methyl-sulfonamido)pyridin-2-yl)-1H-1,2,3-triazol-5-yl)carbamate | 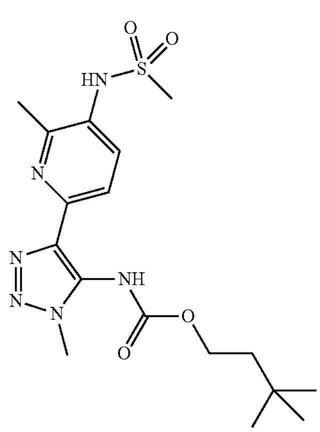 [SMILES: Cc1nc(-c2nnn(C)c2NC(=O)OCCC(C)(C)C)ccc1NS(C)(=O)=O] | | 411.2 | 1H NMR (400 MHz, Methanol-d4) δ 7.84 (s, 2H), 4.24 (s, 2H), 4.03 (s, 3H), 3.06 (s, 3H), 2.62 (s, 3H), 1.59 (s, 2H), 1.10-0.78 (m, 9H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 33 isopentyl (1-methyl-4-(6-methyl-5-(methyl-sulfonamido)pyridin-2-yl)-1H-1,2,3-triazol-5-yl)carbamate | 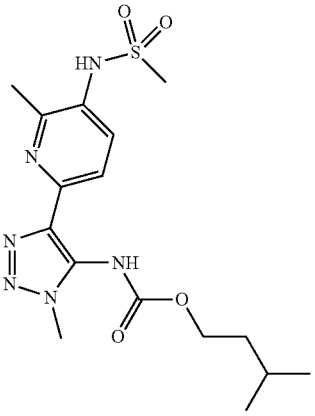 [SMILES: Cc1nc(-c2nnn(C)c2NC(=O)OCCC(C)C)ccc1NS(C)(=O)=O] | 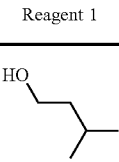 | 397.3 | 1H NMR (400 MHz, Methanol-d4) δ 7.84 (s, 2H), 4.21 (s, 2H), 4.02 (s, 3H), 3.06 (s, 3H), 2.62 (s, 3H), 1.62 (d, J = 59.2 Hz, 3H), 0.93 (s, 6H). |
| Compound 34 2-methoxy-1-phenyl-ethyl (1-methyl-4-(6-methyl-5-(methyl-sulfonamido)pyridin-2-yl)-1H-1,2,3-triazol-5-yl)carbamate | 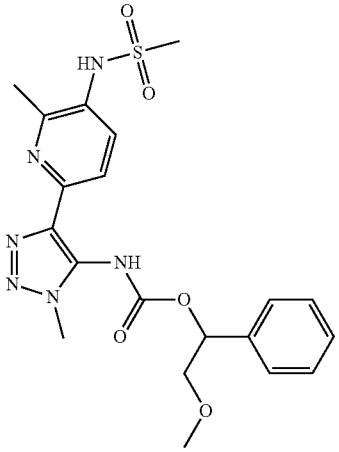 [SMILES: COCC(OC(=O)Nc1c(-c2ccc(NS(C)(=O)=O)c(C)n2)nnn1C)c1ccccc1] | 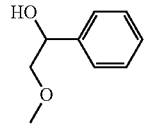 | 461.2 | 1H NMR (400 MHz, Methanol-d4) δ 7.77 (s, 2H), 7.31 (s, 5H), 5.89 (dd, J = 8.3, 3.5 Hz, 1H), 3.97 (s, 3H), 3.82-3.51 (m, 2H), 3.37 (s, 3H), 3.02 (s, 3H), 2.50 (s, 3H). |
| Compound 35 (R)-1-(2-(methoxy-methyl)phenyl)ethyl (1-methyl-4-(6-methyl-5-(methyl-sulfonamido)pyridin-2-yl)-1H-1,2,3-triazol-5-yl)carbamate | 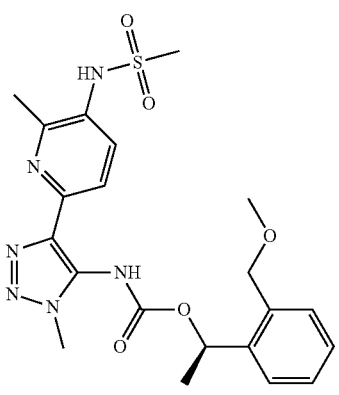 [SMILES: COCc1ccccc1[C@@H](C)OC(=O)Nc1c(-c2ccc(NS(C)(=O)=O)c(C)n2)nnn1C] | 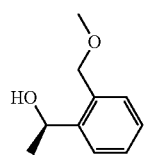 | 475.1 | 1H NMR (400 MHz, Methanol-d4) δ 7.84 (d, J = 8.3 Hz, 1H), 7.73 (d, J = 8.3 Hz, 1H), 7.29 (m, 4H), 6.07 (q, J = 6.3 Hz, 1H), 4.72 (d, J = 11.6 Hz, 1H), 4.36 (d, J = 11.8 Hz, 1H), 3.94 (s, 3H), 3.32 (s, 3H), 3.05 (s, 3H), 2.56 (s, 3H), 1.53 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 36 2,5-difluorobenzyl (1-methyl-4-(6-methyl-5-(methyl-sulfonamido)pyridin-2-yl)-1H-1,2,3-triazol-5-yl)carbamate | 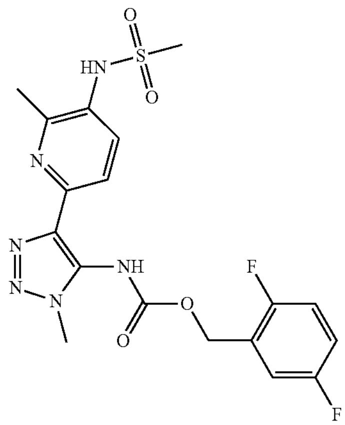 [SMILES: Cc1nc(-c2nnn(C)c2NC(=O)OCc2cc(F)ccc2F)ccc1NS(C)(=O)=O] | 2,5-difluorobenzyl alcohol | 453.2 | 1H NMR (400 MHz, Methanol-d4) δ 7.94-7.65 (m, 2H), 7.11 (m, 3H), 5.24 (s, 2H), 4.00 (s, 3H), 3.03 (s, 3H), 2.53 (s, 3H). |
| Compound 37 3-methylbenzyl (1-methyl-4-(6-methyl-5-(methyl-sulfonamido)pyridin-2-yl)-1H-1,2,3-triazol-5-yl)carbamate | 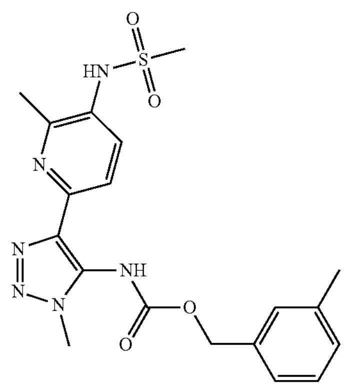 [SMILES: Cc1cccc(COC(=O)Nc2c(-c3ccc(NS(C)(=O)=O)c(C)n3)nnn2C)c1] | 3-methylbenzyl alcohol | 431.1 | 1H NMR (400 MHz, Methanol-d4) δ 7.77 (s, 2H), 7.31-6.93 (m, 4H), 5.14 (s, 2H), 3.98 (s, 3H), 3.00 (s, 3H), 2.52 (s, 3H), 2.31 (s, 3H). |
| Compound 38 2-chloro-5-fluoro-benzyl (1-methyl-4-(6-methyl-5-(methyl-sulfonamido)pyridin-2-yl)-1H-1,2,3-triazol-5-yl)carbamate | 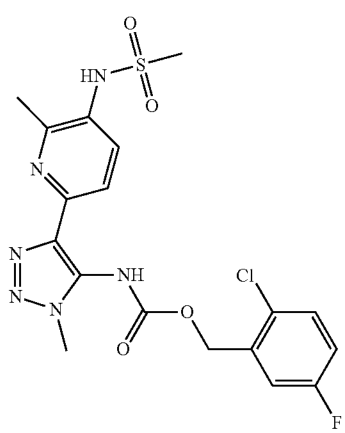 [SMILES: Cc1nc(-c2nnn(C)c2NC(=O)OCc2cc(F)ccc2Cl)ccc1NS(C)(=O)=O] | 2-chloro-5-fluorobenzyl alcohol | 469.1 | 1H NMR (400 MHz, Methanol-d4) δ 7.93-7.69 (m, 2H), 7.60-6.89 (m, 3H), 5.28 (s, 2H), 4.01 (s, 3H), 3.01 (s, 3H), 2.54 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 39 3-chlorobenzyl (1-methyl-4-(6-methyl-5-(methyl-sulfonamido)pyridin-2-yl)-1H-1,2,3-triazol-5-yl)carbamate | 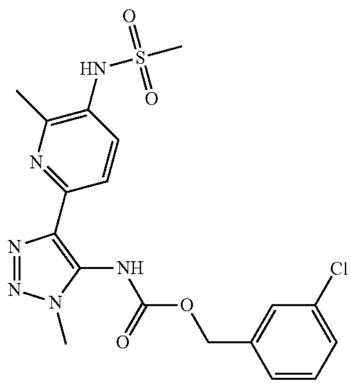 [SMILES: Cc1nc(-c2nnn(C)c2NC(=O)OCc2cccc(Cl)c2)ccc1NS(C)(=O)=O] | | 451.0 | 1H NMR (400 MHz, Methanol-d4) δ 7.83-7.75 (m, 2H), 7.50-6.99 (m, 4H), 5.18 (s, 2H), 3.99 (s, 3H), 3.02 (s, 3H), 2.53 (s, 3H). |
| Compound 40 2-chlorobenzyl (1-methyl-4-(6-methyl-5-(methyl-sulfonamido)pyridin-2-yl)-1H-1,2,3-triazol-5-yl)carbamate | 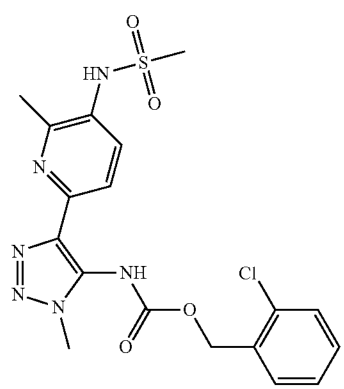 [SMILES: Cc1nc(-c2nnn(C)c2NC(=O)OCc2ccccc2Cl)ccc1NS(C)(=O)=O] | | 451.2 | 1H NMR (400 MHz, Methanol-d4) δ 7.79 (s, 2H), 7.58-7.07 (m, 4H), 5.30 (s, 2H), 4.00 (s, 3H), 3.01 (s, 3H), 2.54 (s, 3H). |
| Compound 41 (R)-1-(3-chloro-phenyl)ethyl (1-methyl-4-(6-methyl-5-(methyl-sulfonamido)pyridin-2-yl)-1H-1,2,3-triazol-5-yl)carbamate | 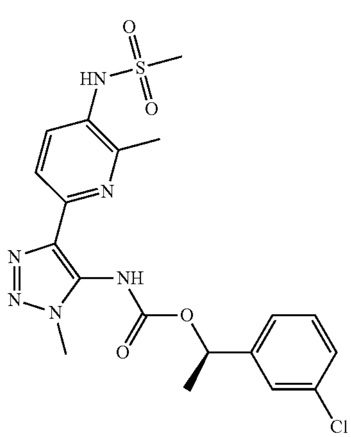 [SMILES: Cc1nc(-c2nnn(C)c2NC(=O)O[C@H](C)c2cccc(Cl)c2)ccc1NS(C)(=O)=O] | | 465.0 | 1H NMR (400 MHz, Methanol-d4) δ 7.79 (s, 2H), 7.37-7.20 (m, 4H), 5.89-5.64 (m, 1H), 3.97 (s, 3H), 3.02 (s, 3H), 2.53 (s, 3H), 1.70-1.44 (m, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 42 (R)-1-(o-tolyl)ethyl (1-methyl-4-(6-methyl-5-(methyl-sulfonamido)pyridin-2-yl)-1H-1,2,3-triazol-5-yl)carbamate | 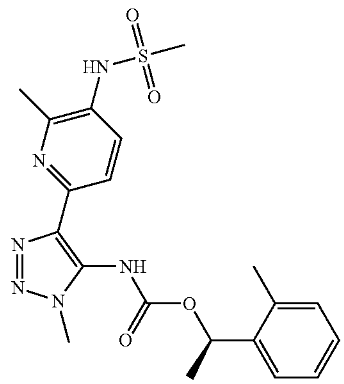 [SMILES: Cc1ccccc1[C@@H](C)OC(=O)Nc1c(-c2ccc(NS(C)(=O)=O)c(C)n2)nnn1C] | | 445 | 1H NMR (400 MHz, Methanol-d4) δ 7.76 (s, 2H), 7.50-7.06 (m, 4H), 6.03 (q, J = 6.6 Hz, 1H), 3.95 (s, 3H), 3.02 (s, 3H), 2.53 (s, 3H), 2.34 (s, 3H), 1.48 (s, 3H). |
| Compound 43 (S)-2-fluoro-1-(3-fluorophenyl)ethyl (1-methyl-4-(6-methyl-5-(methyl-sulfonamido)pyridin-2-yl)-1H-1,2,3-triazol-5-yl)carbamate | 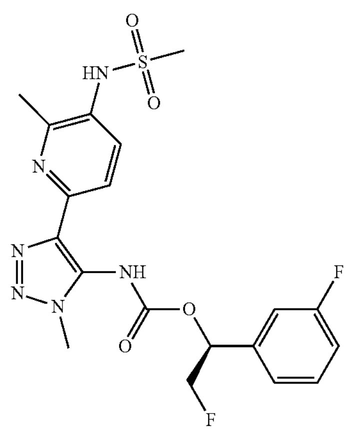 [SMILES: Cc1nc(-c2nnn(C)c2NC(=O)O[C@H](CF)c2cccc(F)c2)ccc1NS(C)(=O)=O] | | 467 | 1H NMR (400 MHz, Methanol-d4) δ 7.89-7.56 (m, 2H), 7.55-6.73 (m, 4H), 6.17-5.87 (m, 1H), 4.67-4.39 (m, 2H), 3.98 (s, 3H), 3.01 (s, 3H), 2.50 (s, 3H). |
| Compound 44 (S)-2-fluoro-1-(2-fluorophenyl)ethyl (1-methyl-4-(6-methyl-5-(methyl-sulfonamido)pyridin-2-yl)-1H-1,2,3-triazol-5-yl)carbamate | 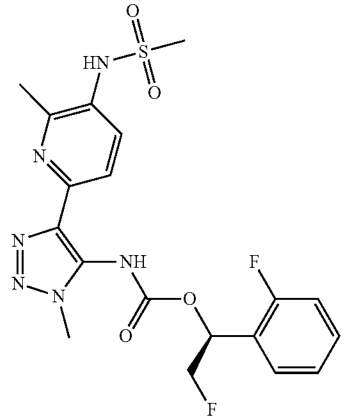 [SMILES: Cc1nc(-c2nnn(C)c2NC(=O)O[C@H](CF)c2ccccc2F)ccc1NS(C)(=O)=O] | | 467.1 | 1H NMR (400 MHz, Methanol-d4) δ 7.88-7.70 (m, 2H), 7.72-6.86 (m, 4H), 6.40-6.06 (m, 1H), 4.79-4.38 (m, 2H), 3.98 (s, 3H), 3.02 (s, 3H), 2.50 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 45 (S)-1-(2,5-difluoro-phenyl)-2-fluoroethyl (1-methyl-4-(6-methyl-5-(methyl-sulfonamido)pyridin-2-yl)-1H-1,2,3-triazol-5-yl)carbamate | 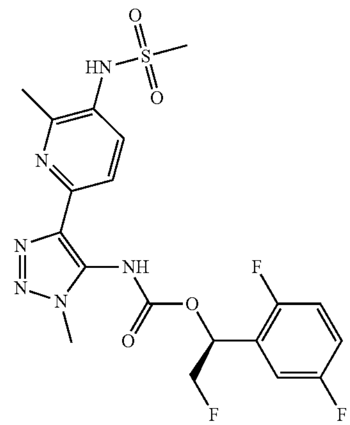 [SMILES: Cc1nc(-c2nnn(C)c2NC(=O)O[C@H](CF)c2cc(F)ccc2F)ccc1NS(C)(=O)=O] | | 485.1 | 1H NMR (400 MHz, Methanol-d4) δ 7.91-7.64 (m, 2H), 7.43-6.83 (m, 3H), 6.43-5.98 (m, 1H), 4.79-4.38 (m, 2H), 3.99 (s, 3H), 3.02 (s, 3H), 2.50 (s, 3H). |
| Compound 46 4-cyclopropyl-1,1,1-trifluoro-butan-2-yl (1-methyl-4-(6-methyl-5-(methyl-sulfonamido)pyridin-2-yl)-1H-1,2,3-triazol-5-yl)carbamate | 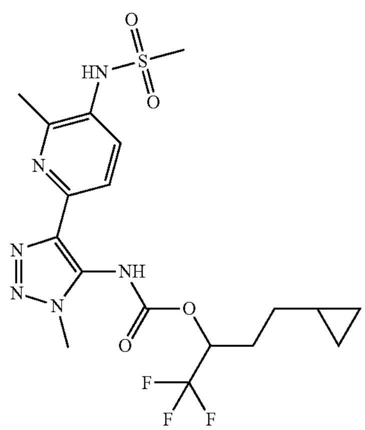 [SMILES: Cc1nc(-c2nnn(C)c2NC(=O)OC(CCC2CC2)C(F)(F)F)ccc1NS(C)(=O)=O] | | 477.1 | 1H NMR (400 MHz, Methanol-d4) δ 7.89-7.69 (m, 2H), 5.49-5.08 (m, 1H), 3.99 (s, 3H), 3.04 (s, 3H), 2.59 (s, 3H), 2.08-1.79 (m, 2H), 1.62-1.10 (m, 2H), 0.90-0.56 (m, 1H), 0.56-0.24 (m, 2H), 0.16-0.17 (m, 2H). |
| Compound 47 (S)-1,1,1-trifluoro-heptan-2-yl (1-methyl-4-(6-methyl-5-(methyl-sulfonamido)pyridin-2-yl)-1H-1,2,3-triazol-5-yl)carbamate | 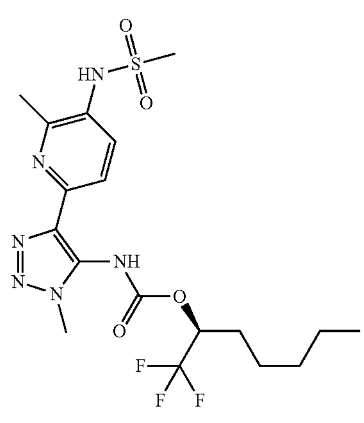 [SMILES: CCCCC[C@H](OC(=O)Nc1c(-c2ccc(NS(C)(=O)=O)c(C)n2)nnn1C)C(F)(F)F] | | 479.1 | 1H NMR (400 MHz, Methanol-d4) δ 7.85-7.78 (m, 2H), 5.41-5.10 (m, 1H), 3.99 (s, 3H), 3.04 (s, 3H), 2.59 (s, 3H), 1.98-1.06 (m, 8H), 1.00-0.63 (m, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 48 1-cyclohexyl-2,2,2-trifluoroethyl (1-methyl-4-(6-methyl-5-(methyl-sulfonamido)pyridin-2-yl)-1H-1,2,3-triazol-5-yl)carbamate | 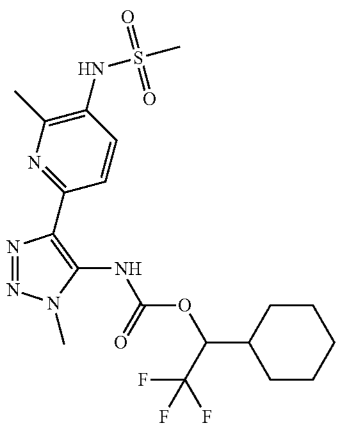 [SMILES: Cc1nc(-c2nnn(C)c2NC(=O)OC(C2CCCCC2)C(F)(F)F)ccc1NS(C)(=O)=O] | | 491.1 | 1H NMR (400 MHz, Methanol-d4) δ 7.93-7.68 (m, 2H), 5.30-5.00 (m, 1H), 3.99 (s, 3H), 3.04 (s, 3H), 2.60 (s, 3H), 2.29-0.56 (m, 11H). |
| Compound 49 (S)-2-chloro-1-phenylethyl (1-methyl-4-(6-methyl-5-(methyl-sulfonamido)pyridin-2-yl)-1H-1,2,3-triazol-5-yl)carbamate | 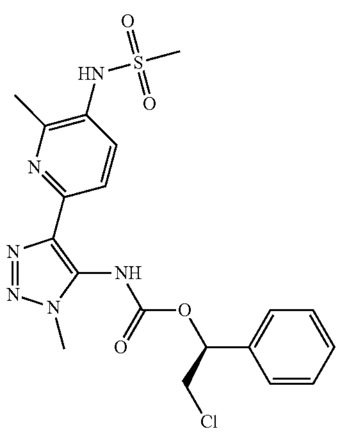 [SMILES: Cc1nc(-c2nnn(C)c2NC(=O)O[C@H](CCl)c2ccccc2)ccc1NS(C)(=O)=O] | | 465.1 | 1H NMR (400 MHz, Methanol-d4) δ 7.77 (s, 2H), 7.33 (s, 5H), 6.00-5.72 (m, 1H), 3.97 (s, 3H), 3.93-3.74 (m, 2H), 3.01 (s, 3H), 2.49 (s, 3H). |
| Compound 50 (R)-2-cyano-1-phenylethyl (1-methyl-4-(6-methyl-5-(methyl-sulfonamido)pyridin-2-yl)-1H-1,2,3-triazol-5-yl)carbamate | 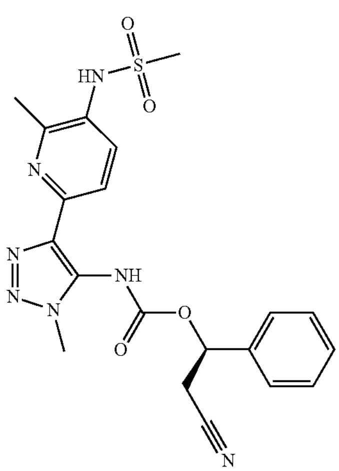 [SMILES: Cc1nc(-c2nnn(C)c2NC(=O)O[C@H](CC#N)c2ccccc2)ccc1NS(C)(=O)=O] | | 456.1 | 1H NMR (400 MHz, Methanol-d4) δ 7.78 (s, 2H), 7.64-7.13 (m, 5H), 6.15-5.90 (m, 1H), 4.71-4.52 (m, 2H), 4.00 (s, 3H), 3.02 (s, 3H), 2.56 (d, J = 31.2 Hz, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 51 (S)-1,1,1-trifluoro-octan-2-yl (1-methyl-4-(6-methyl-5-(methyl-sulfonamido)pyridin-2-yl)-1H-1,2,3-triazol-5-yl)carbamate | 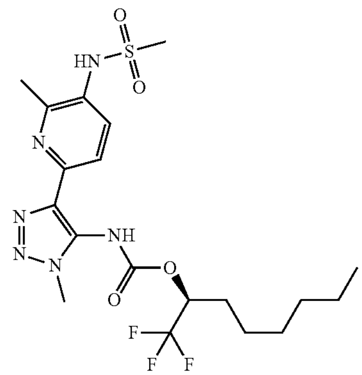 [SMILES: CCCCCC[C@H](OC(=O)Nc1c(-c2ccc(NS(C)(=O)=O)c(C)n2)nnn1C)C(F)(F)F] | | 493.1 | 1H NMR (400 MHz, Methanol-d4) δ 7.90-7.70 (m, 2H), 5.30 (s, 1H), 3.99 (s, 3H), 3.04 (s, 3H), 2.59 (s, 3H), 1.95-1.00 (m, 10H), 0.96-0.77 (m, 3H). |
| Compound 52 (R)-1-(2,5-dichloro-thiophen-3-yl)ethyl (1-methyl-4-(6-methyl-5-(methyl-sulfonamido)pyridin-2-yl)-1H-1,2,3-triazol-5-yl)carbamate | 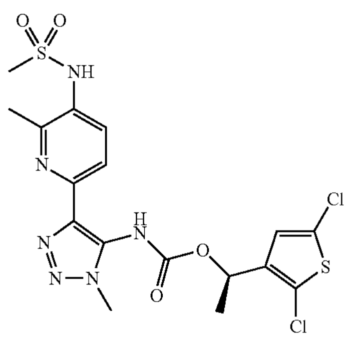 [SMILES: Cc1nc(-c2nnn(C)c2NC(=O)O[C@H](C)c2cc(Cl)sc2Cl)ccc1NS(C)(=O)=O] | | 504.9 | 1H NMR (400 MHz, DMSO-d6) δ 9.67 (s, 1H), 9.37 (s, 1H), 7.81 (d, J = 8.3 Hz, 1H), 7.73 (d, J = 8.3 Hz, 1H), 7.28 (s, 2H), 5.75 (s, 1H), 3.89 (s, 3H), 3.05 (s, 3H), 2.45 (s, 3H), 1.53 (s, 3H). |
| Compound 53 (R)-1-(3,5-difluoro-phenyl)ethyl (1-methyl-4-(6-methyl-5-(methyl-sulfonamido)pyridin-2-yl)-1H-1,2,3-triazol-5-yl)carbamate | 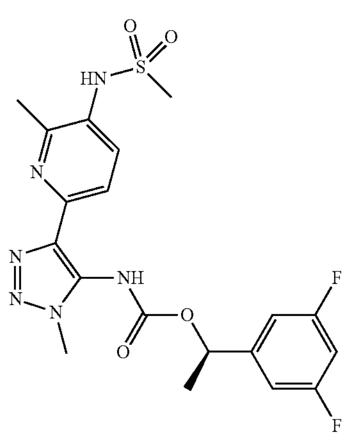 [SMILES: Cc1nc(-c2nnn(C)c2NC(=O)O[C@H](C)c2cc(F)cc(F)c2)ccc1NS(C)(=O)=O] | | 467.1 | 1H NMR (400 MHz, Methanol-d4) δ 7.82 (d, J = 1.9 Hz, 2H), 6.95 (d, J = 54.9 Hz, 3H), 5.84 (s, 1H), 4.00 (s, 3H), 3.05 (s, 3H), 1.57 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 54 (S)-2,2-difluoro-1-(2-fluorophenyl)ethyl (1-methyl-4-(6-methyl-5-(methyl-sulfonamido)pyridin-2-yl)-1H-1,2,3-triazol-5-yl)carbamate | 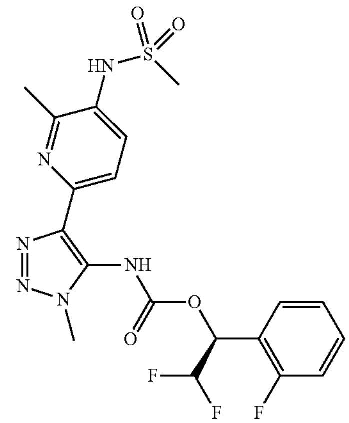 [SMILES: Cc1nc(-c2nnn(C)c2NC(=O)O[C@@H](c2ccccc2F)C(F)F)ccc1NS(C)(=O)=O] | | 485.1 | 1H NMR (400 MHz, Methanol-d4) δ 8.10-6.79 (m, 6H), 6.22 (s, 2H), 4.01 (s, 3H), 3.08 (s, 3H), 2.57 (s, 3H). |
| Compound 55 (R)-1-(2-(methylthio)phenyl)ethyl (1-methyl-4-(6-methyl-5-(methyl-sulfonamido)pyridin-2-yl)-1H-1,2,3-triazol-5-yl)carbamate | 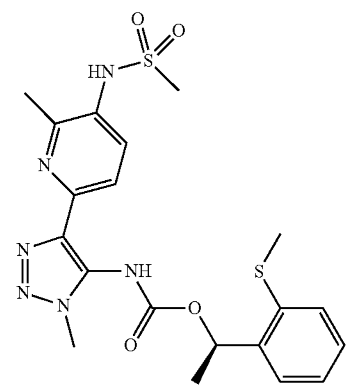 [SMILES: CSc1ccccc1[C@@H](C)OC(=O)Nc1c(-c2ccc(NS(C)(=O)=O)c(C)n2)nnn1C] | | 477.1 | 1H NMR (400 MHz, Methanol-d4) δ 7.80 (s, 2H), 7.63-6.96 (m, 4H), 6.25 (d, J = 6.8 Hz, 1H), 3.99 (s, 3H), 3.05 (s, 3H), 2.57 (s, 3H), 2.49 (s, 3H), 1.53 (s, 3H). |
| Compound 56 (R)-1-(5-chloro-2-fluorophenyl)ethyl (1-methyl-4-(6-methyl-5-(methyl-sulfonamido)pyridin-2-yl)-1H-1,2,3-triazol-5-yl)carbamate | 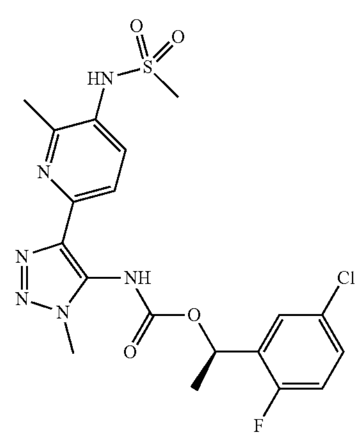 [SMILES: Cc1nc(-c2nnn(C)c2NC(=O)O[C@H](C)c2cc(Cl)ccc2F)ccc1NS(C)(=O)=O] | | 483.1 | 1H NMR (400 MHz, Methanol-d4) δ 7.98-7.70 (m, 2H), 7.22 (d, J = 83.0 Hz, 3H), 6.05 (d, J = 7.0 Hz, 1H), 4.01 (s, 3H), 3.05 (s, 3H), 2.55 (s, 3H), 1.58 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 57 (S)-2,2-difluoro-1-phenylethyl (1-methyl-4-(6-methyl-5-(methylsulfonamido)pyridin-2-yl)-1H-1,2,3-triazol-5-yl)carbamate | | | 467.1 | 1H NMR (400 MHz, Methanol-d4) δ 7.87 (d, J = 8.4 Hz, 1H), 7.76 (s, 1H), 7.66-7.25 (m, 5H), 6.48-5.86 (m, 2H), 3.99 (s, 3H), 3.06 (s, 3H), 2.53 (s, 3H). |
| Compound 58 (S)-2,2-difluoro-1-(3-fluorophenyl)ethyl (1-methyl-4-(6-methyl-5-(methylsulfonamido)pyridin-2-yl)-1H-1,2,3-triazol-5-yl)carbamate | | | 485.1 | 1H NMR (400 MHz, Methanol-d4) δ 7.82 (t, J = 7.1 Hz, 2H), 7.65-6.79 (m, 4H), 6.08 (d, J = 83.3 Hz, 2H), 4.00 (s, 3H), 3.04 (s, 3H), 2.49 (s, 3H). |
| Compound 59 (S)-2-fluoro-1-phenylethyl (1-methyl-4-(6-methyl-5-(methylsulfonamido)pyridin-2-yl)-1H-1,2,3-triazol-5-yl)carbamate | | | 449.2 | 1H NMR (400 MHz, Methanol-d4) δ 7.80 (s, 2H), 7.36 (s, 5H), 6.13-5.86 (m, 1H), 4.62 (d, J = 47.2 Hz, 2H), 3.99 (s, 3H), 3.04 (s, 3H), 2.52 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 60 (R)-1-(2-chloro-5-fluorophenyl)ethyl (1-methyl-4-(6-methyl-5-(methyl-sulfonamido)pyridin-2-yl)-1H-1,2,3-triazol-5-yl)carbamate | 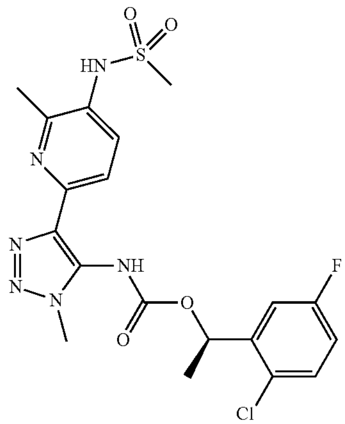 [SMILES: Cc1nc(-c2nnn(C)c2NC(=O)O[C@H](C)c2cc(F)ccc2Cl)ccc1NS(C)(=O)=O] | | 483.1 | 1H NMR (400 MHz, Methanol-d4) δ 7.97 (d, J = 21.8 Hz, 1H), 7.84 (d, J = 8.4 Hz, 1H), 7.42 (s, 1H), 7.08 (s, 1H), 6.13 (d, J = 7.4 Hz, 1H), 4.02 (s, 3H), 3.08 (s, 3H), 2.62 (s, 3H), 1.58 (s, 3H). |
| Compound 61 (R)-1-(2,5-dichloro-phenyl)ethyl (1-methyl-4-(6-methyl-5-(methyl-sulfonamido)pyridin-2-yl)-1H-1,2,3-triazol-5-yl)carbamate | 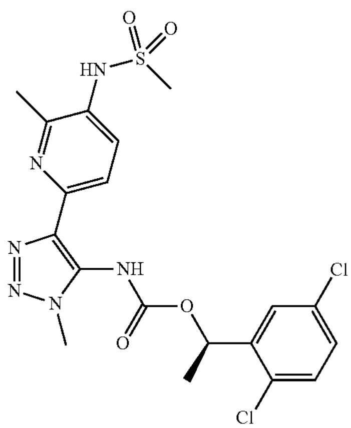 [SMILES: Cc1nc(-c2nnn(C)c2NC(=O)O[C@H](C)c2cc(Cl)ccc2Cl)ccc1NS(C)(=O)=O] | | 499.1 | 1H NMR (400 MHz, Methanol-d4) δ 7.95-7.72 (m, 2H), 7.70-7.16 (m, 3H), 6.14 (s, 1H), 4.02 (s, 3H), 3.04 (s, 3H), 2.56 (s, 3H), 1.57 (s, 3H). |
| Compound 62 (S)-1-(3-chloro-phenyl)-2,2-difluoroethyl (1-methyl-4-(6-methyl-5-(methyl-sulfonamido)pyridin-2-yl)-1H-1,2,3-triazol-5-yl)carbamate | 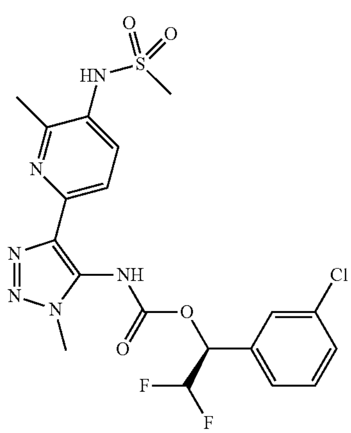 [SMILES: Cc1nc(-c2nnn(C)c2NC(=O)O[C@@H](c2cccc(Cl)c2)C(F)F)ccc1NS(C)(=O)=O] | | 501.1 | 1H NMR (400 MHz, Methanol-d4) δ 7.81 (q, J = 8.4 Hz, 2H), 7.40 (d, J = 22.5 Hz, 4H), 6.08 (d, J = 92.8 Hz, 2H), 4.01 (s, 3H), 3.04 (s, 3H), 2.49 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 63 (R)-1-(2,5-difluoro-phenyl)ethyl (1-methyl-4-(6-methyl-5-(methyl-sulfonamido)pyridin-2-yl)-1H-1,2,3-triazol-5-yl)carbamate | 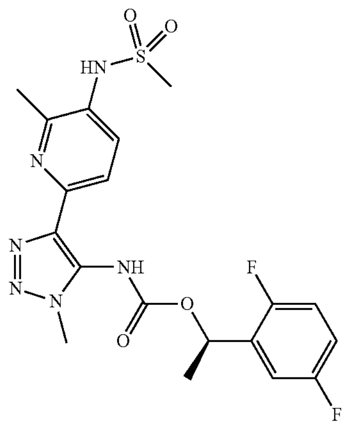 [SMILES: Cc1nc(-c2nnn(C)c2NC(=O)O[C@H](C)c2cc(F)ccc2F)ccc1NS(C)(=O)=O] | | 467.1 | 1H NMR (400 MHz, Methanol-d4) δ 7.92 (d, J = 8.5 Hz, 1H), 7.79 (d, J = 8.4 Hz, 1H), 7.17 (d, J = 70.1 Hz, 3H), 6.04 (d, J = 6.8 Hz, 1H), 3.99 (s, 3H), 3.06 (s, 3H), 2.59 (s, 3H), 1.58 (s, 3H). |
| Compound 64 (R)-N-(2-methyl-6-(1-methyl-5-(3-(2-phenylethyl)ureido)-1H-1,2,3-triazol-4-yl)pyridin-3-yl)methanesulfonamide | 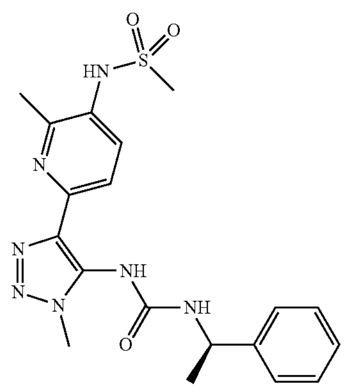 [SMILES: Cc1nc(-c2nnn(C)c2NC(=O)N[C@H](C)c2ccccc2)ccc1NS(C)(=O)=O] | | 430.1 | $^1$H NMR (400 MHz, Methanol-d$_4$) δ 7.87 (q, J = 8.5 Hz, 2H), 7.42-7.31 (m, 4H), 7.31-7.19 (m, 1H), 3.97 (s, 3H), 3.08 (s, 3H), 2.65 (s, 3H), 1.52 (d, J = 7.0 Hz, 3H). |
| Compound 65 (S)-N-(6-(5-(3-(2,2-difluoro-1-phenylethyl)ureido)-1-methyl-1H-1,2,3-triazol-4-yl)-2-methylpyridin-3-yl)methane-sulfonamide | 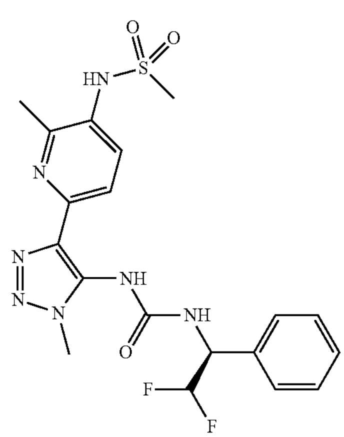 [SMILES: Cc1nc(-c2nnn(C)c2NC(=O)N[C@@H](c2ccccc2)C(F)F)ccc1NS(C)(=O)=O] | | 466.1 | $^1$H NMR (400 MHz, Methanol-d$_4$) δ 7.92-7.80 (m, 2H), 7.54 (s, 1H), 7.46-7.38 (m, 4H), 6.33-5.98 (m, 1H), 5.26 (ddd, J = 16.1, 13.2, 2.7 Hz, 1H), 3.99 (s, 3H), 3.07 (s, 3H), 2.62 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 66 (S)-N-(2-methyl-6-(1-methyl-5-(3-(2,2,2-trifluoro-1-phenylethyl)ureido)-1H-1,2,3-triazol-4-yl)pyridin-3-yl)methanesulfonamide | 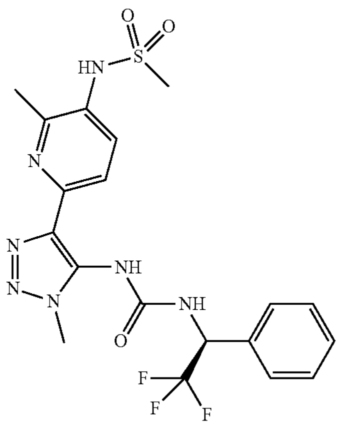 [SMILES: Cc1nc(-c2nnn(C)c2NC(=O)N[C@@H](c2ccccc2)C(F)(F)F)ccc1NS(C)(=O)=O] | | 484.1 | $^1$H NMR (400 MHz, Methanol-d$_4$) δ 7.93 (d, J = 8.5 Hz, 1H), 7.85 (d, J = 8.5 Hz, 1H), 7.56-7.36 (m, 5H), 5.59 (q, J = 8.1 Hz, 1H), 3.99 (s, 3H), 3.07 (s, 3H), 2.60 (s, 3H). |
| Compound 67 (R)-1-(pyridin-3-yl)ethyl (1-methyl-4-(6-methyl-5-(methyl-sulfonamido)pyridin-2-yl)-1H-1,2,3-triazol-5-yl)carbamate | 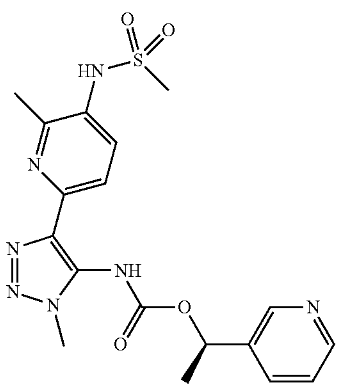 [SMILES: Cc1nc(-c2nnn(C)c2NC(=O)O[C@H](C)c2cccnc2)ccc1NS(C)(=O)=O] | | 432.2 | 1H NMR (400 MHz, Methanol-d4) δ 8.87-8.18 (m, 2H), 8.18-7.63 (m, 3H), 7.55-7.17 (m, 1H), 5.91 (d, J = 7.5 Hz, 1H), 3.99 (s, 3H), 3.06 (s, 3H), 2.53 (s, 3H), 1.79-1.41 (m, 3H). |
| Compound 68 (R)-1-(2-chloro-pyridin-3-yl)ethyl (1-methyl-4-(6-methyl-5-(methyl-sulfonamido)pyridin-2-yl)-1H-1,2,3-triazol-5-yl)carbamate | 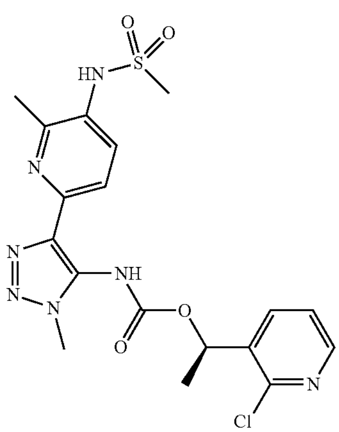 [SMILES: Cc1nc(-c2nnn(C)c2NC(=O)O[C@H](C)c2cccnc2Cl)ccc1NS(C)(=O)=O] | | 466.1 | 1H NMR (400 MHz, Methanol-d4) δ 8.49-6.92 (m, 5H), 6.26-5.93 (m, 1H), 4.01 (s, 3H), 3.06 (s, 3H), 2.56 (s, 3H), 1.60 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 69 (R)-1-(2-chloro-pyridin-3-yl)ethyl (1-methyl-4-(6-methyl-5-(methyl-sulfonamido)pyridin-2-yl)-1H-1,2,3-triazol-5-yl)carbamate | 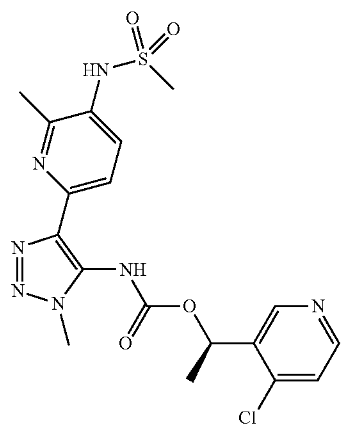 [SMILES: Cc1nc(-c2nnn(C)c2NC(=O)O[C@H](C)c2cnccc2Cl)ccc1NS(C)(=O)=O] | | 466.1 | 1H NMR (400 MHz, Methanol-d4) δ 8.43 (s, 2H), 7.81 (d, J = 2.8 Hz, 2H), 7.51 (s, 1H), 6.19 (s, 1H), 4.01 (s, 3H), 3.06 (s, 3H), 2.55 (s, 3H), 1.65 (s, 3H). |
| Compound 70 (R)-1-(4-methyl-pyrimidin-5-yl)ethyl (1-methyl-4-(6-methyl-5-(methyl-sulfonamido)pyridin-2-yl)-1H-1,2,3-triazol-5-yl)carbamate | 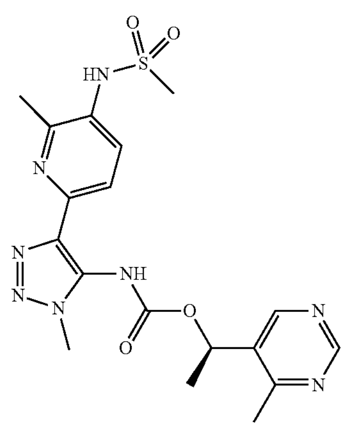 [SMILES: Cc1nc(-c2nnn(C)c2NC(=O)O[C@H](C)c2cncnc2C)ccc1NS(C)(=O)=O] | | 447.2 | 1H NMR (400 MHz, Methanol-d4) δ 8.87 (d, J = 52.7 Hz, 2H), 7.81 (d, J = 1.5 Hz, 2H), 6.05 (s, 1H), 4.00 (s, 3H), 3.07 (s, 3H), 2.57 (d, J = 31.1 Hz, 6H), 1.65 (s, 3H). |
| Compound 71 (R)-heptan-2-yl (1-methyl-4-(6-methyl-5-(methyl-sulfonamido)pyridin-2-yl)-1H-1,2,3-triazol-5-yl)carbamate | 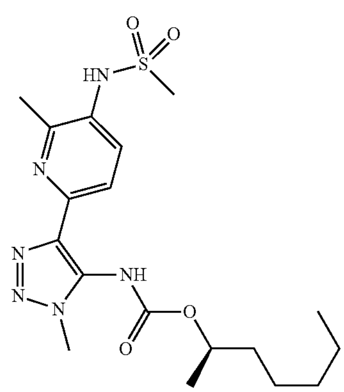 [SMILES: CCCCC[C@@H](C)OC(=O)Nc1c(-c2ccc(NS(C)(=O)=O)c(C)n2)nnn1C] | | 425.2 | 1H NMR (400 MHz, Methanol-d4) δ 7.89-7.70 (m, 2H), 4.02 (s, 3H), 3.01 (s, 3H), 2.60 (s, 3H), 1.79-1.04 (m, 11H), 1.04-0.67 (m, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 72 (R)-4-methylpentan-2-yl (1-methyl-4-(6-methyl-5-(methyl-sulfonamido)pyridin-2-yl)-1H-1,2,3-triazol-5-yl)carbamate | | | 411.2 | 1H NMR (400 MHz, Methanol-d4) δ 7.84 (d, J = 1.2 Hz, 2H), 4.96 (q, J = 6.4 Hz, 1H), 4.02 (s, 3H), 3.06 (s, 3H), 2.62 (s, 3H), 1.31 (d, J = 36.4 Hz, 6H), 0.91 (d, J = 6.5 Hz, 6H). |
| Compound 73 2-fluoro-2,3-dihydro-1H-inden-1-yl (1-methyl-4-(6-methyl-5-(methyl-sulfonamido)pyridin-2-yl)-1H-1,2,3-triazol-5-yl)carbamate | | | 461.2 | 1H NMR (400 MHz, DMSO-d6) δ 9.89 (s, 1H), 9.38 (s, 1H), 7.99-7.64 (m, 2H), 7.34 (s, 4H), 6.05 (s, 1H), 5.47 (d, J = 53.3 Hz, 1H), 3.93 (s, 3H), 3.05 (s, 5H). |
| Compound 74 (R)-1-(2-chloro-5-fluoropyridin-3-yl)ethyl (1-methyl-4-(6-methyl-5-(methyl-sulfonamido)pyridin-2-yl)-1H-1,2,3-triazol-5-yl)carbamate | | | 484.1 | 1H NMR (400 MHz, DMSO-d6) δ 9.85 (s, 1H), 9.56 (s, 1H), 9.36 (s, 1H), 8.46 (s, 1H), 7.83 (d, J = 8.3 Hz, 1H), 7.72 (d, J = 8.4 Hz, 1H), 5.89 (s, 1H), 3.92 (s, 3H), 3.05 (s, 3H), 2.42 (s, 3H), 1.59 (m, 2H). |
| Compound 75 1-(3-chloro-pyridin-4-yl)ethyl (1-methyl-4-(6-methyl-5-(methyl-sulfonamido)pyridin-2-yl)-1H-1,2,3-triazol-5-yl)carbamate | | | 466.1 | 1H NMR (400 MHz, DMSO-d6) δ 9.93 (s, 1H), 9.37 (s, 1H), 8.62 (s, 2H), 7.82 (d, J = 8.4 Hz, 1H), 7.76-7.66 (m, 1H), 7.60 (s, 1H), 6.92 (s, 1H), 5.93 (s, 1H), 3.91 (s, 3H), 3.05 (s, 3H), 2.62 (s, 1H), 2.47 (s, 3H), 1.56 (m, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 76 1-(3-chloro-pyrazin-2-yl)ethyl (1-methyl-4-(6-methyl-5-(methyl-sulfonamido)pyridin-2-yl)-1H-1,2,3-triazol-5-yl)carbamate | 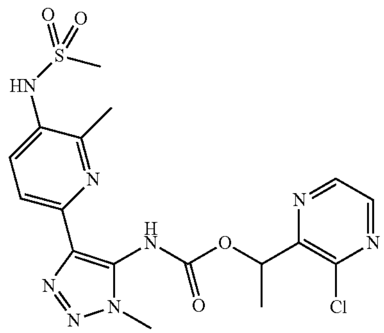 [SMILES: Cc1nc(-c2nnn(C)c2NC(=O)OC(C)c2nccnc2Cl)ccc1NS(C)(=O)=O] | | 467.1 | 1H NMR (400 MHz, DMSO-d6) δ 9.84 (s, 1H), 9.39 (s, 1H), 8.70 (s, 1H), 8.51 (s, 1H), 7.82-7.70 (m, 2H), 6.05 (s, 1H), 3.87 (s, 3H), 3.07 (s, 3H), 2.49 (s, 3H), 1.61 (3, 3H). |
| Compound 77 1-(3-chloro-2-fluoro-pyridin-4-yl)ethyl (1-methyl-4-(6-methyl-5-(methyl-sulfonamido)pyridin-2-yl)-1H-1,2,3-triazol-5-yl)carbamate | 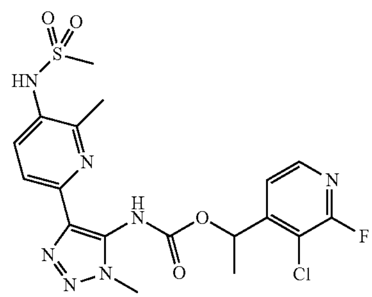 [SMILES: Cc1nc(-c2nnn(C)c2NC(=O)OC(C)c2ccnc(F)c2Cl)ccc1NS(C)(=O)=O] | | 484.0 | 1H NMR (400 MHz, DMSO-d6) δ 9.97 (s, 1H), 9.38 (s, 1H), 8.27 (s, 1H), 7.83 (d, J = 8.4 Hz, 1H), 7.73 (d, J = 8.4 Hz, 1H), 7.56 (s, 1H), 5.97 (s, 1H), 3.91 (s, 3H), 3.05 (s, 3H), 2.45 (s, 3H), 1.58 (m, 3H), 1.08. |
| Compound 78 1-(4-chloro-5-fluoropyridin-3-yl)ethyl (1-methyl-4-(6-methyl-5-(methyl-sulfonamido)pyridin-2-yl)-1H-1,2,3-triazol-5-yl)carbamate | 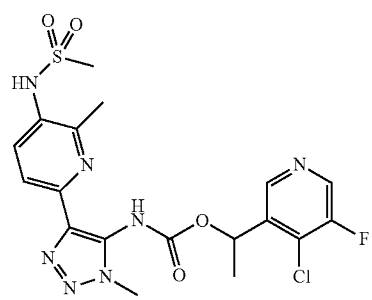 [SMILES: Cc1nc(-c2nnn(C)c2NC(=O)OC(C)c2cncc(F)c2Cl)ccc1NS(C)(=O)=O] | | 484.0 | 1H NMR (400 MHz, DMSO-d6) δ 9.89 (s, 1H), 9.35 (s, 1H), 8.63 (m, 2H), 7.81 (d, J = 8.3 Hz, 1H), 7.71 (d, J = 8.4 Hz, 1H), 6.01 (s, 1H), 3.90 (s, 3H), 3.05 (s, 3H), 2.43 (s, 3H), 1.63 (s, 3H). |
| Compound 79 1-(2-fluoropyridin-3-yl)ethyl (1-methyl-4-(6-methyl-5-(methyl-sulfonamido)pyridin-2-yl)-1H-1,2,3-triazol-5-yl)carbamate | 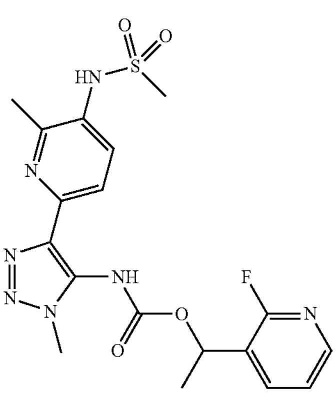 [SMILES: Cc1nc(-c2nnn(C)c2NC(=O)OC(C)c2cccnc2F)ccc1NS(C)(=O)=O] | | 450.1 | 1H NMR (400 MHz, Methanol-d4) δ 8.34-7.59 (m, 4H), 7.29 (s, 1H), 5.99 (s, 1H), 3.98 (s, 3H), 3.04 (s, 3H), 2.53 (s, 3H), 1.60 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 80 1-(2-fluoropyridin-3-yl)ethyl (1-methyl-4-(6-methyl-5-(methyl-sulfonamido)pyridin-2-yl)-1H-1,2,3-triazol-5-yl)carbamate | 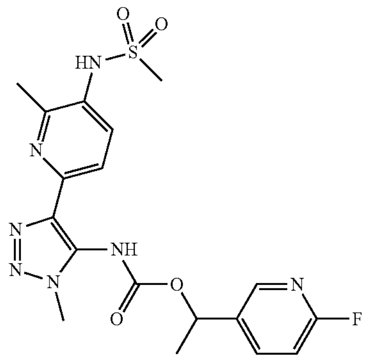 [SMILES: Cc1nc(-c2nnn(C)c2NC(=O)OC(C)c2ccc(F)nc2)ccc1NS(C)(=O)=O] | | 450.1 | 1H NMR (400 MHz, Methanol-d4) δ 7.81 (s, 4H), 7.07 (s, 1H), 5.92 (s, 1H), 3.99 (s, 3H), 3.06 (s, 3H), 2.54 (s, 3H), 1.61 (s, 3H). |
| Compound 81 1-(2-methylpyridin-3-yl)ethyl (1-methyl-4-(6-methyl-5-(methyl-sulfonamido)pyridin-2-yl)-1H-1,2,3-triazol-5-yl)carbamate | 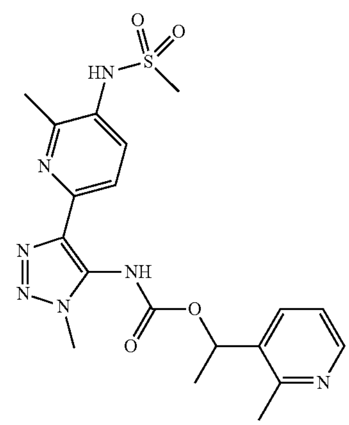 [SMILES: Cc1nc(-c2nnn(C)c2NC(=O)OC(C)c2cccnc2C)ccc1NS(C)(=O)=O] | | 446.0 | 1H NMR (400 MHz, Methanol-d4) δ 8.34 (s, 1H), 7.81 (d, J = 1.4 Hz, 3H), 6.04 (s, 1H), 3.99 (s, 3H), 3.06 (s, 3H), 2.64-2.45 (m, 6H), 1.73-1.42 (m, 3H). |
| Compound 82 1-(4-methyl-pyridin-3-yl)ethyl (1-methyl-4-(6-methyl-5-(methyl-sulfonamido)pyridin-2-yl)-1H-1,2,3-triazol-5-yl)carbamate | 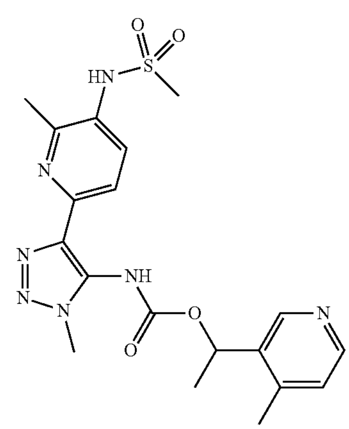 [SMILES: Cc1ccncc1C(C)OC(=O)Nc1c(-c2ccc(NS(C)(=O)=O)c(C)n2)nnn1C] | | 446.0 | 1H NMR (400 MHz, Methanol-d4) δ 8.83-8.11 (m, 2H), 7.80 (s, 2H), 7.23 (d, J = 12.9 Hz, 1H), 6.09 (s, 1H), 3.99 (s, 3H), 3.06 (s, 3H), 2.60-2.29 (m, 6H), 1.77-1.42 (m, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 83 1-(5-chloropyridin-3-yl)ethyl (1-methyl-4-(6-methyl-5-(methyl-sulfonamido)pyridin-2-yl)-1H-1,2,3-triazol-5-yl)carbamate | | | 466.1 | 1H NMR (400 MHz, Methanol-d4) δ 8.50 (s, 2H), 8.16-7.45 (m, 3H), 5.92 (s, 1H), 4.00 (s, 3H), 3.06 (s, 3H), 2.53 (s, 3H), 1.62 (s, 3H). |
| Compound 84 1-(2,5-dichloro-pyridin-3-yl)ethyl (1-methyl-4-(6-methyl-5-(methyl-sulfonamido)pyridin-2-yl)-1H-1,2,3-triazol-5-yl)carbamate | | | 500.1 | 1H NMR (400 MHz, Methanol-d4) δ 8.55-7.55 (m, 4H), 6.06 (s, 1H), 4.02 (s, 3H), 3.05 (s, 3H), 2.55 (s, 3H), 1.86-1.30 (m, 3H). |
| Compound 85 1-(2-(trifluoromethyl)pyridin-3-yl)ethyl (1-methyl-4-(6-methyl-5-(methyl-sulfonamido)pyridin-2-yl)-1H-1,2,3-triazol-5-yl)carbamate | | | 500.1 | 1H NMR (400 MHz, Methanol-d4) δ 9.08-7.12 (m, 5H), 6.23 (d, J = 7.2 Hz, 1H), 3.99 (s, 3H), 3.06 (s, 3H), 2.52 (s, 3H), 1.61 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 122 (R)-1-(2-methoxy-pyridin-3-yl)ethyl (1-methyl-4-(6-methyl-5-(methyl-sulfonamido)pyridin-2-yl)-1H-1,2,3-triazol-5-yl)carbamate | 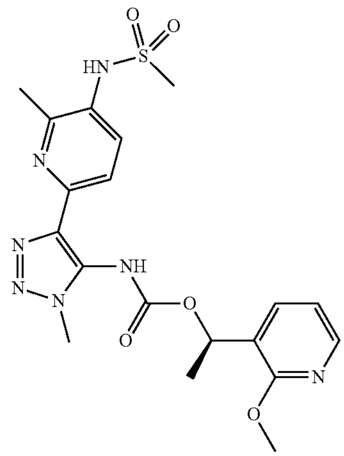 [SMILES: COc1ncccc1[C@@H](C)OC(=O)Nc1c(-c2ccc(NS(C)(=O)=O)c(C)n2)nnn1C] | | 461.9 | 1H NMR (400 MHz, Methanol-d4) δ 8.08 (s, 1H), 7.93 (d, 1H), 7.83 (m, 2H), 6.96 (s, 1H), 6.03 (d, J = 7.8 Hz, 1H), 4.02 (s, 3H), 3.95 (s, 3H), 3.08 (s, 3H), 2.60 (s, 3H), 1.53 (s, 3H). |
| Compound 123 (R)-1-(5-chloro-2-fluoropyridin-4-yl)ethyl (1-methyl-4-(6-methyl-5-(methyl-sulfonamido)pyridin-2-yl)-1H-1,2,3-triazol-5-yl)carbamate | 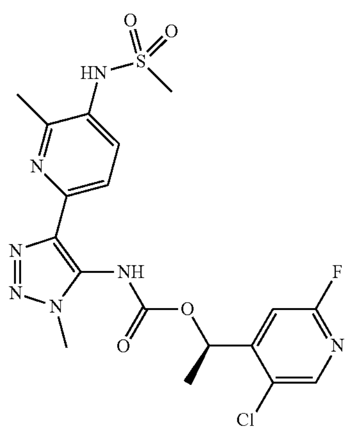 [SMILES: Cc1nc(-c2nnn(C)c2NC(=O)O[C@H](C)c2cc(F)ncc2Cl)ccc1NS(C)(=O)=O] | | 484.1 | 1H NMR (400 MHz, DMSO-d6) d 9.93 (s, 1H), 9.35 (s, 1H), 8.36 (s, 1H), 7.83 (d, J = 8.3 Hz, 1H), 7.71 (d, J = 8.4 Hz, 1H), 7.38 (s, 1H), 5.90 (s, 1H), 3.92 (s, 3H), 3.66-3.43 (m, 3H), 3.32 (s, 3H), 3.04 (s, 3H), 2.43 (s, 3H). |
| Compound 124 1-(2-(difluoromethyl)pyridin-3-yl)ethyl (1-methyl-4-(6-methyl-5-(methyl-sulfonamido)pyridin-2-yl)-1H-1,2,3-triazol-5-yl)carbamate | 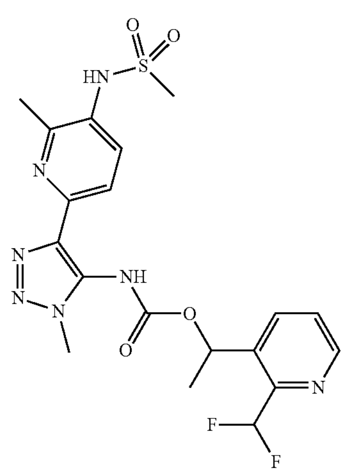 [SMILES: Cc1nc(-c2nnn(C)c2NC(=O)OC(C)c2cccnc2C(F)F)ccc1NS(C)(=O)=O] | | 482.0 | 1H NMR (400 MHz, DMSO-d6) d 9.76 (s, 1H), 9.36 (s, 1H), 8.62 (s, 1H), 8.15 (s, 1H), 7.81 (d, J = 8.3 Hz, 1H), 7.72 (d, J = 8.3 Hz, 1H), 7.11 (t, J = 53.8 Hz, 1H), 6.15 (s, 1H), 3.88 (s, 2H), 3.05 (s, 3H), 2.40 (s, 3H), 1.56 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 125 (R)-1-(5-bromo-2-fluoropyridin-3-yl)ethyl (1-methyl-4-(6-methyl-5-(methyl-sulfonamido)pyridin-2-yl)-1H-1,2,3-triazol-5-yl)carbamate | 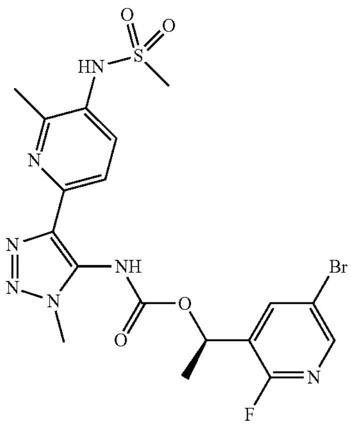 [SMILES: Cc1nc(-c2nnn(C)c2NC(=O)O[C@H](C)c2cc(Br)cnc2F)ccc1NS(C)(=O)=O] | | 528.1 | 1H NMR (400 MHz, DMSO-d6) d 9.80 (s, 1H), 9.61 (s, 0H), 9.35 (s, 1H), 8.35 (s, 1H), 7.83 (d, J = 8.3 Hz, 1H), 7.72 (d, J = 8.4 Hz, 1H), 5.84 (s, 1H), 3.90 (s, 3H), 3.05 (s, 3H), 2.40 (s, 3H), 1.60 (s, 3H). |
| Compound 126 1-(2-bromo-5-fluoro-pyridin-3-yl)ethyl (1-methyl-4-(6-methyl-5-(methyl-sulfonamido)pyridin-2-yl)-1H-1,2,3-triazol-5-yl)carbamate | 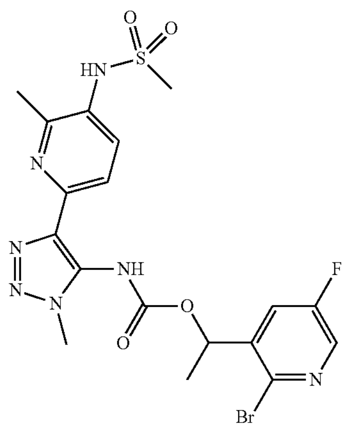 [SMILES: Cc1nc(-c2nnn(C)c2NC(=O)OC(C)c2cc(F)cnc2Br)ccc1NS(C)(=O)=O] | | 528.1 | 1H NMR (400 MHz, DMSO-d6) d 9.89 (s, 1H), 9.44 (s, 1H), 9.36 (s, 1H), 8.46 (s, 1H), 7.85 (d, J = 8.4 Hz, 1H), 7.71 (d, J = 8.4 Hz, 1H), 5.81 (s, 1H), 3.92 (s, 3H), 3.04 (s, 3H), 2.40 (s, 3H), 1.56 (s, 3H). |
| Compound 127 (R)-1-(2-vinyl-pyridin-3-yl)ethyl (1-methyl-4-(6-methyl-5-(methyl-sulfonamido)pyridin-2-yl)-1H-1,2,3-triazol-5-yl)carbamate | 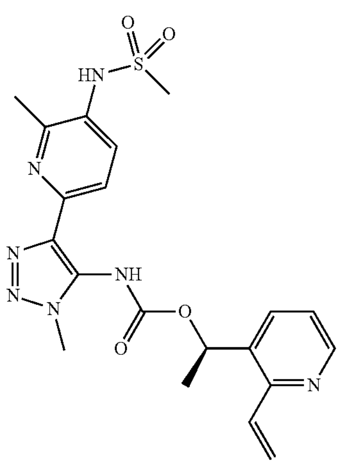 [SMILES: C=Cc1ncccc1[C@@H](C)OC(=O)Nc1c(-c2ccc(NS(C)(=O)=O)c(C)n2)nnn1C] | | 458.1 | 1H NMR (400 MHz, Methanol-d4) δ 8.45 (s, 1H), 7.87-7.67 (m, 2H), 7.53-6.92 (m, 2H), 6.36-6.02 (m, 2H), 5.69-5.46 (m, 1H), 3.99 (s, 3H), 3.05 (s, 3H), 2.52 (s, 3H), 1.61 (s 3H) |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 128 (R)-1-(2-fluoro-pyridin-3-yl)ethyl (1-methyl-4-(6-methyl-5-(methyl-sulfonamido)pyridin-2-yl)-1H-1,2,3-triazol-5-yl)carbamate | 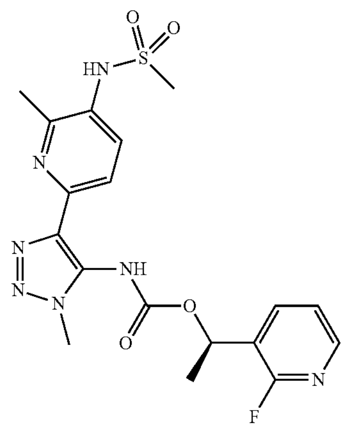 [SMILES: Cc1nc(-c2nnn(C)c2NC(=O)O[C@H](C)c2cccnc2F)ccc1NS(C)(=O)=O] | | 450.1 | 1H NMR (400 MHz, Methanol-d4) δ 7.80 (s, 4H), 7.31 (s, 1H), 6.01 (s, 1H), 4.00 (s, 3H), 3.05 (s, 3H), 2.54 (s, 3H), 1.61 (s, 3H). |
| Compound 129 1-(4-chloro-6-fluoropyridin-3-yl)ethyl (1-methyl-4-(6-methyl-5-(methyl-sulfonamido)pyridin-2-yl)-1H-1,2,3-triazol-5-yl)carbamate | 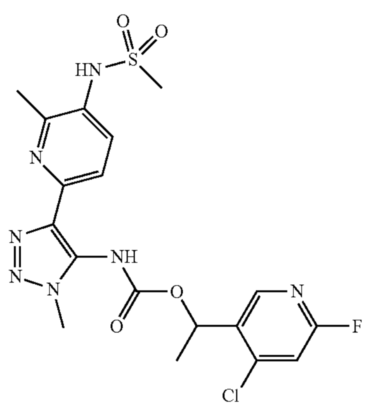 [SMILES: Cc1nc(-c2nnn(C)c2NC(=O)OC(C)c2cnc(F)cc2Cl)ccc1NS(C)(=O)=O] | | 484.0 | 1H NMR (400 MHz, DMSO-d6) d 9.85 (s, 1H), 9.37 (s, 1H), 8.47 (s, 1H), 7.81 (d, J = 8.3 Hz, 1H), 7.72 (d, J = 8.3 Hz, 1H), 5.99 (s, 1H), 3.90 (s, 3H), 3.05 (s, 3H), 2.43 (s, 3H), 1.62 (s, 3H). |
| Compound 130 1-(5-bromo-2-chloro-pyridin-3-yl)ethyl (1-methyl-4-(6-methyl-5-(methyl-sulfonamido)pyridin-2-yl)-1H-1,2,3-triazol-5-yl)carbamate | 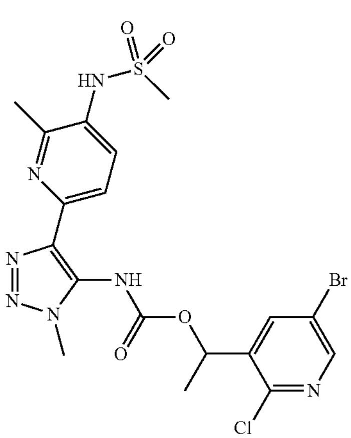 [SMILES: Cc1nc(-c2nnn(C)c2NC(=O)OC(C)c2cc(Br)cnc2Cl)ccc1NS(C)(=O)=O] | | 544.0 | 1H NMR (400 MHz, DMSO-d6) d 9.86 (s, 1H), 9.56 (s, 0H), 9.34 (s, 1H), 8.56 (s, 1H), 8.23 (s, 1H), 7.83 (d, J = 8.3 Hz, 1H), 7.71 (s, 1H), 7.39 (s, 0H), 5.88 (s, 2H), 3.92 (s, 3H), 3.04 (s, 3H), 2.40 (s, 4H), 1.59 (s, 2H), 1.24 (s, 2H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 131 1-(3-chloropyridin-2-yl)ethyl (1-methyl-4-(6-methyl-5-(methyl-sulfonamido)pyridin-2-yl)-1H-1,2,3-triazol-5-yl)carbamate | 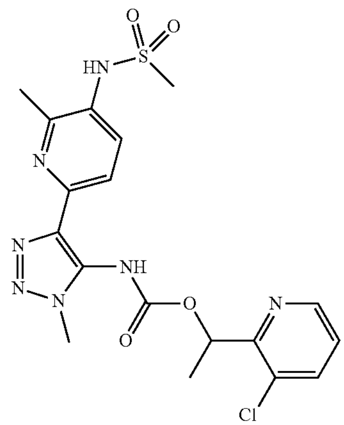 [SMILES: Cc1nc(-c2nnn(C)c2NC(=O)OC(C)c2ncccc2Cl)ccc1NS(C)(=O)=O] | | 465.9 | 1H NMR (400 MHz, Methanol-d4) δ 8.49 (s, 1H), 7.91-7.77 (m, 3H), 7.37 (dd, J = 8.1, 4.7 Hz, 1H), 6.20 (s, 1H), 3.99 (s, 3H), 3.07 (s, 3H), 2.61 (s, 3H), 1.60 (s, 3H). |
| Compound 132 1-(3-fluoropyridin-4-yl)ethyl (1-methyl-4-(6-methyl-5-(methyl-sulfonamido)pyridin-2-yl)-1H-1,2,3-triazol-5-yl)carbamate | 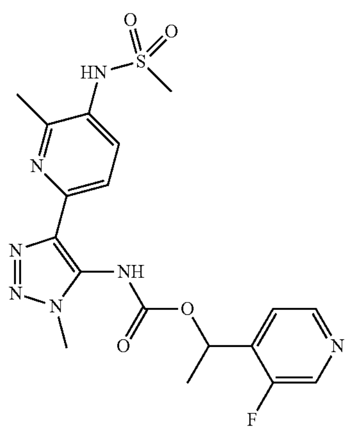 [SMILES: Cc1nc(-c2nnn(C)c2NC(=O)OC(C)c2ccncc2F)ccc1NS(C)(=O)=O] | | 450.1 | 1H NMR (400 MHz, Methanol-d4) δ 8.44 (s, 2H), 7.99-7.17 (m, 3H), 6.08 (s, 1H), 4.01 (s, 3H), 3.06 (s, 3H), 2.57 (s, 3H), 1.63 (s, 3H). |
| Compound 133 1-(2,4-dichloro-pyrimidin-5-yl)ethyl (1-methyl-4-(6-methyl-5-(methyl-sulfonamido)pyridin-2-yl)-1H-1,2,3-triazol-5-yl)carbamate | 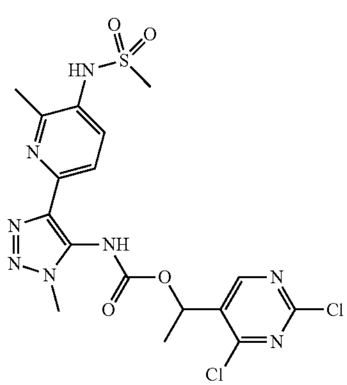 [SMILES: Cc1nc(-c2nnn(C)c2NC(=O)OC(C)c2cnc(Cl)nc2Cl)ccc1NS(C)(=O)=O] | | 501.0 | 1H NMR (400 MHz, DMSO-d6) d 9.88 (s, 1H), 9.39 (s, 1H), 8.95 (s, 1H), 7.83 (d, J = 8.3 Hz, 1H), 7.73 (d, J = 8.4 Hz, 1H), 5.89 (s, 1H), 3.91 (s, 3H), 3.06 (s, 3H), 2.44 (s, 3H), 1.63 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 134 1-(3,6-dichloro-pyridazin-4-yl)ethyl (1-methyl-4-(6-methyl-5-(methyl-sulfonamido)pyridin-2-yl)-1H-1,2,3-triazol-5-yl)carbamate | 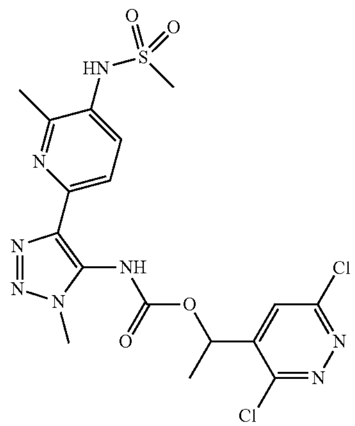 [SMILES: Cc1nc(-c2nnn(C)c2NC(=O)OC(C)c2cc(Cl)nnc2Cl)ccc1NS(C)(=O)=O] | | 501.0 | 1H NMR (400 MHz, DMSO-d6) d 9.95 (s, 1H), 9.37 (s, 1H), 7.85 (d, J = 8.5 Hz, 1H), 7.73 (d, J = 8.3 Hz, 1H), 7.34 (s, 1H), 5.81 (s, 1H), 3.93 (s, 3H), 3.04 (d, J = 8.2 Hz, 4H), 2.46-2.39 (m, 3H), 1.62 (s, 3H). |
| Compound 135 (R)-1-(1-methyl-1H-pyrazol-5-yl)ethyl (1-methyl-4-(6-methyl-5-(methyl-sulfonamido)pyridin-2-yl)-1H-1,2,3-triazol-5-yl)carbamate | 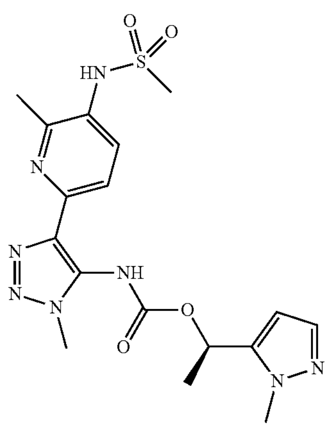 [SMILES: Cc1nc(-c2nnn(C)c2NC(=O)O[C@H](C)c2ccnn2C)ccc1NS(C)(=O)=O] | | 434.9 | 1H NMR (400 MHz, Methanol-d4) δ 7.81 (d, J = 1.0 Hz, 2H), 7.41 (s, 1H), 6.38 (s, 1H), 6.04 (d, J = 5.2 Hz, 1H), 4.00 (s, 3H), 3.95-3.75 (m, 3H), 3.06 (s, 3H), 2.55 (s, 3H), 1.66 (s, 3H). |
| Compound 136 1-(3-methyl-isoxazol-4-yl)ethyl (1-methyl-4-(6-methyl-5-(methyl-sulfonamido)pyridin-2-yl)-1H-1,2,3-triazol-5-yl)carbamate | 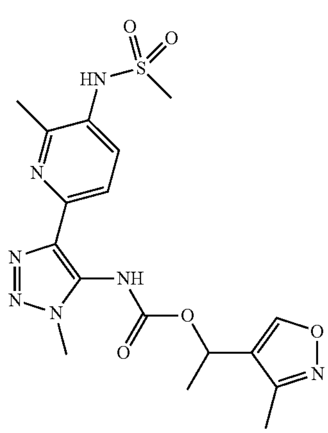 [SMILES: Cc1nc(-c2nnn(C)c2NC(=O)OC(C)c2conc2C)ccc1NS(C)(=O)=O] | | 436.0 | 1H NMR (400 MHz, Methanol-d4) δ 8.62 (s, 1H), 7.82 (s, 2H), 5.87 (d, J = 6.3 Hz, 1H), 4.01 (s, 3H), 3.07 (s, 3H), 2.55 (s, 3H), 2.30 (s, 3H), 1.62 (s, 3H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 137 1-(2-chloropyridin-3-yl)-2,2-difluoro-ethyl (1-methyl-4-(6-methyl-5-(methyl-sulfonamido)pyridin-2-yl)-1H-1,2,3-triazol-5-yl)carbamate | 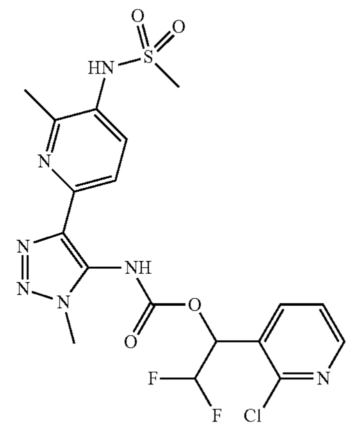 [SMILES: Cc1nc(-c2nnn(C)c2NC(=O)OC(c2cccnc2Cl)C(F)F)ccc1NS(C)(=O)=O] | | 502.0 | 1H NMR (400 MHz, Methanol-d4) δ 8.85-6.83 (m, 6H), 6.61-6.08 (m, 1H), 4.01 (s, 3H), 3.05 (s, 3H), 2.52 (s, 3H). |
| Compound 138 (R)-1-(4-chloro-thiophen-3-yl)ethyl (1-methyl-4-(6-methyl-5-(methyl-sulfonamido)pyridin-2-yl)-1H-1,2,3-triazol-5-yl)carbamate | 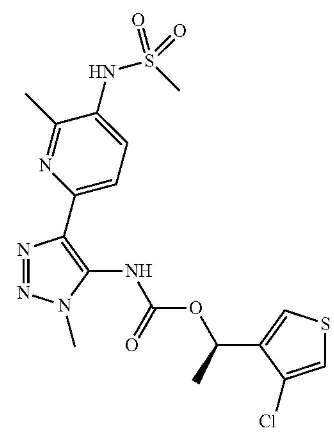 [SMILES: Cc1nc(-c2nnn(C)c2NC(=O)O[C@H](C)c2cscc2Cl)ccc1NS(C)(=O)=O] | | 470.9 | 1H NMR (400 MHz, Methanol-d4) δ 7.94 (d, J = 8.5 Hz, 1H), 7.83 (d, J = 8.5 Hz, 1H), 7.43-7.39 (m, 1H), 7.30 (d, J = 3.5 Hz, 1H), 5.94 (q, J = 6.6 Hz, 1H), 4.02 (s, 3H), 3.09 (s, 3H), 2.63 (s, 3H), 1.62 (s, 3H). |
| Compound 139 (R)-1-(2,5-dichloro-thiazol-4-yl)ethyl (1-methyl-4-(6-methyl-5-(methyl-sulfonamido)pyridin-2-yl)-1H-1,2,3-triazol-5-yl)carbamate | 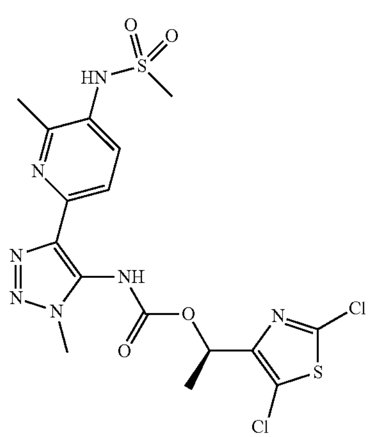 [SMILES: Cc1nc(-c2nnn(C)c2NC(=O)O[C@H](C)c2nc(Cl)sc2Cl)ccc1NS(C)(=O)=O] | | 506.0 | 1H NMR (400 MHz, Methanol-d4) δ 7.97 (d, J = 8.5 Hz, 1H), 7.83 (d, J = 8.5 Hz, 1H), 5.96 (d, J = 7.5 Hz, 1H), 4.02 (s, 3H), 3.10 (s, 3H), 2.64 (s, 3H), 1.60 (s, 3H), 1.49 (d, J = 6.6 Hz, 1H). |

TABLE 4-continued

Exemplary compounds prepared according to Scheme B2a (using Intermediate 10)

| Name | Structure | Reagent 1 | LCMS M/Z (M + 1) | NMR |
|---|---|---|---|---|
| Compound 140 (R)-1-(4-chloro-thiazol-5-yl)ethyl (1-methyl-4-(6-methyl-5-(methyl-sulfonamido)pyridin-2-yl)-1H-1,2,3-triazol-5-yl)carbamate | 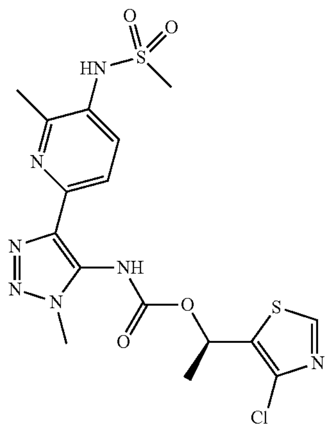 [SMILES: Cc1nc(-c2nnn(C)c2NC(=O)O[C@H](C)c2scnc2Cl)ccc1NS(C)(=O)=O] | | 472.0 | 1H NMR (400 MHz, Methanol-d4) δ 8.91 (d, J = 24.4 Hz, 1H), 7.89 (d, J = 8.7 Hz, 1H), 7.82 (d, J = 8.4 Hz, 1H), 6.19 (s, 1H), 4.01 (s, 3H), 3.09 (s, 3H), 2.59 (s, 3H), 1.78-1.48 (m, 3H). |
| Compound 141 (R)-1-(2-methyl-pyridin-3-yl)ethyl (1-methyl-4-(6-methyl-5-(methyl-sulfonamido)pyridin-2-yl)-1H-1,2,3-triazol-5-yl)carbamate | 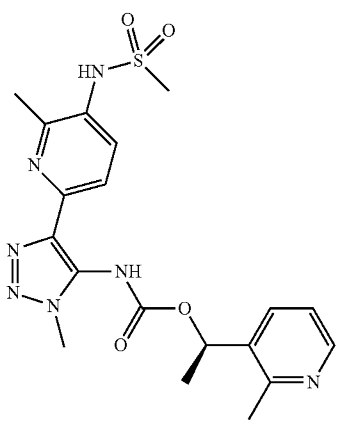 [SMILES: Cc1nc(-c2nnn(C)c2NC(=O)O[C@H](C)c2cccnc2C)ccc1NS(C)(=O)=O] | | 446.0 | 1H NMR (400 MHz, Methanol-d4) δ 8.58-6.91 (m, 5H), 6.04 (s, 1H), 3.98 (s, 3H), 3.06 (s, 3H), 2.56 (d, J = 24.1 Hz, 6H), 1.58 (s, 3H). |
| Compound 142 (R)-1-(2,5-dichloro-pyridin-3-yl)ethyl (1-methyl-4-(6-methyl-5-(methyl-sulfonamido)pyridin-2-yl)-1H-1,2,3-triazol-5-yl)carbamate | 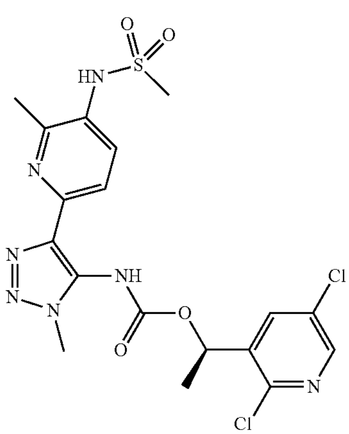 [SMILES: Cc1nc(-c2nnn(C)c2NC(=O)O[C@H](C)c2cc(Cl)cnc2Cl)ccc1NS(C)(=O)=O] | | 500.0 | 1H NMR (400 MHz, Methanol-d4) δ 8.56-7.59 (m, 4H), 6.07 (s, 1H), 4.02 (s, 3H), 3.05 (s, 3H), 2.54 (s, 3H), 1.61 (s, 3H). |

TABLE 4-continued

Exemplary compounds prepared according to Scheme B2a (using Intermediate 10)

| Name | Structure | Reagent 1 | LCMS M/Z (M + 1) | NMR |
|------|-----------|-----------|------------------|-----|
| Compound 143 (R)-1-(6-fluoro-2-methylpyridin-3-yl)ethyl (1-methyl-4-(6-methyl-5-(methylsulfonamido)pyridin-2-yl)-1H-1,2,3-triazol-5-yl)carbamate | | | 464.0 | 1H NMR (400 MHz, Methanol-d4) δ 7.81 (s, 3H), 6.90 (s, 1H), 6.03 (s, 1H), 3.98 (s, 3H), 3.06 (s, 3H), 2.53 (d, J = 6.3 Hz, 6H), 1.77-1.35 (m, 3H). |

TABLE 5

Exemplary compounds prepared according to Scheme B2a (using Intermediate 11)

| Name | Structure | Reagent 1 | LCMS M/Z (M + 1) | NMR |
|------|-----------|-----------|------------------|-----|
| Compound 86 (R)-1-(2-chlorophenyl)ethyl(1-methyl-4-(6-methyl-5-(N-methylmethylsulfonamido)pyridin-2-yl)-1H-1,2,3-triazol-5-yl)carbamate | 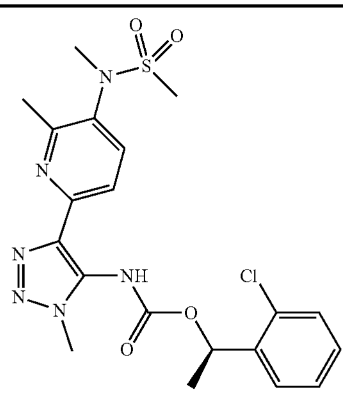 | | 479.2 | 1H NMR (400 MHz, DMSO-d6) δ 9.79 (bs, 1H), 7.93 (d, J = 8.4 Hz, 1H), 7.86 (d, J = 8.2 Hz, 1H), 7.76-7.11 (bm, 4H), 6.00 (bs, 1H), 3.89 (s, 3H), 3.16 (s, 3H), 3.10 (s, 3H), 2.44 (s, 3H), 1.52 (bs, 3H). |

Example 23: Preparation of Compounds 87 to 100

Compounds 87 to 100 were generally prepared according to Scheme B2b. For example, (R)-1-(2,3-difluorophenyl)ethyl (1-methyl-4-(6-methyl-5-(methylsulfonamido)pyridin-2-yl)-1H-1,2,3-triazol-5-yl)carbamate (Compound 87) was prepared as follows.

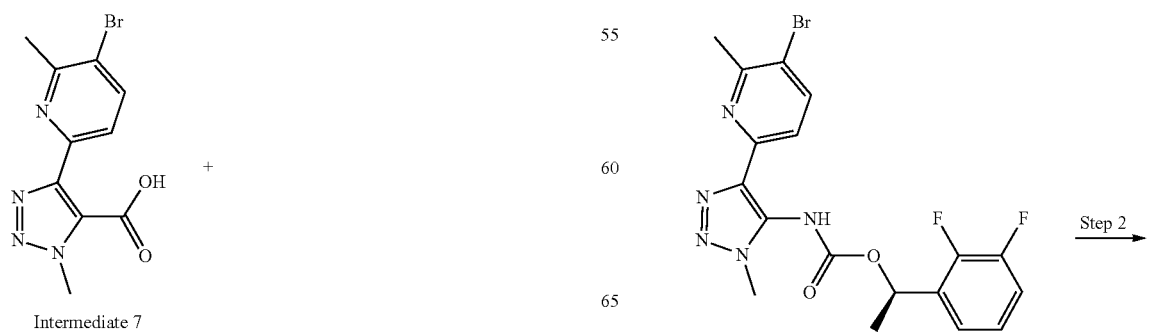

-continued

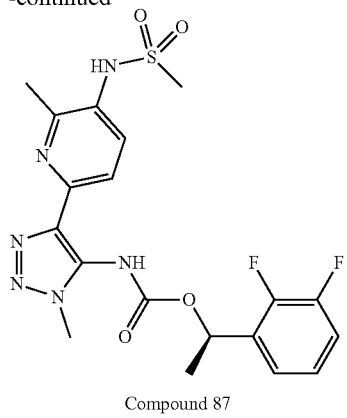

Compound 87

Step 1: (R)-1-(2,3-difluorophenyl)ethyl(4-(5-bromo-6-methylpyridin-2-yl)-1-methyl-1H-1,2,3-triazol-5-yl)carbamate To a solution of 4-(5-bromo-6-methylpyridin-2-yl)-1-methyl-1H-1,2,3-triazole-5-carboxylic acid (Intermediate 7) (0.673 mmol) in THF (2 mL) was added triethylamine (1.35 mmol), 50% v/v propanephosphonic acid anhydride ($T_3P$) (1.57 M) in THF (1.01 mmol), and azidotrimethylsilane (1.01 mmol). The mixture was stirred for 30 min at 70° C. The mixture was then cooled to room temperature and (R)-1-(2,3-difluorophenyl)ethan-1-ol (Reagent 1) (0.336 mmol) was added. The mixture was then reheated to 70° C. for 1 h. The reaction solution was cooled to room temperature, the volatiles removed in vacuo and the remaining residue was chromatographed by silica gel column chromatography to provide (R)-1-(2,3-difluorophenyl)ethyl (4-(5-bromo-6-methylpyridin-2-yl)-1-methyl-1H-1,2,3-triazol-5-yl)carbamate.

Step 2: (R)-1-(2,3-difluorophenyl)ethyl(1-methyl-4-(6-methyl-5-(methylsulfonamido) pyridin-2-yl)-1H-1,2,3-triazol-5-yl)carbamate (Compound 87)

A 5 ml microwave vial, fitted with a stir bar, was charged with (R)-1-(2,3-difluorophenyl)ethyl (4-(5-bromo-6-methylpyridin-2-yl)-1-methyl-1H-1,2,3-triazol-5-yl) carbamate (0.526 mmol), methanesulphonamide (Reagent 2) (1.05 mmol), allylpalladium chloride dimer (0.053 mmol), 2-di-tert-butylphosphino-2',4',6'-triisopropylbiphenyl (0.210 mmol), potassium carbonate (1.32 mmol), and THF (3 mL). The mixture was degassed for 5 min, sealed under an atmosphere of argon and heated to 80° C. for 2 h. The crude mixture was cooled to room temperature, filtered and the volatiles removed in vacuo. The crude material was purified by preparative HPLC (continuous gradient 30% to 90% MeCN/$H_2O$ with 0.1% v/v TFA) to give (R)-1-(2,3-difluorophenyl)ethyl (1-methyl-4-(6-methyl-5-(methylsulfonamido) pyridin-2-yl)-1H-1,2,3-triazol-5-yl)carbamate Compounds 87 to 100 were similarly prepared according to Scheme B2b by reacting Intermediate 5 (Example 7), Intermediate 7 (Example 9), Intermediate 8 (Example 10), or Intermediate 9 (Example 11) with a Reagent 1 listed in Table 6 and methanesulphonamide (Reagent 2) following the general process described for Compound 87

TABLE 6

Compounds prepared according to Scheme B2b

| Name | Structure | Reagent 1 | LCMS M/Z (M + 1) | NMR |
|---|---|---|---|---|
| Compound 87 (R)-1-(2,3-difluorophenyl)ethyl(1-methyl-4-(6-methyl-5-(methylsulfonamido) pyridin-2-yl)-1H-1,2,3-triazol-5-yl)carbamate | | | 467.1 | 1H NMR (400 MHz, Methanol-d4) δ 7.93 (d, J = 8.5 Hz, 1H), 7.79 (d, J = 8.4 Hz, 1H), 7.20 (s, 3H), 6.23-5.90 (m, 1H), 3.98 (s, 3H), 3.07 (s, 3H), 2.60 (s, 3H), 1.60 (s, 3H). |

TABLE 6-continued

Compounds prepared according to Scheme B2b

| Name | Structure | Reagent 1 | LCMS M/Z (M + 1) | NMR |
|---|---|---|---|---|
| Compound 88 (R)-1-(3-fluorophenyl) ethyl(4-(3-fluoro-5-(methylsulfonamido) pyridin-2-yl)-1-methyl-1H-1,2,3-triazol-5-yl)carbamate | 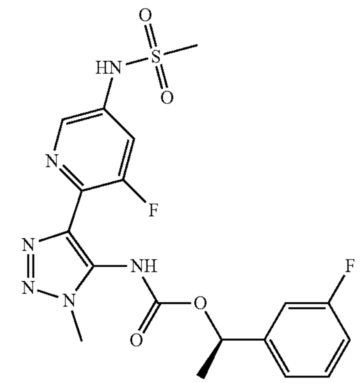 [SMILES: C[C@@H](OC(=O)Nc1c(-c2ncc(NS(C)(=O)=O)cc2F)nnn1C)c1cccc(F)c1] | | 453.1 | 1H NMR (400 MHz, Methanol-d4) δ 8.27 (s, 1H), 7.54 (dd, J = 11.9, 2.2 Hz, 1H), 7.46-6.86 (m, 4H), 5.76 (q, J = 6.8 Hz, 1H), 3.97 (s, 3H), 3.07 (s, 3H), 1.53 (s, 3H). |
| Compound 89 (R)-1-(2-chlorophenyl) ethyl(4-(3-fluoro-5-(methylsulfonamido) pyridin-2-yl)-1-methyl-1H-1,2,3-triazol-5-yl)carbamate | 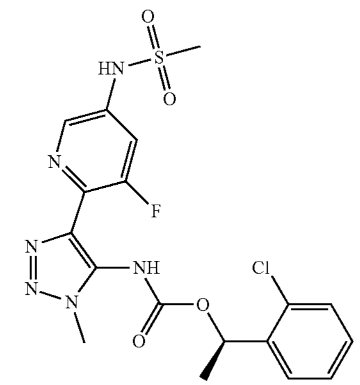 [SMILES: C[C@@H](OC(=O)Nc1c(-c2ncc(NS(C)(=O)=O)cc2F)nnn1C)c1ccccc1Cl] | | 469.1 | 1H NMR (400 MHz, Methanol-d4) δ 8.28 (s, 1H), 7.73-7.09 (m, 5H), 6.10 (q, J = 6.5 Hz, 1H), 3.97 (s, 3H), 3.07 (s, 3H), 1.50 (s, 3H). |
| Compound 90 (R)-1-(2,4,5-trifluoro-phenyl)ethyl(1-methyl-4-(6-methyl-5-(methyl-sulfonamido)pyridin-2-yl)-1H-1,2,3-triazol-5-yl)carbamate | 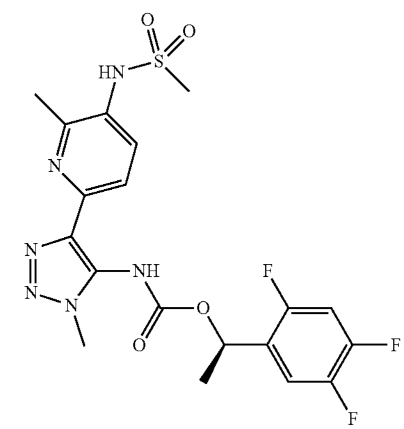 [SMILES: Cc1nc(-c2nnn(C)c2NC(=O)O[C@H](C)c2cc(F)c(F)cc2F)ccc1NS(C)(=O)=O] | | 485.1 | 1H NMR (400 MHz, Methanol-d4) δ 8.01-7.76 (m, 2H), 7.31 (d, J = 112.4 Hz, 2H), 6.01 (d, J = 6.9 Hz, 1H), 3.99 (s, 3H), 3.06 (s, 3H), 2.58 (s, 3H), 1.57 (s, 3H). |
| Compound 91 3-fluorobenzyl(1-methyl-4-(6-methyl-5-(methylsulfonamido) pyridin-2-yl)-1H-1,2,3-triazol-5-yl)carbamate | 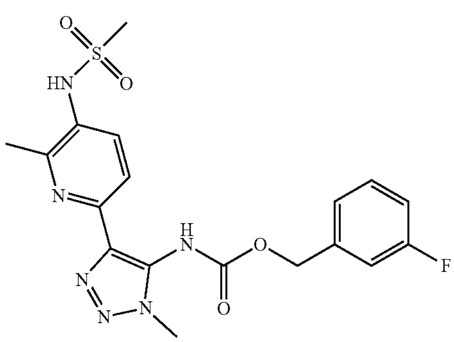 [SMILES: Cc1nc(-c2nnn(C)c2NC(=O)OCc2cccc(F)c2)ccc1NS(C)(=O)=O] | | 435.1 | 1H NMR (400 MHz, Methanol-d4) δ 7.90 (d, J = 8.4 Hz, 1H), 7.82 (d, J = 8.4 Hz, 1H), 7.51-6.85 (m, 4H), 5.20 (s, 2H), 4.00 (s, 3H), 3.05 (s, 3H), 2.58 (s, 3H). |

TABLE 6-continued

Compounds prepared according to Scheme B2b

| Name | Structure | Reagent 1 | LCMS M/Z (M + 1) | NMR |
|---|---|---|---|---|
| Compound 92 (R)-1-(3-fluorophenyl) ethyl(1-methyl-4-(6-methyl-5-(methylsulfonamido) pyridin-2-yl)-1H-1,2,3-triazol-5-yl)carbamate | 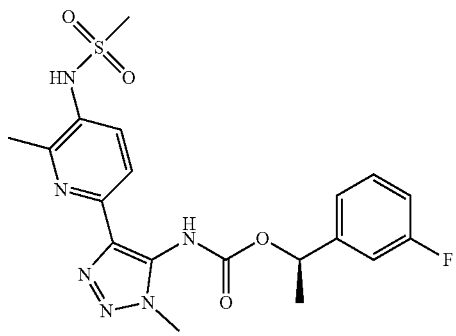 [SMILES: Cc1nc(-c2nnn(C)c2NC(=O)O[C@H](C)c2cccc(F)c2)ccc1NS(C)(=O)=O] | | 449.1 | 1H NMR (400 MHz, Methanol-d4) δ 7.79 (s, 2H), 7.50-6.83 (m, 4H), 5.89-5.71 (m, 1H), 3.97 (s, 3H), 3.03 (s, 3H), 2.53 (s, 3H), 1.54 (s, 3H). |
| Compound 93 (R)-1-(2-fluorophenyl) ethyl(1-methyl-4-(6-methyl-5-(methyl-sulfonamido) pyridin-2-yl)-1H-1,2,3-triazol-5-yl)carbamate | 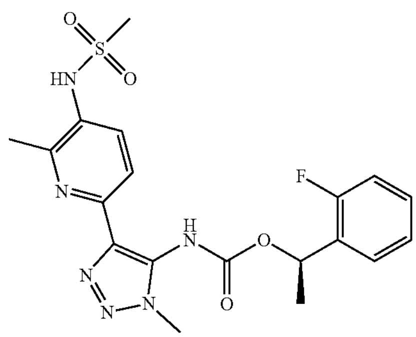 [SMILES: Cc1nc(-c2nnn(C)c2NC(=O)O[C@H](C)c2ccccc2F)ccc1NS(C)(=O)=O] | | 449.1 | 1H NMR (400 MHz, Methanol-d4) δ 7.80 (s, 2H), 7.67-6.80 (m, 4H), 6.20-5.99 (m, 1H), 3.99 (s, 3H), 3.05 (s, 3H), 2.56 (s, 3H), 1.59 (s, 3H). |
| Compound 94 (S)-2,2,2-trifluoro-1-phenylethyl(1-methyl-4-(6-methyl-5-(methylsulfonamido) pyridin-2-yl)-1H-1,2,3-triazol-5-yl)carbamate | 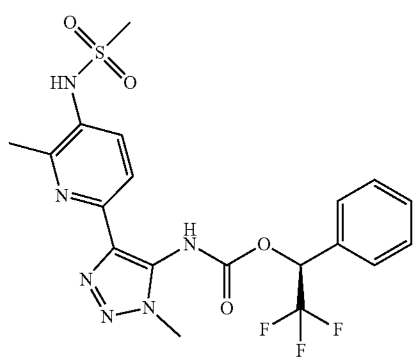 [SMILES: Cc1nc(-c2nnn(C)c2NC(=O)O[C@@H](c2ccccc2)C(F)(F)F)ccc1NS(C)(=O)=O] | | 485.1 | 1H NMR (400 MHz, Methanol-d4) δ 7.79 (s, 2H), 7.67-7.30 (m, 4H), 7.23 (t, J = 8.3 Hz, 1H), 6.23 (s, 1H), 3.98 (d, J = 11.4 Hz, 3H), 3.02 (s, 3H), 2.44 (s, 3H). |
| Compound 95 (R)-1-(3-fluorophenyl) ethyl(1-methyl-4-(5-(methylsulfonamido) pyridin-2-yl)-1H-1,2,3-triazol-5-yl)carbamate | 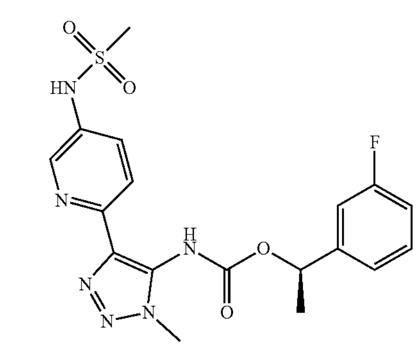 [SMILES: C[C@@H](OC(=O)Nc1c(-c2ccc(NS(C)(=O)=O)cn2)nnn1C)c1cccc(F)c1] | | 435.1 | 1H NMR (400 MHz, Methanol-d4) δ 8.44 (d, J = 2.5 Hz, 1H), 7.88 (d, J = 8.7 Hz, 1H), 7.72 (dd, J = 8.6, 2.7 Hz, 1H), 7.49-6.84 (m, 4H), 5.80 (t, J = 6.5 Hz, 1H), 3.95 (s, 3H), 3.02 (s, 3H), 1.55 (s, 3H). |

TABLE 6-continued

Compounds prepared according to Scheme B2b

| Name | Structure | Reagent 1 | LCMS M/Z (M + 1) | NMR |
|---|---|---|---|---|
| Compound 96 (R)-1-(2-chlorophenyl) ethyl(1-(cyanomethyl)-4-(6-methyl-5-(methylsulfonamido)pyridin-2-yl)-1H-1,2,3-triazol-5-yl)carbamate | 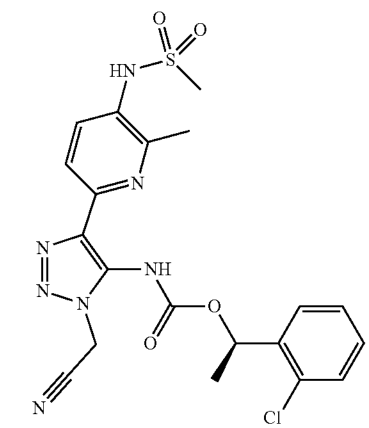 [SMILES: Cc1nc(-c2nnn(CC#N)c2NC(=O)O[C@H](C)c2ccccc2Cl)ccc1NS(C)(=O)=O] | | 490.1 | $^1$H NMR (400 MHz, Methanol-d$_4$) δ 7.86 (m, J = 8.2 Hz, 3H), 7.37 (s, 2H), 7.28 (s, 1H), 6.19 (s, 1H), 5.58 (d, J = 2.8 Hz, 2H), 3.05 (s, 3H), 2.59 (s, 3H), 1.59 (s, 3H). |
| Compound 97 (S)-2,2,2-trifluoro-1-(2-fluorophenyl)ethyl(1-methyl-4-(6-methyl-5-(methylsulfonamido)pyridin-2-yl)-1H-1,2,3-triazol-5-yl)carbamate | 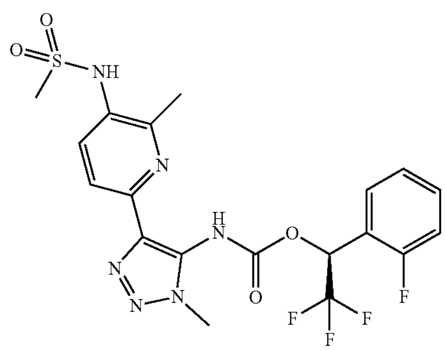 [SMILES: Cc1nc(-c2nnn(C)c2NC(=O)O[C@@H](c2ccccc2F)C(F)(F)F)ccc1NS(C)(=O)=O] | | 503.0 | $^1$H NMR (400 MHz, Acetonitrile-d$_3$) δ 8.12 (m, 1H), 7.93 (d, J = 8.4 Hz, 1H), 7.79 (d, J = 8.4 Hz, 1H), 7.52 (m, 2H), 7.24 (m, 3H), 6.52 (q, J = 6.6 Hz, 1H), 3.96 (s, 3H), 3.62 (s, 3H), 3.10 (s, 1H). |
| Compound 98 (R)-1-(2-(trifluoromethyl)phenyl)ethyl (1-methyl-4-(6-methyl-5-(methylsulfonamido)pyridin-2-yl)-1H-1,2,3-triazol-5-yl)carbamate | | | 490.0 | 1H NMR (400 MHz, DMSO-d6) δ 9.69 (s, 1H), 9.32 (s, 1H), 7.78 (d, J = 8.4 Hz, 1H), 7.70 (d, J = 8.4 Hz, 3H), 7.50 (s, 1H), 6.05 (s, 1H), 3.85 (s, 3H), 3.02 (s, 3H), 2.39 (s, 3H), 1.55-1.47 (m, 2H). |
| Compound 99 (R)-1-phenylethyl(1-(cyanomethyl)-4-(6-methyl-5-(methylsulfonamido)pyridin-2-yl)-1H-1,2,3-triazol-5-yl)carbamate | | | 456.2 | 1H NMR (400 MHz, Methanol-d4) δ 7.85 (s, 2H), 7.31 (d, J = 16.5 Hz, 5H), 5.86 (s, 1H), 5.57 (d, J = 1.0 Hz, 2H), 3.05 (s, 3H), 2.56 (s, 3H), 1.58 (s, 3H). |

TABLE 6-continued

Compounds prepared according to Scheme B2b

| Name | Structure | Reagent 1 | LCMS M/Z (M + 1) | NMR |
|---|---|---|---|---|
| Compound 100 (S)-2,2-difluoro-1-phenylethyl(1-(cyanomethyl)-4-(6-methyl-5-(methylsulfonamido)pyridin-2-yl)-1H-1,2,3-triazol-5-yl)carbamate | | | 492.1 | 1H NMR (400 MHz, Methanol-d4) δ 7.87 (d, J = 8.4 Hz, 1H), 7.81 (d, J = 8.6 Hz, 1H), 7.41 (s, 5H), 5.95 (s, 1H), 5.56 (s, 2H), 3.04 (s, 3H), 2.51 (s, 3H). |

Example 24: Preparation of Compounds 101 to 109

Compounds 101 to 109 were generally prepared according to Scheme B2b. For example, (R)-1-(3-fluorophenyl)ethyl (4-(5-(ethylsulfonamido)-6-methylpyridin-2-yl)-1-methyl-1H-1,2,3-triazol-5-yl)carbamate (Compound 101) was prepared as follows.

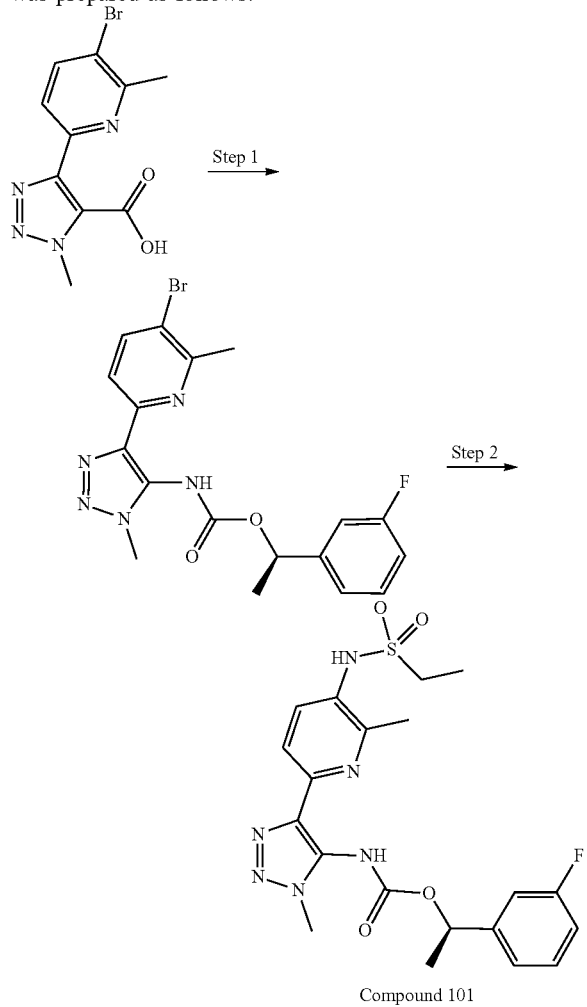

Compound 101

Step 1: (R)-1-(3-fluorophenyl)ethyl (4-(5-bromo-6-methylpyridin-2-yl)-1-methyl-1H-1,2,3-triazol-5-yl) carbamate To a flask charged with (4-(5-bromo-6-methylpyridin-2-yl)-1-methyl-1H-1,2,3-triazole-5-carboxylic acid (Intermediate 7) (3.37 mmol), 1-propanephosphonic acid cyclic anhydride (50% in DMF, 5.05 mmol), azidotrimethysilane (5.05 mmol) acid and THF (10.0 ml) was added Triethylamine (6.73 mmol) dropwise. The reaction mixture was stirred at room temperature for 30 min. (1R)-1-(3-fluorophenyl)ethanol was then added (5.05 mmol), the flask was fitted with a condenser and the reaction was heated at 90° C. for 2 h. The reaction was cooled to room temperature, diluted with water, extracted with EtOAc (3×), washed with brine, dried over MgSO$_4$, filtered and concentrated. The residue was purified by silica gel chromatography to afford (R)-1-(3-fluorophenyl)ethyl(4-(5-bromo-6-methylpyridin-2-yl)-1-methyl-1H-1,2,3-triazol-5-yl) carbamate. LCMS-ESI+ (m/z): [M+H]$^+$ 434.0.

Step 2: (R)-1-(3-fluorophenyl)ethyl (4-(5-(ethylsulfonamido)-6-methylpyridin-2-yl)-1-methyl-1H-1,2,3-triazol-5-yl)carbamate (Compound 101)

A vial was charged with (R)-1-(3-fluorophenyl)ethyl (4-(5-bromo-6-methylpyridin-2-yl)-1-methyl-1H-1,2,3-triazol-5-yl)carbamate (0.115 mmol), ethanesulfonamide (0.345 mmol), potassium carbonate (0.345 mmol), t-butyl-Xphos Pd G3 (0.012 mmol) and THF (2.00 ml). The reaction mixture was degassed with nitrogen, sealed and heated at 70° C. for 45 min. The reaction was cooled to room temperature, diluted with ACN/water, filtered, concentrated and purified by reverse phase chromatography (30-98% ACN/water with 0.1% TFA). The residue was lyophilized to afford (R)-1-(3-fluorophenyl)ethyl (4-(5-(ethylsulfonamido)-6-methylpyridin-2-yl)-1-methyl-1H-1,2,3-triazol-5-yl)carbamate (Compound 87). 1H NMR (400 MHz, DMSO-d6) δ 9.70 (bs, 1H), 9.36 (s, 1H), 7.79 (d, J=8.4 Hz, 1H), 7.70 (d, J=8.4 Hz, 1H), 7.61-6.68 (bm, 4H), 5.76 (bs, 1H), 3.88 (s, 3H), 3.13 (q, J=7.3 Hz, 2H), 2.43 (s, 3H), 1.52 (bs, 3H), 1.26 (t, J=7.3 Hz, 3H). LCMS-ESI+ (m/z): [M+H]$^+$ 463.1.

Compounds 102 to 109 were similarly prepared according to Scheme B2b by reacting Intermediate 7 with a Reagent 1 and a Reagent 2 listed in Table 7 following the general process described for Compound 101.

TABLE 7

Compounds prepared according to Scheme B2b

| Name | Structure | Reagent 1 | Reagent 2 | LCMS M/Z (M + 1) | NMR |
|---|---|---|---|---|---|
| Compound 101 (R)-1-(3-fluorophenyl)ethyl(4-(5-(ethyl-sulfonamido)-6-methyl-pyridin-2-yl)-1-methyl-1H-1,2,3-triazol-5-yl)carbamate | 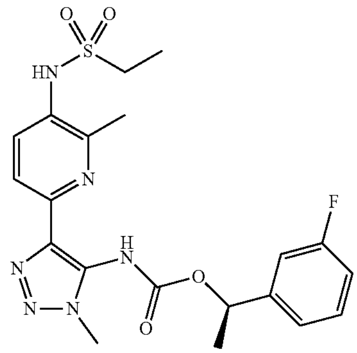 [SMILES: CCS(=O)(=O)Nc1ccc(-c2nnn(C)c2NC(=O)O[C@H](C)c2cccc(F)c2)nc1C] | | | 463.0 | 1H NMR (400 MHz, DMSO-d6) δ 9.70 (bs, 1H), 9.36 (s, 1H), 7.79 (d, J = 8.4 Hz, 1H), 7.70 (d, J = 8.4 Hz, 1H), 7.61-6.68 (bm, 4H), 5.76 (bs, 1H), 3.88 (s, 3H), 3.13 (q, J = 7.3 Hz, 2H), 2.43 (s, 3H), 1.52 (bs, 3H), 1.26 (t, J = 7.3 Hz, 3H). |
| Compound 102 (R)-1-(2-chloro-phenyl)ethyl (4-(5-((cyano-methyl)sulfonamido)-6-methyl-pyridin-2-yl)-1-methyl-1H-1,2,3-triazol-5-yl)carbamate | 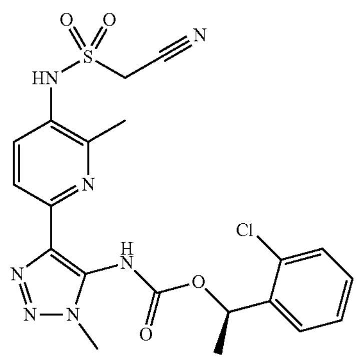 [SMILES: Cc1nc(-c2nnn(C)c2NC(=O)O[C@H](C)c2ccccc2Cl)ccc1NS(=O)(=O)CC#N] | | | 490.0 | 1H NMR (400 MHz, DMSO-d6) δ 10.38 (s, 1H), 9.81 (bs, 1H), 7.83 (d, J = 8.4 Hz, 1H), 7.74 (d, J = 8.4 Hz, 1H), 7.71-7.03 (m, 4H), 6.01 (bs, 1H), 4.96 (s, 2H), 3.89 (s, 3H), 2.48 (s, 3H), 1.54 (bs, 3H). |
| Compound 103 (R)-1-(2-chloro-phenyl)ethyl(4-(5-(cyclopropane-sulfonamido)-6-methylpyridin-2-yl)-1-methyl-1H-1,2,3-triazol-5-yl)carbamate | 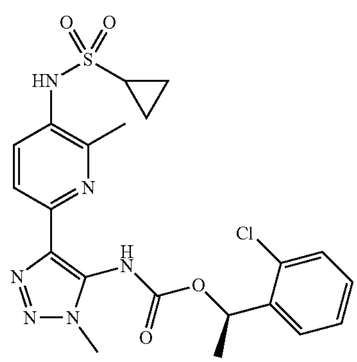 [SMILES: Cc1nc(-c2nnn(C)c2NC(=O)O[C@H](C)c2ccccc2Cl)ccc1NS(=O)(=O)C1CC1] | | | 491.1 | 1H NMR (400 MHz, DMSO-d6) δ 9.79 (bs, 1H), 9.40 (s, 1H), 7.80 (d, J = 8.3 Hz, 1H), 7.72 (d, J = 8.4 Hz, 1H), 7.70-7.11 (bm, 4H), 6.00 (bs, 1H), 3.89 (s, 3H), 2.75-2.60 (m, 1H), 2.48 (s, 3H), 1.54 (bs, 3H), 1.03-0.69 (m, 4H). |
| Compound 104 (R)-1-(3-fluoro-phenyl)ethyl(4-(5-(cyclobutane-sulfonamido)-6-methylpyridin-2-yl)-1-methyl-1H-1,2,3-triazol-5-yl)carbamate | 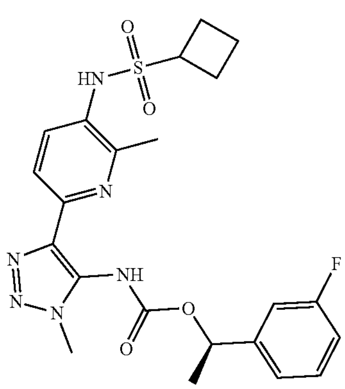 [SMILES: Cc1nc(-c2nnn(C)c2NC(=O)O[C@H](C)c2cccc(F)c2)ccc1NS(=O)(=O)C1CCC1] | | | 489.1 | 1H NMR (400 MHz, DMSO-d6) δ 9.68 (bs, 1H), 9.32 (s, 1H), 7.78 (d, J = 8.3 Hz, 1H), 7.67 (d, J = 8.3 Hz, 1H), 7.60-6.64 (bm, 4H), 5.76 (bs, 1H), 4.00-3.80 (m, 4H), 2.41 (s, 3H), 2.37-2.16 (m, 4H), 2.01-1.82 (m, 2H), 1.52 (bs, 3H). |

TABLE 7-continued

Compounds prepared according to Scheme B2b

| Name | Structure | Reagent 1 | Reagent 2 | LCMS M/Z (M + 1) | NMR |
|---|---|---|---|---|---|
| Compound 105 (R)-1-(3-fluoro-phenyl)ethyl(1-methyl-4-(6-methyl-5-((1-methylethyl) sulfonamido) pyridin-2-yl)-1H-1,2,3-triazol-5-yl)carbamate | 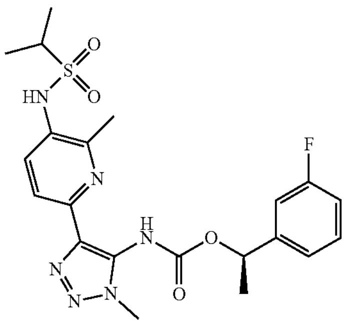 [SMILES: Cc1nc(-c2nnn(C)c2NC(=O)O[C@H](C)c2cccc(F)c2)ccc1NS(=O)(=O)C(C)C] | | | 477.1 | 1H NMR (400 MHz, DMSO-d6) δ 9.69 (bs, 1H), 9.32 (s, 1H), 7.90-7.66 (m, 2H), 7.66-6.60 (m, 4H), 5.76 (s, 1H), 3.88 (s, 3H), 3.28 (m, 1H), 2.44 (s, 3H), 1.49 (bs, 3H), 1.29 (d, J = 6.8 Hz, 6H). |
| Compound 106 (R)-1-(3-fluoro-phenyl)ethyl(4-(5-(cyclopropane-sulfonamido)-6-methylpyridin-2-yl)-1-methyl-1H-1,2,3-triazol-5-yl)carbamate | 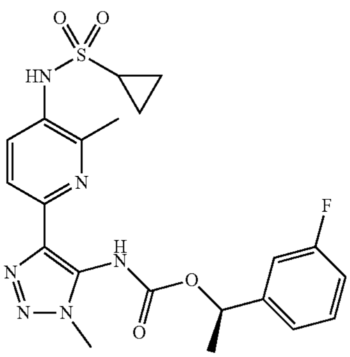 [SMILES: Cc1nc(-c2nnn(C)c2NC(=O)O[C@H](C)c2cccc(F)c2)ccc1NS(=O)(=O)C1CC1] | | | 475.1 | 1H NMR (400 MHz, DMSO-d6) δ 9.69 (bs, 1H), 9.39 (s, 1H), 7.80 (d, J = 8.3 Hz, 1H), 7.72 (d, J = 8.3 Hz, 1H), 7.64-6.58 (bm, 4H), 5.76 (bs, 1H), 3.89 (s, 3H), 2.76-2.59 (m, 1H), 2.47 (s, 3H), 1.52 (bs, 3H), 1.04-0.66 (m, 4H). |
| Compound 107 (R)-1-(3-fluoro-phenyl)ethyl (1-methyl-4-(6-methyl-5-((2-methylthiazole)-5-sulfonamido) pyridin-2-yl)-1H-1,2,3-triazol-5-yl)carbamate | 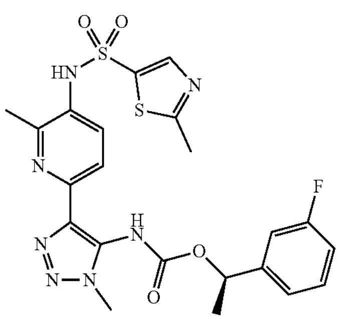 [SMILES: Cc1ncc(S(=O)(=O)Nc2ccc(-c3nnn(C)c3NC(=O)O[C@H](C)c3cccc(F)c3)nc2C)s1] | | | 532.1 | 1H NMR (400 MHz, DMSO-d6) δ 10.32 (bs, 1H), 9.70 (bs, 1H), 7.92 (s, 1H), 7.79 (d, J = 8.3 Hz, 1H), 7.51 (d, J = 8.3 Hz, 1H), 7.45-6.81 (m, 4H), 5.74 (bs, 1H), 3.88 (s, 3H), 2.71 (s, 3H), 2.22 (s, 3H), 1.51 (bs, 3H). |
| Compound 108 (R)-1-(3-fluoro-phenyl)ethyl (4-(5-((3-methoxy-azetidine)-1-sulfonamido)-6-methylpyridin-2-yl)-1-methyl-1H-1,2,3-triazol-5-yl)carbamate | 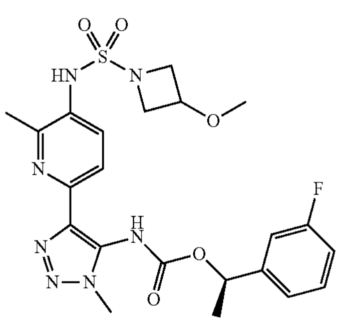 [SMILES: COC1CN(S(=O)(=O)Nc2ccc(-c3nnn(C)c3NC(=O)O[C@H](C)c3cccc(F)c3)nc2C)C1] | | | 520.1 | 1H NMR (400 MHz, DMSO-d6) δ 9.71 (bs, 1H), 9.55 (s, 1H), 7.77 (q, J = 8.4 Hz, 2H), 7.59-6.99 (bm, 4H), 5.77 (bs, 1H), 4.15 (m, 1H), 3.95 (m, 2H), 3.88 (s, 3H), 3.68 (dd, J = 8.8, 5.0 Hz, 2H), 3.19 (s, 3H), 2.44 (s, 3H), 1.53 (bs, 3H). |

TABLE 7-continued

Compounds prepared according to Scheme B2b

| Name | Structure | Reagent 1 | Reagent 2 | LCMS M/Z (M + 1) | NMR |
|---|---|---|---|---|---|
| Compound 109 (R)-1-(3-fluorophenyl)ethyl (1-methyl-4-(6-methyl-5-(oxetane-3-sulfonamido)pyridin-2-yl)-1H-1,2,3-triazol-5-yl)carbamate | 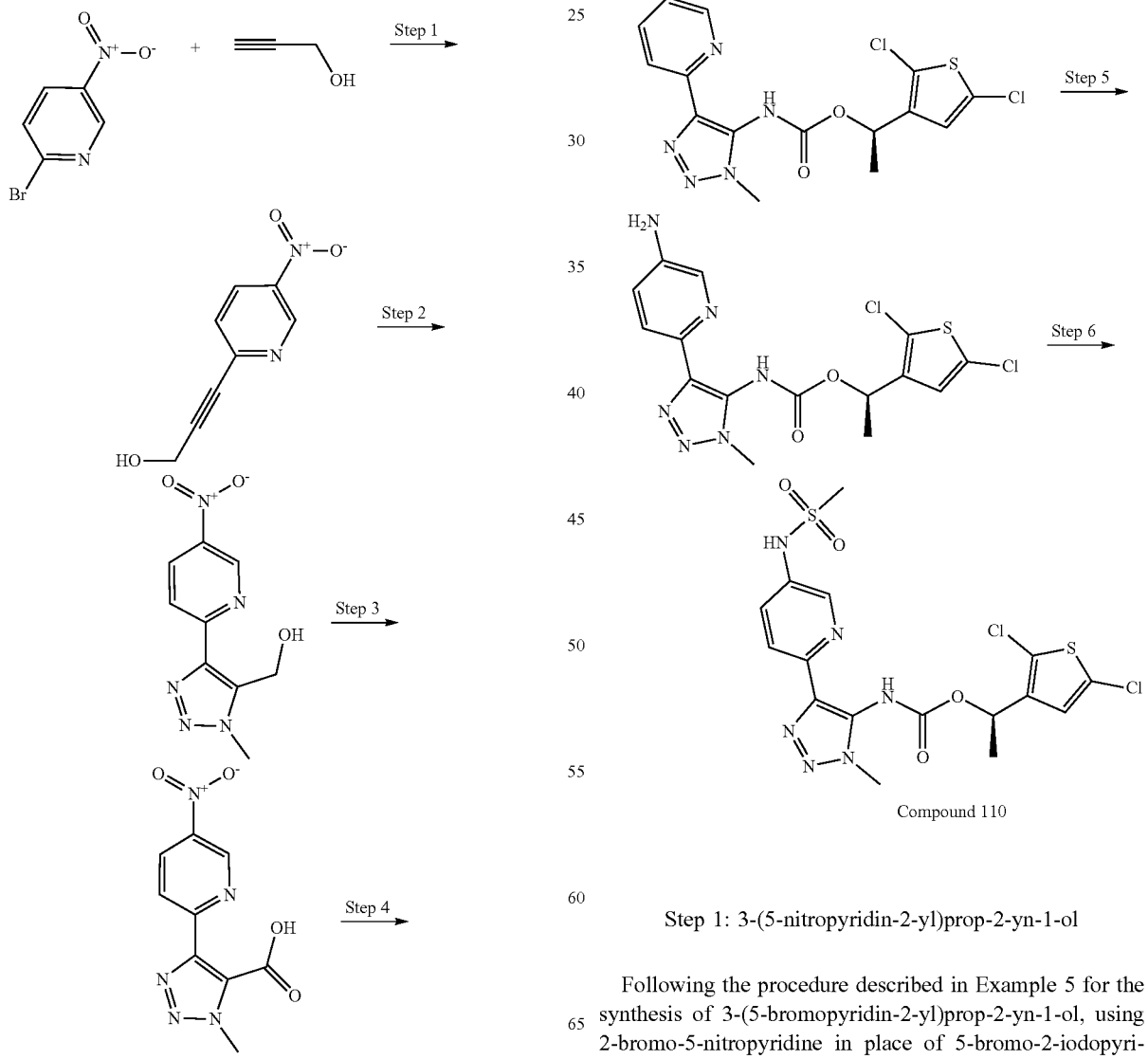 | | | 491.0 | 1H NMR (400 MHz, DMSO-d6) δ 9.71 (s, 2H), 7.79 (d, J = 8.3 Hz, 1H), 7.66 (d, J = 8.3 Hz, 1H), 7.55-6.84 (bm, 4H), 5.76 (bs, 1H), 4.87-4.76 m, 2H), 4.76-4.54 (m, 3H), 3.88 (s, 3H), 2.40 (s, 3H), 1.51 (bs, 3H). |

Example 25: Preparation of (R)-1-(2,5-dichlorothiophen-3-yl)ethyl (1-methyl-4-(5-(methylsulfonamido)pyridin-2-yl)-1H-1,2,3-triazol-5-yl)carbamate (Compound 110)

Step 1: 3-(5-nitropyridin-2-yl)prop-2-yn-1-ol

Following the procedure described in Example 5 for the synthesis of 3-(5-bromopyridin-2-yl)prop-2-yn-1-ol, using 2-bromo-5-nitropyridine in place of 5-bromo-2-iodopyridine, 3-(5-nitropyridin-2-yl)prop-2-yn-1-ol was obtained.

Step 2: (1-methyl-4-(5-nitropyridin-2-yl)-1H-1,2,3-triazol-5-yl)methanol

Following the procedure described in Example 8 for the synthesis of 3-(5-bromo-3-fluoro-2-pyridyl)prop-2-yn-1-ol, using 3-(5-nitropyridin-2-yl)prop-2-yn-1-ol in place of 3-(5-bromo-6-methylpyridin-2-yl)prop-2-yn-1-ol, (1-methyl-4-(5-nitropyridin-2-yl)-1H-1,2,3-triazol-5-yl)methanol was obtained.

Step 3: 1-methyl-4-(5-nitropyridin-2-yl)-1H-1,2,3-triazole-5-carboxylic acid Following the procedure described in Example 7 for the synthesis of 4-(5-bromo-6-methylpyridin-2-yl)-1-methyl-1H-1,2,3-triazole-5-carboxylic acid (Intermediate 6), using (1-methyl-4-(5-nitropyridin-2-yl)-1H-1,2,3-triazol-5-yl)methanol in place of (4-(5-bromo-6-methylpyridin-2-yl)-1-methyl-1H-1,2,3-triazol-5-yl)methanol, methyl-4-(5-nitropyridin-2-yl)-1H-1,2,3-triazole-5-carboxylic acid was obtained.

Step 4: (R)-1-(2,5-dichlorothiophen-3-yl)ethyl (1-methyl-4-(5-nitropyridin-2-yl)-1H-1,2,3-triazol-5-yl)carbamate 3-methyl-5-(5-nitro-2-pyridyl)triazole-4-carboxylic acid (1.08 mmol) suspended in toluene (7 mL) was treated with trimethylamine (2.15 mmol), followed by diphenyl phosphoryl azide (1.63 mmol) and (R)-1-(2,5-dichlorothiophen-3-yl)ethan-1-ol (1.68 mmol). The reaction mixture was heated at 55° C. overnight. After cooling to room temperature, the reaction mixture was diluted with ethyl acetate and washed with water. The organic layer was dried over sodium sulfate, filtered, and concentrated. The residue was purified by column chromatography to provide (R)-1-(2,5-dichlorothiophen-3-yl)ethyl (1-methyl-4-(5-nitropyridin-2-yl)-1H-1,2,3-triazol-5-yl)carbamate.

Step 5: (R)-1-(2,5-dichlorothiophen-3-yl)ethyl(4-(5-aminopyridin-2-yl)-1-methyl-1H-1,2,3-triazol-5-yl)carbamate (R)-1-(2,5-dichlorothiophen-3-yl)ethyl(1-methyl-4-(5-nitropyridin-2-yl)-1H-1,2,3-triazol-5-yl)carbamate (0.135 mmol) dissolved in acetic acid (2 mL) was treated with Zinc powder (1.76 mmol). The reaction mixture was stirred at room temperature for 3 h. The reaction mixture was treated first with saturated NaHCO₃, followed by saturated Na₂CO₃ solution until pH=8. The reaction mixture was then extracted with ethyl acetate. The organic layer was dried over sodium sulfate, filtered, and concentrated to provide (R)-1-(2,5-dichlorothiophen-3-yl)ethyl(4-(5-aminopyridin-2-yl)-1-methyl-1H-1,2,3-triazol-5-yl)carbamate.

Step 6: (R)-1-(2,5-dichlorothiophen-3-yl)ethyl(1-methyl-4-(5-(methylsulfonamido)pyridin-2-yl)-1H-1,2,3-triazol-5-yl)carbamate (R)-1-(2,5-dichlorothiophen-3-yl)ethyl(4-(5-aminopyridin-2-yl)-1-methyl-1H-1,2,3-triazol-5-yl)carbamate (0.109 mmol) dissolved in dichloromethane (1 ml) was cooled to 0° C. and then treated with pyridine (0.372 mmol) followed by methanesulfonic anhydride (0.138 mmol). The reaction mixture was stirred for 15 min and concentrated. The residue was purified by HPLC to provide (R)-1-(2,5-dichlorothiophen-3-yl)ethyl(1-methyl-4-(5-(methylsulfonamido)pyridin-2-yl)-1H-1,2,3-triazol-5-yl)carbamate. (MS (m/z) 491.4 [M+H]⁺). 1H NMR (400 mhz, DMSO-d6) δ 10.09 (s, 1H), 8.39 (d, J=2.6 Hz, 1H), 7.94 (d, J=8.6 Hz, 1H), 7.70 (dd, J=8.6, 2.7 Hz, 1H), 5.72 (s, 1H), 3.88 (s, 3H), 3.08 (s, 3H), 1.50 (s, 3H).

Example 26: Preparation of (R)-1-(2,5-dichloropyridin-3-yl)ethyl (1-methyl-4-(6-methyl-5-(methylsulfonamido)pyridin-2-yl)-1H-1,2,3-triazol-5-yl)carbamate (Compound 142)

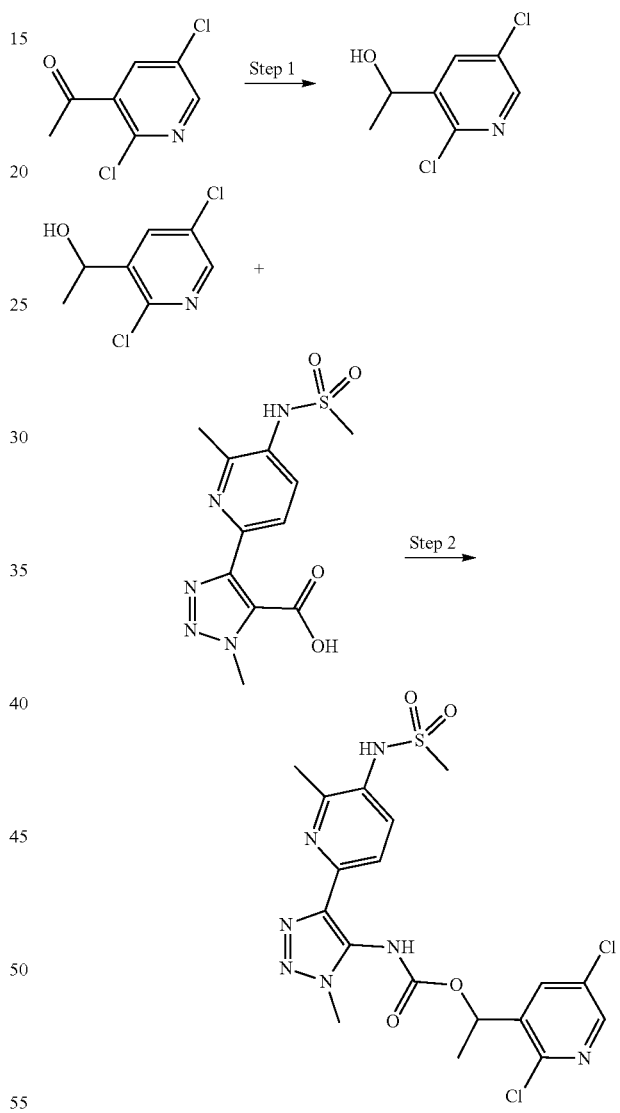

Step 1: 1-(2,5-dichloropyridin-3-yl)ethan-1-ol

A 40 ml vial, equipped with a stir bar, was charged with 1 mmol of 1-(2,5-dichloropyridin-3-yl)ethan-1-one, 5 ml methanol, 2 mmol sodium borohydride and allowed to stir overnight. The next day the reaction mixture was quenched with 10 ml deionized water, transferred to a separator funnel and extracted three times with dichloromethane. The combined extracts were dried over sodium sulphate, concentrated in vacuo and purified by column chromatography to give rac-1-(2,5-dichloropyridin-3-yl)ethan-1-ol.

Step 2: (R)-1-(2,5-dichloropyridin-3-yl)ethyl (1-methyl-4-(6-methyl-5-(methylsulfonamido) pyridin-2-yl)-1H-1,2,3-triazol-5-yl)carbamate To a solution of 1-methyl-4-(5-(methylsulfonamido)pyridin-2-yl)-1H-1,2,3-triazole-5-carboxylic acid (Intermediate 6) (0.064 mmol) and rac-1-(2,5-dichloropyridin-3-yl)ethan-1-ol (0.128 mmol) in THF (1 ml) was added triethylamine (0.225 mmol), 50% v/v propanephosphonic acid anhydride (1.57 M) in THE (0.128 mmol), and trimethylsilyl azide (0.128 mmol). The mixture was heated to 80° C. for 2 h. The reaction solution was cooled to room temperature, the volatiles removed in vacuo and the remaining residue was chromatographed by silica gel column chromatography to give rac-1-(2,5-dichloro-3-pyridyl)ethyl N-[5-[5-(methanesulfonamido)-6-methyl-2-pyridyl]-3-methyl-triazol-4-yl]carbamate. Rac-1-(2,5-dichloro-3-pyridyl)ethyl N-[5-[5-(methanesulfonamido)-6-methyl-2-pyridyl]-3-methyl-triazol-4-yl]carbamate was then separated into its individual enantiomers by chiral SFC. LCMS-ESI+ (m/z): [M+H]+ 500.0. 1H NMR (400 MHz, Methanol-d4) δ 8.56-7.59 (m, 4H), 6.07 (s, 1H), 4.02 (s, 3H), 3.05 (s, 3H), 2.54 (s, 3H), 1.61 (s, 3H).

Example 27: Preparation of (R)-1-(6-fluoro-2-methylpyridin-3-yl)ethan-1-ol

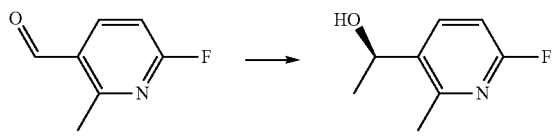

A 50 ml round bottom flask, equipped with a stir bar, was charged with 1 ml dimethylzinc (2 M in toluene), 5 ml toluene under an atmosphere of argon and cooled to 0° C. in an ice bath. (S)-(+)-2-Piperidino-1,1,2-triphenylethanol (0.1 mmol) was then added and the mixture allowed to equilibriate for 5 min. 6-fluoro-2-methylnicotinaldehyde (1 mmol) was added dropwise to the stirring reaction mixture over 20 min as a 0.5 M solution in toluene. The reaction mixture was then left to warm to room temperature overnight. The next day the reaction mixture was quenched with 10 ml saturated ammonium chloride solution transferred to a separator funnel and extracted three times with dichloromethane. The combined extracts were dried over sodium sulphate, concentrated in vacuo and purified by silica gel column chromatography to give (R)-1-(6-fluoro-2-methylpyridin-3-yl)ethan-1-ol (93:7 e.r.).

Example 28: Preparation of (R)-1-(2-methylpyridin-3-yl)ethyl (1-methyl-4-(6-methyl-5-(methylsulfonamido)pyridin-2-yl)-1H-1,2,3-triazol-5-yl)carbamate (Compound 141)

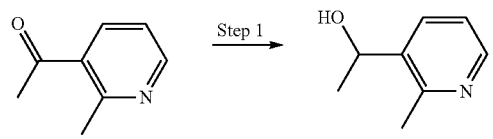

Step 1: 1-(2-methylpyridin-3-yl)ethan-1-ol

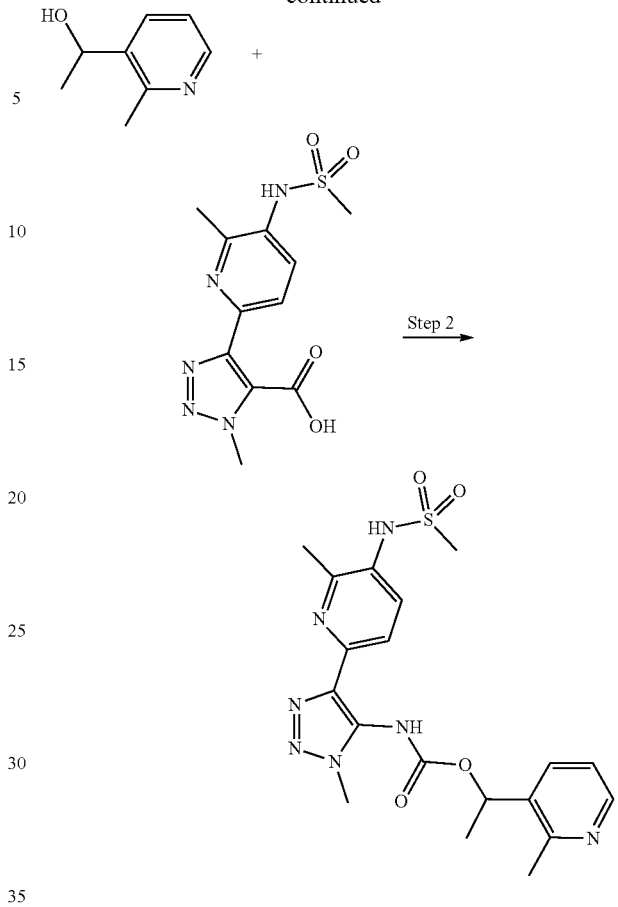

A 50 ml round bottom flask, equipped with a stir bar, was charged with 2-methylnicotinaldehyde (2.06 mmol), 5 ml THF, placed under an atmosphere of argon and cooled to 0° C. in an ice bath. Methylmagnesium bromide, 3 M in diethyleather, (3.1 mmol) was added dropwise and the reaction mixture allowed to stir for 20 min. The reaction was quenched with 20 ml saturated ammonium chloride solution transferred to a separator funnel and extracted three times with ethyl-acetate. The combined extracts were dried over sodium sulphate, concentrated in vacuo and purified by silica gel column chromatography to give rac-1-(2-methylpyridin-3-yl)ethan-1-ol.

Step 2: 1-(2-methylpyridin-3-yl)ethyl (1-methyl-4-(6-methyl-5-(methylsulfonamido)pyridin-2-yl)-1H-1,2,3-triazol-5-yl)carbamate To a solution of 1-methyl-4-(5-(methylsulfonamido)pyridin-2-yl)-1H-1,2,3-triazole-5-carboxylic acid (Intermediate 6) (0.064 mmol) and rac-1-(2-methylpyridin-3-yl)ethan-1-ol (0.128 mmol) in THE (1 ml) was added triethylamine (0.225 mmol), 50% v/v propanephosphonic acid anhydride (1.57 M) in THE (0.128 mmol), and trimethylsilyl azide (0.128 mmol). The mixture was heated to 80° C. for 2 h. The reaction solution was cooled to room temperature, the volatiles removed in vacuo and the remaining residue was chromatographed by silica gel column chromatography to give rac-1-(2-methylpyridin-3-yl)ethyl (1-methyl-4-(6- methyl-5-(methylsulfonamido)pyridin-2-yl)-1H-1,2,3-triazol-5-yl)carbamate. Rac-1-(2-methylpyridin-3-yl)ethyl (1-methyl-4-(6-methyl-5-(methylsulfonamido)pyridin-2-yl)-1H-1,2,3-triazol-5-yl)carbamate was then separated into its individual enantiomers by chiral SFC.

Example 29: Preparation of (R)-1-(5-chloro-2-methylpyridin-3-yl)ethyl (1-methyl-4-(5-(methylsulfonamido)pyridin-2-yl)-1H-1,2,3-triazol-5-yl)carbamate (Compound 113)

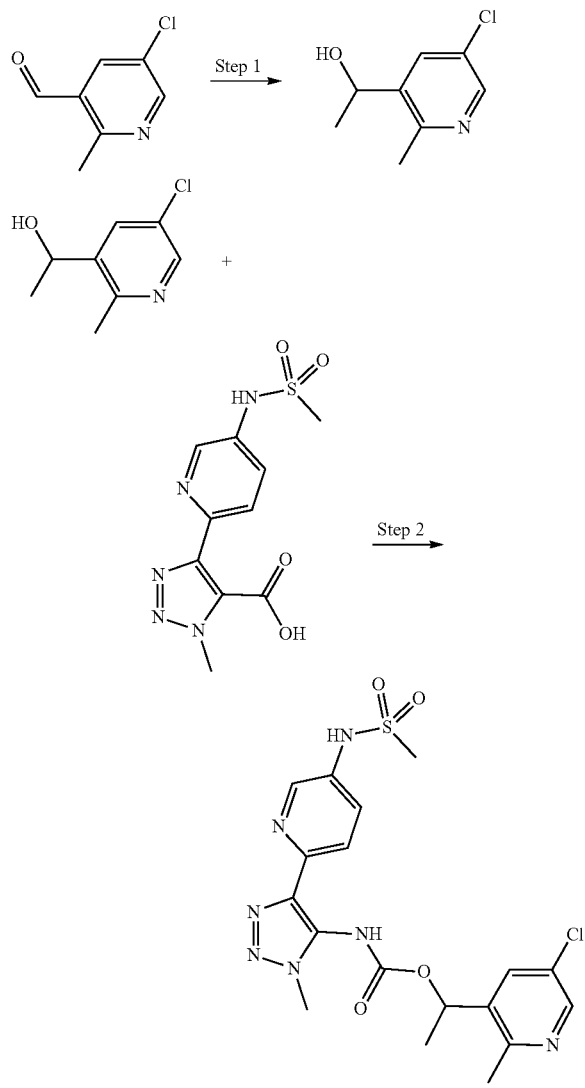

Step 1: 1-(5-chloro-2-methylpyridin-3-yl)ethan-1-ol

A 50 ml round bottom flask, equipped with a stir bar, was charged with 5-chloro-2-methylnicotinaldehyde (2 mmol), 5 ml THF, placed under an atmosphere of argon and cooled to 0° C. in an ice bath. Methylmagnesium bromide, 3 M in diethylether, (3 mmol) was added dropwise and the reaction mixture allowed to stir for 20 min. The reaction was quenched with 20 ml saturated ammonium chloride solution transferred to a separator funnel and extracted three times with ethyl-acetate. The combined extracts were dried over sodium sulphate, concentrated in vacuo and purified by silica gel column chromatography to give rac-1-(5-chloro-2-methylpyridin-3-yl)ethan-1-ol Step 2: 1-(5-chloro-2-methylpyridin-3-yl)ethyl (1-methyl-4-(5-(methylsulfonamido)pyridin-2-yl)-1H-1,2,3-triazol-5-yl)carbamate To a solution of 1-methyl-4-(5-(methylsulfonamido)pyridin-2-yl)-1H-1,2,3-triazole-5-carboxylic acid (0.33 mmol) and rac-1-(5-chloro-2-methylpyridin-3-yl)ethan-1-ol (0.61 mmol) in THF (1 ml) was added triethylamine (1.18 mmol), 50% v/v propanephosphonic acid anhydride (1.57 M) in THF (0.67 mmol), and trimethylsilyl azide (0.67 mmol). The mixture was heated to 80° C. for 2 h. The reaction solution was cooled to room temperature, the volatiles removed in vacuo and the remaining residue was chromatographed by silica gel column chromatography to give rac-1-(5-chloro-2-methylpyridin-3-yl)ethyl (1-methyl-4-(5-(methylsulfonamido)pyridin-2-yl)-1H-1,2,3-triazol-5-yl) carbamate. Rac-1-(5-chloro-2-methylpyridin-3-yl)ethyl (1-methyl-4-(5-(methylsulfonamido)pyridin-2-yl)-1H-1,2,3-triazol-5-yl)carbamate was then separated into its individual enantiomers by chiral SFC. LCMS-ESI+ (m/z): [M+H]+ 466.0. 1H NMR (400 MHz, Methanol-d4) δ 8.40 (d, J=32.3 Hz, 2H), 8.17-7.48 (m, 3H), 5.98 (d, J=6.7 Hz, 1H), 3.98 (s, 3H), 3.05 (s, 3H), 2.57 (s, 3H), 1.59 (s, 3H).

Example 30: Preparation of (R)-1-(3-chloroisothiazol-4-yl)ethan-1-ol

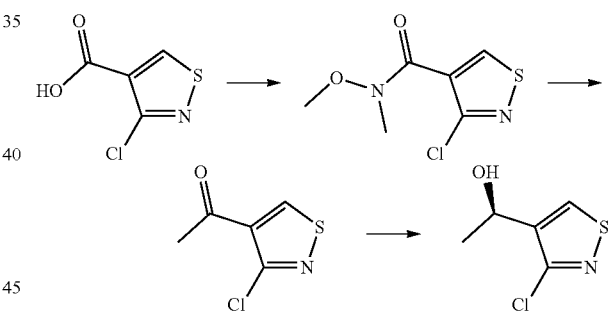

Step 1: 3-chloro-N-methoxy-N-methylisothiazole-4-carboxamide 3-chloroisothiazole-4-carboxylic acid (600 mg, 3.67 mmol) suspended in dichloromethane (30 ml) was treated with HATU (1800 mg, 4.73 mmol), n,o-dimethylhydroxylamine hydrochloride (370 mg, 3.79 mmol), and N-Ethyldiisopropylamine (900 µl, 5.17 mmol). The reaction mixture was stirred at room temperature overnight.

The reaction mixture was diluted with ethyl acetate and washed with water. The organic layer was concentrated. The residue was purified by column chromatography to give 3-chloro-N-methoxy-N-methylisothiazole-4-carboxamide.

Step 2: 1-(3-chloroisothiazol-4-yl)ethan-1-one 3-chloro-N-methoxy-N-methylisothiazole-4-carboxamide (504 mg, 2.44 mmol) dissolved in methyl tetrahydrofuran (20 ml) was cooled to 0° C. and then methylmagnesium iodide solution (3.0 M, 3500 μl, 10.5 mmol) was added. The reaction mixture was warmed to room temperature and stirred for 2 h.

The reaction mixture was quenched with addition of 1N hydrochloride solution, and then diluted with ethyl acetate and washed with water. The organic layer was concentrated. The residue was purified by column chromatography to give 1-(3-chloroisothiazol-4-yl)ethan-1-one.

Step 3: (R)-1-(3-chloroisothiazol-4-yl)ethan-1-ol 1-(3-Chloroisothiazol-4-yl)ethan-1-one (130 mg, 0.804 mmol) dissolved in dichloromethane (10 ml) was cooled to 0° C. and then treated with (S)-(−)-2-Methyl-CBS-oxazaborolidine (25 mg, 0.0902 mmol) followed by borane dimethyl sulfide complex solution (2.0 M in THF, 900 μl, 1.80 mmol). The reaction mixture was warmed to room temperature and stirred for 3 h.

The reaction mixture was quenched with addition of methanol and concentrated after 10 min. The residue was re-dissolved in methanol and then concentrated again. The residue was purified by column chromatography to give the product.

Example 31: Preparation of 1-(2-chloro-6-fluoropyridin-3-yl)ethan-1-ol

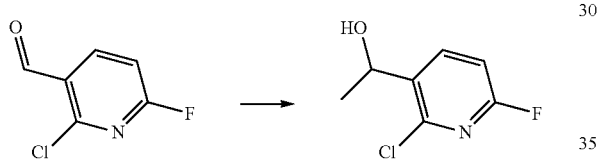

2-Chloro-6-fluoronicotinaldehyde (400 mg, 2.51 mmol) dissolved in methyl tetrahydrofuran (20 ml) was cooled in an ice/acetonitrile bath and then methylmagnesium bromide solution (3.0 M, 2400 μl, 7.20 mmol) was added dropwise.

The reaction mixture was quenched with addition of ethanol, and then diluted with ethyl acetate and washed with 10% citric acid. The organic layer was concentrated. The residue was purified by column chromatography to give 1-(2-chloro-6-fluoropyridin-3-yl)ethan-1-ol.

Example 31: Preparation of the tail group: (R)-1-(2-methoxypyridin-3-yl)ethan-1-ol

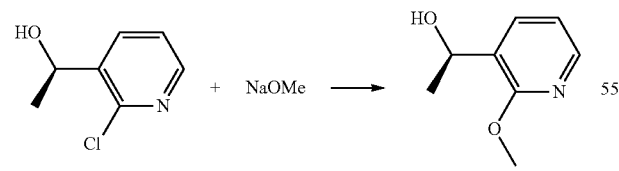

A solution of (R)-1-(2-chloropyridin-3-yl)ethan-1-ol (1 mmol) and sodium methoxide (25 percent solution in meoh, 0.6 ml) was stirred in sealed tube at 100° C. for 20 hrs. The reaction mixture was diluted with ethyl acetate, washed with brine, dried over sodium sulfate and concentrated. The residue was purified by flash chromatography on silica gel eluting with 0 to 20 percent meoh in DCM to give the product.

Example 32: Preparation of (R)-1-(2-vinylpyridin-3-yl)ethan-1-ol

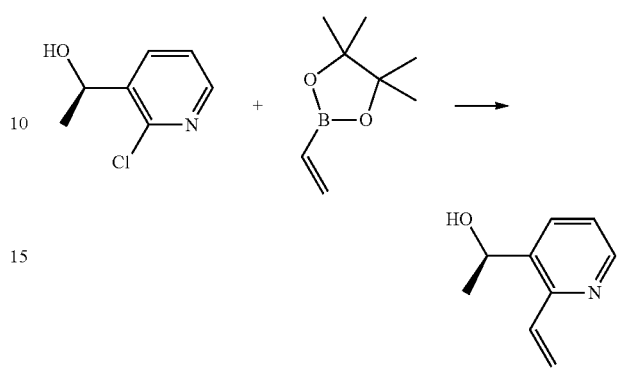

(R)-1-(2-chloropyridin-3-yl)ethan-1-ol (0.3 mmol, 1 eq), boronic acid ester (2 eq), sodium carbonate (3 eq) and tetrakis(triphenylphosphine)palladium (0) (0.05 eq) were combined, diluted with dioxane (1 ml) and water (250 μl). The reaction vial was purged with argon, heated to 90 C and stirred for 24 hours. The reaction was allowed to cool, purified by silica gel column to give the product.

Example 32: Preparation of (R)-1-(2-Chloro-5-fluoropyridin-3-yl)ethyl (4-(6-(methoxymethyl)-5-(methylsulfonamido)pyridin-2-yl)-1-methyl-1H-1,2,3-triazol-5-yl)carbamate (Compound 144)

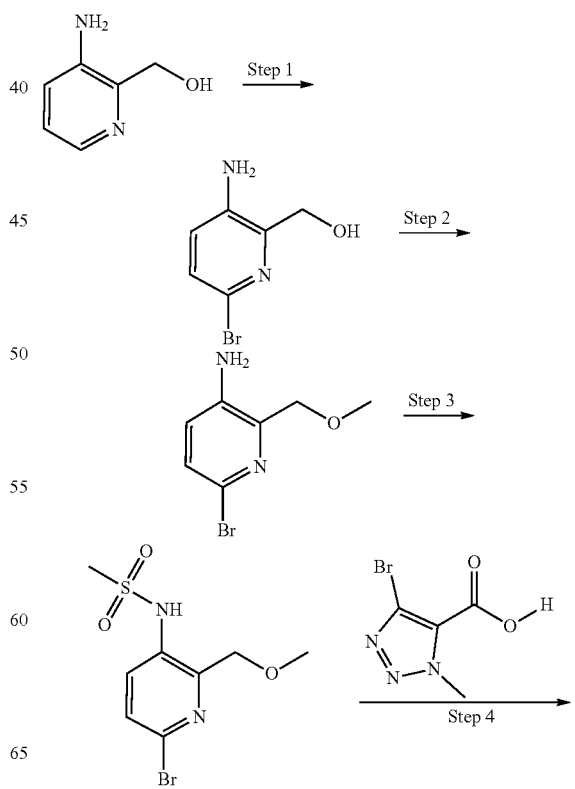

-continued

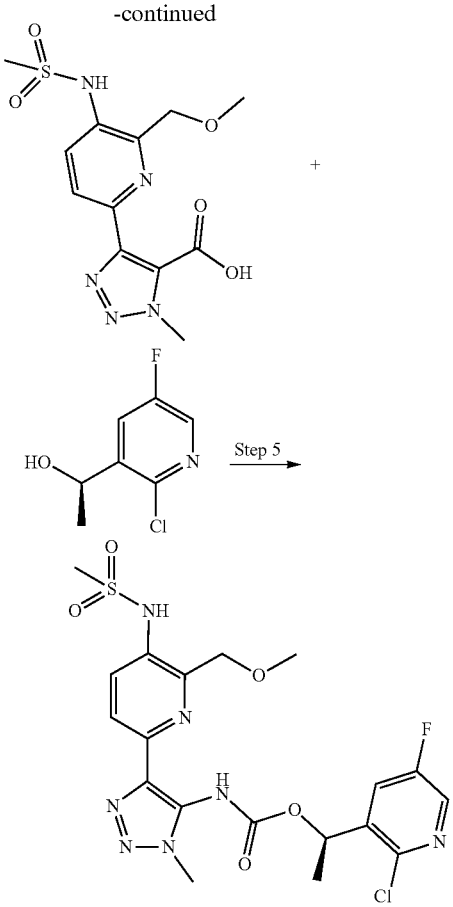

Step 1: (3-Amino-6-bromopyridin-2-yl)methanol

A mixture of (3-aminopyridin-2-yl)methanol (1.02 g, 8.22 mmol), NBS (1.48 g, 8.3 mmol) in CH₃CN (12 ml) was stirred at room temperature overnight. The reaction mixture was concentrated in vacuo, the residue was purified by silica gel column chromatography with 0-80% etoac in hexanes to give the product.

Step 2: 6-Bromo-2-(methoxymethyl)pyridin-3-amine

A mixture of (3-amino-6-bromopyridin-2-yl) methanol (325 mg, 1.6 mmol), 188 mg of concentrated sulfuric acid, and 12 ml of methanol was stirred at 50° C. for 2 hours. After the reaction mixture was cooled to 0° C., 150 mg of sodium hydroxide was added, and the mixture was concentrated under reduced pressure. Then sodium carbonate and water were added, and the mixture was extracted with etoac. The organic phase was collected, dried over Na₂SO₄, filtered and concentrated under reduced pressure, the residue was purified by silica gel column chromatography with 0-80% etoac in hexanes to give the product (219 mg, 63%).

Step 3: N-(6-Bromo-2-(methoxymethyl)pyridin-3-yl)methanesulfonamide

6-Bromo-2-(methoxymethyl)pyridin-3-amine (216 mg, 1 mmol) was dissolved in a mixture of pyridine (2 ml) and anhydrous dichloromethane (6 ml), treated with methanesulfonyl chloride (204 mg, 1.8 mmol), and stirred at ambient temperature for 24 h. The reaction mixture was treated with meoh, concentrated to dryness. The residue was purified by silica gel column chromatography with 0-60% etoac in hexanes to give the product (300 mg, 100%).

Step 4: 4-(6-(Methoxymethyl)-5-(methylsulfonamido)pyridin-2-yl)-1-methyl-1H-1,2,3-triazole-5-carboxylic acid To a solution of 4-bromo-1-methyl-1H-1,2,3-triazole-5-carboxylic acid (112 mg, 0.54 mmol) in THF (3.5) in a microwave vial at −78° C. was added n-BuLi (2.5 M solution, 0.65 ml, 1.63 mmol) very slowly dropwise. The reaction mixture was stirred at −78° C. for 15 min. A 1.9 M solution of ZnCl₂ in 2-MeTHF (0.86 ml, 1.63 mmol) was added slowly dropwise at −78° C. Then the mixture was warmed to room temperature for 10 min.

After 20 min, N-(6-bromo-2-(methoxymethyl)pyridin-3-yl)methanesulfonamide (150 mg, 0.51 mmol) and 1,1'-bis(diphenylphosphino)ferrocene-palladium(II)dichloride dichloromethane complex (45 mg, 0.054 mmol) were added in one portion. The mixture was sealed and heated to 70° C. for 2 h. The mixture was cooled to room temperature, then quenched with 1 ml H₂O. The aqueous layer was acidified to pH 4 with 1 M HCl solution, then diluted with meoh, filtered through Celite. The filtrate was concentrated to a smaller volume, then purified by prep HPLC to give the product.

Step 5: (R)-1-(2-Chloro-5-fluoropyridin-3-yl)ethyl (4-(6-(methoxymethyl)-5-(methylsulfonamido)pyridin-2-yl)-1-methyl-1H-1,2,3-triazol-5-yl)carbamate To a flask charged with 4-(6-(methoxymethyl)-5-(methylsulfonamido)pyridin-2-yl)-1-methyl-1H-1,2,3-triazole-5-carboxylic acid (0.03 mmol), 1-propanephosphonic acid cyclic anhydride (50% in DMF, 0.06 mmol), azidotrimethysilane (0.06 mmol) acid and THE (1.0 ml) was added triethylamine (0.09 mmol) dropwise. The reaction mixture was stirred at 65° C. for 30 min before (R)-1-(2-chloro-5-fluoropyridin-3-yl)ethan-1-ol (0.03 mmol) was added and the flask was heated at 65° C. for 90 min. The reaction was concentrated, and purified by reverse phase HPLC to provide the title compound. LCMS-ESI+ (m/z): 514. 1H NMR (400 MHz, Methanol-d4) δ 8.40-8.14 (m, 1H), 8.06-7.75 (m, 3H), 6.06 (s, 1H), 4.71 (s, 2H), 4.02 (s, 3H), 3.44 (s, 3H), 3.08 (s, 3H), 1.97-1.43 (m, 3H).

Example 33: Preparation of (R)-1-(2-chloropyridin-3-yl)ethyl (4-(6-(methoxymethyl)-5-(methylsulfonamido)pyridin-2-yl)-1-methyl-1H-1,2,3-triazol-5-yl) carbamate (Compound 145)

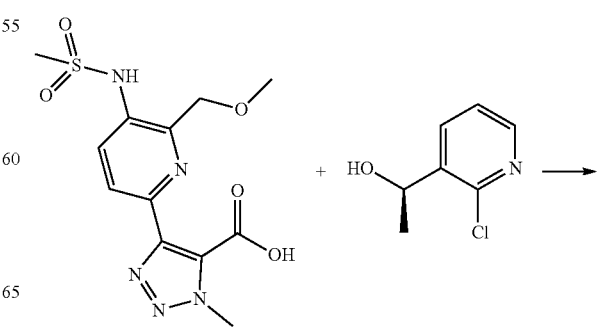

-continued

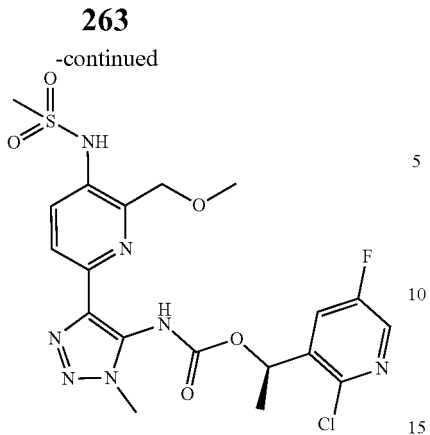

To a flask charged with 4-(6-(methoxymethyl)-5-(methylsulfonamido)pyridin-2-yl)-1-methyl-1H-1,2,3-triazole-5-carboxylic acid (0.03 mmol), 1-propanephosphonic acid cyclic anhydride (50% in DMF, 0.06 mmol), azidotrimethysilane (0.06 mmol) acid and THF (1.0 ml) was added triethylamine (0.09 mmol) dropwise. The reaction mixture was stirred at 65° C. for 30 min before (R)-1-(2-chloropyridin-3-yl)ethan-1-ol (0.03 mmol) was added and the flask was heated at 65° C. for 90 min. The reaction was concentrated, and purified by reverse phase HPLC to provide the title compound. LCMS-ESI+ (m/z): 496. 1H NMR (400 MHz, Methanol-d4) δ 8.46-8.23 (m, 1H), 7.96 (m, 3H), 7.59-7.19 (m, 1H), 6.11 (s, 1H), 4.71 (s, 2H), 4.01 (s, 3H), 3.43 (s, 3H), 3.09 (s, 3H), 1.98-1.40 (m, 3H).

Example 34: Preparation of (R)-1-(2-chloropyridin-3-yl)ethyl (4-(6-methoxy-5-(methylsulfonamido)pyridin-2-yl)-1-methyl-1H-1,2,3-triazol-5-yl)carbamate (Compound 146)

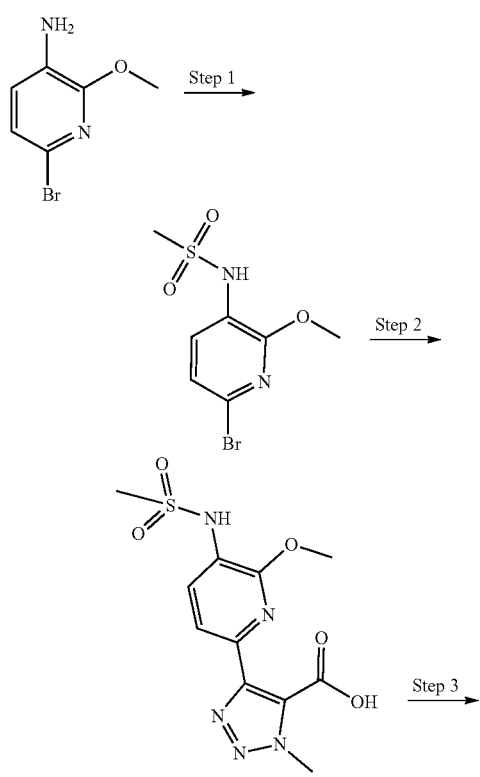

-continued

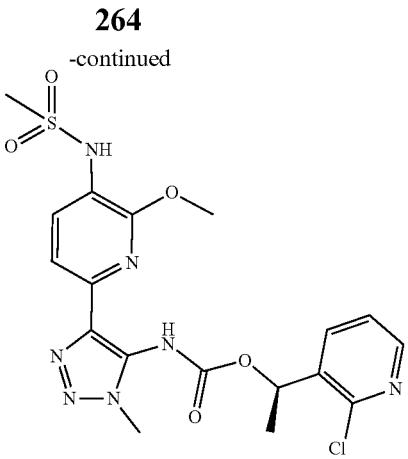

Step 1: N-(6-Bromo-2-methoxypyridin-3-yl)methanesulfonamide

6-Bromo-2-methoxypyridin-3-amine (2 g, 9.85 mmol) was dissolved in anhydrous dichloromethane (20 ml) and pyridine (4 ml), treated with methanesulfonyl chloride (2.02 g, 17.7 mmol). The mixture was stirred at ambient temperature overnight. The reaction was quenched with methanol. The mixture was concentrated in vacuo and the residue was purified by silica gel column chromatography with 0-80% ethyl acetate in hexanes to give a mixture of mono- and bismesylated products. To the aforementioned mixture of bismesylated products was added methanol (100 ml) followed by sodium methoxide (25 percent, 4 ml) at ambient temperature leading to an almost complete solution. Stirring was continued for 1 hour then the solution was concentrated under reduced pressure followed by addition of water, saturated aq. NH4Cl and ethyl acetate. The combined organic layers were washed with brine, dried over Na2SO4, filtered, and the filtrate concentrated in vacuo giving the title compound (1.84 g, 52%).

Step 2: 4-(6-Methoxy-5-(methylsulfonamido)pyridin-2-yl)-1-methyl-1H-1,2,3-triazole-5-carboxylic acid To a solution of 4-bromo-1-methyl-1H-1,2,3-triazole-5-carboxylic acid (490 mg, 2.38 mmol) in THF (24 ml) at −78° C. was added n-BuLi (2.5 M solution, 2.85 ml, 7.14 mmol) very slowly dropwise. The reaction mixture was stirred at −78° C. for 15 min. A 1.9 M solution of ZnCl2 in 2-MeTHF (3.76 ml, 7.14 mmol) was added slowly dropwise at −78° C. Then the mixture was warmed to room temperature for 10 min. After 20 min, N-(6-bromo-2-methoxypyridin-3-yl)methanesulfonamide (600 mg, 2.13 mmol) and 1,1'-Bis(diphenylphosphino)ferrocene-palladium(II)dichloride dichloromethane complex (197 mg, 0.238 mmol) were added in one portion. The mixture was sealed and heated to 70° C. for 2 h. The mixture was cooled to room temperature, then quenched with H2O. The aqueous layer was acidified to pH 4 with 1 M HCl solution, then diluted with methanol, filtered through Celite. The filtrate was concentrated to a smaller volume, then purified by silica gel column chromatography with 0-15% methanol in DCM to give the product.

Step 3: (R)-1-(2-chloropyridin-3-yl)ethyl (4-(6-methoxy-5-(methylsulfonamido)pyridin-2-yl)-1-methyl-1H-1,2,3-triazol-5-yl)carbamate To a flask charged with 4-(6-methoxy-5-(methylsulfonamido)pyridin-2-yl)-1-methyl-1H-1,2,3-triazole-5-carboxylic acid (0.03 mmol), 1-propanephosphonic acid cyclic anhydride (50% in DMF, 0.06 mmol), azidotrimethysilane (0.06 mmol) acid and THF (1.0 ml) was added triethylamine (0.09 mmol) dropwise. The reaction mixture was stirred at 65° C. for 30 min before (R)-1-(2-chloropyridin-3-yl)ethan-1-ol (0.03 mmol) was added and the flask was heated at 65° C. for 90 min. The reaction was concentrated and purified by reverse phase HPLC to provide the title compound. LCMS-ESI+ (m/z): 482.1. 1H NMR (400 MHz, Methanol-d4) δ 8.27 (m, 1H), 8.07 (m, 1H), 7.80 (m, 1H), 7.62-6.90 (m, 2H), 6.13 (s, 1H), 3.99 (s, 6H), 3.02 (s, 3H), 1.44 (m, 3H).

Example 35: Preparation of (R)-1-(2-chloro-5-fluoropyridin-3-yl)ethyl (4-(6-ethyl-5-(methylsulfonamido)pyridin-2-yl)-1-methyl-1H-1,2,3-triazol-5-yl) carbamate (Compound 147)

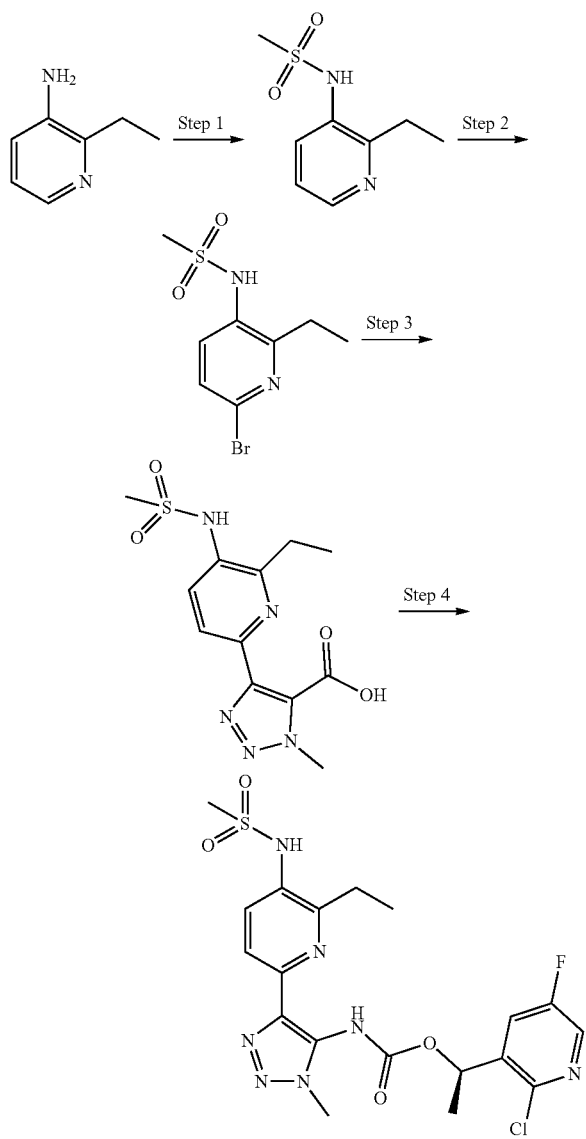

Step 1: N-(2-ethylpyridin-3-yl)methanesulfonamide

2-Ethylpyridin-3-amine (0.5 g, 4.1 mmol) was dissolved in anhydrous dichloromethane (20 ml) under argon, treated with methanesulfonyl chloride (1.14 g, 10 mmol), a 0.8 ml of anhydrous pyridine, stirred at ambient temperature for 24 h. The mixture was concentrated to dryness.

To the aforementioned mixture of bismesylated products was added methanol (29 ml) followed by sodium methoxide (25 percent, 1.1 mL) at ambient temperature. Stirring was continued for 1 hour then the solution was concentrated under reduced pressure followed by addition of water, $NH_4Cl$ (sat. aq.) and ethyl acetate. The combined organic layers washed with brine, dried over $Na_2SO_4$, filtered, and the filtrate concentrated in vacuo giving the title compound.

Step 2:
N-(6-Bromo-2-ethylpyridin-3-yl)methanesulfonamide

A mixture of N-(2-ethylpyridin-3-yl)methanesulfonamide (0.22 g, 1.1 mmol), NBS (0.198 g, 1.11 mmol) in $CH_3CN$ (4 ml) was stirred at room temperature overnight. The reaction mixture was diluted with DCM and washed with water and $Na_2S_2O_3$. The organic layer was collected, dried over $Na_2SO_4$, filtered, and concentrated in vacuo. The residue was purified by silica gel column chromatography with 0-80% ethyl acetate in hexanes to give the product.

Step 3: 4-(6-Ethyl-5-(methylsulfonamido)pyridin-2-yl)-1-methyl-1H-1,2,3-triazole-5-carboxylic acid To a solution of 4-bromo-1-methyl-1H-1,2,3-triazole-5-carboxylic acid (934 mg, 4.53 mmol) in THF (40 ml) at −78° C. was added n-BuLi (2.5 M solution, 5.4 ml, 13.6 mmol) very slowly dropwise. The reaction mixture was stirred at −78° C. for 15 min. A 1.9 M solution of $ZnCl_2$ in 2-MeTHF (7.16 ml, 13.6 mmol) was added slowly dropwise at −78° C. Then the mixture was warmed to room temperature for 10 min. After 20 min, N-(6-bromo-2-ethylpyridin-3-yl)methanesulfonamide (1.24 g, 4.4 mmol) and 1,1'-bis(diphenylphosphino)ferrocene-palladium(II)dichloride dichloromethane complex (375 mg, 0.453 mmol) were added in one portion. The mixture was sealed and heated to 70° C. for 2 h. The mixture was cooled to room temperature, then quenched with $H_2O$. The aqueous layer was acidified to pH 4 with 1 M HCl solution, then diluted with methanol, filtered through Celite. The filtrate was concentrated to a smaller volume, then purified by silica gel column chromatography with 0-15% methanol in DCM to give the product.

Step 4: (R)-1-(2-chloro-5-fluoropyridin-3-yl)ethyl (4-(6-ethyl-5-(methylsulfonamido)pyridin-2-yl)-1-methyl-1H-1,2,3-triazol-5-yl)carbamate To a flask charged with 4-(6-ethyl-5-(methylsulfonamido)pyridin-2-yl)-1-methyl-1H-1,2,3-triazole-5-carboxylic acid (0.03 mmol), 1-propanephosphonic acid cyclic anhydride (50% in DMF, 0.06 mmol), azidotrimethysilane (0.06 mmol) acid and THF (1.0 ml) was added triethylamine (0.09 mmol) dropwise. The reaction mixture was stirred at 65° C. for 30 min before (R)-1-(2-chloro-5-fluoropyridin-3-yl)ethan-1-ol (0.03 mmol) was added and the flask was heated at 65° C. for 90 min. The reaction was concentrated, and purified by reverse phase HPLC to provide the title compound. LCMS-ESI+ (m/z): 498. 1H NMR (400 MHz, Methanol-d4) δ 8.44-8.12 (m, 1H), 7.99-7.73 (m, 3H), 6.08 (s, 1H), 4.03 (s, 3H), 3.07 (s, 3H), 2.94 (s, 2H), 1.83-1.46 (m, 3H), 1.30 (s, 3H).

Example 36: Preparation of (R)-1-(2-chloro-5-fluoropyridin-3-yl)ethyl (4-(6-ethyl-5-(methylsulfonamido)pyridin-2-yl)-1-methyl-1H-1,2,3-triazol-5-yl)carbamate (Compound 148)

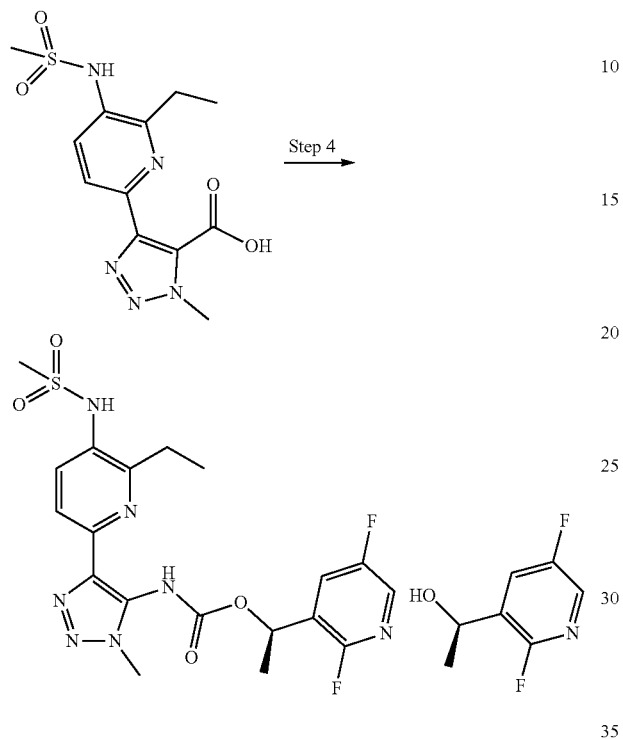

To a flask charged with 4-(6-ethyl-5-(methylsulfonamido)pyridin-2-yl)-1-methyl-1H-1,2,3-triazole-5-carboxylic acid (0.03 mmol), 1-propanephosphonic acid cyclic anhydride (50% in DMF, 0.06 mmol), azidotrimethysilane (0.06 mmol) acid and THF (1.0 ml) was added triethylamine (0.09 mmol) dropwise. The reaction mixture was stirred at 65° C. for 30 min before (R)-1-(2,5-difluoropyridin-3-yl)ethan-1-ol (0.03 mmol) was added and the flask was heated at 65° C. for 90 min. The reaction was concentrated, and purified by reverse phase HPLC to provide the title compound. LCMS-ESI+ (m/z): 482. 1H NMR (400 MHz, Methanol-d4) δ 8.14-7.97 (m, 1H), 7.87 (m, 3H), 5.98 (d, J=8.1 Hz, 1H), 4.03 (s, 3H), 3.07 (s, 3H), 2.94 (d, 2H), 1.84-1.44 (m, 3H), 1.41-1.19 (m, 3H).

Example 37: Preparation of (R)-1-(2-chloropyridin-3-yl)ethyl (4-(6-cyclopropyl-5-(methylsulfonamido)pyridin-2-yl)-1-methyl-1H-1,2,3-triazol-5-yl)carbamate (Compound 149)

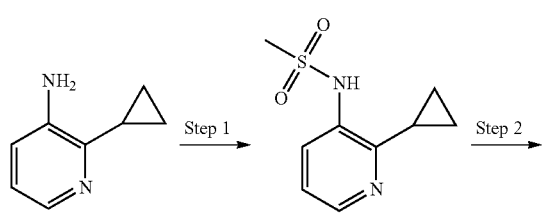

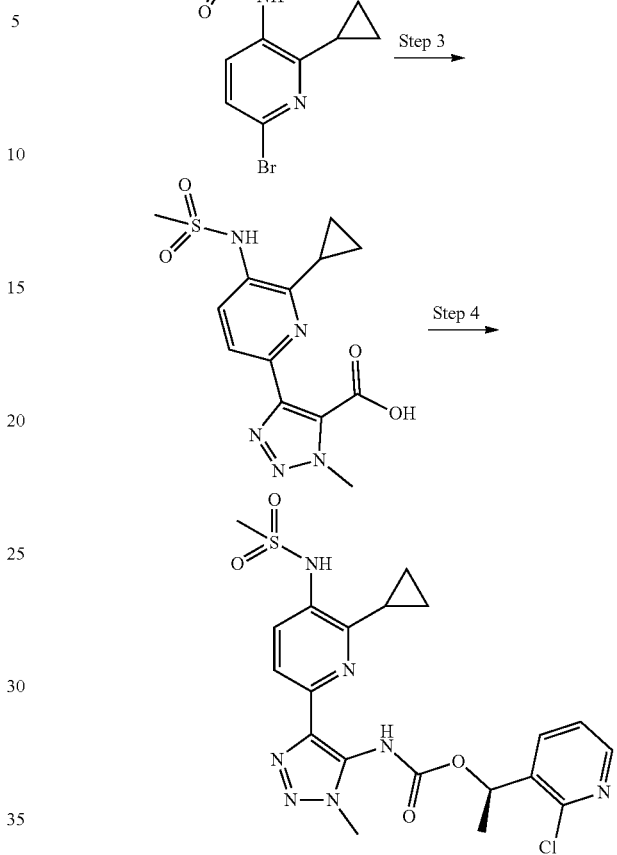

Step 1: N-(2-Cyclopropylpyridin-3-yl)methanesulfonamide

2-Cyclopropylpyridin-3-amine (548 mg, 4.1 mmol) was dissolved in anhydrous dichloromethane (20 ml) under argon, treated with methanesulfonyl chloride (0.77 ml, 10 mmol), and pyridine (0.8 ml, 10 mmol). The mixture was stirred at ambient temperature for 24 h and then concentrated to dryness. To the aforementioned mixture of mono- and bis-mesylated products was added methanol (29 ml) followed by sodium methoxide (25 percent, 1.1 ml) at ambient temperature. Stirring was continued for 1 hour then the solution was concentrated under reduced pressure followed by addition of water, NH4Cl (sat. aq.) and ethyl acetate. The combined organic layers washed with brine, dried over Na2SO4, filtered, and the filtrate concentrated in vacuo giving the title compound.

Step 2: N-(6-Bromo-2-cyclopropylpyridin-3-yl)methanesulfonamide

A mixture of N-(6-bromo-2-cyclopropylpyridin-3-yl)methanesulfonamide (0.34 g, 1.6 mmol), NBS (0.288 g, 1.62 mmol) in CH3CN (4 ml) was stirred at room temperature overnight. The reaction mixture was diluted with DCM and washed with water and Na2S2O3. The organic layer was collected, dried over Na2SO4, filtered, and concentrated in vacuo. The residue was purified by silica gel column chromatography with 0-80% ethyl acetate in hexanes to give the product.

Step 3: 4-(6-Cyclopropyl-5-(methylsulfonamido)pyridin-2-yl)-1-methyl-1H-1,2,3-triazole-5-carboxylic acid To a solution of 4-bromo-1-methyl-1H-1,2,3-triazole-5-carboxylic acid (80 mg, 0.388 mmol) in THF (4 ml) at −78° C. was added n-BuLi (2.5 M solution, 0.47 ml, 1.17 mmol) very slowly dropwise. The reaction mixture was stirred at −78° C. for 15 min. A 1.9 M solution of $ZnCl_2$ in 2-MeTHF (0.61 ml, 1.17 mmol) was added slowly dropwise at −78° C. Then the mixture was warmed to room temperature for 10 min. After 20 min, N-(6-bromo-2-cyclopropylpyridin-3-yl)methanesulfonamide (107 mg, 0.367 mmol) and 1,1'-bis(diphenylphosphino)ferrocene-palladium(II)dichloride dichloromethane complex (32 mg, 0.039 mmol) were added in one portion. The mixture was sealed and heated to 70° C. for 2 h. The mixture was cooled to room temperature, then quenched with $H_2O$. The aqueous layer was acidified to pH 4 with 1 M HCl solution, then diluted with methanol, filtered through Celite. The filtrate was concentrated to a smaller volume, then purified by prep HPLC to give the product.

Step 4: (R)-1-(2-chloropyridin-3-yl)ethyl (4-(6-cyclopropyl-5-(methylsulfonamido)pyridin-2-yl)-1-methyl-1H-1,2,3-triazol-5-yl)carbamate To a flask charged with 4-(6-Cyclopropyl-5-(methylsulfonamido)pyridin-2-yl)-1-methyl-1H-1,2,3-triazole-5-carboxylic acid (0.03 mmol), 1-propanephosphonic acid cyclic anhydride (50% in DMF, 0.06 mmol), azidotrimethysilane (0.06 mmol) acid and THF (1.0 ml) was added triethylamine (0.09 mmol) dropwise. The reaction mixture was stirred at 65° C. for 30 min before (R)-1-(2-chloropyridin-3-yl)ethan-1-ol (0.03 mmol) was added and the flask was heated at 65° C. for 90 min. The reaction was concentrated, and purified by reverse phase HPLC to provide the title compound. LCMS-ESI+ (m/z): 492.1. 1H NMR (400 MHz, Methanol-d4) δ 8.35 (s, 1H), 8.11 (s, 1H), 7.87-7.70 (m, 2H), 7.50 (s, 1H), 6.16 (s, 1H), 3.99 (s, 3H), 3.05 (s, 3H), 2.48 (s, 1H), 1.64 (s, 3H), 1.15 (m, 2H), 0.95 (m, 2H).

Example 38: Preparation of (R)-1-phenylethyl (4-(6-(difluoromethyl)-5-(methylsulfonamido)pyridin-2-yl)-1-methyl-1H-1,2,3-triazol-5-yl)carbamate (Compound 150)

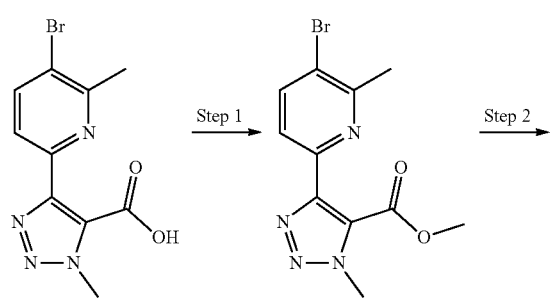

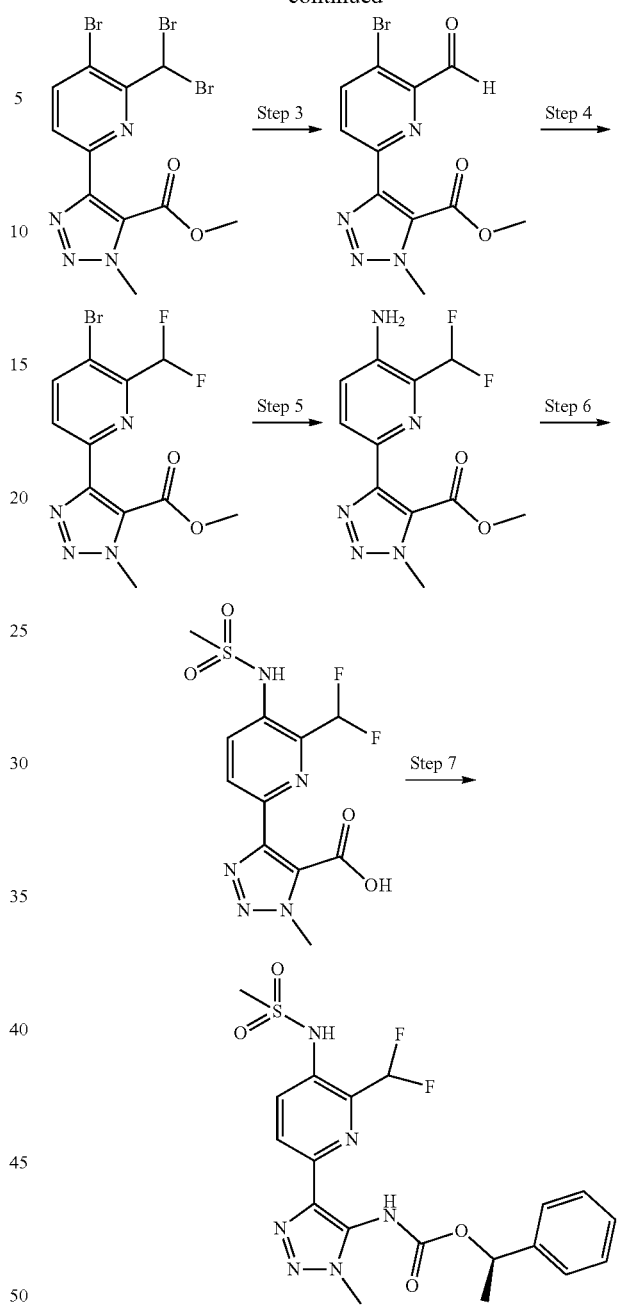

Step 1: Methyl 4-(5-bromo-6-methylpyridin-2-yl)-1-methyl-1H-1,2,3-triazole-5-carboxylate To 4-(5-bromo-6-methylpyridin-2-yl)-1-methyl-1H-1,2,3-triazole-5-carboxylic acid (3 g, 10.1 mmol) was added meoh (17 ml) and THF (5 ml) followed by dropwise addition of $H_2SO_4$ (3 ml) over 5 minutes. The reaction was heated reflux overnight. The reaction was cooled and concentrated, quenched with water and extracted with DCM. The organic phase was dried over Na2SO4, filtered and concentrated in vacuo. The residue was purified by silica gel column with 0-80% ethyl acetate in hexanes to give the ester as a solid.

Step 2: Methyl 4-(5-bromo-6-(dibromomethyl)pyridin-2-yl)-1-methyl-1H-1,2,3-triazole-5-carboxylate To a suspension of methyl 4-(5-bromo-6-methylpyridin-2-yl)-1-methyl-1 h-1,2,3-triazole-5-carboxylate (311 mg, 1 mmol), and n-bromosuccinimide (205 mg, 1.15 mmol) in CCl$_4$ (4 ml) was added benzoyl peroxide (12 mg, 0.05 eq). The resulting mixture was stirred at reflux overnight. The mixture was cooled to room temperature. Filtered and the filtrate was concentrated to dryness. The residue was slowly purified by silica gel column chromatography with 0-40 etoac in hexanes. The desired product was separated from a mixture. 1H NMR (400 mhz, chloroform-d) δ 7.98 (d, j=8.3 hz, 1 h), 7.89 (s, 1 h), 7.17 (s, 1 h), 4.30 (s, 3 h), 4.04 (s, 3 h).

Step 3: Methyl 4-(5-bromo-6-formylpyridin-2-yl)-1-methyl-1H-1,2,3-triazole-5-carboxylate Methyl 4-(5-bromo-6-(dibromomethyl)pyridin-2-yl)-1-methyl-1H-1,2,3-triazole-5-carboxylate (0.2 g, 0.427 mmol) in morpholine (0.35 ml) was stirred at room temperature overnight. The mixture was partitioned between DCM and water. The organic phase was washed with brine, dried over sodium sulfate, filtered and concentrated in vacuo. The residue was purified by flash column chromatography eluting with a gradient of 3%-10% methanol in dichloromethane to provide the product.

Step 4: Methyl 4-(5-bromo-6-(difluoromethyl)pyridin-2-yl)-1-methyl-1H-1,2,3-triazole-5-carboxylate To a stirred solution of methyl 4-(5-bromo-6-formylpyridin-2-yl)-1-methyl-1H-1,2,3-triazole-5-carboxylate (200 mg, 0.615 mmol) in chloroform (6 ml) at 0° C. was added DAST (0.163 ml, 1.23 mmol). The reaction mixture was stirred at room temperature overnight. The mixture was treated with aq. NaHCO$_3$ solution and extracted with CH$_2$Cl$_2$. The organic phase was separated, dried over Na2SO4, filtered, and concentrated. The residue was purified by flash chromatography (10-40% ethyl acetate in hexane as eluent) to afford the title compound.

Step 5: Methyl 4-(5-amino-6-(difluoromethyl)pyridin-2-yl)-1-methyl-1H-1,2,3-triazole-5-carboxylate Proline (30 mg, 0.258 mmol), NaN$_3$ (26 mg, 0.4 mmol), CuI (38 mg, 0.2 mmol), and methyl 4-(5-bromo-6-(difluoromethyl)pyridin-2-yl)-1-methyl-1 h-1,2,3-triazole-5-carboxylate (69 mg, 0.2 mmol) were combined in a flask that was then purged with argon. DMSO (0.4 ml) was added while flushing with argon. The flask was stirred at 100° C. for 2 hours. The dark solution was cooled to room temperature and quenched by the addition of aq NH$_4$Cl (1.5 ml) and ethyl acetate (1 ml). This biphasic mixture was stirred at room temperature for 1 h. The resulting solution was filtered through a pad of celite, which was subsequently washed with ethyl acetate and water. The filtrate was extracted with ethyl acetate and washed with brine. Finally, the organic phases were combined, dried with Na$_2$SO$_4$, filtered, and concentrated to dryness. The residue was purified by prep-HPLC to give the product.

Step 6: 4-(6-(Difluoromethyl)-5-(methylsulfonamido)pyridin-2-yl)-1-methyl-1H-1,2,3-triazole-5-carboxylic acid Pyridine (0.15 ml, 1.84 mmol), methyl 4-(5-amino-6-(difluoromethyl)pyridin-2-yl)-1-methyl-1H-1,2,3-triazole-5-carboxylate (26 mg, 0.092 mmol) in DCM (1 ml) were combined. methanesulfonic anhydride (48 mg, 0.27 mmol) was added at 0° C. Then the reaction was run at 90° C. for 2 min and room temperature for 3 h. The crude mixture was quenched by addition of water and DCM. The organic phase was separated, drying over Na$_2$SO$_4$ and evaporation afforded the crude material which was taken to the next step. To the aforementioned mixture of mono and bismesylated products was added methanol (0.7 ml) followed by sodium methoxide (25 percent, 22 ul, 0.12 mmol,) at ambient temperature. The mixture was stirred at room temperature for 5 h. Then the solution was concentrated under reduced pressure, followed by addition of water, NH$_4$Cl (sat. aq.) and ethyl acetate. The organic phase was concentrated. The residue was dissolved in 0.4 ml of 1M sodium hydroxide solution, and 1 ml THF. The solution was stirred vigorously for 30 minutes. After completion, the solution was neutralized to pH ~5 with conc. HCl. Brine was added, and the mixture was extracted with ethyl acetate (2×) to provide the product.

Step 7: (R)-1-phenylethyl (4-(6-(difluoromethyl)-5-(methylsulfonamido)pyridin-2-yl)-1-methyl-1H-1,2,3-triazol-5-yl)carbamate To a flask charged with 4-(6-(Difluoromethyl)-5-(methylsulfonamido)pyridin-2-yl)-1-methyl-1H-1,2,3-triazole-5-carboxylic acid (0.03 mmol), 1-propanephosphonic acid cyclic anhydride (50% in DMF, 0.06 mmol), azidotrimethysilane (0.06 mmol) acid and THF (1.0 ml) was added triethylamine (0.09 mmol) dropwise. The reaction mixture was stirred at 65° C. for 30 min before (R)-1-phenylethan-1-ol (0.03 mmol) was added and the flask was heated at 65° C. for 90 min. The reaction was concentrated, and purified by reverse phase HPLC to provide the title compound. LCMS-ESI+ (m/z): 466.9. 1H NMR (400 MHz, Methanol-d4) δ 8.15 (d, J=8.6 Hz, 1H), 8.05 (d, J=8.6 Hz, 1H), 7.35 (m, 5H), 6.94 (t, J=54.0 Hz, 1H), 5.83 (m, 1H), 3.99 (s, 3H), 3.08 (s, 3H), 1.56 (s, 3H).

Example 39: Preparation of (R)-1-(2-ethylpyridin-3-yl)ethyl (1-methyl-4-(6-methyl-5-(methylsulfonamido)pyridin-2-yl)-1H-1,2,3-triazol-5-yl)carbamate (Compound 151)

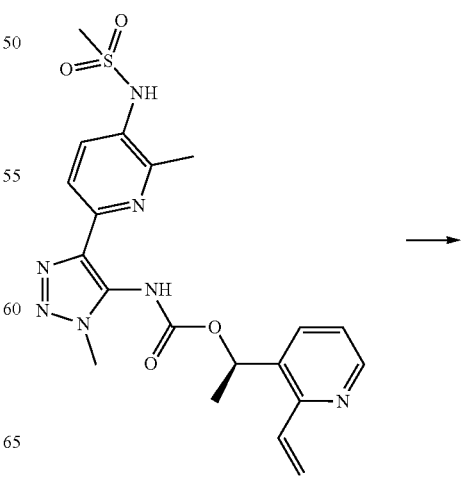

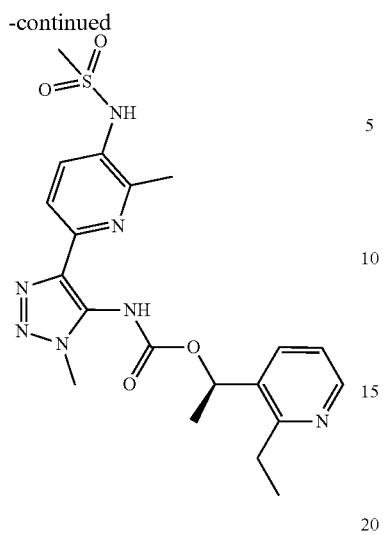

To a solution of (R)-1-(2-vinylpyridin-3-yl)ethyl (1-methyl-4-(6-methyl-5-(methylsulfonamido)pyridin-2-yl)-1H-1,2,3-triazol-5-yl)carbamate (0.024 mmol) in 2 mL MeOH was added Pd/C (10%, 0.01 g) under nitrogen atmosphere. The mixture was hydrogenated at room temperature for 4 h under hydrogen atmosphere using a hydrogen balloon, filtered through a celite pad and concentrated under reduced pressure. The residue was purified by prep-HPLC to give the title product. LCMS-ESI+ (m/z): 460.1. 1H NMR (400 MHz, Methanol-d4) δ 8.67 (s, 1H), 7.82 (s, 4H), 6.13 (m, 1H), 3.99 (s, 3H), 3.27-3.15 (m, 2H), 3.10 (s, 3H), 2.57 (s, 3H), 1.94-1.56 (m, 3H), 1.42 (t, J=7.6 Hz, 3H).

Example 40: Preparation of 1-(2-cyano-5-fluoropyridin-3-yl)ethyl (1-methyl-4-(6-methyl-5-(methylsulfonamido)pyridin-2-yl)-1H-1,2,3-triazol-5-yl)carbamate (Compound 152)

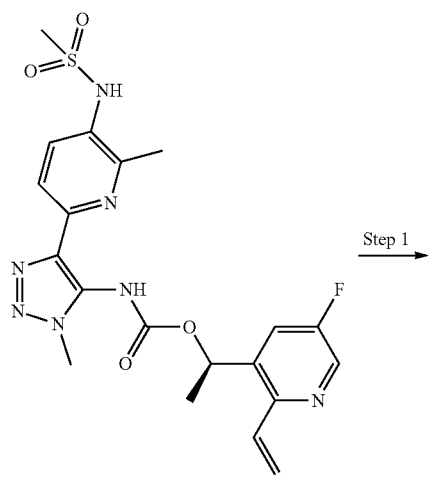

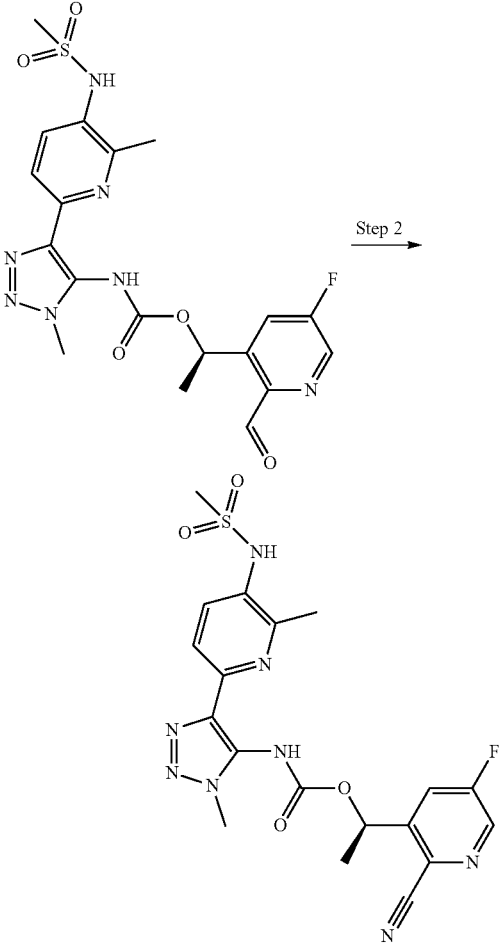

Step 1: (R)-1-(5-fluoro-2-formylpyridin-3-yl)ethyl (1-methyl-4-(6-methyl-5-(methylsulfonamido)pyridin-2-yl)-1H-1,2,3-triazol-5-yl)carbamate OsO4 (2.5 wt. percent sol. in tert-butanol) (0.35 mL, 2.7 mmol) was added to a stirred solution of (R)-1-(5-fluoro-2-vinylpyridin-3-yl)ethyl (1-methyl-4-(6-methyl-5-(methylsulfonamido)pyridin-2-yl)-1H-1,2,3-triazol-5-yl)carbamate (0.276 mmol) and 4-methylmorpholine-N-oxide (1.5 eq) in a mixture of acetone and water (1 mL:1 mL). The reaction mixture was stirred in acetone/water (1/1 mL) at 0° C. The reaction mixture was allowed to stir for 30 min at ambient temperature. The reaction was stirred at room temperature overnight.

Then NaIO4 (225 mg, 4 eq) was added and the reaction mixture was allowed to stir for additional 4 h at ambient temperature. The reaction mixture was diluted with ice cold water and extracted with ethyl acetate. The combined organic layers were washed with brine, dried over Na2SO4 and concentrated under reduced pressure. The crude residue was purified by flash column chromatography on silica gel, eluting with 5-50 percent ethyl acetate in hexanes to give the product.

Step 2: 1-(2-cyano-5-fluoropyridin-3-yl)ethyl (1-methyl-4-(6-methyl-5-(methylsulfonamido) pyridin-2-yl)-1H-1,2,3-triazol-5-yl)carbamate To a solution of (R)-1-(5-fluoro-2-formylpyridin-3-yl) ethyl (1-methyl-4-(6-methyl-5-(methylsulfonamido)pyridin-2-yl)-1H-1,2,3-triazol-5-yl)carbamate (0.04 mmol) and ammonium acetate (0.4 mmol) in MeCN (1 mL), was added trimethylphenylammonium tribromide (2 eq) at room temperature. After stirring for 21 h at room temperature, reaction mixture was filtered, and the filtrate was concentrated. The residue was purified by prep-HPLC to give the product. LCMS-ESI+ (m/z): 475.1. 1H NMR (400 MHz, Methanol-d4) δ 8.60 (m, 1H), 7.97 (s, 1H), 7.84 (s, 2H), 6.09 (s, 1H), 4.02 (s, 3H), 3.07 (s, 2H), 2.57 (s, 3H), 1.72 (m, 3H).

Example 41: (R)-1-(2-chloropyridin-3-yl)ethyl (4-(6-fluoro-5-(methylsulfonamido)pyridin-2-yl)-1-methyl-1H-1,2,3-triazol-5-yl)carbamate (Compound 153)

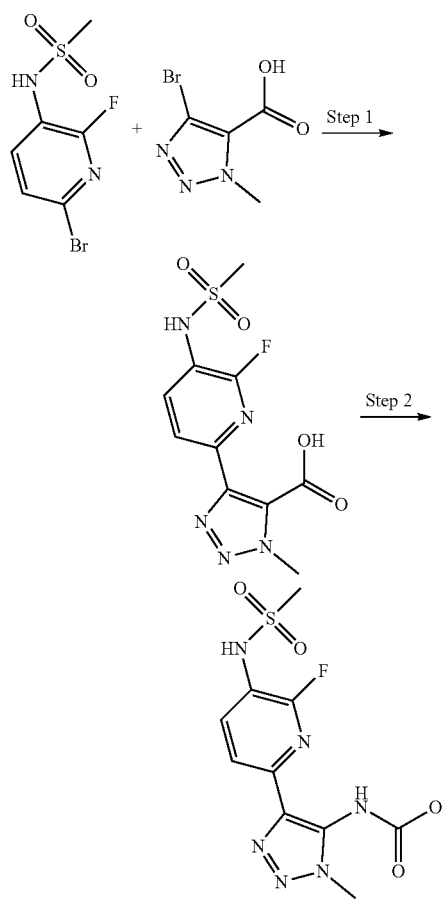

Step 1: 4-(6-fluoro-5-(methylsulfonamido)pyridin-2-yl)-1-methyl-1H-1,2,3-triazole-5-carboxylic acid 4-bromo-1-methyl-1H-1,2,3-triazole-5-carboxylic acid (0.73 mmol) was dissolved in 15 mL of tetrahydrofuran and submerged in a −78° C. bath for 15 min. A 1.6 M solution of n-butyllithium (2.2 mmol) in hexanes was added dropwise over 20 min and allowed to stir for an additional 1 h. A 1.9 M solution of zinc chloride (2.2 mmol) in 2-methyl tetrahydrofuran was added dropwise over 15 min. The reaction mixture was warmed to ambient temperature and allowed to stir for 30 min. The resulting mixture was sparged with argon gas for 10 min, and then N-(6-bromo-2-fluoro-3-pyridyl)methanesulfonamide (0.73 mmol) and [1,1′-Bis(diphenylphosphino)ferrocene]dichloropalladium(II), complex with dichloromethane (0.07 mmol) were added. The reaction was heated at 70° C. for 1 h, and then cooled to ambient temperature. The reaction was diluted with 20 mL ethyl acetate, and quenched with 1 mL AcOH, and Brine. The organic layer was separated, and the aqueous layer was washed with THF (30 mL×2). The combined organics were dried over Na₂SO₄, concentrated to provide 4-(6-fluoro-5-(methylsulfonamido)pyridin-2-yl)-1-methyl-1H-1,2,3-triazole-5-carboxylic acid which was used in the next step without further purification.

Step 2: (R)-1-(2-chloropyridin-3-yl)ethyl (4-(6-fluoro-5-(methylsulfonamido)pyridin-2-yl)-1-methyl-1H-1,2,3-triazol-5-yl)carbamate 4-(6-fluoro-5-(methylsulfonamido)pyridin-2-yl)-1-methyl-1H-1,2,3-triazole-5-carboxylic acid (0.16 mmol), Azidotrimethylsilane (0.32 mmol), and T3P (50% in DMF) (0.32 mmol) was dissolved in THF (5 mL). Triethyl amine (0.48 mmol) was added dropwise at room temperature resulting. The reaction was heated to 70° C. for 20 minutes before (R)-1-(2-chloropyridin-3-yl)ethan-1-ol (0.32 mmol) was added and the reaction was heated at 70° C. for another 2 h. Water and ethyl acetate was added and layers separated. The organic was concentrated and then purified by column and reverse phase HPLC to provide (R)-1-(2-chloropyridin-3-yl)ethyl (4-(6-fluoro-5-(methylsulfonamido)pyridin-2-yl)-1-methyl-1H-1,2,3-triazol-5-yl)carbamate. LCMS-ESI+ (m/z): 470. 1H NMR (400 MHz, Methanol-d4) δ 8.32 (s, 1H), 8.24-7.91 (m, 2H), 7.87 (d, J=8.3 Hz, 1H), 7.63-7.23 (m, 1H), 6.21-5.93 (m, 1H), 3.98 (s, 3H), 3.09 (s, 3H), 1.65 (s, 3H).

Example 42: (R)-1-(2-chloropyridin-3-yl)ethyl (4-(6-chloro-5-(methylsulfonamido)pyridin-2-yl)-1-methyl-1H-1,2,3-triazol-5-yl)carbamate (Compound 154)

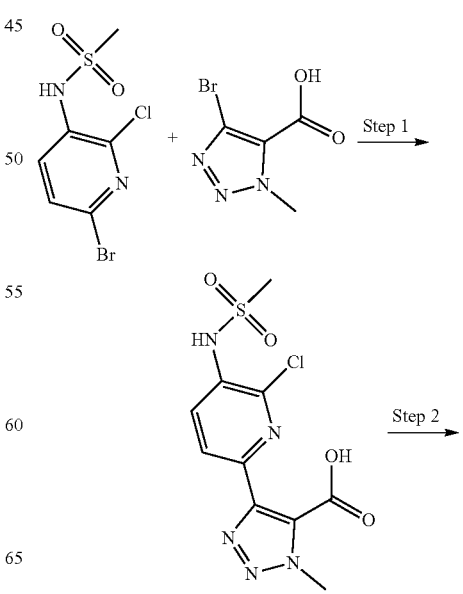

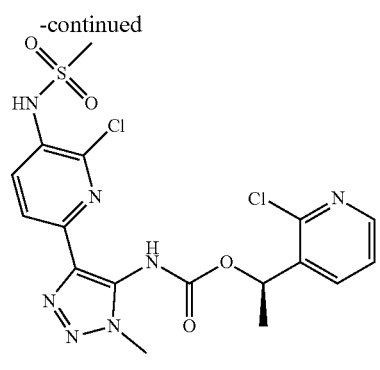

Step 1: 4-(6-chloro-5-(methylsulfonamido)pyridin-2-yl)-1-methyl-1H-1,2,3-triazole-5-carboxylic acid 4-bromo-1-methyl-1H-1,2,3-triazole-5-carboxylic acid (0.73 mmol) was dissolved in 15 mL of tetrahydrofuran and submerged in a −78° C. bath for 15 min. A 1.6 M solution of n-butyllithium (2.2 mmol) in hexanes was added dropwise over 20 min and allowed to stir for an additional 1 h. A 1.9 M solution of zinc chloride (2.2 mmol) in 2-methyl tetrahydrofuran was added dropwise over 15 min. The reaction mixture was warmed to ambient temperature and allowed to stir for 30 min. The resulting mixture was sparged with argon gas for 10 min, and then N-(6-bromo-2-chloro-3-pyridyl)methanesulfonamide (0.73 mmol) and [1,1'-bis(diphenylphosphino)ferrocene]dichloropalladium(II), complex with dichloromethane (0.07 mmol) were added. The reaction was heated at 70° C. for 1 h, and then cooled to ambient temperature. The reaction was diluted with 20 mL ethyl acetate, and quenched with 1 mL AcOH, and Brine. The organic was separated, and the aqeuous layer was washed with THF (30 mL×2). The combined organics were dried over $Na_2SO_4$, concentrated to provide 4-(6-chloro-5-(methylsulfonamido)pyridin-2-yl)-1-methyl-1H-1,2,3-triazole-5-carboxylic acid which was used in the next step without further purification.

Step 2: (R)-1-(2-chloropyridin-3-yl)ethyl (4-(6-chloro-5-(methylsulfonamido)pyridin-2-yl)-1-methyl-1H-1,2,3-triazol-5-yl)carbamate 4-(6-chloro-5-(methylsulfonamido)pyridin-2-yl)-1-methyl-1H-1,2,3-triazole-5-carboxylic acid (0.16 mmol), azidotrimethylsilane (0.32 mmol), and T3P (50% in DMF) (0.32 mmol) was dissolved in THF (5 mL). Triethyl amine (0.48 mmol) was added dropwise at room temperature. The reaction was heated to 70° C. for 20 minutes before (R)-1-(2-chloropyridin-3-yl)ethan-1-ol (0.32 mmol) was added and the reaction was heated at 70° C. for another 2 h. Water and ethyl acetate was added and layers separated. The organic was concentrated and then purified by column and reverse phase HPLC to provide (R)-1-(2-chloropyridin-3-yl)ethyl (4-(6-chloro-5-(methylsulfonamido)pyridin-2-yl)-1-methyl-1H-1,2,3-triazol-5-yl)carbamate. LCMS-ESI+ (m/z): 486. 1H NMR (400 MHz, Methanol-d4) δ 8.50-8.26 (m, 1H), 8.21-7.10 (m, 4H), 6.30-5.92 (m, 1H), 3.99 (s, 3H), 3.07 (s, 3H), 1.66 (s, 3H).

Example 43: (S)-2-fluoro-1-phenylethyl (1-methyl-4-(6-(methylamino)-5-(methylsulfonamido) pyridin-2-yl)-1H-1,2,3-triazol-5-yl)carbamate (Compound 155)

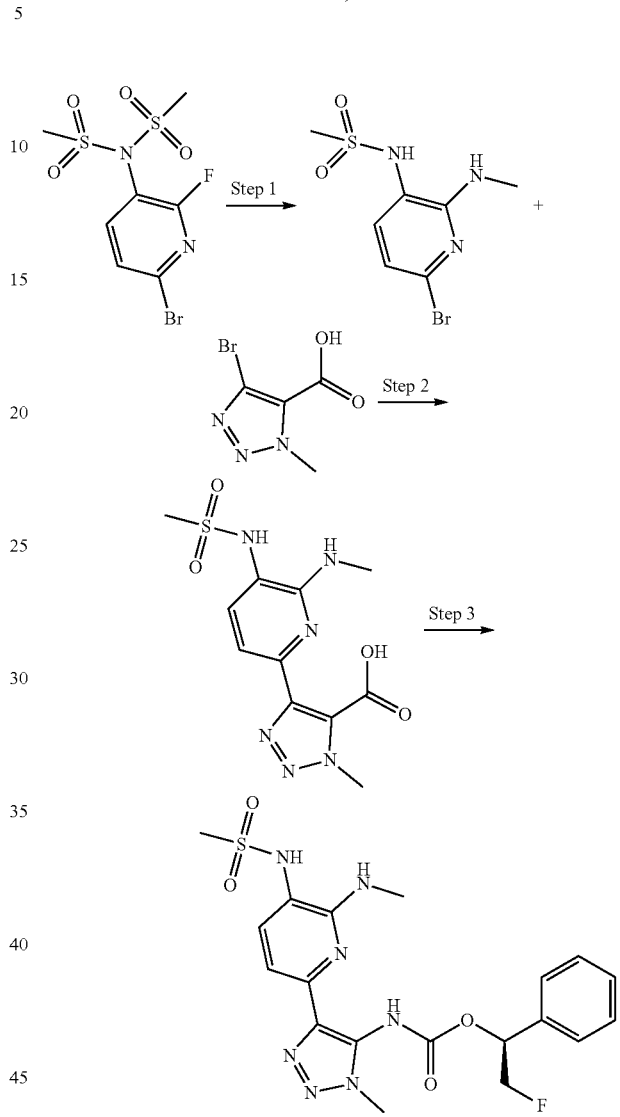

Step 1: N-(6-bromo-2-(methylamino)pyridin-3-yl) methanesulfonamide

N-(6-bromo-2-fluoropyridin-3-yl)-N-(methylsulfonyl) methanesulfonamide (2.9 mmol) was dissolved in THF (25 mL), and 2 M solution of methyl amine in THF (14 mmol) was added dropwise. The reaction was stirred at room temperature for 16 h, and concentrated and purified by column chromatography to provide N-(6-bromo-2-(methylamino)pyridin-3-yl)methanesulfonamide.

Step 2: 1-methyl-4-(6-(methylamino)-5-(methylsulfonamido)pyridin-2-yl)-1H-1,2,3-triazole-5-carboxylic acid 4-bromo-1-methyl-1H-1,2,3-triazole-5-carboxylic acid (0.73 mmol) was dissolved in 15 mL of tetrahydrofuran and submerged in a −78° C. bath for 15 min. A 1.6 M solution of n-butylithium (2.2 mmol) in hexanes was added dropwise over 20 min and allowed to stir for an additional 1 h. A 1.9 M solution of zine chloride (2.2 mmol) in 2-methyl tetrahydrofuran was added dropwise over 15 min. The reaction mixture was warmed to ambient temperature and allowed to stir for 30 min. The resulting mixture was sparged with argon gas for 10 min, and then N-(6-bromo-2-(methylamino)pyridin-3-yl)methanesulfonamide. (0.55 mmol) and [1,1'-Bis(diphenylphosphino)ferrocene]dichloropalladium (II), complex with dichloromethane (0.07 mmol) were added. The reaction was heated at 70° C. for 1 h, and then cooled to ambient temperature. The reaction was diluted with 20 mL ethyl acetate, and quenched with 1 mL AcOH, and Brine. The organic was separated, and the aqeuous layer was washed with THE (30 mL×2). The combined organics were dried over Na$_2$SO$_4$, concentrated to provide 1-methyl-4-(6-(methylamino)-5-(methylsulfonamido)pyridin-2-yl)-1H-1,2,3-triazole-5-carboxylic acid which was used in the next step without further purification.

Step 3: (S)-2-fluoro-1-phenylethyl (1-methyl-4-(6-(methylamino)-5-(methylsulfonamido)pyridin-2-yl)-1H-1,2,3-triazol-5-yl)carbamate 1-methyl-4-(6-(methylamino)-5-(methylsulfonamido) pyridin-2-yl)-1H-1,2,3-triazole-5-carboxylic acid (0.12 mmol), azidotrimethylsilane (0.25 mmol), and T3P (50% in DMF) (0.25 mmol) was dissolved in THE (5 mL). Triethyl amine (0.36 mmol) was added dropwise at room temperature. The reaction was heated to 70° C. for 20 minutes before (S)-2-fluoro-1-phenylethan-1-ol (0.32 mmol) was added and the reaction was heated at 70° C. for another 2 h. Water and ethyl acetate was added and layers separated. The organic was concentrated and then purified by column and reverse phase HPLC to provide (S)-2-fluoro-1-phenylethyl (1-methyl-4-(6-(methylamino)-5-(methylsulfonamido)pyridin-2-yl)-1H-1,2,3-triazol-5-yl)carbamate. LCMS-ESI+ (m/z): 464.1. 1H NMR (400 MHz, Methanol-d4) δ 7.65-7.12 (m, 7H), 6.11-5.87 (m, 1H), 4.74-4.51 (m, 2H), 3.99 (s, 3H), 3.00 (s, 3H), 2.94 (s, 3H).

Example 44: (S)-2-fluoro-1-phenylethyl (4-(3-fluoro-6-methyl-5-(methylsulfonamido)pyridin-2-yl)-1-methyl-1H-1,2,3-triazol-5-yl)carbamate (Compound 156)

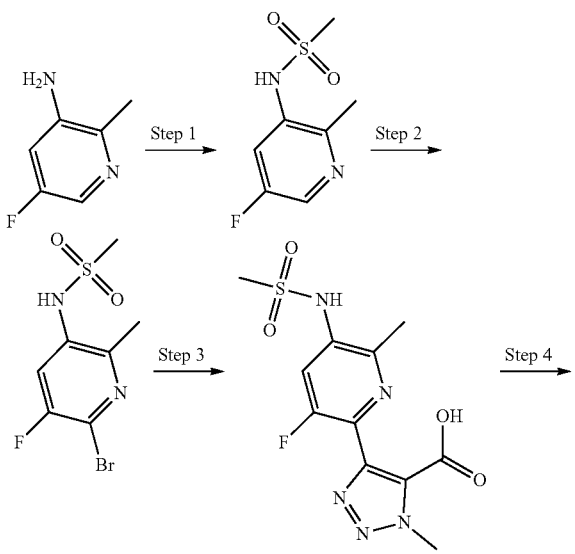

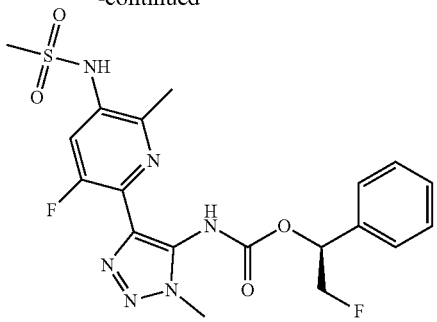

Step 1: N-(5-fluoro-2-methylpyridin-3-yl)methanesulfonamide 5-fluoro-2-methylpyridin-3-amine (9.1 mmol) was dissolved in DCM (40 mL) and pyridine (5 mL). Methanesulfonyl chloride (18 mmol) was added dropwise and the solution was stirred at room temperature for 16 h. The reaction was quenched with aq. sodium bicarbonate, and extracted with DCM. The combined organics were dried over sodium sulfate, concentrated, and purified by column chromatography to provide N-(5-fluoro-2-methylpyridin-3-yl)methanesulfonamide.

Step 2: N-(6-bromo-5-fluoro-2-methylpyridin-3-yl) methanesulfonamide

N-(5-fluoro-2-methylpyridin-3-yl)methanesulfonamid (1.2 mmol) was dissolved in MeCN (10 mL) and N-Bromo succinimide (1.5 mmol) was added. The reaction was stirred at room temperature for 12 h, and concentrated and purified by column chromatography to provide N-(6-bromo-5-fluoro-2-methylpyridin-3-yl)methanesulfonamide.

Step 3: 4-(3-fluoro-6-methyl-5-(methylsulfonamido) pyridin-2-yl)-1-methyl-1H-1,2,3-triazole-5-carboxylic acid 4-bromo-1-methyl-1H-1,2,3-triazole-5-carboxylic acid (0.73 mmol) was dissolved in 15 mL of tetrahydrofuran and submerged in a −78° C. bath for 15 min. A 1.6 M solution of n-butylithium (2.2 mmol) in hexanes was added dropwise over 20 min and allowed to stir for an additional 1 h. A 1.9 M solution of zine chloride (2.2 mmol) in 2-methyl tetrahydrofuran was added dropwise over 15 min. The reaction mixture was warmed to ambient temperature and allowed to stir for 30 min. The resulting mixture was sparged with argon gas for 10 min, and then N-(6-bromo-5-fluoro-2-methylpyridin-3-yl)methanesulfonamide (0.69 mmol) and [1,1'-Bis(diphenylphosphino)ferrocene]dichloropalladium (II), complex with dichloromethane (0.07 mmol) were added. The reaction was heated at 70° C. for 1 h, and then cooled to ambient temperature. The reaction was diluted with 20 mL ethyl acetate, and quenched with 1 mL AcOH, and Brine. The organic was separated, and the aqueous layer was washed with THE (30 mL×2). The combined organics were dried over Na$_2$SO$_4$, concentrated to provide 4-(3-fluoro-6-methyl-5-(methylsulfonamido)pyridin-2-yl)-1-methyl-1H-1,2,3-triazole-5-carboxylic acid which was used in the next step without further purification.

Step 4: (S)-2-fluoro-1-phenylethyl (4-(3-fluoro-6-methyl-5-(methylsulfonamido)pyridin-2-yl)-1-methyl-1H-1,2,3-triazol-5-yl)carbamate 4-(3-fluoro-6-methyl-5-(methylsulfonamido)pyridin-2-yl)-1-methyl-1H-1,2,3-triazole-5-carboxylic acid (0.17 mmol), azidotrimethylsilane (0.35 mmol), and T3P (50% in DMF) (0.35 mmol) was dissolved in THF (5 mL). Triethyl amine (0.52 mmol) was added dropwise at room temperature. The reaction was heated to 70° C. for 20 minutes before (S)-2-fluoro-1-phenylethan-1-ol (0.32 mmol) was added and the reaction was heated at 70° C. for another 2 h. Water and ethyl acetate was added and layers separated. The organic was concentrated and then purified by column and reverse phase HPLC to provide (S)-2-fluoro-1-phenylethyl (4-(3-fluoro-6-methyl-5-(methylsulfonamido)pyridin-2-yl)-1-methyl-1H-1,2,3-triazol-5-yl)carbamate. LCMS-ESI+(m/z): 467. 1H NMR (400 MHz, Methanol-d4) δ 7.65 (d, J=11.7 Hz, 1H), 7.58-7.05 (m, 5H), 6.08-5.78 (m, 1H), 4.72-4.46 (m, 2H), 4.01 (s, 3H), 3.07 (s, 3H), 2.48 (s, 3H).

Example 45: (R)-1-(2-chloropyridin-3-yl)ethyl (1-ethyl-4-(6-methyl-5-(methylsulfonamido) pyridin-2-yl)-1H-1,2,3-triazol-5-yl)carbamate (Compound 157)

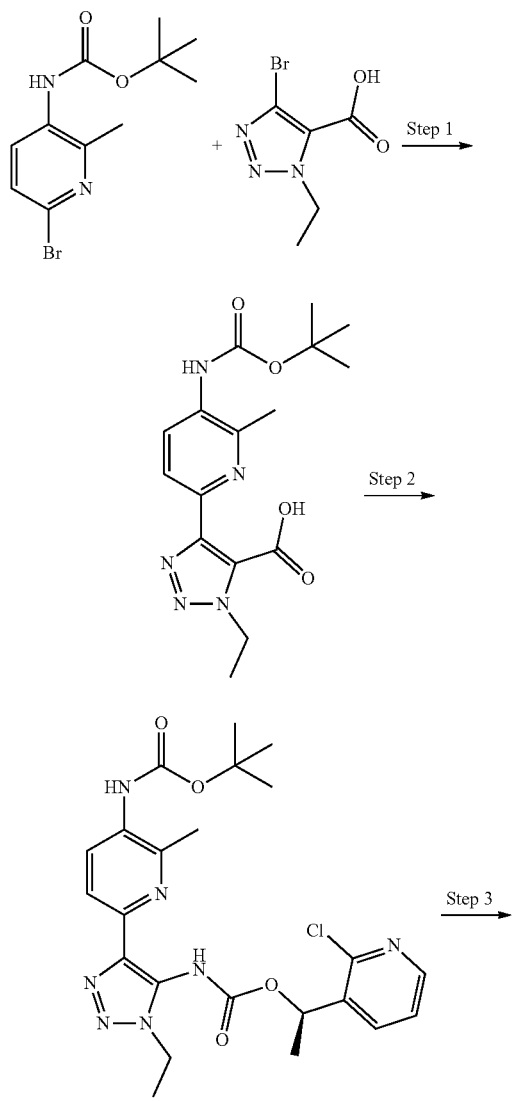

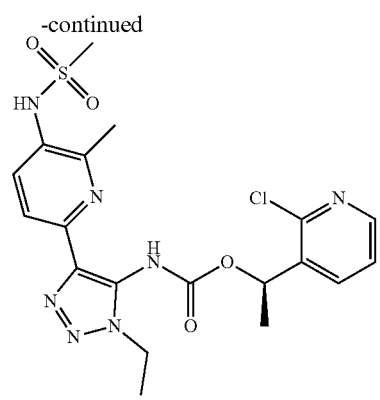

Step 1: 4-(5-((tert-butoxycarbonyl)amino)-6-methylpyridin-2-yl)-1-ethyl-1H-1,2,3-triazole-5-carboxylic acid 4-bromo-1-propyl-1H-1,2,3-triazole-5-carboxylic acid (0.86 mmol) (obtained following the procedure described in Example 1 for the synthesis of 4-bromo-1-methyl-1H-1,2,3-triazole-5-carboxylic acid, using 1-bromoethane in place of iodomethane, and using DMF in place of THF) was dissolved in 15 mL of tetrahydrofuran and submerged in a −78° C. bath for 15 min. A solution of lithium bis(trimethylsilyl)amide (0.86 mmol) in THF was added followed by a 1.6 M solution of n-butyllithium (1.7 mmol) in hexanes dropwise over 20 min and allowed to stir for an additional 1 h. A 1.9 M solution of zinc chloride (1.7 mmol) in 2-methyl tetrahydrofuran was added dropwise over 15 min. The reaction mixture was warmed to ambient temperature and allowed to stir for 30 min. The resulting mixture was sparged with argon gas for 10 min, and then tert-butyl (6-bromo-2-methylpyridin-3-yl)carbamate (1.1 mmol) and [1,1'-bis(diphenylphosphino)ferrocene]dichloropalladium (II), complex with dichloromethane (0.09 mmol) were added. The reaction was heated at 70° C. for 1 h, and then cooled to ambient temperature. The reaction was diluted with 20 mL ethyl acetate, and quenched with 1 mL AcOH, and Brine. The organic was separated, and the aqueous layer was washed with THF (30 mL×2). The combined organics were dried over Na₂SO₄, concentrated to provide 4-(5-((tert-butoxycarbonyl)amino)-6-methylpyridin-2-yl)-1-ethyl-1H-1,2,3-triazole-5-carboxylic acid which was used in the next step without further purification.

Step 2: (R)-1-(2-chloropyridin-3-yl)ethyl (4-(5-((tert-butoxycarbonyl)amino)-6-methylpyridin-2-yl)-1-ethyl-1H-1,2,3-triazol-5-yl)carbamate 4-(5-((tert-butoxycarbonyl)amino)-6-methylpyridin-2-yl)-1-ethyl-1H-1,2,3-triazole-5-carboxylic acid (0.17 mmol), azidotrimethylsilane (0.35 mmol), and T3P (50% in DMF) (0.35 mmol) was dissolved in THF (5 mL). Triethyl amine (0.52 mmol) was added dropwise at room temperature. The reaction was heated to 70° C. for 20 minutes before (S)-2-fluoro-1-phenylethan-1-ol (0.32 mmol) was added and the reaction was heated at 70° C. for another 2 h. Water and EtOAc were added and layers separated. The organic was concentrated and then purified by column to provide (R)-1-(2-chloropyridin-3-yl)ethyl (4-(5-((tert-butoxycarbonyl)amino)-6-methylpyridin-2-yl)-1-ethyl-1H-1,2,3-triazol-5-yl)carbamate.

Step 3: (R)-1-(2-chloropyridin-3-yl)ethyl (1-ethyl-4-(6-methyl-5-(methylsulfonamido) pyridin-2-yl)-1H-1,2,3-triazol-5-yl)carbamate (R)-1-(2-chloropyridin-3-yl)ethyl (4-(5-((tert-butoxycarbonyl)amino)-6-methylpyridin-2-yl)-1-ethyl-1H-1,2,3-triazol-5-yl)carbamate (0.04 mmol) was added 4M HCl in dioxanes. The resulting mixture was stirred at room temperature for 2 h. The reaction mixture was concentrated to dryness, and then treated with 3 mL of 1:4 pyridine/dichloromethane. Methanesulfonyl chloride (0.12 mmol) was added, and the reaction stirred for 1 h. The reaction was quenched with sodium bicarbonate, and extracted with ethyl acetate. The combined organics were dried, concentrated, and purified by reverse phase hplc to provide (R)-1-(2-chloropyridin-3-yl)ethyl (1-ethyl-4-(6-methyl-5-(methylsulfonamido)pyridin-2-yl)-1H-1,2,3-triazol-5-yl)carbamate. LCMS-ESI+ (m/z): 480. 1H NMR (400 MHz, Methanol-d4) δ 8.45-7.83 (m, 2H), 7.89-7.68 (m, 2H), 7.65-7.08 (m, 1H), 6.21-6.01 (m, 1H), 4.44-4.31 (m, 2H), 3.06 (s, 3H), 2.52 (s, 3H), 1.78-1.42 (m, 6H).

Example 46: (R)-1-(2-chloropyridin-3-yl)ethyl (4-(4-fluoro-5-(methylsulfonamido)pyridin-2-yl)-1-methyl-1H-1,2,3-triazol-5-yl)carbamate (Compound 158)

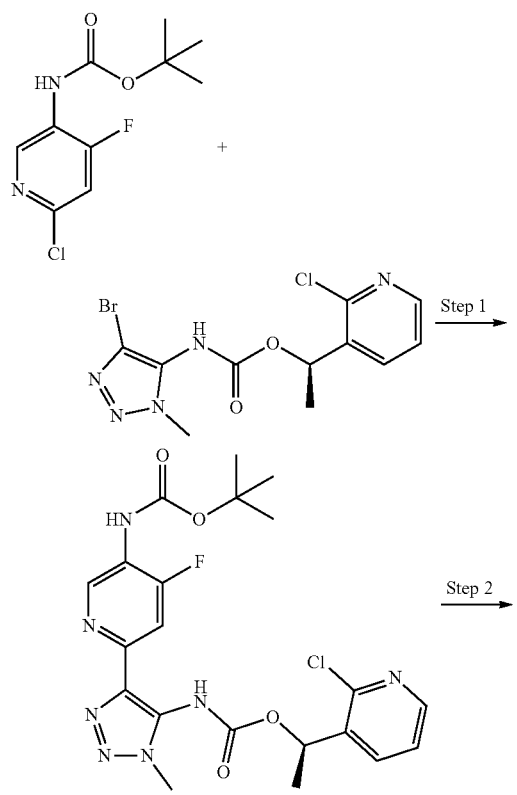

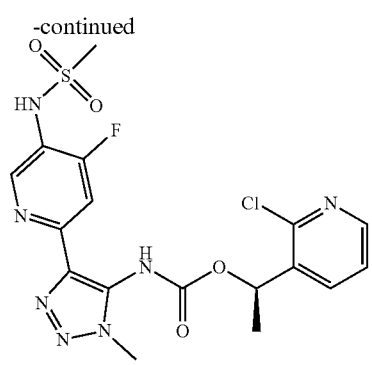

Step 1: tert-butyl (R)-(6-(5-(((1-(2-chloropyridin-3-yl)ethoxy)carbonyl)amino)-1-methyl-1H-1,2,3-triazol-4-yl)-4-fluoropyridin-3-yl)carbamate To a mixture of (R)-1-(2-chloropyridin-3-yl)ethyl (4-bromo-1-methyl-1H-1,2,3-triazol-5-yl)carbamate (1 mmol) in tetrahydrofuran (15 mL) at −78° C. was added a 1M solution of lithium bis(trimethylsilyl)amide (1.2 mmol) in tetrahydrofuran. After 10 minutes, a 2.5 M solution of n-butyllithium (2.5 mmol) in hexanes was added. After 45 minutes, a 1.9 M solution of zinc chloride (2.5 mmol) in 2-methyl tetrahydrofuran was added, and the reaction was warmed to and stirred at room temperature for 30 minutes. The reaction mixture was sparged with argon gas for 5 minutes, and then added tert-butyl (6-chloro-4-fluoropyridin-3-yl)carbamate (1.2 mmol) and [1,1'-bis(diphenylphosphino)ferrocene]dichloropalladium(II) (0.1 mmol). The reaction mixture was heated to 70° C. for 1 h. After completion of the reaction, the mixture was cooled and quenched with 1N aqueous hydrochloric acid (20 mL). The aqueous layer was extracted with ethyl acetate (3×10 mL). The combined organic layers were dried over anhydrous sodium sulfate and concentrated under reduced pressure to provide (R)-1-(2-chloropyridin-3-yl)ethyl (4-(5-((tert-butoxycarbonyl)amino)-4-fluoropyridin-2-yl)-1-methyl-1H-1,2,3-triazol-5-yl)carbamate which was used in the next step without further purification.

Step 2: (R)-1-(2-chloropyridin-3-yl)ethyl (4-(4-fluoro-5-(methylsulfonamido)pyridin-2-yl)-1-methyl-1H-1,2,3-triazol-5-yl)carbamate 4M HCl in 1,4-dioxane (1 mL) was added to (R)-1-(2-chloropyridin-3-yl)ethyl (4-(5-((tert-butoxycarbonyl)amino)-4-fluoropyridin-2-yl)-1-methyl-1H-1,2,3-triazol-5-yl)carbamate (0.49 mmol). The resulting suspension was stirred for 4 h at room temperature. The reaction was concentrated to afford (R)-1-(2-chloropyridin-3-yl)ethyl (4-(5-amino-4-fluoropyridin-2-yl)-1-methyl-1H-1,2,3-triazol-5-yl)carbamate as the hydrochloride salt, which was treated with 6 mL of 1:4 pyridine/dichloromethane. Methanesulfonyl chloride (0.12 mmol) was added, and the reaction stirred for 1 h. The reaction was quenched with sodium bicarbonate, and extracted with ethyl acetate. The combined organics were dried, concentrated, and purified by reverse phase hplc to provide (R)-1-(2-chloropyridin-3-yl)ethyl (4-(4-fluoro-5-(methylsulfonamido)pyridin-2-yl)-1-methyl-1H-1,2,3-triazol-5-yl)carbamate. LCMS-ESI+ (m/z): [M+H]+ 469.92. 1H NMR (400 MHz, Methanol-d4) δ 8.66 (d, J=10.2 Hz, 1H), 8.33 (d, J=4.7 Hz, 1H), 8.06 (s, 1H), 7.82 (d, J=11.2 Hz, 1H), 7.48 (s, 1H), 6.09 (q, J=6.6 Hz, 1H), 3.99 (s, 3H), 3.08 (s, 3H), 1.62 (s, 3H).

Example 47: Preparation of (R)-1-(2-chloropyridin-3-yl)ethyl (4-(5-aminopyridin-2-yl)-1-methyl-1H-1,2,3-triazol-5-yl)carbamate (Intermediate 12)

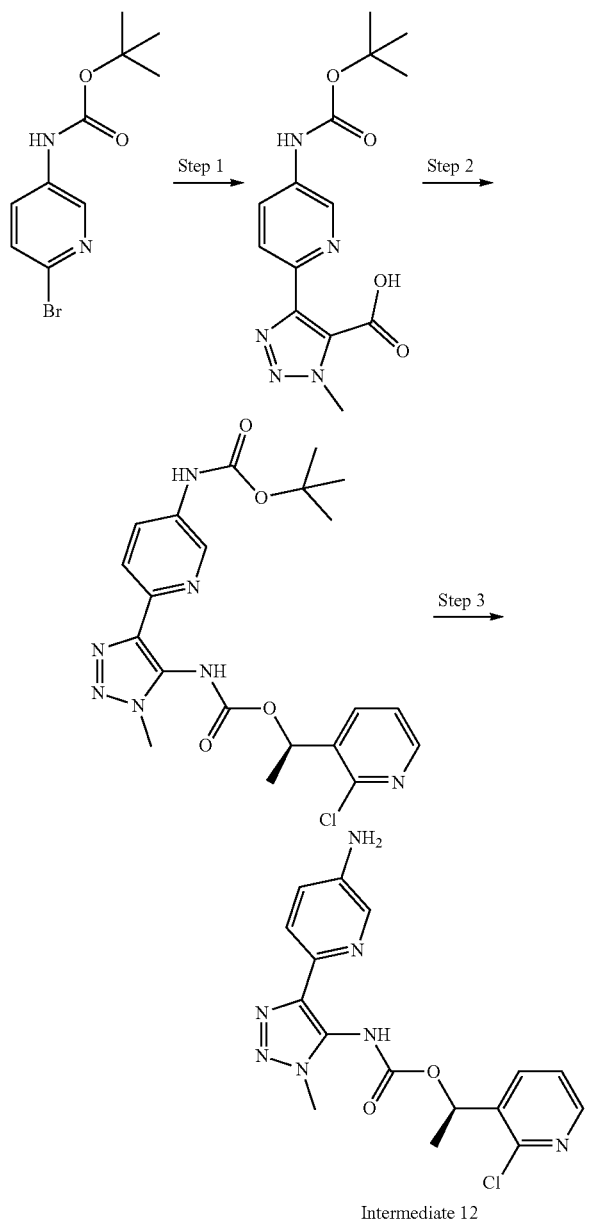

Intermediate 12

Step 1: 4-(5-((tert-butoxycarbonyl)amino)pyridin-2-yl)-1-methyl-1H-1,2,3-triazole-5-carboxylic acid 4-bromo-1-methyl-1H-1,2,3-triazole-5-carboxylic acid (50 mmol) was dissolved in 500 mL of tetrahydrofuran and submerged in a −78° C. bath for 15 minutes. A 1 M solution of lithium bis(trimethylsilyl)amide in tetrahydrofuran (54 mmol) was added dropwise over 15 minutes. A 2.5 M solution of n-butyllithium (105 mmol) in hexanes was added dropwise over 20 minutes and allowed to stir for an additional 1 hour. A 1.9 M solution of zinc chloride (105 mmol) in 2-methyl tetrahydrofuran was added dropwise over 15 minutes. The reaction mixture was warmed to ambient temperature by submerging in a water bath and allowed to stir for 30 minutes. The resulting mixture was sparged with argon gas for 10 min, and then tert-butyl (6-bromopyridin-3-yl)carbamate (50 mmol) and [1,1'-bis(diphenylphosphino)ferrocene]dichloropalladium(II), complex with dichloromethane (5 mmol) were added. The reaction was heated at 75° C. for 3 hours, and then cooled to ambient temperature. The reaction was diluted with 350 mL of a 2 M aqueous solution of sodium hydroxide and 300 mL of diethyl ether. The aqueous layer was separated, and the organic layer was extract with a 1 M aqueous solution of sodium hydroxide (100 mL). The combined aqueous layer was washed with a 1:1 mixture of ethyl acetate and diethyl ether (150 mL×2). 80 mL of concentrated hydrochloric acid was dropwise over 10 min under vigorous stirring to adjust pH to 4. The mixture was filtered, and the filter cake was washed with water (100 mL) and a 1:1 mixture of ethyl acetate and diethyl ether (100 mL×2). The precipitate was dried under reduced pressure to provide 4-(5-((tert-butoxycarbonyl)amino)pyridin-2-yl)-1-methyl-1H-1,2,3-triazole-5-carboxylic acid Step 2: (R)-1-(2-chloropyridin-3-yl)ethyl (4-(5-((tert-butoxycarbonyl)amino)pyridin-2-yl)-1-methyl-1H-1,2,3-triazol-5-yl)carbamate To a mixture of 4-(5-((tert-butoxycarbonyl)amino)pyridin-2-yl)-1-methyl-1H-1,2,3-triazole-5-carboxylic acid (9.4 mmol), 1-propanephosphonic acid cyclic anhydride (50% in THF, 14.1 mmol), and azidotrimethysilane (14.1 mmol) acid in THF (100 mL) was added triethylamine (23.5 mmol) dropwise. The reaction mixture was heated at 70° C. for 1 hour followed by addition of (R)-1-(2-chloropyridin-3-yl)ethan-1-ol (18.8 mmol) at the same temperature. After heating for 24 hours, the reaction was cooled to room temperature, concentrated and purified by silica gel chromatography to provide (R)-1-(2-chloropyridin-3-yl)ethyl (4-(5-((tert-butoxycarbonyl)amino)pyridin-2-yl)-1-methyl-1H-1,2,3-triazol-5-yl)carbamate. (MS (m/z) 474.12 [M+H]+). 1H NMR (400 MHz, Methanol-d4) δ 8.67 (s, 1H), 8.31 (s, 1H), 8.08 (s, 1H), 7.94 (dd, J=8.7, 2.6 Hz, 1H), 7.84 (dd, J=8.6, 0.8 Hz, 1H), 7.47 (s, 1H), 6.07 (d, J=6.7 Hz, 1H), 3.98 (s, 3H), 1.75-1.46 (m, 12H).

Step 3: (R)-1-(2-chloropyridin-3-yl)ethyl (4-(5-aminopyridin-2-yl)-1-methyl-11H-1,2,3-triazol-5-yl) carbamate (Intermediate 12)

4 M HCl in 1,4-dioxane (20 mL) was added to (R)-1-(2-chloropyridin-3-yl)ethyl (4-(5-((tert-butoxycarbonyl)amino)pyridin-2-yl)-1-methyl-1H-1,2,3-triazol-5-yl)carbamate (6.9 mmol). The resulting suspension was stirred for 18 hour at room temperature. The reaction was concentrated to afford (R)-1-(2-chloropyridin-3-yl)ethyl (4-(5-aminopyridin-2-yl)-1-methyl-1H-1,2,3-triazol-5-yl)carbamate (Intermediate 12) as the hydrochloride salt.

Example 48: Preparation of (R)-1-(2-chloropyridin-3-yl)ethyl (4-(5-((N-cyclopropylsulfamoyl) amino)pyridin-2-yl)-1-methyl-1H-1,2,3-triazol-5-yl)carbamate (Compound 159)

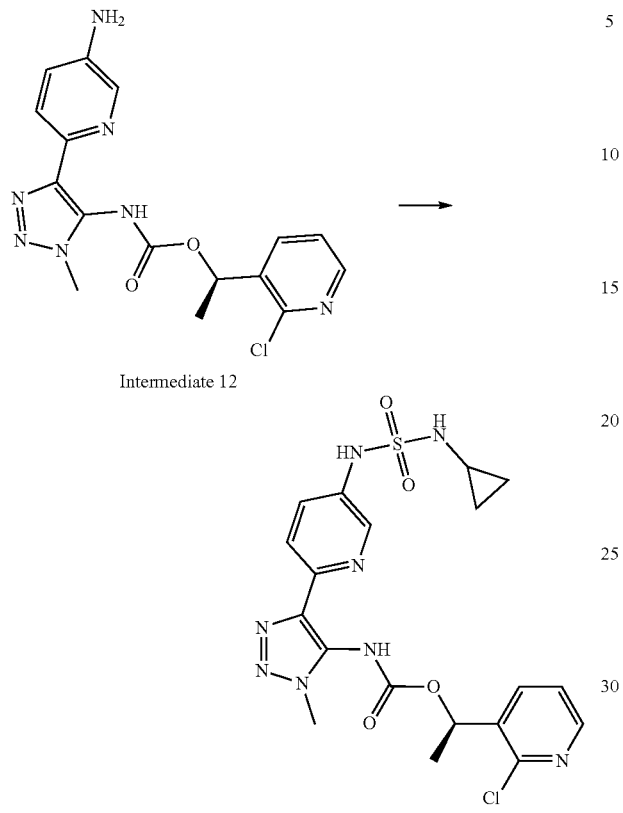

Intermediate 12

To a solution of (R)-1-(2-chloropyridin-3-yl)ethyl (4-(5-aminopyridin-2-yl)-1-methyl-1H-1,2,3-triazol-5-yl)carbamate (Intermediate 12) as the hydrochloride salt (0.032 mmol) in pyridine (1.0 mL) was added N-cyclopropylsulfamoyl chloride (4.9 mg, 0.032 mmol). The solution was stirred at room temperature for 18 hours, concentrated and purified by reverse-phase chromatography to afford (R)-1-(2-chloropyridin-3-yl)ethyl (4-(5-((N-cyclopropylsulfamoyl)amino)pyridin-2-yl)-1-methyl-1H-1,2,3-triazol-5-yl)carbamate. LCMS-ESI+ (m/z): [M+H]+ 493.2. $^1$H NMR (400 MHz, DMSO-d$_6$) δ 10.22 (s, 1H), 9.80 (bs, 1H), 8.37 (d, J=2.7 Hz, 2H), 8.05 (s, 1H), 7.90 (d, J=8.6 Hz, 1H), 7.70-7.30 (m, 3H), 5.86 (bs, 1H), 3.87 (s, 3H), 2.32-2.21 (m, 1H), 1.56 (bs, 3H), 0.62-0.46 (m, 2H), 0.44-0.29 (m, 2H).

Example 49: Preparation of (R)-1-(2-chloropyridin-3-yl)ethyl (4-(5-((N-isopropylsulfamoyl) amino)pyridin-2-yl)-1-methyl-1H-1,2,3-triazol-5-yl)carbamate (Compound 160)

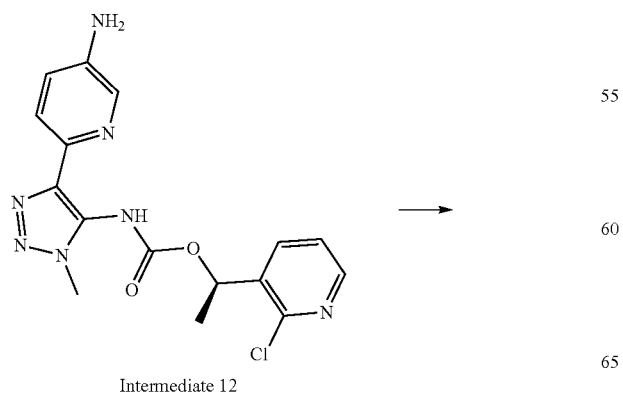

Intermediate 12

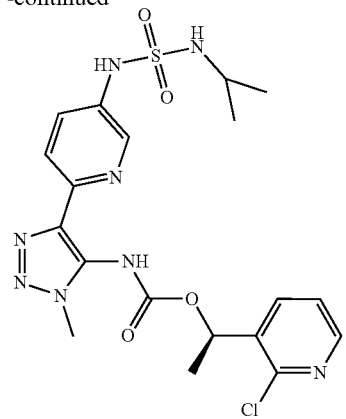

To a solution of (R)-1-(2-chloropyridin-3-yl)ethyl (4-(5-aminopyridin-2-yl)-1-methyl-1H-1,2,3-triazol-5-yl)carbamate (Intermediate 12) as the hydrochloride salt (16 mg, 0.039 mmol) in pyridine (1.0 mL) was added N-isopropylsulfamoyl chloride (6.2 mg, 0.039 mmol). The solution was stirred at room temperature for 18 hours, concentrated and purified by reverse-phase chromatography to afford (R)-1-(2-chloropyridin-3-yl)ethyl (4-(5-((N-isopropylsulfamoyl)amino)pyridin-2-yl)-1-methyl-1H-1,2,3-triazol-5-yl)carbamate. LCMS-ESI+ (m/z): [M+H]+ 495.3. $^1$H NMR (400 MHz, DMSO-d$_6$) δ 10.03 (s, 1H), 9.78 (bs, 1H), 8.36 (d, J=2.7 Hz, 2H), 8.00 (bs, 1H), 7.89 (d, J=8.6 Hz, 1H), 7.71-7.14 (m, 3H), 5.86 (bs, 1H), 3.87 (s, 3H), 3.44-3.29 (m, 1H), 1.56 (bs, 3H), 1.01 (dd, J=8.7, 6.5 Hz, 6H).

Example 50: Preparation of (R)-1-(2-chloropyridin-3-yl)ethyl (4-(5-(azetidine-3-sulfonamido) pyridin-2-yl)-1-methyl-1H-1,2,3-triazol-5-yl)carbamate (Compound 161)

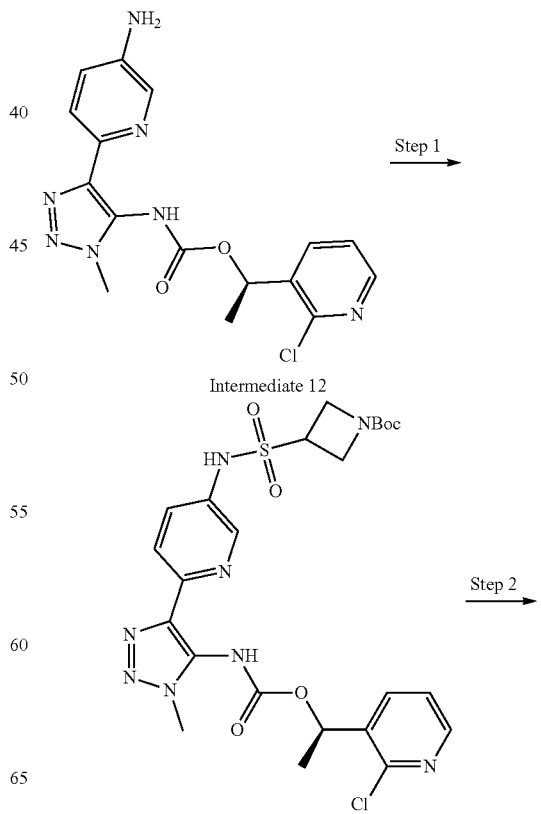

-continued

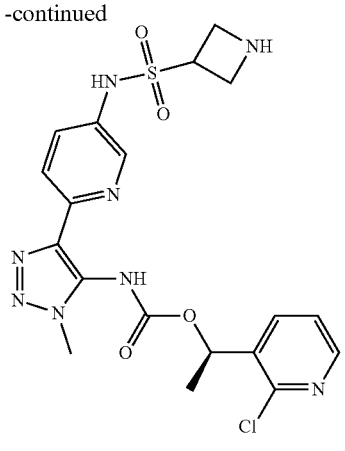

Step 1: tert-butyl (R)-3-(N-(6-(5-(((1-(2-chloropyridin-3-yl)ethoxy)carbonyl)amino)-1-methyl-1H-1,2,3-triazol-4-yl)pyridin-3-yl)sulfamoyl)azetidine-1-carboxylate To a solution of (R)-1-(2-chloropyridin-3-yl)ethyl (4-(5-aminopyridin-2-yl)-1-methyl-1H-1,2,3-triazol-5-yl)carbamate (Intermediate 12) as the hydrochloride salt (0.078 mmol) in pyridine (2.0 mL) was added tert-butyl 3-chlorosulfonylazetidine-1-carboxylate (0.12 mmol). The reaction was incomplete after stirring the solution at room temperature for 6 hours. An additional 30 mg (0.12 mmol) of tert-butyl 3-chlorosulfonylazetidine-1-carboxylate was added. The solution was stirred at room temperature for 48 hours, concentrated and purified by reverse-phase chromatography to afford tert-butyl (R)-3-(N-(6-(5-(((1-(2-chloropyridin-3-yl)ethoxy)carbonyl)amino)-1-methyl-1H-1,2,3-triazol-4-yl)pyridin-3-yl)sulfamoyl)azetidine-1-carboxylate. LCMS-ESI+ (m/z): [M+H]+ calcd 593.17; found 593.02.

Step 2: (R)-1-(2-chloropyridin-3-yl)ethyl (4-(5-(azetidine-3-sulfonamido)pyridin-2-yl)-1-methyl-1H-1,2,3-triazol-5-yl)carbamate A solution of tert-butyl (R)-3-(N-(6-(5-(((1-(2-chloropyridin-3-yl)ethoxy)carbonyl)amino)-1-methyl-1H-1,2,3-triazol-4-yl)pyridin-3-yl)sulfamoyl)azetidine-1-carboxylate (0.025 mmol) in DCM (1.0 mL) and TFA (0.30 mL) was stirred at room temperature for 2 hours. The reaction was concentrated and the crude mixture was purified by reverse-phase chromatography to afford (R)-1-(2-chloropyridin-3-yl)ethyl (4-(5-(azetidine-3-sulfonamido)pyridin-2-yl)-1-methyl-1H-1,2,3-triazol-5-yl)carbamate as the trifluoroacetic acid salt. LCMS-ESI+ (m/z): [M+H]+ 493.1. $^1$H NMR (400 MHz, DMSO-d$_6$, as TFA salt) δ 10.61 (s, 1H), 9.85 (bs, 1H), 9.40-9.20 (bs, 1H), 9.20-9.00 (bs, 1H), 8.49-8.27 (m, 2H), 8.17-7.86 (m, 2H), 7.73-7.35 (m, 2H), 5.88 (bs, 1H), 4.58-4.41 (m, 1H), 4.32 (bs, 2H), 4.14 (bs, 2H), 3.88 (s, 3H), 1.56 (bs, 3H).

Example 51: Preparation of (R)-1-(2-chloro-5-fluoropyridin-3-yl)ethyl (4-(5-aminopyridin-2-yl)-1-methyl-1H-1,2,3-triazol-5-yl)carbamate (Intermediate 13)

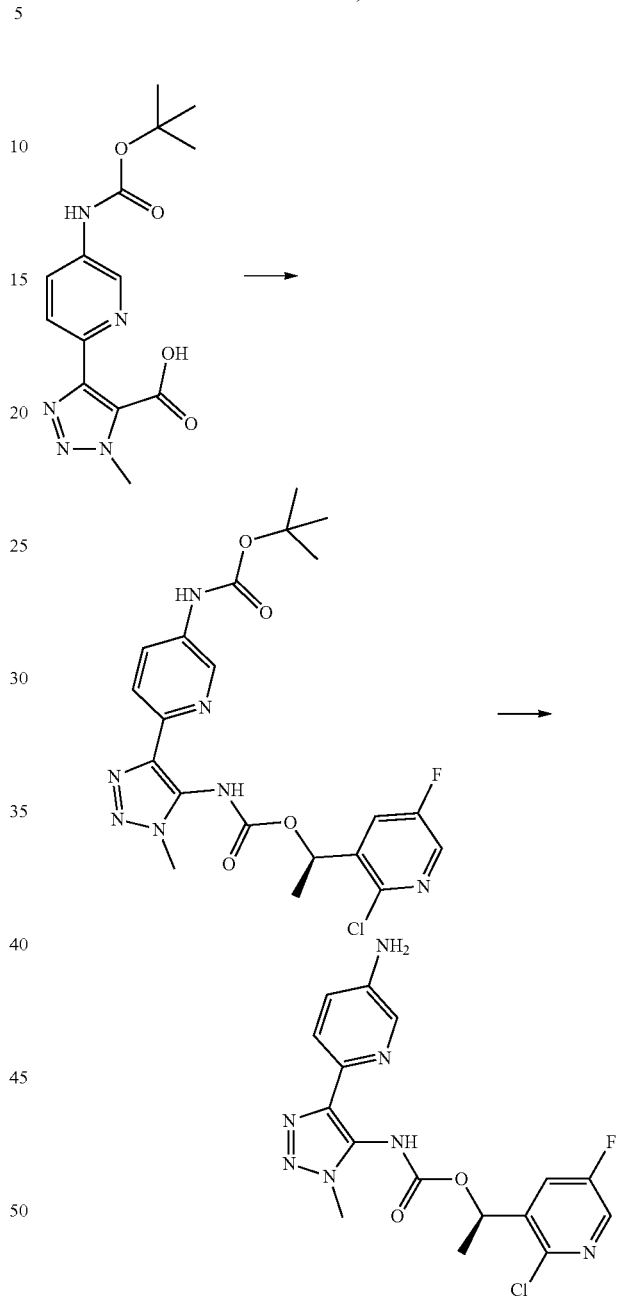

Intermediate 13

Following the procedure described in Example 47 for the preparation of (R)-1-(2,5-difluoropyridin-3-yl)ethyl (4-(5-aminopyridin-2-yl)-1-methyl-1H-1,2,3-triazol-5-yl)carbamate (Intermediate 12), using (R)-1-(2-chloro-5-fluoropyridin-3-yl)ethan-1-ol (1.7 mmol), in place of (R)-1-(2,5-difluoropyridin-3-yl)ethan-1-ol, (R)-1-(2-chloro-5-fluoropyridin-3-yl)ethyl (4-(5-aminopyridin-2-yl)-1-methyl-1H-1,2,3-triazol-5-yl)carbamate (Intermediate 13) was obtained.

Example 52: Preparation of Example 51x: Preparation of (R)-1-(2-chloro-5-fluoropyridin-3-yl)ethyl (4-(5-aminopyridin-2-yl)-1-methyl-1H-1,2,3-triazol-5-yl)carbamate (Compound 162)

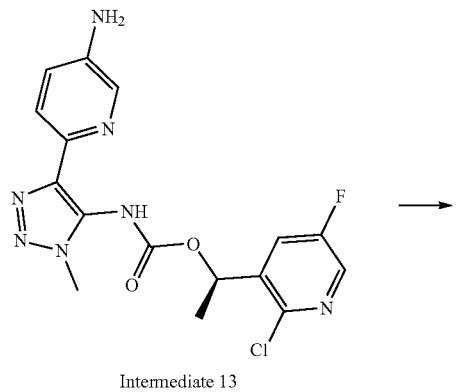

Intermediate 13

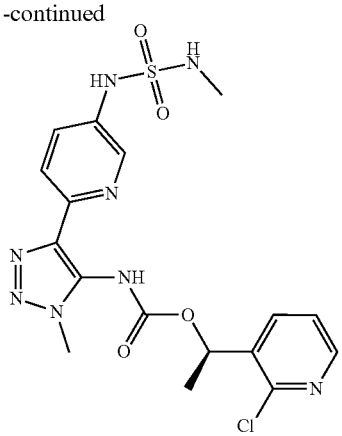

To a solution of (R)-1-(2-chloro-5-fluoropyridin-3-yl)ethyl (4-(5-aminopyridin-2-yl)-1-methyl-1H-1,2,3-triazol-5-yl)carbamate (Intermediate 13) as the hydrochloride salt (30 mg, 0.065 mmol) in pyridine (3.0 mL) was added N-methylsulfamoyl chloride (17 mg, 0.13 mmol). The solution was stirred at room temperature for 18 hours, concentrated and purified by reverse-phase chromatography to afford (R)-1-(2-chloro-5-fluoropyridin-3-yl)ethyl (1-methyl-4-(5-((N-methylsulfamoyl)amino)pyridin-2-yl)-1H-1,2,3-triazol-5-yl)carbamate. LCMS-ESI+ (m/z): [M+H]+ 485.2. $^1$H NMR (400 MHz, DMSO-d$_6$) δ 10.17-9.41 (bs, 2H), 8.53-8.37 (bs, 1H), 8.33 (s, 1H), 8.07-7.83 (m, 2H), 7.62 (dd, J=8.6, 2.7 Hz, 1H), 7.53-7.40 (m, 1H), 5.83 (bs, 1H), 3.88 (s, 3H), 2.48 (s, 3H), 1.57 (bs, 3H).

Example 53: Preparation of (R)-1-(2-chloropyridin-3-yl)ethyl (1-methyl-4-(6-methyl-5-((N-methylsulfamoyl)amino)pyridin-2-yl)-1H-1,2,3-triazol-5-yl)carbamate (Compound 163)

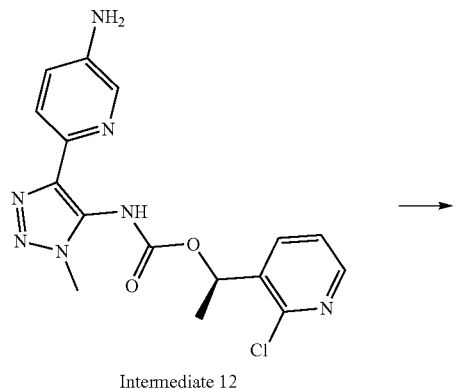

Intermediate 12

To a solution of (R)-1-(2-chloropyridin-3-yl)ethyl (4-(5-aminopyridin-2-yl)-1-methyl-1H-1,2,3-triazol-5-yl)carbamate (Intermediate xx) as the hydrochloride salt (11 mg, 0.027 mmol) in pyridine (1.0 mL) was added methylsulfamoyl chloride (3.5 mg, 0.027 mmol). The solution was stirred at room temperature for 20 minutes, concentrated and purified by reverse-phase chromatography to afford (R)-1-(2-chloropyridin-3-yl)ethyl (1-methyl-4-(5-((N-methylsulfamoyl)amino)pyridin-2-yl)-1H-1,2,3-triazol-5-yl)carbamate. LCMS-ESI+ (m/z): [M+H]+ 481.2. $^1$H NMR (400 MHz, DMSO-d$_6$) δ 9.82 (bs, 1H), 9.10 (bs, 1H), 8.36 (bs, 1H), 8.02 (bs, 1H), 7.77 (d, J=8.4 Hz, 1H), 7.70 (d, J=8.4 Hz, 1H), 7.50 (s, 1H), 7.21 (s, 1H), 5.91 (bs, 1H), 3.88 (s, 3H), 2.54 (d, J=4.9 Hz, 3H), 2.41 (s, 3H), 1.57 (bs, 3H).

Example 54: Preparation of (R)-1-(2-chloropyridin-3-yl)ethyl (1-methyl-4-(6-methyl-5-(N-(methyl-d3) methylsulfonamido)pyridin-2-yl)-1H-1,2,3-triazol-5-yl)carbamate (Compound 164)

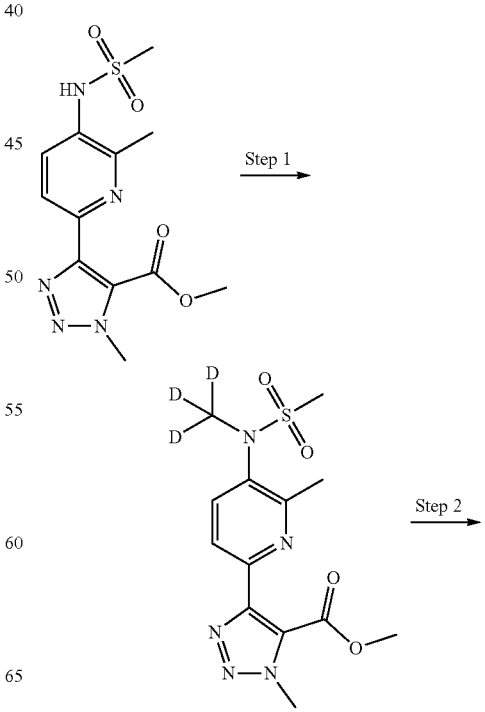

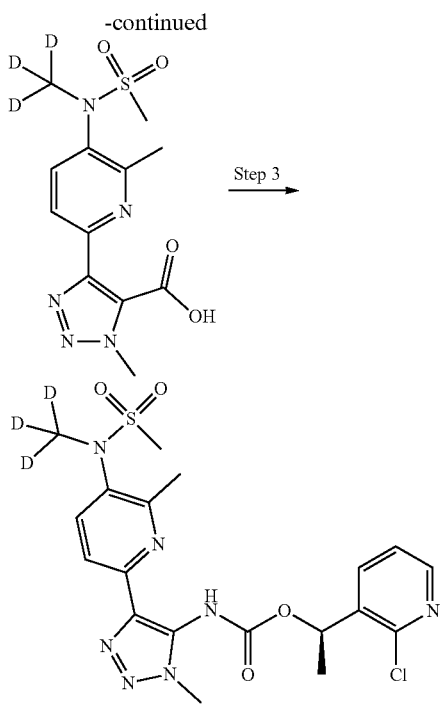

Step 1: Methyl 1-methyl-4-(6-methyl-5-(N-(methyl-d)methylsulfonamido)pyridin-2-yl)-1H-1,2,3-triazole-5-carboxylate A 50 mL round bottom flask was charged with methyl 1-methyl-4-(6-methyl-5-(methylsulfonamido)pyridin-2-yl)-1H-1,2,3-triazole-5-carboxylate (200 mg, 0.615 mmol) (Example 12, Step 2), cesium carbonate (220 mg, 0.676 mmol) and acetonitrile (5.0 mL). Iodomethane-d3 (40 μL, 0.65 mmol) was added and the reaction was stirred at room temperature for 5 hours. The reaction was diluted with water, extracted with EtOAc (3×), dried over MgSO₄, filtered and concentrated. The crude product was used without further purification. LCMS-ESI+ (m/z): [M+H]+ calcd 343.13; found 343.15.

Step 2: 1-Methyl-4-(6-methyl-5-(N-(methyl-d₃) methylsulfonamido)pyridin-2-yl)-1H-1,2,3-triazole-5-carboxylicacid To a solution of methyl 1-methyl-4-(6-methyl-5-(N-(methyl-d3)methylsulfonamido)pyridin-2-yl)-1H-1,2,3-triazole-5-carboxylate (210 mg, 0.613 mmol) in THF/MeOH/water (1:1:1, 9.0 mL) was added lithium hydroxide monohydrate (129 mg, 3.07 mmol). The mixture was stirred at room temperature for 18 hours. The solution was adjusted to pH 3 with 1N HCl(aq) and stirred gently until precipitation of solid ceased. The mixture was filtered, washed with water and dried over a frit under nitrogen to afford methyl 1-methyl-4-(6-methyl-5-(N-(methyl-d3)methylsulfonamido)pyridin-2-yl)-1H-1,2,3-triazole-5-carboxylate. The solid was used without further purification. LCMS-ESI+ (m/z): [M+H]+ calcd 329.11; found 329.09.

Step 3: (R)-1-(2-chloropyridin-3-yl)ethyl (1-methyl-4-(6-methyl-5-(N-(methyl-d₃) methylsulfonamido) pyridin-2-yl)-1H-1,2,3-triazol-5-yl)carbamate To a mixture of 1-methyl-4-(6-methyl-5-(N-(methyl-d3) methylsulfonamido)pyridin-2-yl)-1H-1,2,3-triazole-5-carboxylic acid (65.0 mg, 0.198 mmol), 1-propanephosphonic acid cyclic anhydride (50% in DMF, 378 μL, 0.594 mmol) and azidotrimethysilane (53 μL, 0.40 mmol) in THF (3.0 mL) was added triethylamine (83 μL, 0.60 mmol) dropwise. The reaction mixture was heated at 70° C. for 45 minutes followed by addition of (R)-1-(2-chloropyridin-3-yl)ethan-1-ol (31 L, 0.24 mmol). The solution was heated for an additional 60 minutes at 70° C. The reaction mixture was concentrated and purified by reverse-phase chromatography to afford (R)-1-(2-chloropyridin-3-yl)ethyl (1-methyl-4-(6-methyl-5-(N-(methyl-d3)methylsulfonamido)pyridin-2-yl)-1H-1,2,3-triazol-5-yl)carbamate. LCMS-ESI+ (m/z): [M+H]+ 483.2. $^1$H NMR (400 MHz, DMSO-$d_6$) δ 9.85 (bs, 1H), 8.34 (bs, 1H), 8.15-7.65 (m, 3H), 7.65-7.17 (m, 1H), 5.92 (bs, 1H), 3.90 (s, 3H), 3.09 (s, 3H), 2.43 (s, 3H), 1.75-1.38 (m, 3H).

Example 55: Calcium Assay

In vitro LPAR1 activity was measured in an intracellular calcium mobilization assay.

CHO-K1 EDG2 cells (DiscoverX cat #93-0644C₂) expressing human LPAR1 (NM_001401.3) were seeded in a total volume of 20 μL of AssayComplete™ Cell Culture media (DiscoverX cat #92-3108G) into Poly-D-lysine coated 384-well microplates (Corning cat #356697) at 11,500 cells/well and incubated at 37° C. overnight. Prior to testing cell media were aspirated from the cells and replaced with 20 μL Calcium Dye Loading Buffer (DiscoverX Calcium NoWash$^{PLUS}$ Assay Kit cat #90-0091) and 2.5 mM Probenecid (Sigma Aldrich cat #P8761, prepared fresh) in HBSS/20 mM Hepes for 60 min at 37° C.

Agonist dose curves of LPA 18:1 (Cayman Chemical cat #10010093, 0.05 nM to 1 μM) were recorded to determine the LPA 18:1 EC₈₀ for subsequent antagonist assays. For agonist dose curves, cells were removed from the incubator after dye loading and 10 μL HBSS/20 mM Hepes including 3× vehicle was added. Cells were incubated for 30 min at room temperature in the dark to equilibrate plate temperatures. An intermediate LPA dilution series was prepared in assay buffer to generate 4× stock. Calcium mobilization was monitored on a FLIPR Tetra (MDS, San Jose, Calif.) for 2 min and 10 μL 4×LPA in HBSS/20 mM Hepes was added to the cells 5 s into the assay.

To determine the LPAR1 antagonist activity of test compounds, cells were pre-incubated with test compound at a dose range of 0.5 nM to 10 μM, followed by an LPA 18:1 challenge at the EC₈₀ concentration (typically 18 nM). An intermediate antagonist dilution series was prepared as 3× samples in assay buffer. After dye loading, cells were removed from the incubator and 10 μL 3× antagonist was added. Cells were incubated for 30 min at room temperature in the dark to equilibrate plate temperatures. The final vehicle (DMSO) concentration was 1%. Compound antagonist activities was measured on a FLIPR Tetra. Calcium mobilization was monitored for 2 min and 10 μL EC₈₀ agonist in HBSS/20 mM Hepes was added to the cells 5 s into the assay. Compound activity was analyzed using CBIS data analysis suite (ChemInnovation Software, San Diego, Calif.).

To assess the antagonistic potential of exemplified compounds EC₅₀ values were determined for Compounds 1 to 110 in the LPAR1 calcium mobilization assay. Results are shown in Table 8 (LPAR1 EC₅₀). The compound numbers correspond to the compound numbers in Tables 1 to 7.

TABLE 8

| Compound | LPAR1 (EC$_{50}$) |
|---|---|
| Compound 1 | 323.2 |
| Compound 2 | 269.5 |
| Compound 3 | 165.8 |
| Compound 4 | 61.7 |
| Compound 5 | 34.3 |
| Compound 6 | 71.3 |
| Compound 7 | 112.2 |
| Compound 8 | 84.9 |
| Compound 9 | 31.9 |
| Compound 10 | 37.4 |
| Compound 11 | 23.8 |
| Compound 12 | 221.0 |
| Compound 13 | 71.4 |
| Compound 14 | 66.3 |
| Compound 15 | 8.2 |
| Compound 16 | 5.3 |
| Compound 17 | 5.0 |
| Compound 18 | 46.1 |
| Compound 19 | 284.4 |
| Compound 20 | 116.6 |
| Compound 21 | 37.8 |
| Compound 22 | 8.7 |
| Compound 23 | 36.0 |
| Compound 24 | 276.5 |
| Compound 25 | 18.7 |
| Compound 26 | 34.1 |
| Compound 27 | 57.7 |
| Compound 28 | 171.2 |
| Compound 29 | 325.2 |
| Compound 30 | 666.9 |
| Compound 31 | 1220.7 |
| Compound 32 | 1694.9 |
| Compound 33 | 3675.2 |
| Compound 34 | 469.0 |
| Compound 35 | 327.4 |
| Compound 36 | 219.6 |
| Compound 37 | 172.1 |
| Compound 38 | 167.3 |
| Compound 39 | 89.5 |
| Compound 40 | 87.0 |
| Compound 41 | 65.0 |
| Compound 42 | 46.1 |
| Compound 43 | 18.4 |
| Compound 44 | 50.0 |
| Compound 45 | 55.8 |
| Compound 46 | 91.3 |
| Compound 47 | 132.3 |
| Compound 48 | 161.6 |
| Compound 49 | 202.7 |
| Compound 50 | 729.6 |
| Compound 51 | 1251.9 |
| Compound 52 | 16.7 |
| Compound 53 | 170.2 |
| Compound 54 | 90.6 |
| Compound 55 | 64.9 |
| Compound 56 | 59.9 |
| Compound 57 | 48.5 |
| Compound 58 | 43.9 |
| Compound 59 | 37.7 |
| Compound 60 | 31.3 |
| Compound 61 | 30.0 |
| Compound 62 | 29.0 |
| Compound 63 | 23.4 |
| Compound 64 | 2744.7 |
| Compound 65 | 1018.9 |
| Compound 66 | 539.6 |
| Compound 67 | 1628.0 |
| Compound 68 | 217.8 |
| Compound 69 | 295.1 |
| Compound 70 | 1587.2 |
| Compound 71 | 1739.0 |
| Compound 72 | 115.3 |
| Compound 73 | 3215.7 |
| Compound 74 | 110.0 |
| Compound 75 | 154.9 |
| Compound 76 | 929.1 |
| Compound 77 | 79.2 |
| Compound 78 | 378.1 |
| Compound 79 | 589.2 |
| Compound 80 | 2841.7 |
| Compound 81 | 876.3 |
| Compound 82 | 2303.5 |
| Compound 83 | 622.6 |
| Compound 84 | 192.6 |
| Compound 85 | 2466.4 |
| Compound 86 | 55.4 |
| Compound 87 | 312.4 |
| Compound 88 | 255.5 |
| Compound 89 | 31.4 |
| Compound 90 | 282.2 |
| Compound 91 | 72.6 |
| Compound 92 | 49.7 |
| Compound 93 | 41.3 |
| Compound 94 | 38.6 |
| Compound 95 | 28.4 |
| Compound 96 | 18.1 |
| Compound 97 | 387.1 |
| Compound 98 | 69.9 |
| Compound 99 | 44.6 |
| Compound 100 | 114.0 |
| Compound 101 | 261.5 |
| Compound 102 | 88.4 |
| Compound 103 | 56.3 |
| Compound 104 | 434.5 |
| Compound 105 | 277.9 |
| Compound 106 | 313.0 |
| Compound 107 | 1124.0 |
| Compound 108 | 10000.0 |
| Compound 109 | 705.5 |
| Compound 110 | 12.3 |
| Compound 111 | 42.1 |
| Compound 112 | 105.8 |
| Compound 113 | 83.0 |
| Compound 114 | 48.8 |
| Compound 115 | 83.9 |
| Compound 116 | 128.6 |
| Compound 117 | 218.5 |
| Compound 118 | 57.8 |
| Compound 119 | 50.2 |
| Compound 120 | 87.0 |
| Compound 121 | 461.4 |
| Compound 122 | 919.7 |
| Compound 123 | 86.1 |
| Compound 124 | 1077.6 |
| Compound 125 | 186.5 |
| Compound 126 | 232.0 |
| Compound 127 | 1415.2 |
| Compound 128 | 265.1 |
| Compound 129 | 271.2 |
| Compound 130 | 271.6 |
| Compound 131 | 675.3 |
| Compound 132 | 1134.3 |
| Compound 133 | 1701.9 |
| Compound 134 | 1834.3 |
| Compound 135 | 2980.2 |
| Compound 136 | 3765.7 |
| Compound 137 | 493.4 |
| Compound 138 | 23.0 |
| Compound 139 | 163.4 |
| Compound 140 | 305.2 |
| Compound 141 | 723.0 |
| Compound 142 | 141.6 |
| Compound 143 | 330.0 |
| Compound 144 | 235.4 |
| Compound 145 | 492.6 |
| Compound 146 | 579.7 |
| Compound 147 | 126.7 |
| Compound 148 | 190.1 |
| Compound 149 | 303.6 |
| Compound 150 | 1047.8 |
| Compound 151 | 587.8 |
| Compound 152 | 1303.5 |
| Compound 153 | 206.8 |
| Compound 154 | 277.8 |

TABLE 8-continued

| Compound | LPAR1 (EC$_{50}$) |
|---|---|
| Compound 155 | 84.7 |
| Compound 156 | 162.5 |
| Compound 157 | 373.6 |
| Compound 158 | 78.1 |
| Compound 159 | 240.4 |
| Compound 160 | 267.4 |
| Compound 161 | 5253.2 |
| Compound 162 | 81.7 |
| Compound 163 | 208.1 |
| Compound 164 | 437.8 |

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A compound of Formula (II),

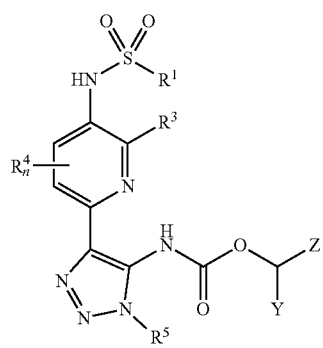

(II)

or a pharmaceutically acceptable salt thereof, wherein:
  $R^1$ is $C_{1-6}$ alkyl optionally substituted with 1 to 3 substituents independently selected from halogen, cyano, and $C_{1-3}$ alkoxy;
  $R^3$ is hydrogen, halogen, $C_{1-6}$ alkyl, $C_{3-6}$ cycloalkyl, —O—$R^{3A}$, or —N($R^{3A}$)$_2$, wherein the $C_{1-6}$ alkyl is optionally substituted with 1 to 3 substituents independently selected from $C_{1-3}$ alkoxy and halogen, and wherein each $R^{3A}$ is independently $C_{1-3}$ alkyl optionally substituted with 1 to 3 halogens;
  each $R^4$ is independently deuterium, halogen, $C_{1-6}$ alkyl, $C_{3-10}$ cycloalkyl, or $C_{1-3}$ alkoxy, wherein the $C_{1-6}$ alkyl or $C_{3-10}$ cycloalkyl, is optionally substituted with 1 to 3 halogens:
  n is 0, 1 or 2;
  $R^5$ is $C_{1-6}$ alkyl optionally substituted with 1 to 3 substituents independently selected from halogen, cyano, $C_{1-3}$ alkoxy, —C(O)N($R^{1A}$), and —N($R^{1A}$)$_2$ wherein each $R^{1A}$ is independently H, $C_{1-6}$ alkyl, or $C_{3-10}$ cycloalkyl; or
  $R^5$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents independently selected from halogen, cyano, $C_{1-3}$ alkyl and $C_{1-3}$ alkoxy;
  Y is hydrogen or $C_{1-6}$ alkyl optionally substituted with 1 to 3 substituents independently selected from halogen, cyano, $C_{1-3}$ alkynyl, $C_{1-3}$ alkoxy, and —C(O)NH—$R^y$, wherein $R^y$ is $C_{1-3}$ alkyl; and
  Z is $C_{6-10}$ aryl optionally substituted with 1 to 3 substituents independently selected from halogen, $C_{1-3}$ alkyl, or $C_{1-3}$ alkoxy, wherein the $C_{1-3}$ alkyl is optionally substituted with 1 to 3 substituents independently selected from halogen and $C_{1-3}$ alkoxy.

2. The compound or pharmaceutically acceptable salt thereof of claim 1, wherein the compound is of Formula (IIa):

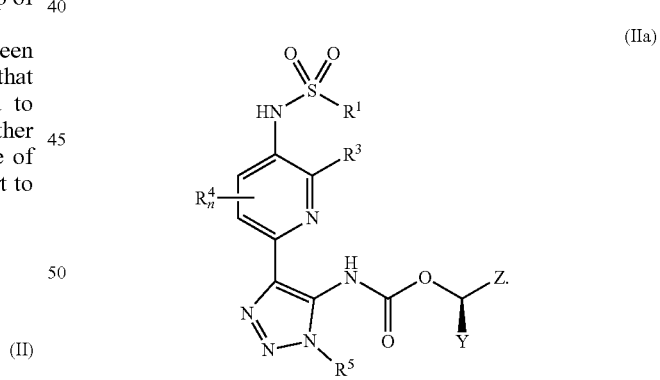

(IIa)

3. The compound or pharmaceutically acceptable salt thereof of claim 1, wherein $R^1$ is $C_{1-3}$ alkyl optionally substituted with 1 to 3 substituents independently selected from F and cyano.

4. The compound or pharmaceutically acceptable salt thereof of claim 1, wherein $R^1$ is $C_{1-3}$ alkyl optionally substituted with cyano.

5. The compound or pharmaceutically acceptable salt thereof of claim 1, wherein $R^1$ is methyl, ethyl, isopropyl, or cyanomethyl.

6. The compound or pharmaceutically acceptable salt thereof of claim 1, wherein $R^3$ is hydrogen.

7. The compound or pharmaceutically acceptable salt thereof of claim 1, wherein $R^3$ is halogen, $C_{1-6}$ alkyl, $C_{3-6}$ cycloalkyl, —O—$R^{3A}$, or —N($R^{3A}$)$_2$, wherein the $C_{1-6}$ alkyl is optionally substituted with 1 to 3 substituents independently selected from halogen and $C_{1-3}$ alkoxy, and wherein each $R^{3A}$ is independently —H or $C_{1-3}$ alkyl optionally substituted with 1 to 3 halogens.

8. The compound or pharmaceutically acceptable salt thereof of claim 1, wherein $R^3$ is halogen, $C_{1-6}$ alkyl, —O—$R^{3A}$, or —N($R^{3A}$)$_2$, wherein the $C_{1-6}$ alkyl is optionally substituted with 1 to 3 substituents independently selected from halogen and $C_{1-3}$ alkoxy, and wherein each $R^{3A}$ is independently H or $C_{1-3}$ alkyl optionally substituted with 1 to 3 halogens.

9. The compound or pharmaceutically acceptable salt thereof of claim 1, wherein $R^3$ is halogen, $C_{1-6}$ alkyl, $C_{3-6}$ cycloalkyl —O—$R^{3A}$, —N($R^{3A}$)$_2$, wherein the $C_{1-6}$ alkyl is optionally substituted with 1 to 3 substituents independently selected from halogen and $C_{1-3}$ alkoxy, wherein each $R^{3A}$ is $C_{1-3}$ alkyl optionally substituted with 1 to 3 halogens.

10. The compound or pharmaceutically acceptable salt thereof of claim 1, wherein $R^3$ is halogen, $C_{1-6}$ alkyl, or —O—$R^{3A}$, wherein the $C_{1-6}$ alkyl is optionally substituted with 1 to 3 substituents independently selected from halogen and $C_{1-3}$ alkoxy, wherein $R^{3A}$ is $C_{1-3}$ alkyl optionally substituted with 1 to 3 halogens.

11. The compound or pharmaceutically acceptable salt thereof of claim 1, wherein $R^3$ is —F, —Cl, —CH$_3$, —C$_2$H$_5$, —CHF$_2$, —CH$_2$—OCH$_3$, —O—CH$_3$, —NH—CH$_3$, or

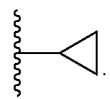 [SMILES: *C1CC1]

12. The compound or pharmaceutically acceptable salt thereof of claim 1, wherein $R^3$ is —F, —Cl, —CH$_3$, or —O—CH$_3$.

13. The compound or pharmaceutically acceptable salt thereof of claim 1, wherein n is 0 or 1.

14. The compound or pharmaceutically acceptable salt thereof of claim 1, wherein n is 0.

15. The compound or pharmaceutically acceptable salt thereof of claim 1, wherein $R^4$ is halogen or $C_{1-3}$ alkyl optionally substituted with 1 to 3 halogens.

16. The compound or pharmaceutically acceptable salt thereof of claim 1, wherein $R^4$ is halogen.

17. The compound or pharmaceutically acceptable salt thereof of claim 1, wherein $R^4$ is —F.

18. The compound or pharmaceutically acceptable salt thereof of claim 1, wherein $R^5$ is $C_{1-3}$ alkyl optionally substituted with 1 to 3 substituents independently selected from cyano and —F.

19. The compound or pharmaceutically acceptable salt thereof of claim 1, wherein $R^5$ is methyl, ethyl or propyl, each optionally substituted with cyano.

20. The compound or pharmaceutically acceptable salt thereof of claim 1, wherein $R^5$ is —CH$_3$.

21. The compound or pharmaceutically acceptable salt thereof of claim 1, wherein Y is hydrogen.

22. The compound or pharmaceutically acceptable salt thereof of claim 1, wherein Y is $C_{1-3}$ alkyl optionally substituted with 1 to 3 substituents independently selected from halogen, cyano, and $C_{1-3}$ alkoxy.

23. The compound or pharmaceutically acceptable salt thereof of claim 1, wherein Y is methyl optionally substituted with 1 to 3 substituents independently selected from —F, —Cl, cyano, and methoxy.

24. The compound or pharmaceutically acceptable salt thereof of claim 1, wherein Y is —CH$_3$, —CH$_2$F, —CHF$_2$, —CF$_3$, —CH$_2$Cl, —CH$_2$—O—CH$_3$, or —CH$_2$—CN.

25. The compound or pharmaceutically acceptable salt thereof of claim 1, wherein Z is phenyl optionally substituted with 1 to 3 substituents independently selected from halogen, $C_{1-3}$ alkyl, or $C_{1-3}$ alkoxy, wherein the $C_{1-3}$ alkyl is optionally substituted with 1 to 3 substituents independently selected from halogen and $C_{1-3}$ alkoxy.

26. The compound or pharmaceutically acceptable salt thereof of claim 1, wherein Z is phenyl optionally substituted with 1 to 3 substituents independently selected from —F, —Cl, —CH$_3$, —CF$_3$, —CH$_2$—O—CH$_3$, and —O—CH$_3$.

27. The compound or pharmaceutically acceptable salt thereof of claim 1, wherein Z is

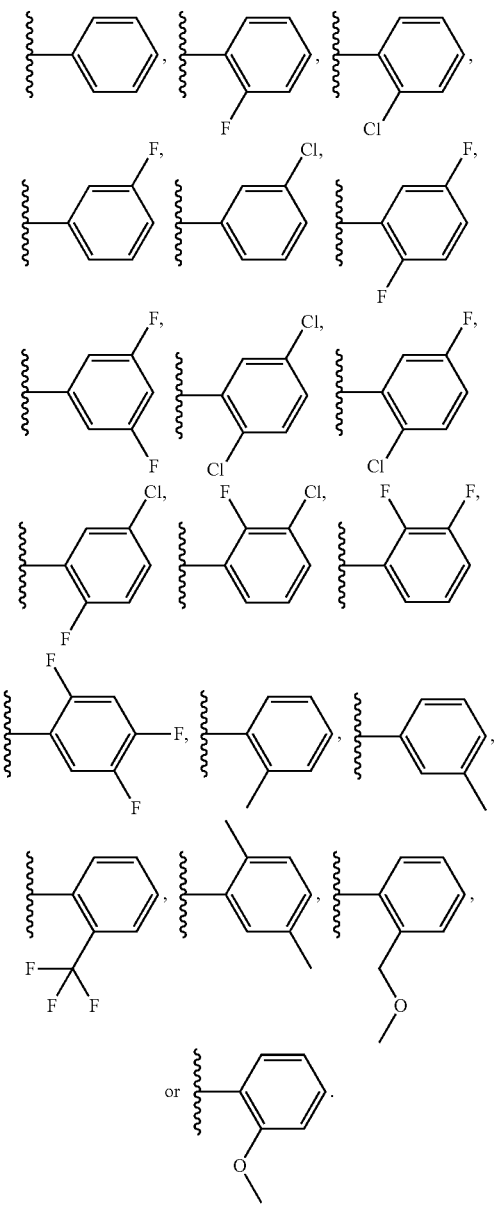

28. The compound or pharmaceutically acceptable salt thereof of claim 1, wherein the compound is selected from the group consisting of:
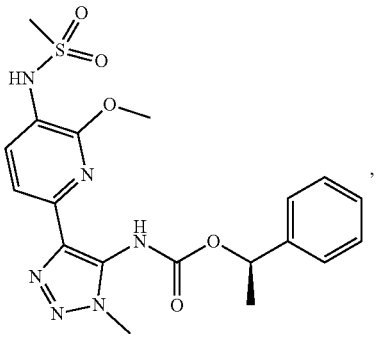
,
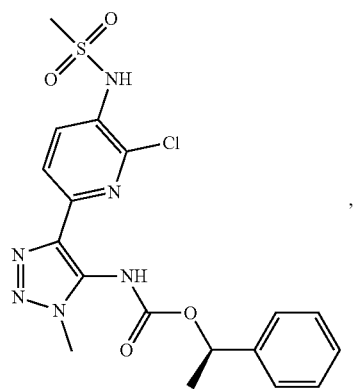
,
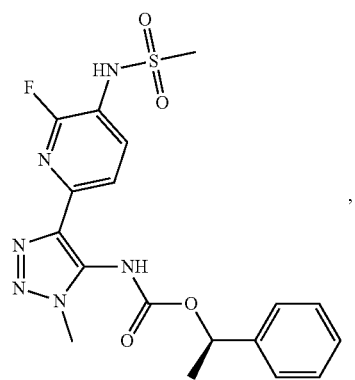
,
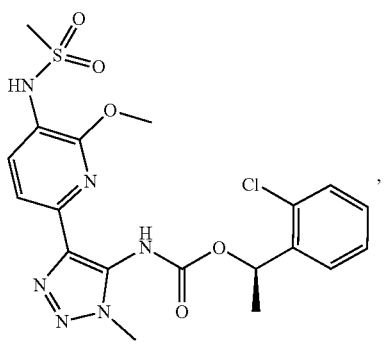
,
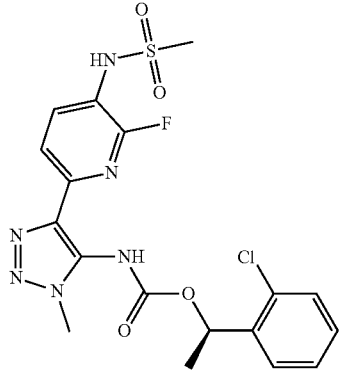
,
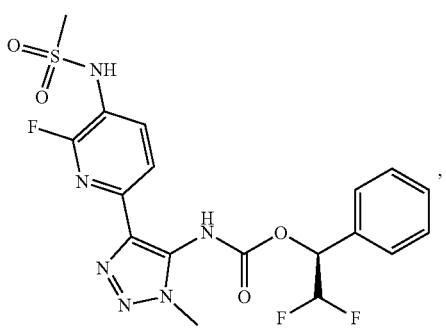
,
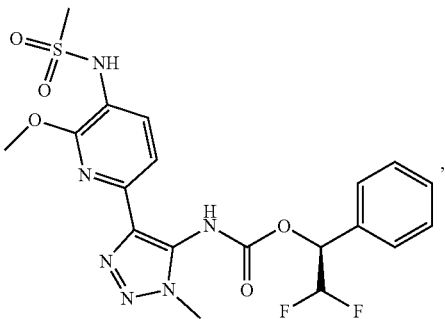
,
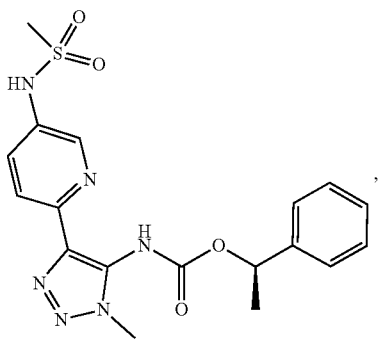
,

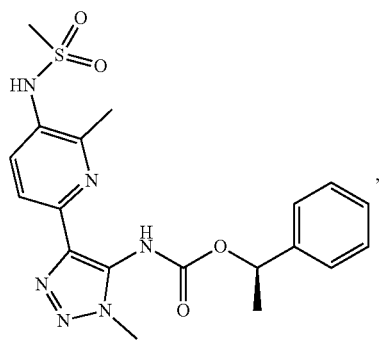
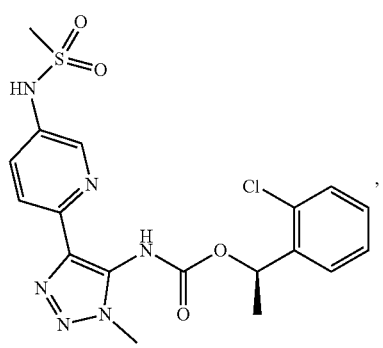
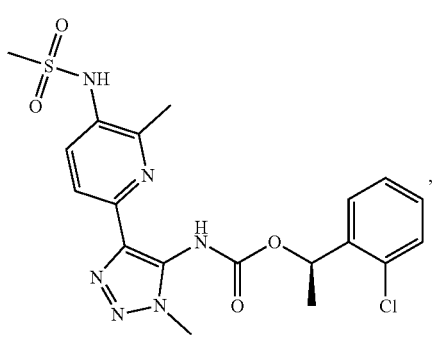
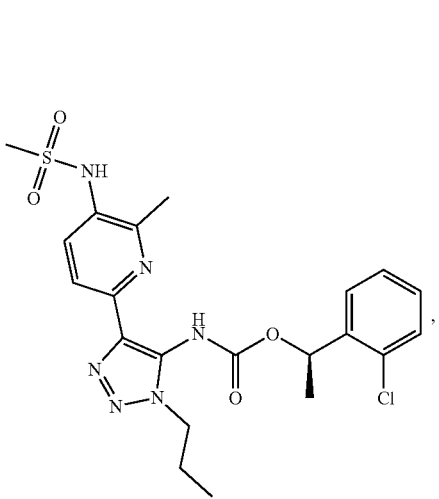
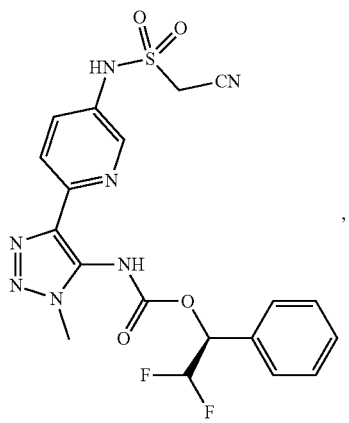
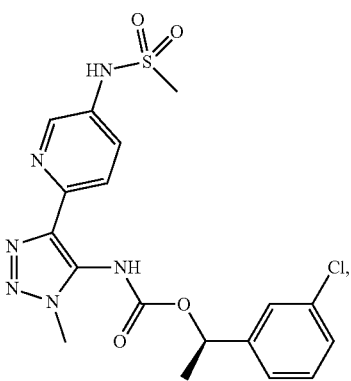
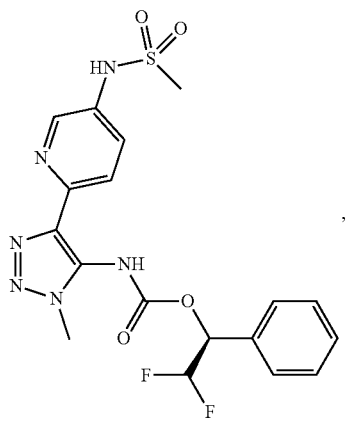
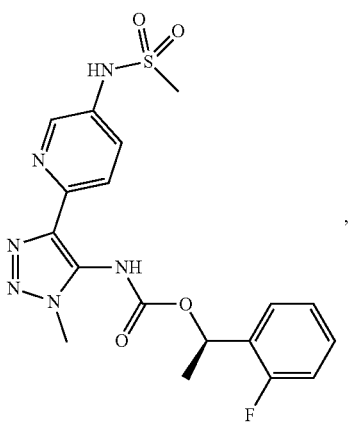

305
-continued
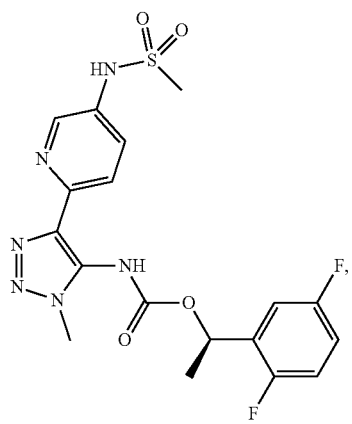
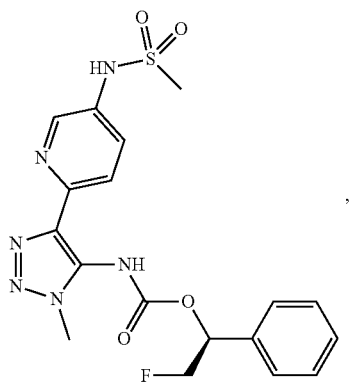
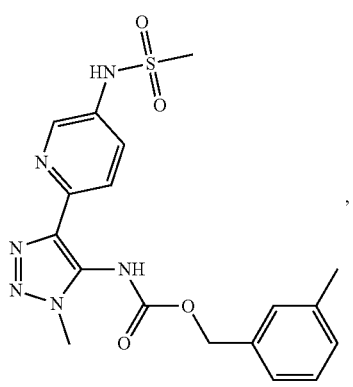
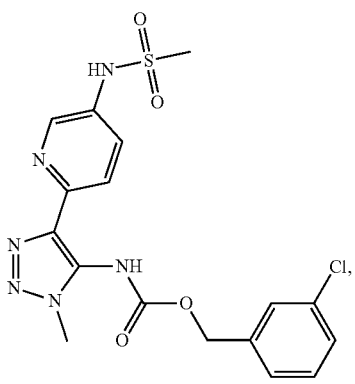
306
-continued
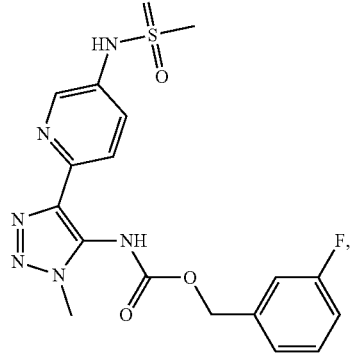
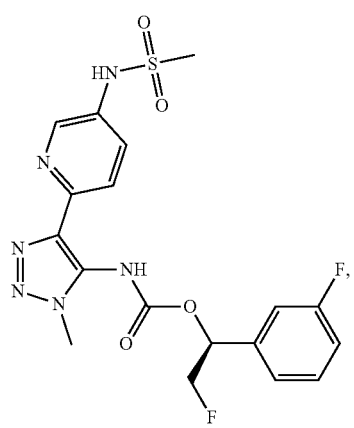
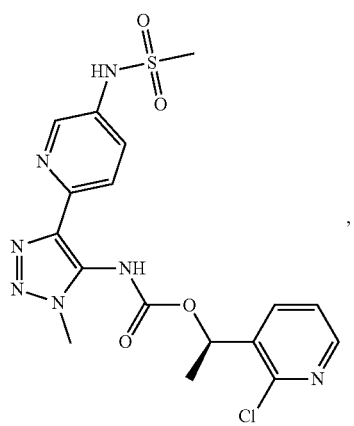
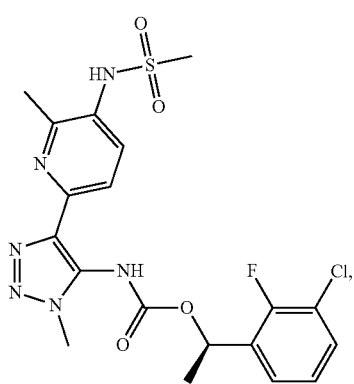

307
-continued
308
-continued
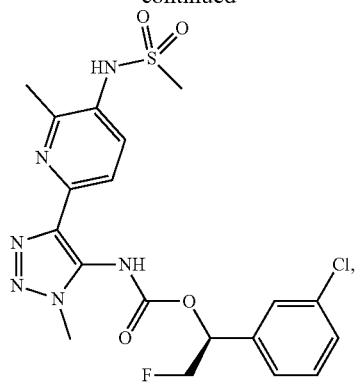
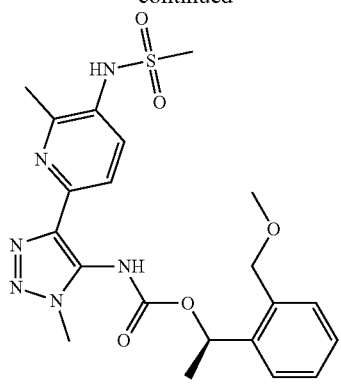

309
-continued
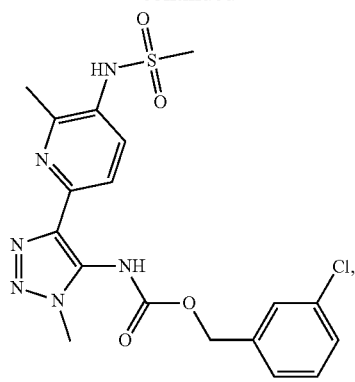
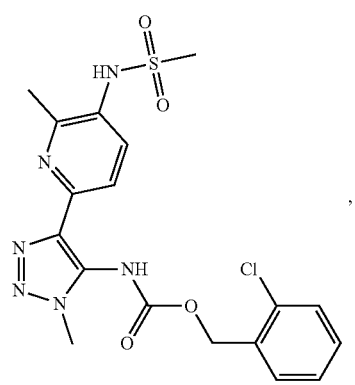
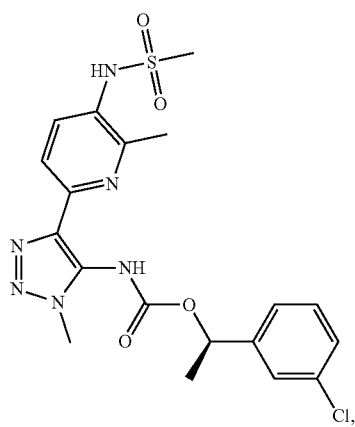
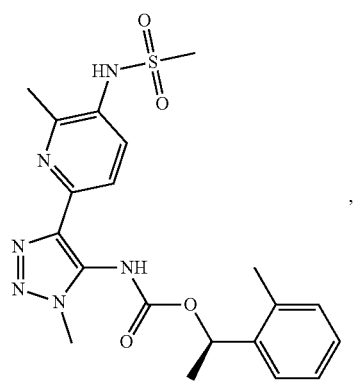
310
-continued
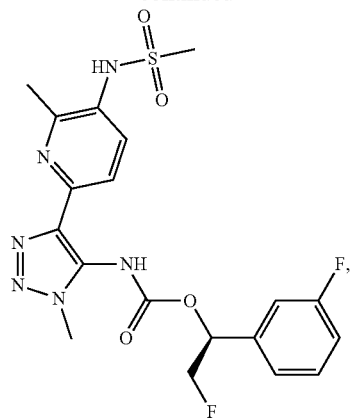
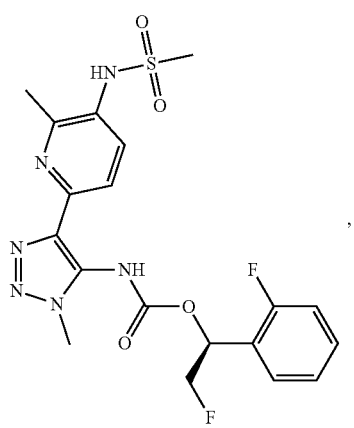
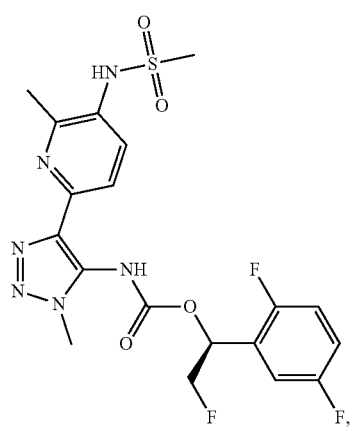
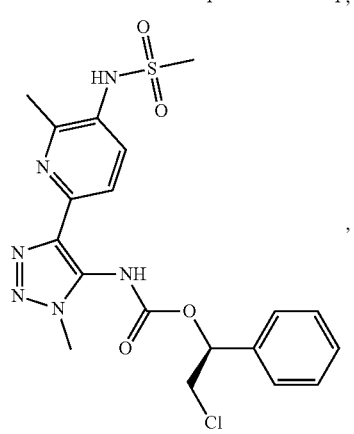

311
-continued
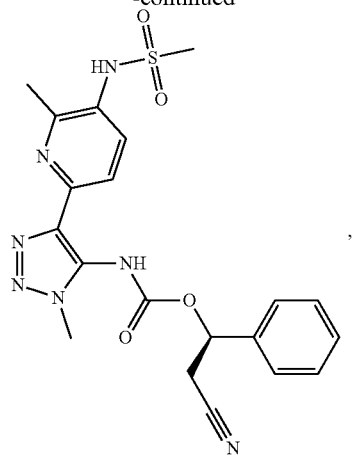
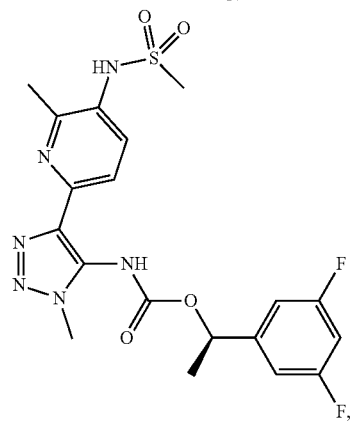
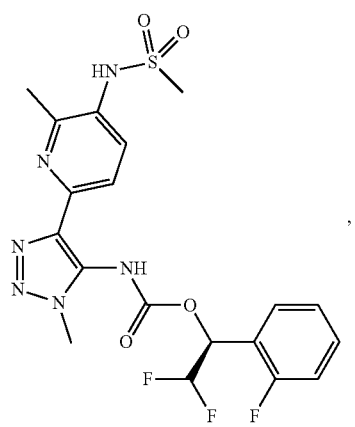
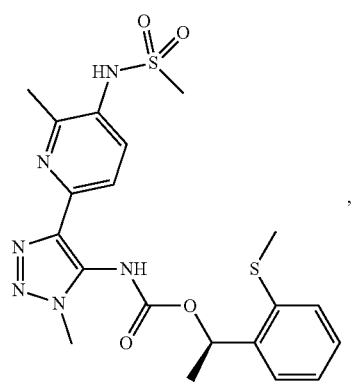
312
-continued
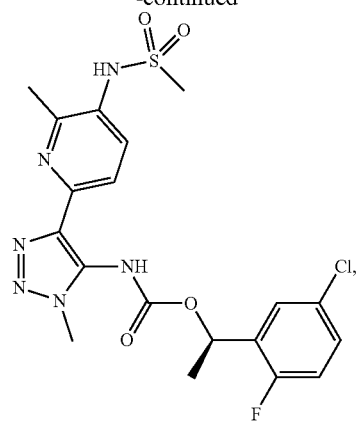
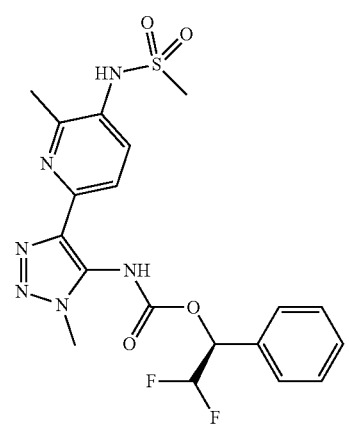
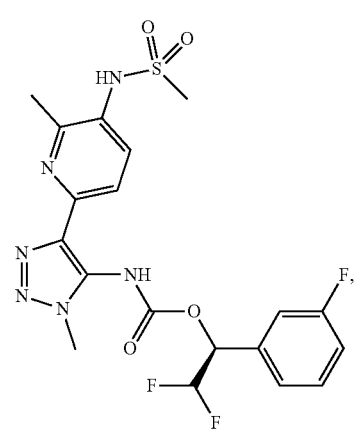
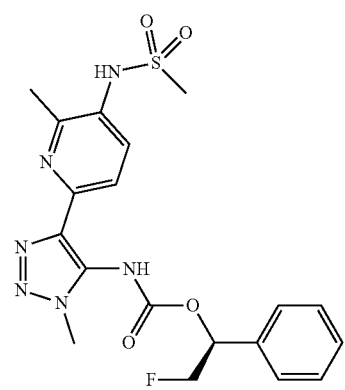

313
-continued
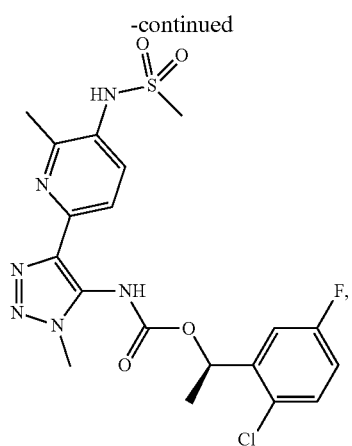
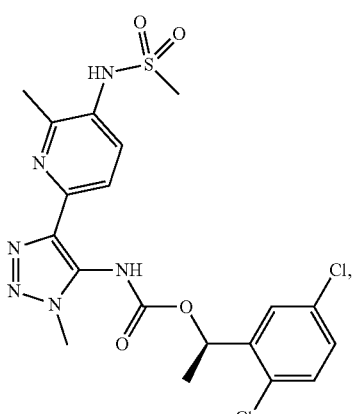
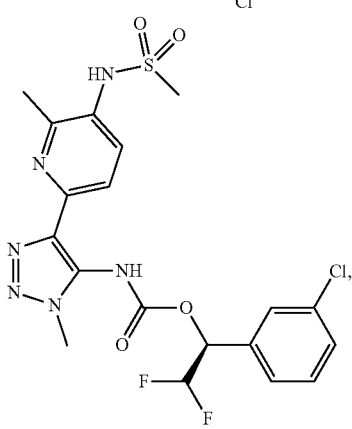
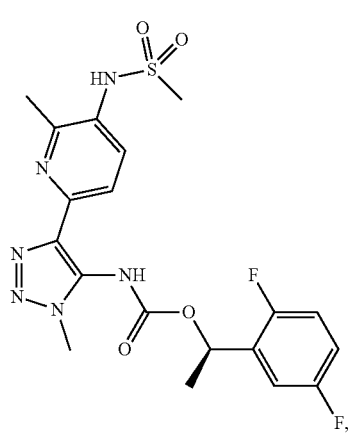
314
-continued
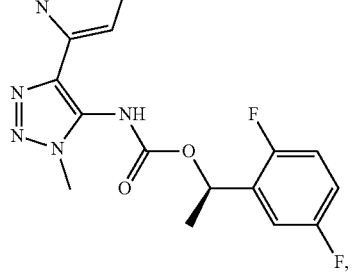
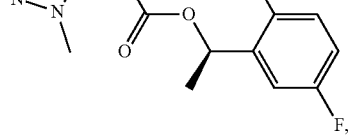
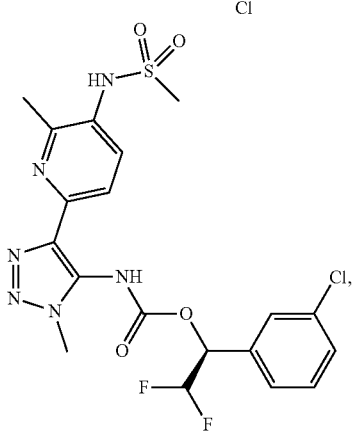
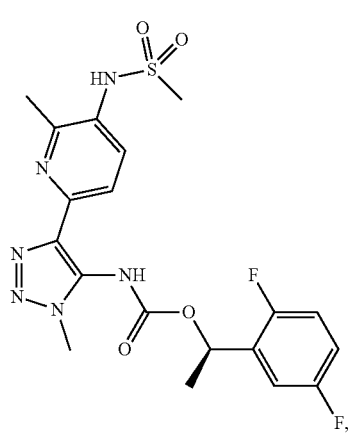

315
-continued
316
-continued
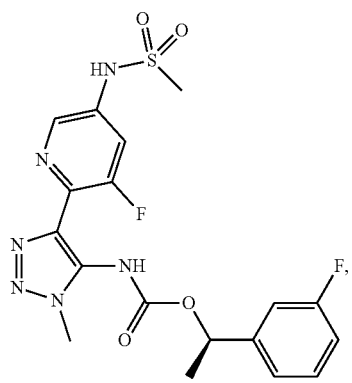
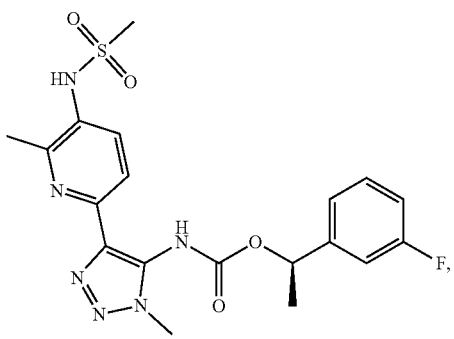
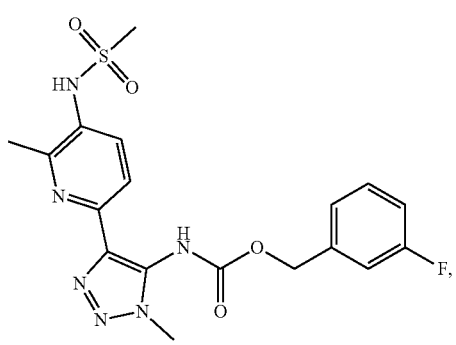
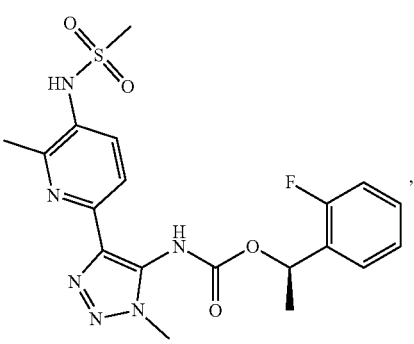
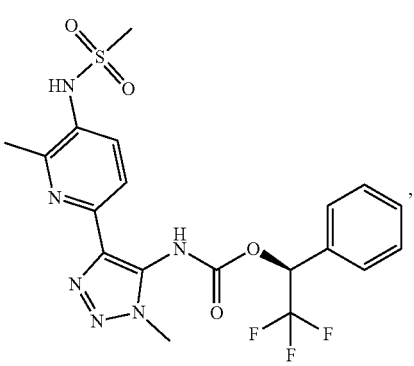

317
-continued
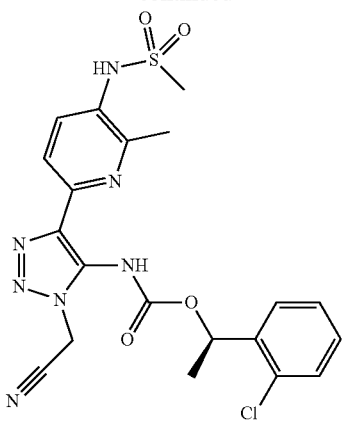
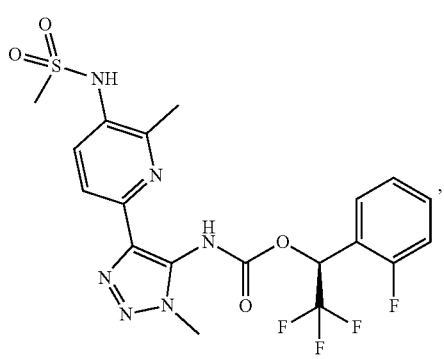
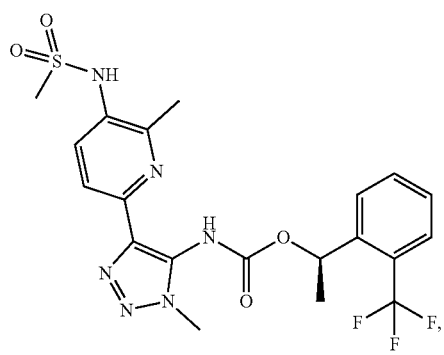
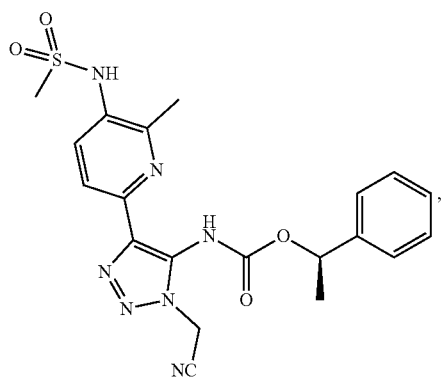
318
-continued
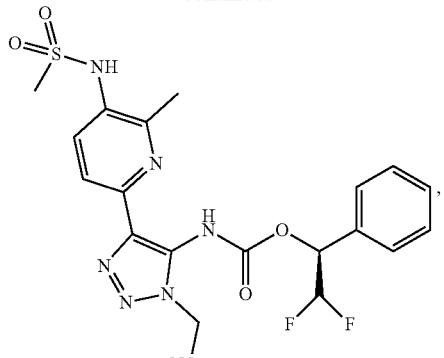
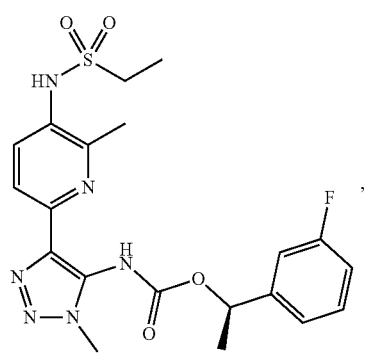
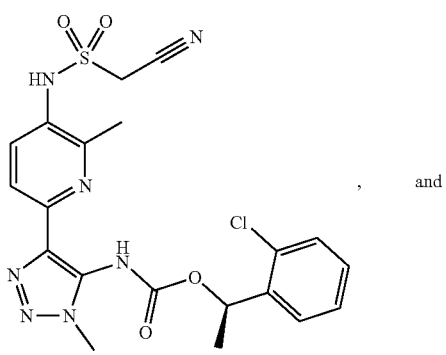
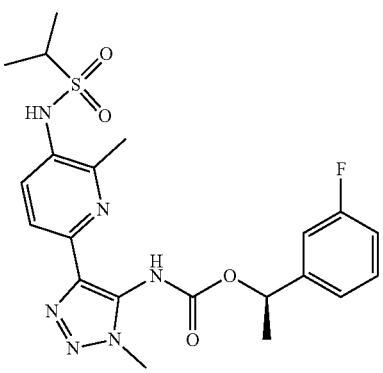
and
29. The compound or pharmaceutically acceptable salt thereof of claim 1, wherein the compound is selected from the group consisting of:

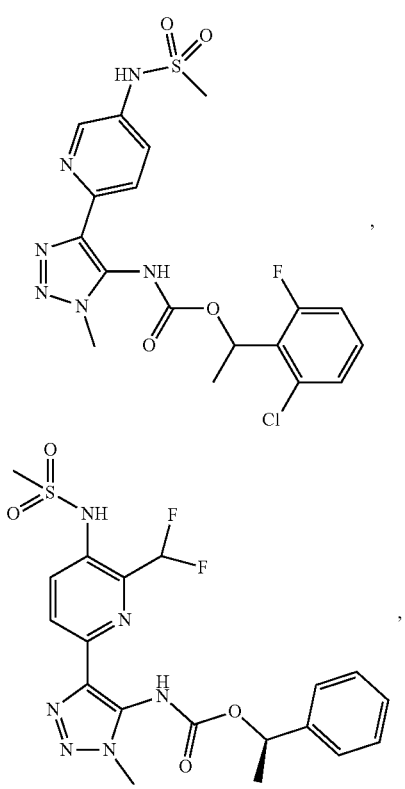
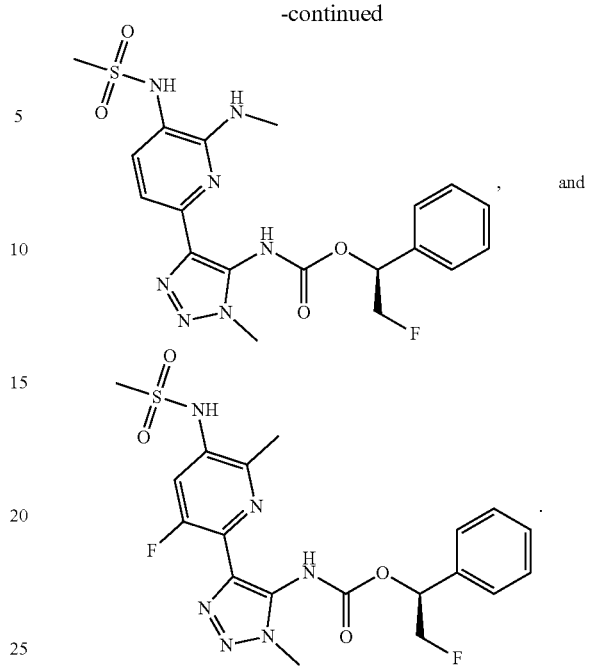
30. A pharmaceutical composition comprising a therapeutically effective amount of a compound, or pharmaceutically acceptable salt thereof, of claim 1, and a pharmaceutically acceptable excipient.
* * * * *

UNITED STATES PATENT AND TRADEMARK OFFICE
CERTIFICATE OF CORRECTION

PATENT NO. : 11,548,871 B2
APPLICATION NO. : 17/096150
DATED : January 10, 2023
INVENTOR(S) : Brian P. Bestvater et al.

Page 1 of 1

It is certified that error appears in the above-identified patent and that said Letters Patent is hereby corrected as shown below:

In the Claims

Column 306, Lines 35-50, Claim 28, delete " 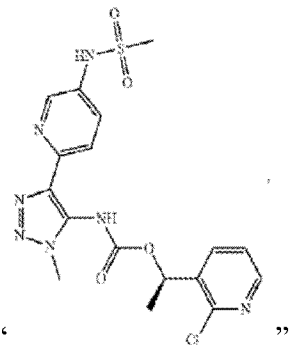 "

Signed and Sealed this
Fifteenth Day of August, 2023

Katherine Kelly Vidal
Director of the United States Patent and Trademark Office